(12) United States Patent
Jaffrey et al.

(10) Patent No.: US 12,103,952 B2
(45) Date of Patent: *Oct. 1, 2024

(54) METHODS FOR EXPRESSING PROTEINS IN AXONS

(71) Applicant: Cornell University, Ithaca, NY (US)

(72) Inventors: Samie R. Jaffrey, New York, NY (US); Ulrich Hengst, New York, NY (US)

(73) Assignee: Cornell University, Ithaca, NY (US)

( * ) Notice: Subject to any disclaimer, the term of this patent is extended or adjusted under 35 U.S.C. 154(b) by 670 days.

This patent is subject to a terminal disclaimer.

(21) Appl. No.: 17/168,774

(22) Filed: Feb. 5, 2021

(65) Prior Publication Data

US 2021/0246180 A1    Aug. 12, 2021

Related U.S. Application Data

(63) Continuation of application No. 12/832,698, filed on Jul. 8, 2010, now Pat. No. 10,941,186.

(51) Int. Cl.
| | | |
|---|---|---|
| *A61K 48/00* | (2006.01) | |
| *C07K 14/47* | (2006.01) | |
| *C12N 15/113* | (2010.01) | |
| *C12N 15/86* | (2006.01) | |

(52) U.S. Cl.
CPC ...... *C07K 14/4705* (2013.01); *A61K 48/0075* (2013.01); *C12N 15/113* (2013.01); *C12N 15/86* (2013.01); *C12N 2310/14* (2013.01); *C12N 2770/36143* (2013.01); *C12N 2840/203* (2013.01)

(58) Field of Classification Search
CPC .................................................. A61K 48/00
See application file for complete search history.

(56) References Cited

U.S. PATENT DOCUMENTS

| | | |
|---|---|---|
| 6,509,190 B2 | 1/2003 | Kandel et al. |
| 10,941,186 B2 | 3/2021 | Jaffrey et al. |
| 2002/0119140 A1 | 8/2002 | Mckerracher et al. |
| 2003/0118557 A1 | 6/2003 | Bomze et al. |
| 2004/0197313 A1 | 10/2004 | Wang et al. |
| 2005/0019346 A1 | 1/2005 | Boulis |
| 2005/0136036 A1 | 6/2005 | During et al. |
| 2007/0166820 A1 | 7/2007 | Smith et al. |
| 2010/0330038 A1 | 12/2010 | Jaffrey et al. |

FOREIGN PATENT DOCUMENTS

| | | |
|---|---|---|
| WO | WO-2003031630 A1 | 4/2003 |
| WO | WO-09089040 A1 | 7/2009 |

OTHER PUBLICATIONS

Finkbeiner et al. (1997, Neuron, vol. 19 pp. 1031-1047). (Year: 1997).*

"U.S. Appl. No. 10/804,331, Non-Final Office Action mailed Sep. 12, 2007", 16.
"U.S. Appl. No. 12/832,698, Advisory Action mailed Jun. 13, 2019", 3 pgs.
"U.S. Appl. No. 12/832,698, Advisory Action mailed Aug. 1, 2017", 3 pgs.
"U.S. Appl. No. 12/832,698, Advisory Action mailed Aug. 26, 2015", 4 pgs.
"U.S. Appl. No. 12/832,698, Examiner Interview Summary mailed Sep. 18, 2014", 3 pgs.
"U.S. Appl. No. 12/832,698, Final Office Action mailed Jan. 25, 2019", 7 pgs.
"U.S. Appl. No. 12/832,698, Final Office Action mailed Feb. 27, 2017", 23 pgs.
"U.S. Appl. No. 12/832,698, Final Office Action mailed Apr. 24, 2015", 10 pgs.
"U.S. Appl. No. 12/832,698, Non Final Office Action mailed May 2, 2018", 33 pgs.
"U.S. Appl. No. 12/832,698, Non Final Office Action mailed May 12, 2020", 9 pgs.
"U.S. Appl. No. 12/832,698, Non Final Office Action mailed Jun. 16, 2016", 16 pgs.
"U.S. Appl. No. 12/832,698, Non Final Office Action mailed Sep. 18, 2014", 23 pgs.
"U.S. Appl. No. 12/832,698, Non Final Office Action mailed Nov. 25, 2013", 9 pgs.
"U.S. Appl. No. 12/832,698, Non Final Office Action mailed Nov. 26, 2012", 19 pgs.
"U.S. Appl. No. 12/832,698, Notice of Allowance mailed Oct. 30, 2020", 10 pgs.
"U.S. Appl. No. 12/832,698, Response filed Feb. 25, 2014 to Non Final Office Action mailed Nov. 25, 2013", 9 pgs.
"U.S. Appl. No. 12/832,698, Response filed Feb. 26, 2013 to Non Final Office Action mailed Nov. 26, 2012", 20 pgs.
"U.S. Appl. No. 12/832,698, Response filed Jun. 27, 2017 to Final Office Action mailed Feb. 27, 2017", 15 pgs.
"U.S. Appl. No. 12/832,698, Response filed Jul. 18, 2012 to Restriction Requirement mailed Jan. 19, 2012", 10 pgs.
"U.S. Appl. No. 12/832,698, Response filed Jul. 23, 2015 to Final Office Action mailed Apr. 24, 2015", 15 pgs.
"U.S. Appl. No. 12/832,698, Response filed Aug. 11, 2020 to Non Final Office Action mailed May 12, 2020", 6 pgs.
"U.S. Appl. No. 12/832,698, Response filed Aug. 23, 2017 to Advisory Action mailed Aug. 1, 2017", 16 pgs.
"U.S. Appl. No. 12/832,698, Response filed Sep. 22, 2015 to Advisory Action Action mailed Aug. 26, 2015", 13 pgs.
"U.S. Appl. No. 12/832,698, Response filed Oct. 2, 2018 to Non Final Office Action mailed May 2, 2018", 25 pgs.
"U.S. Appl. No. 12/832,698, Response filed Oct. 17, 2016 to Non Final Office Action mailed Jun. 16, 2016", 12 pgs.

(Continued)

*Primary Examiner* — Anoop K Singh
*Assistant Examiner* — David A Montanari
(74) *Attorney, Agent, or Firm* — Schwegman Lundberg & Woessner, P.A.

(57) ABSTRACT

The invention relates to expressing proteins in the axons of mammalian neurons. The invention provides nucleic acids that can be used to express a selected polypeptide in neuronal axons, viruses that can be used deliver nucleic acids of the invention into neuronal axons, as well as methods for doing so. Thus, the invention provides pharmaceutical compositions comprising viruses of the invention, as well as their use in methods of treating injured axons or conditions associated with aberrant axon growth or function.

19 Claims, 28 Drawing Sheets

Specification includes a Sequence Listing.

(56) References Cited

OTHER PUBLICATIONS

"U.S. Appl. No. 12/832,698, Response filed Dec. 18, 2014 to Non Final Office Action mailed Sep. 18, 2014", 16 pgs.
"U.S. Appl. No. 12/832,698, Response filed Apr. 25, 2019 to Final Office Action mailed Jan. 25, 2019", 8 pgs.
"U.S. Appl. No. 12/832,698, Response filed Jun. 25, 2019 to Advisory Action mailed Jun. 13, 2019", 8 pgs.
"U.S. Appl. No. 12/832,698, Restriction Requirement Mailed Jan. 19, 2012", 10 pgs.
"International Application Serial No. PCT/US2009/000118, International Search Report mailed Mar. 27, 2009".
"International Application Serial No. PCT/US2009/000118, Written Opinion mailed Mar. 27, 2009".
"International Application Serial No. PCT/US2009/000181, International Search Report mailed Mar. 27, 2009".
"International Application Serial No. PCT/US2009/000181, Written Opinion mailed Mar. 27, 2009".
Bieniasz, et al., "", J. Virology, vol. 69(11)., (1995), 7295-7299.
Czarneski, et al., "", Immunological Res., vol. 27(2)., (2003), 469-479.
Gao, Ying, et al., "Activated CREB Is Sufficient to Overcome Inhibitors in Myelin and Promote Spinal Axon Regeneration in Vivo", Neuron, vol. 44, (2004), 609-621.
Hengst, U., et al., "Function and translational regulation of mRNA in developing axons", Semin Cell Dev Biol., 18(2), (Apr. 2007), 209-15.
Kleiman, Robin, et al., "Subcellular distribution of rRNA and ploly(A) RNA in hippocampal neurons in culture", Molecular Brain Research, 20, (1993), 305-312.
Liu, Guofa, et al., "Netrin Requires Focal Adhesion Kinase and Src Family Kinases for Axon Outgrowth and Attraction", Nature Neuroscience. vol. 7(11), (2004), 1222-1232.
Lundstrom, K. J, "", Stem Cell Res. Ther., vol. S4, (2012), 1-5.
Nakai, Sadamu, et al., "Effects of BDNF Infusion on the Axon Terminals of Locus Coeruleus Neurons of Aging Rats", Neuroscience Res., vol. 54, (2006), 213-219.
Woolf, Clifford J, et al., "Neuropathic Pain", Aetiology, Symptoms, Mechanisms, and Management. vol. 353. Lancet, (1999), 1959-1964.
Wu, K. Y, et al., "Local translation of RhoA regulates growth cone collapse", Nature, 436(7053), (Aug. 18, 2005), 1020-4.
Wu, Karen Y, et al., "Soluble Adenylyl Cyclase is Required for Netrin-1 Signaling in Nerve Growth Cones", Nature Neuroscience, vol. 9(10), (2006), 1257-1264.
Yamashita, et al., "", Virology, vol. 344., (2006).
Ziemba, K. S, et al., "Targeting axon growth from neuronal transplants along preformed guidance pathways in the adult CNS", J Neurosci., 28(2), (Jan. 9, 2008), 340-8.

* cited by examiner

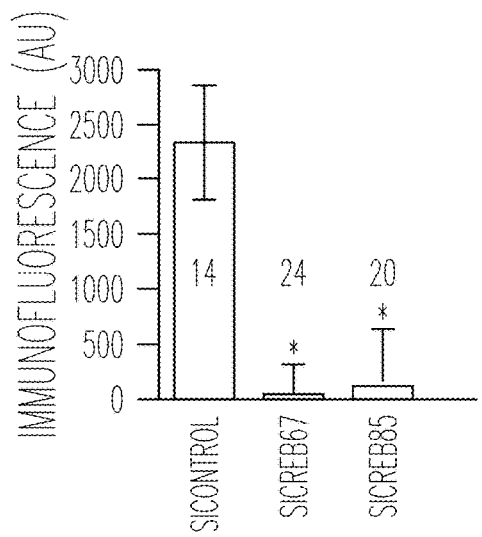
*Fig. 1K*
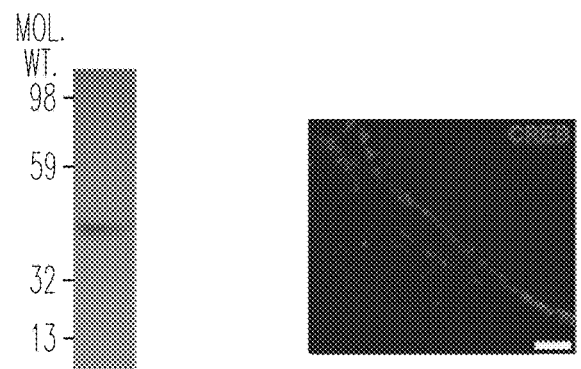
*Fig. 1L*          *Fig. 1M*
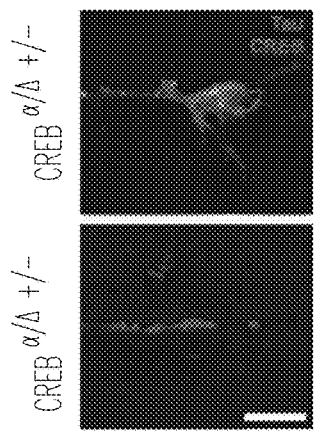
*Fig. 1N*
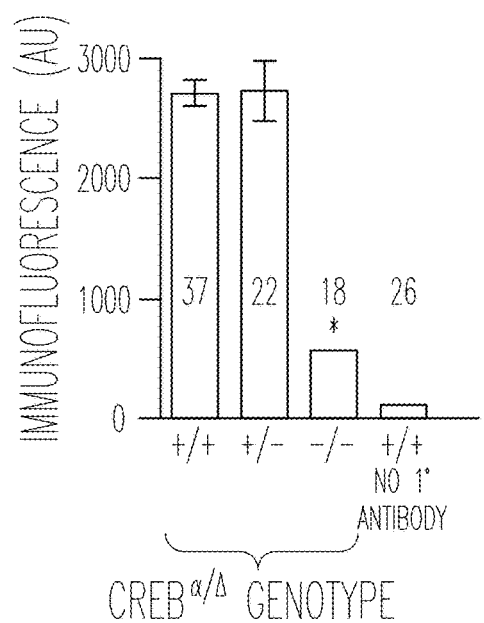
*Fig. 1O*

▲ DENDRA
■ DENDRA-CREB
● DENDRA-CREB + ETHACRYNIC ACID
▼ DENDRA-CREB + COLCHICINE

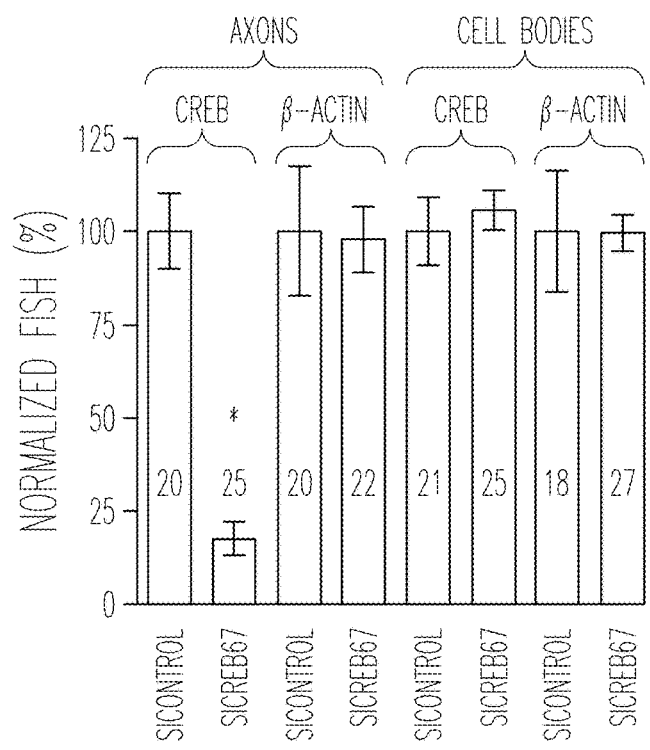
Fig. 10B
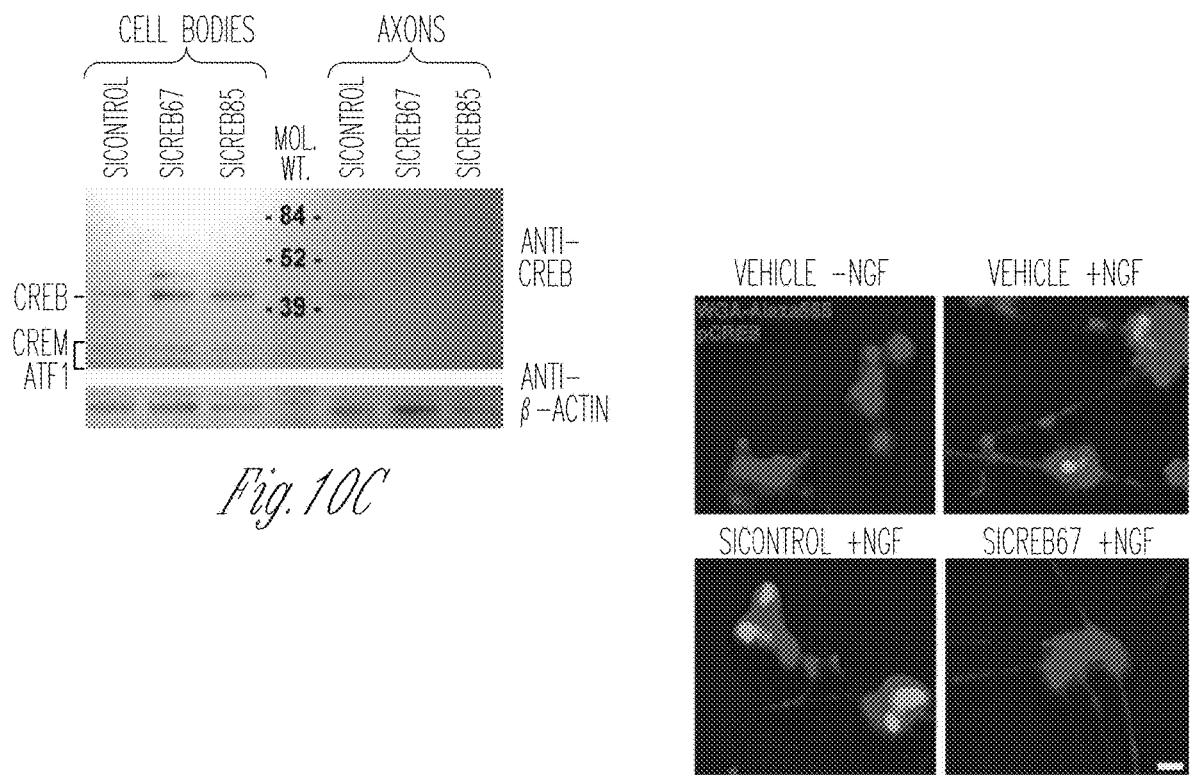
Fig. 10C
Fig. 10D

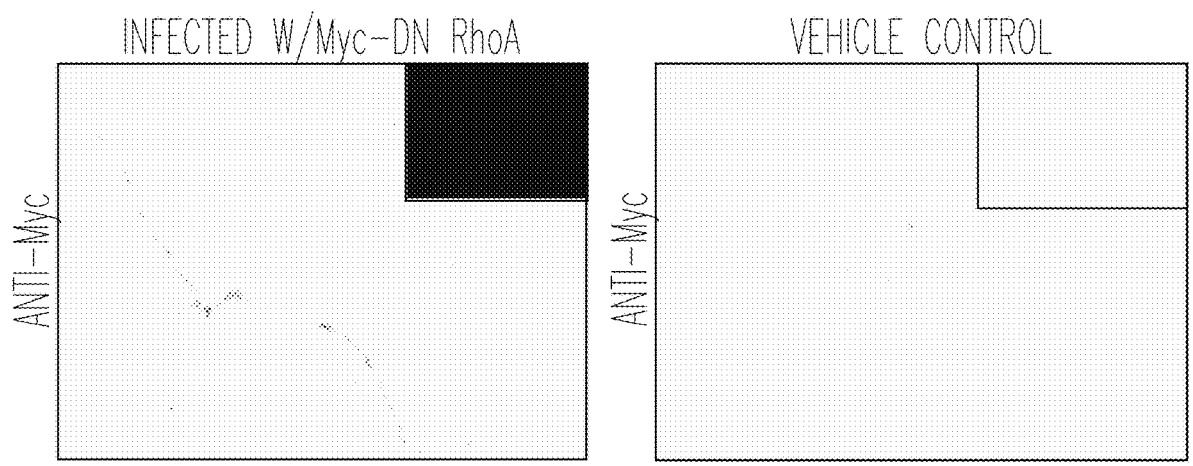
*Fig.13A*    *Fig.13C*
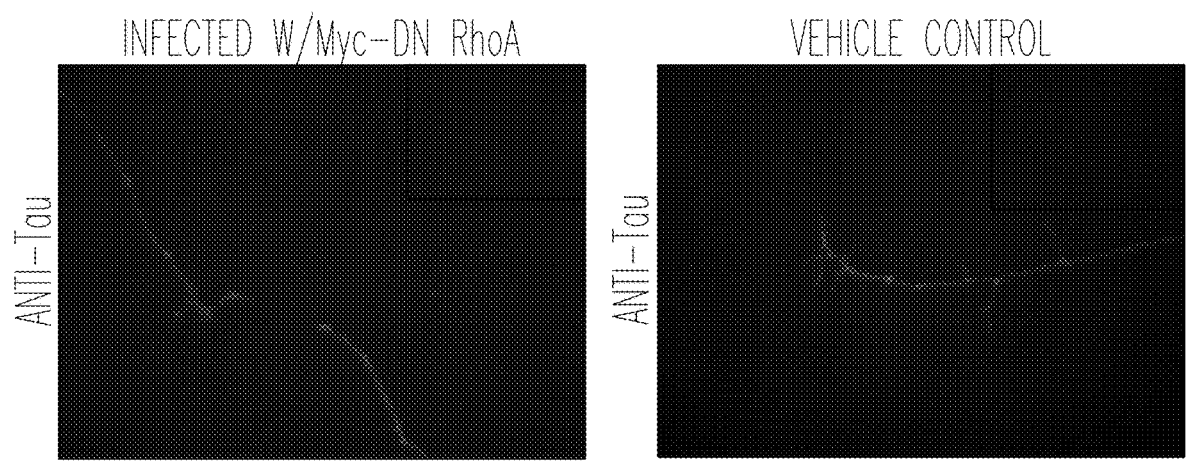
*Fig.13B*    *Fig.13D*

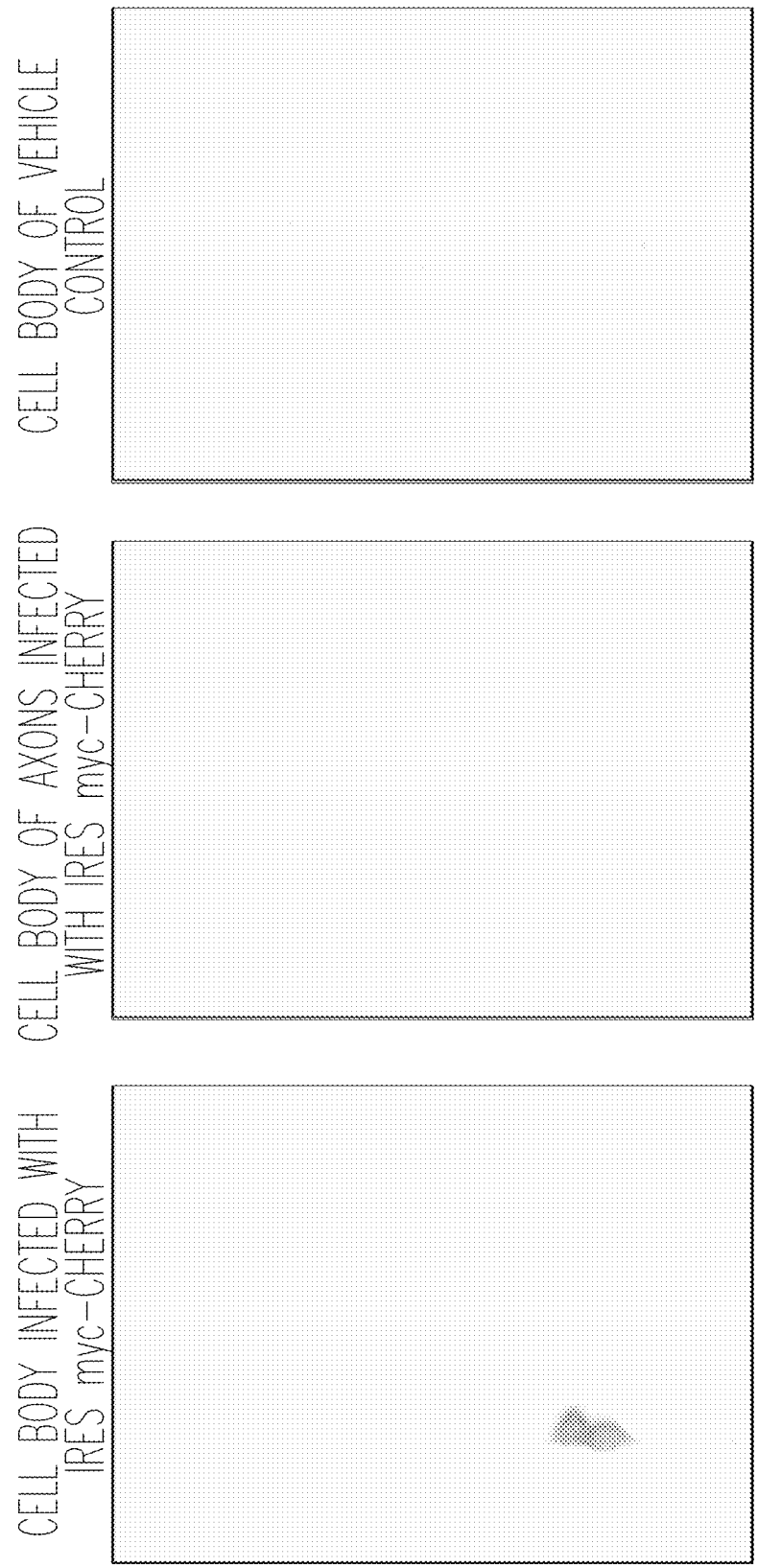

Fig. 17

```
 9951            tgactaatac tacaacacca ccacctctag
10001 attccGCCCC TCTCCCTCCC CCCCCCTAA CGTTACTGGC CGAAGCCGCT
10051 TGGAATAAGG CCGGTGTGCG TTTGTCTATA TGTTATTTTC CACCATATTG
10101 CCGTCTTTG GCAATGTGAG GGCCCGGAAA CCTGGCCCTG TCTTCTTGAC
10151 GAGCATTCCT AGGGGTCTTT CCCCTCTCGC CAAAGGAATG CAAGGTCTGT
10201 TGAATGTCGT GAAGGAAGCA GTTCCTCTGG AAGCTTCTTG AAGACAAACA
10251 ACGTCTGTAG CGACCCTTTG CAGGCAGCGG AACCCCCCAC CTGGCGACAG
10301 GTGCCCTCGC GGCCAAAAGC CGCCACGTT AGATACACCT GCAAAGGCGG
10351 CACAACCCCA GTGCCACGTT GTGAGTTGGA TAGTTGTGGA AAGAGTCAAA
10401 TGGCTCTCCT CAAGCGTATT CAACAAGGGG CTGAAGGATG CCCAGAAGGT
10451 ACCCCATGT ATGGGATCTG ATCTGGGGCC TCGGTGCACA TGCTTTACAT
10501 GTGTTTAGTC GAGGTTAAAA AAACGTCTAG GCCCCCGAA CCACGGGAC
10501 GTGGTTTTCC TTTGAAAAAC ACGatgataa gcttgccaca a (SEQ. ID NO. 66)
    1                                             cgcgtagat
   10 ctcacgtgag catgcaggcc ttgggcccaa tgatccgacc agcaaaactc
   60 gatgtacttc cgaggaactg atgtgcataa tgcatcaggc tggtacatta
  110 gatccccgct taccgcgggc aatatagcaa cactaaaaac tcgatgtact
  160 tccgaggaag cgcagtgcat aatgctgcgc agtgttgcca cataaccact
  210 atattaacca tttatctagc ggacgccaaa aactcaatgt atttctgagg
  260 aagcgtggtg cataatgcca cgcagcgtct gcataacttt tattattct
  310 tttattaatc aacaaaattt tgtttttaac atttcaaaaa aaaaaaaaaa
  360 aaaaaaaaa aaaaaaaaaa aagggaattc ctcgattaat taagcggccg
  410 ctcgagggga a (SEQ. ID NO. 67)
```

METHODS FOR EXPRESSING PROTEINS IN AXONS

CROSS-REFERENCE TO RELATED APPLICATIONS

This application is a continuation of U.S. application Ser. No. 12/832,698, filed Jul. 8, 2010, which is a national stage application under 35 U.S.C. § 371 of PCT/US2009/00118, filed Jan. 9, 2009 and published as WO 2009/089040 on Jul. 16, 2009, which claims priority to U.S. Provisional Application Ser. No. 61/010,720, filed Jan. 11, 2008, the contents of which applications are specifically incorporated herein by reference in their entirety.

STATEMENT REGARDING FEDERALLY SPONSORED RESEARCH OR DEVELOPMENT

Work relating to this application was supported by a grant from the National Institutes of Mental Health (5R01MH066204-05). The government may have certain rights in the invention.

BACKGROUND OF THE INVENTION

Neurons have axons, which are long extensions that typically connect the neuron to a target cell, such as another neuron, or a muscle cell. Axons can be very long. For example, while the cell body may be 40 microns in diameter, the axon of many sensory neurons can be a meter or longer in adults.

There are several types of medical conditions that are associated with axonal injury. These include numerous types of axonopathies, ranging from Charcot-Marie-Tooth disease to diabetic neuropathy, as well as traumatic injuries of axons, such as spinal cord injury (SCI). SCI is caused by injury to axonal tracts that descend from the brain. These axons are derived from upper motor neurons that are situated in the cortex that send axons through the brain, down through the spinal cord, where they eventually synapse on lower motor neurons in the spinal cord. Injury to these descending axons, results in the loss of innervation of motor neurons, and therefore paralysis of the muscles that are innervated by those motor neurons.

Thus, there is a need for methods of promoting axonal regeneration or growth after injury.

SUMMARY OF THE INVENTION

The invention is based on the discovery that proteins can be expressed in the axons of a mammalian neuron. More specifically, the invention involves the discovery that a protein coding sequence operably linked to an internal ribosome entry site (IRES) in an RNA viral genome can be expressed in a mammalian axon when the RNA genome is transduced into the axon. Thus, the invention provides isolated recombinant nucleic acids such as DNA and RNA molecules, as well as RNA viruses that can be used to deliver selected polypeptide-coding sequences into the axons of mammalian neurons for expression of the encoded polypeptides in the axons. The invention also provides methods for expressing polypeptides in the axons of mammalian neurons as well as methods of treating injured axons or treating conditions associated with aberrant axon function.

In one aspect, the invention provides an isolated nucleic acid that has (a) a mammalian translation initiation element; (b) a polypeptide coding sequence operably-linked to the mammalian translation initiation element, and (c) a viral packaging sequence. The coding sequence encodes a polypeptide that, when expressed in the axon of a mammalian neuron, modulates the growth or function of an axon. In some embodiments, the viral packaging sequence is that of an alphavirus. In some embodiments, the alphavirus is a Sindbis virus or a Semliki forest virus. In some embodiments, the nucleic acid further includes one or more viral structural protein coding sequences such as an alphavirus protein coding sequence, which can be a capsid protein or a glycoprotein involved in viral assembly and packaging.

In some embodiments, the nucleic acid is a recombinant RNA molecule. In some embodiments, the RNA molecule includes a poly-adenylyl tail. In some embodiments, mammalian translation initiation element of the recombinant RNA molecule is a 5'CAP. In other embodiments, it is an internal ribosome entry site (IRES).

In some embodiments, the nucleic acid is a recombinant DNA molecule that further comprises a mammalian promoter sequence located 5' of the mammalian translation initiation element and wherein the mammalian translation initiation element is an IRES.

In some embodiments, the IRES of the a nucleic acid of the invention can be a viral IRES, such as the IRES from encephalomyocarditis, Sindbis virus or a Semliki forest virus. In other embodiments, the IRES can be a prokaryotic or eukaryotic sequence. In some embodiments, the IRES has the sequence of any one of SEQ ID NO: 29-35. In some embodiments, the RNA molecule is a single-stranded genome of a virus or an attenuated mutant thereof that is capable of infecting the axon of a mammalian neuron and transducing the recombinant RNA molecule into the axon.

In some embodiments, the polypeptide encoded by a nucleic acid of the invention promotes the growth of an injured axon. In one embodiment, the polypeptide-coding sequence encodes a kinase or a transcription factor. The kinase can be a src kinase, the transcription factor can be a cyclic AMP-response element-binding protein (CREB) or nervy. In some embodiments, the polypeptide-coding sequence encodes a C3-ADP-ribosyltransferase, a dominant-negative RhoA mutant polypeptide, a cAMP-producing enzyme, glutamic acid decarboxylase, human proenkephalin, an inhibitor of a dominant-negative Vps24, an intestinal peptide (VIP), brain-derived neurotrophic factor (BDNF), neurotrophin-3 (NT-3), glial-derived neurotropic factor (GDNF), GAP 43 or CAP23. The dominant-negative RhoA mutant polypeptide can be N19-RhoA polypeptide. The cAMP-producing enzyme can be a soluble adenylyl cyclase. In some embodiments, the polypeptide comprises the sequence of any one of SEQ ID NO: 36 to 47. In some embodiments, the polypeptide-coding sequence comprises the sequence of any one of SEQ ID NO: 49 to 60.

In one aspect, the invention provides a recombinant RNA virus capable of infecting the axon of a mammalian neuron, the virus comprising the RNA molecule of the invention. In some embodiments, the RNA molecule encodes a polypeptide having the sequence of any one of SEQ ID NO: 36 to 47. In some embodiments, the RNA molecule comprises the sequence of any one of SEQ ID NO: 49 to 60. The virus can be an alphavirus or an attenuated form thereof such as a Semliki forest virus or an attenuated form thereof In one aspect, the invention provides a composition comprising a recombinant RNA virus of the invention and a pharmaceutically acceptable carrier.

In one aspect, the invention provides a method for expressing a polypeptide in the axon of a mammalian neuron comprising contacting the axon with a virus or composition of the invention, under conditions effective for the transduction of the recombinant RNA molecule in the virus into the axon. The polypeptide can be any one described here including one capable of modulating the growth or function of an axon, e.g. one capable of promoting the growth of an injured axon or reducing the activity of the axon of a neuron. Examples include a kinase such as src or a transcription factor such as a cyclic AMP-response element-binding protein (CREB) or nervy. In some embodiments, the polypeptide is C3-ADP-ribosyltransferase, a dominant-negative RhoA mutant polypeptide, a cAMP-producing enzyme, glutamic acid decarboxylase, human proenkephalin, an inhibitor of a dominant-negative Vps24, an intestinal peptide (VIP), brain-derived neurotrophic factor (BDNF), neurotrophin-3 (NT-3), glial-derived neurotropic factor (GDNF), GAP 43, CAP23, a myc-tagged soluable adenylyl cyclase, a green fluorescent protein (GFP), a myristoylated GFP, a destabilized enhanced GFP (dEGFP), a myristoylated dEGFP, Cherry, or a myc-tagged Cherry. The polypeptide can be the dominant-negative RhoA mutant polypeptide is N19-RhoA polypeptide, a soluble adenylyl cyclase.

In some embodiments, the method further comprises contacting the axon with a brain-derived neurotrophic factor (BDNF), neurotrophin-3 (NT-3), glial-derived neurotropic factor (GDNF) or nerve growth factor.

The axon to which the methods of the invention can be applied is that of a sensory neuron, an upper motor neuron or a dorsal root ganglion. In some embodiments, the sensory neuron is a peripheral sensory neuron. In some embodiments, the virus is applied to the axon at the site of injury.

In one aspect, the invention provides a method of treating a condition in a mammal associated with aberrant axon function comprising administering to the mammal a virus or a composition of the invention. The virus or composition is can be administered locally to one or more selected axons. In some embodiments, the condition is axon injury associated with spinal cord injury, laceration, a stroke or multiple sclerosis. In some embodiments, the condition is axonal degeneration associated with axonal injury, diabetic peripheral neuropathy, neuropathic pain or inflammatory pain.

In one aspect, the invention provides an isolated mammalian neuron, the axon of which comprises a nucleic acid of the invention. As used herein, the term isolated in reference to an isolated neuron means that the neuron is not within the body of a mammal. In some embodiments, the mammalian neuron expresses a polypeptide encoded by the nucleic acid. The expressed polypeptide is one that modulates the growth or function of the axon of a mammalian neuron when it is expressed in the axon.

In one aspect, the invention provides a method for introducing an isolated nucleic acid into the axon of a neuron comprising contacting an alphavirus comprising the isolated nucleic acid with the axon. In some embodiments, the alphavirus is Sindbis virus or Semliki forest virus. In some embodiments, the nucleic acid is a nucleic acid of the invention.

Any feature or combination of features described herein are included within the scope of the present invention provided that the features included in any such combination are not mutually inconsistent as will be apparent from the context, this specification and the knowledge of one of ordinary skill in the art.

Methods and materials similar or equivalent to those described herein can be used to practice the invention. Suitable methods and materials are described below. These materials, methods, and examples are illustrative only and not intended to be limiting. All publications, patent applications, patents and other references mentioned herein are incorporated by reference in their entirety.

Other features and advantages of the invention will be apparent from the following detailed description and from the claims.

DESCRIPTION OF DRAWINGS

FIGS. 10A-G are data showing selective CREB knockdown in distal axons, but not proximal axons determined by compartmentalized siRNA transfection. (A) Neurons transfected with CREB-specific siRNAs exhibited a specific abolishment of CREB mRNA FISH signal in the axon compartment ("Axon"), but no significant change in CREB mRNA FISH signals in proximal axons in the cell body compartment ("Cell Body"). (B) Quantification of data in (A). FISH levels in each compartment were normalized to fluorescence signals from cultures treated with non-targeting siRNA. β-actin mRNA FISH signals were unaffected by CREB-specific siRNA. *p<0.001. Numbers on bars represent n axons per condition. (C) Transfection was as in FIG. 9A, except CREB knockdown was assessed by Western blot instead of immunofluorescence. Lysates (10 μg protein) were prepared from the axon compartment of CREB-specific siRNA-treated compartmented cultures and analyzed by Western blot using a CREB-specific antibody. (D) DRGs in compartmented cultures (5 DIV) were incubated in NGF-free media, supplemented with BAF to prevent apoptosis. Axon compartments were transfected with CREB-specific or non-targeting siRNA. After 48 hours, 30 ng/ml NGF was added to the axon compartment for 20 min, after which cells were fixed and subjected to immunofluorescence analysis of nuclear pCREB. (E) DRGs in compartmented cultures were treated as in (D, FIG. 9A), after which pTrkA levels in nuclei were quantified by immunofluorescence. (F) DRGs in compartmented chambers were treated as in (D, E, FIG. 9A) and pErk5 levels in nuclei were quantified by immunofluorescence. (G) Dissociated DRG neurons (5 DIV) were infected with equal infectious units of recombinant CRE-luciferase adenovirus and incubated in various concentrations of NGF. After 24 hours, cells were fixed and analyzed by immunofluorescence for luciferase production. n=36 (0NGF), 29 (1 ng/ml NGF), 38 (5 ng/ml NGF), 29 (10 ng/ml NGF), 35 (20 ng/ml NGF), 35 (50 ng/ml NGF), 45 (100 ng/ml NGF) cells.

FIGS. 13A-D are results showing that adult axons can express a potentially therapeutic protein. Rat postnatal sensory neurons harvested at 6 days after birth (P6) were cultured. At this age, the axons of these neurons have completed axonal pathfinding. Axons that have completed axonal pathfinding are thought to no longer contain ribosomes and to have reduced or absent capacity for protein synthesis. P6 neurons were grown in compartmentalized chambers, and a Sindbis IRES virus expressing a dominant negative (DN)-RhoA protein was applied exclusively to axons. As in FIG. 12, myc labeling was seen in axons (A) demonstrating that the virus led to the production of protein in axons. No labeling was seen in the cell body (A, inset) demonstrating that the virus was not trafficked back to the cell body, where myc-DN RhoA was synthesized and subsequently anterograde trafficked to the axon. (B) shows the outline of the axons. (C) & (D) are controls showing the absence of endogenous red labeling thereby establishing the specificity of the labeling seen in (A).

FIGS. 14A-C are results confirming that Sindbis-IRES viruses were not trafficked from the axon to the cell body where protein expression occurred. In (A), a Sindbis IRES virus expressing myc-Cherry was applied directly to cell bodies, resulting in clear myc-Cherry expression in the cell body. However, when the virus is applied to axons (B), the cell bodies do not express any myc-Cherry (although axons were expressing myc-Cherry, data not shown) demonstrating that expression in the axons did not occur by a process involving the virus being trafficked to the cell body, with subsequent expression of the transgene in the cell body. Background level of Cherry staining is shown in (C). Similarity of staining in (B) & (C) further demonstrates the absence of expression of the transgenes in the cell body in (B). The image is shown with inverted contrast so that red fluorescence appears black on a white background.

FIG. 17 is the sequence of the region in pSinRep5-IRES (FIG. 16) that includes the IRES (shown in capital letters), restriction enzyme recognition sites (bolded), and the ATG start codon (underlined).

DETAILED DESCRIPTION OF THE INVENTION

Figure 1A:
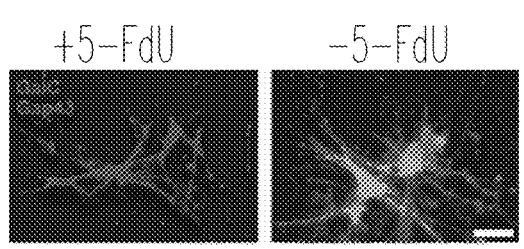
FIGS. 1A-O are data showing that the compartmentalization of DRGs enables axon-specific manipulations and quantitative measurement using fluorescent probes. (A) Immunofluorescence analysis of 3 DIV DRG cultures+/−5-FdU. Inclusion of 5-FdU effectively abolishes Schwann cell proliferation in DRG cultures. Scale bar, 50 µm. (B) Immunofluorescence analysis of 3 DIV DRG cultures demonstrates strong labeling of cell bodies and all projections with axon marker GAP43. Dendrite/cell body marker MAP2 is restricted to cell bodies, indicating the absence of MAP2-staining dendrites in DRG cultures and demonstrates that the neurites seen in axonal compartments are axons and not dendrites. Scale bar, 50 µm. (C) Immunofluorescence analysis of compartmented cultures (montage micrographs). Retrogradely labeled (WGA-Alexa555, red) DRG axons fasciculate and grow under the 1 mm divider into the axon compartment. Axons defasciculate as they enter the axon compartment. Cell bodies (DAPI, blue) are restricted to the cell body compartment. Only WGA-Alexa555 labeled cell bodies are included in data sets, as they comprise the population of neurons extending axons across the divider. (D) Dissociated DRG neurons (5 DIV) in compartmented cultures were treated with NGF in either or both compartments. NGF was capable of supporting DRG survival when applied to either axons or cell bodies individually, corroborating the presence of functional TrkA complexes throughout the developing neuron. Numbers on bars represent n cells per condition. (E, F) DRG axons in compartmented cultures were infected with a Sindbis virus encoding myr-dEGFP under the control of an IRES by applying the virus to both cell body and axonal compartments. Myr-dEGFP does not translocate from the site of its synthesis (Wu paper). Thus, the presence of fluorescence signal in the axon indicates that the protein was synthesized directly in the axon most likely as a result of viral application. Addition of cycloheximide or anisomycin for 48 hrs to the axonal compartment elicited a loss of myr-EGFP fluorescence in the axonal compartment, with no significant effect on myr-EGFP levels in the cell body compartment. All compartments were maintained in identical NGF-containing media throughout the course of the experiment. Scale bar, 50 µm (G) DIV3 E13 DRG neurons from CREB$^{\alpha/\Delta+/-}$ mouse embryos demonstrated robust CREB mRNA FISH signal in axons, while neurons from CREB$^{\alpha/\Delta-/-}$ embryos demonstrated an 86.3% loss of CREB mRNA FISH signal. Incomplete abolishment of FISH signals, relative to siRNA-treated axons, reflects residual alternatively-spliced CREBβ transcripts in these hypomorphic animals (Blendy et al., *EMBO Journal* 15, 1098-1106 (1996)). Additionally, axonal mRNAs are trafficked as mRNA-ribosome complexes, and impaired CREBβ mRNA-ribosome interactions due to the poor Kozak site (Blendy et al., *EMBO Journal* 15, 1098-1106 (1996)) in this transcript may lead to inefficient trafficking. Scale bar, 10 µm. (H) Quantification of data in (G). *p<0.0001. Numbers on bars represent n axons per condition. (I) Similar to the experiment in FIG. 4A, except equivalent numbers of cell bodies and axon terminals were used for Western blotting. DRG explants were cultured in Boyden chambers, and the upper compartment was incubated in 0 ng/ml NGF. The lower compartment was incubated in either 0 ng/ml NGF or 100 ng/ml NGF for 3 hours. Axon lysates (~$10^4$ cells) were prepared from the underside of the membrane and analysed by Western blot. As in FIG. 4A, only CREB was detected in axons, and CREB localization in 22 axons was dependent on NGF in the culture media. (J) DRG cultures were transfected with CREB siRNA and CREB levels were detected using a CREB antibody. Neurons transfected with nontargeting siRNA exhibited CREB immunoreactivity in axons, while neurons transfected with CREB specific siRNAs exhibited a near-complete abolishment of CREB immunoreactivity. Scale bar, 20 µm. (K) Quantification of data in (J). *$p<0.001$. Numbers on bars represent n axons per condition. (L) E15 DRG neuronal lysate (10 µg) was subjected to immunoblotting with the CST-9192 CREB antibody. (M) CREB was detected by immunofluorescence using CREB antibody sc-186 (see I, FIG. 4A, and Table S4). Scale bar 10 µm. (N) DIV3 E13 DRG neurons from CREB$^{\alpha/\Delta+/-}$ embryos exhibited robust CREB immunoreactivity in axons, while neurons from CREB$^{\alpha/\Delta-/-}$ embryos demonstrated an 84.8% loss of CREB IF signal. The greater degree of reduction in CREB immunofluorescence following siRNA treatment (see K) than in the CREB mutant mice likely reflects the more complete abolition of CREB following siRNA transfection than in the hypomorphic animal. Scale bar, 10 µm. (O) Quantification of data in (M). *$p<0.0001$. Numbers on bars represent n axons per condition.

The invention is based on the discovery that proteins can be expressed in the axons of a mammalian neuron. More specifically, the invention involves the discovery that a protein coding sequence operably linked to an internal ribosome entry site (IRES) in an RNA viral genome can be expressed in a mammalian axon when the RNA viral genome is transduced into the axon. Thus, the invention provides isolated recombinant nucleic acids such as DNA and RNA molecules, as well as RNA viruses that can be used to deliver selected polypeptide-coding sequences into the axons of mammalian neurons for expression of the encoded polypeptides in the axons. The invention also provides methods for expressing polypeptides in the axons of mammalian neurons, as well as methods of treating injured axons or treating conditions associated with aberrant axon function.

Nucleic Acids of the Invention

The invention provides isolated nucleic acids and viruses that can be used to deliver selected polypeptide-coding sequences into the axons of mammalian neurons for expression of the encoded polypeptides in the axons.

As used herein, the term "nucleic acid" refers to a polymer of deoxyribose nucleic acids (DNA), as well as ribose nucleic acids (RNA). The term includes linear molecules, as well as covalently closed circular molecules. It includes single stranded molecules, as well as double stranded molecules. The term "isolated" means that a select nucleic acid sequence is not contiguous with sequences that encode other genes or those involved in the expression of these other genes that flank the 5' and 3' ends of the select nucleic acid sequence in the naturally-occurring genome of the organism from which the select nucleic acid sequence is derived. An "isolated nucleic acid" has a structure that is different from that of any naturally occurring nucleic acid. The term "isolated nucleic acid" does not include nucleic acids present in mixtures of DNA molecules, transfected cells and cell clones such as in a cDNA or genomic DNA library.

A nucleic acid of the invention is also a recombinant molecule. As used herein, the term "recombinant" in reference to a nucleic acid means that the nucleic acid has a structure that is different from that of any naturally-occurring nucleic acid. A recombinant nucleic acid molecule is the product of the joining of at least two unrelated nucleic acid sequences using recombinant DNA techniques known to those of skill in the art such as described in MOLECULAR CLONING: A LABORATORY MANUAL, Sambrook & Russell eds., Cold Spring Harbor Laboratory Press, Cold Spring Harbor, New York (2001) [hereinafter MOLECULAR CLONING] or CURRENT PROTOCOLS IN MOLECULAR BIOLOGY, eds. Ausubel et al., John Wiley & Sons, Inc. (1994) [hereinafter CURRENT PROTOCOLS]. Sequences are unrelated if they are derived from different sources. Non-limiting examples of different sources from which unrelated nucleic acids can be derived include different organisms, different species, or different isolates. Two sequences are also unrelated if they come from different regions within a larger naturally-occurring nucleic acid molecule. Discontinuous sequences, for example, are also unrelated. Thus, unrelated sequences include those that encode different genes or those involved in the expression of different genes, as well as those that do not immediately flank the 5' and 3' ends of a selected sequence in the naturally-occurring genome of the organism from which this sequence is obtained.

A recombinant nucleic acid of the invention can be (1) a linear or covalently-closed circular DNA plasmid or expression vector that is capable of replicating in a prokaryotic or eukaryotic host cell and has incorporated within a sequence encoding a selected mammalian polypeptide so that the plasmid or expression vector is not identical to any naturally-occurring plasmid or vector; (2) a nucleic acid incorporated into the genomic RNA of a virus or incorporated into the genome of a prokaryotic or eukaryotic host cell in a manner such that the resulting genome is not identical to any naturally-occurring genome; (3) a molecule such as a cDNA, a polyadenylyl RNA, a genomic fragment, a fragment produced by polymerase chain reaction (PCR), or a restriction fragment; and (4) an RNA molecule that has a viral packaging sequence, a translation initiation element, e.g. 5' CAP or internal ribosome entry site, and a coding sequence for a mammalian protein operably-linked to the translation initiation element.

Thus, a recombinant nucleic acid of the invention can be a DNA or RNA molecule. A recombinant DNA molecule of the invention includes (1) a mammalian promoter; (2) an internal ribosome entry site (IRES) located 3' of the promoter; (3) a selected polypeptide-coding sequence 3' of the IRES, and (4) a viral packaging sequence. The polypeptide coding sequence can be operably linked to the IRES for expression of the polypeptide in the axon of a mammalian neuron. A recombinant RNA molecule of the invention includes (1) a translation initiation element; (2) a selected polypeptide-coding sequence and (3) a viral packaging sequence. The polypeptide coding sequence is operably-linked to the translation initiation element, which can be an IRES or a mammalian 5' CAP. The recombinant RNA molecule can also have a 3' polyadenylated tail.

As used herein, two components are "operably-linked" if they are linked in a manner that permits each component to function in its intended manner. When a polypeptide coding sequence and an IRES are operably-linked, the polypeptide coding sequence and the IRES are linked in such a way that, in the absence of an operably-linked 5' CAP structure, the IRES functions to enable translation of the polypeptide coding sequence into a polypeptide when ribosomes, amino acids and other cellular components required for protein synthesis are present.

As used herein, the term "internal ribosome entry site" or "IRES" refers to a sequence within a nucleic acid molecule that is capable of recruiting ribosomes for initiation of protein translation from a polypeptide coding sequence. IRES can promote translation from any polypeptide coding sequence that is downstream of the IRES sequence. Generally, IRES's can be found in the 5' untranslated regions of polypeptide-coding sequences and allow translation of the RNA in a 5'CAP-independent manner. In a recombinant RNA molecule of the invention, the IRES can be within the 5' untranslated region of the RNA molecule or it can be inserted into different parts of the RNA molecule as long as it is located 5' of a polypeptide coding sequence. The IRES can be less than 10 nucleotides upstream or 5' of the start codon of a coding sequence that is operably linked to it, or it can be as distant as 200 to 300 nucleotides or more upstream of the first start codon of a coding sequence that is operably linked to it.

IRES can be found in viral RNA genomes, as well as in sequences from eukaryotic origin. Non-limiting examples of viral IRES sequences include those found in: (1) picornaviruses, e.g., poliovirus (PV) or the human enterovirus 71, e.g. strains 74231MS187 and BrCr thereof; (2) encephalomyocarditis virus (EMCV); (3) foot-and-mouth disease virus (FMDV); (4) flaviviruses, e.g., hepatitis C virus (HCV); (5) pestiviruses, e.g., classical swine fever virus (CSFV); (6) retroviruses, e.g., murine leukemia virus (MLV); and (7) lentiviruses, e.g., simian immunodeficiency virus (SIV).

Non-limiting examples of non-viral IRES sequences can be found in cellular mRNA such as those encoding (1) translation initiation factors, e.g., eIF4G or DAPS; (2) transcription factors, e.g., c-Myc (Yang and Sarnow, *Nucleic Acids Research* 25: 2800-2807 (1997)) or NF-KB-repressing factor (NRF); (3) growth factors, e.g., vascular endothelial growth factor (VEGF), fibroblast growth factor (FGF-2) and platelet-derived growth factor B (PDGF B); (4) homeotic genes, e.g., *Antennapedia*; (5) survival proteins, e.g., X-linked inhibitor of apoptosis (XIAP) or Apaf-1; and (6) chaperones, e.g., immunoglobulin heavy-chain binding protein BiP (Martinez-Salas et al., *Journal of General Virology* 82: 973-984, (2001)). IRES can also be found in plant viral sequences. Any IRES now known or later identified can be used to practice the invention.

Non-limiting examples of IRES sequences can be found in the following viral sequences: encephalomyocarditis virus (EMCV. GenBank accession #NC001479), cricket paralysis virus (GenBank accession #AF218039), Drosophila C virus (GenBank accession #AF014388), *Plautia stali* intestine virus (GenBank accession #AB006531), *Rhopalosiphum padi* virus (GenBank accession #AF022937), Himetobi P virus (GenBank accession #AB017037), acute bee paralysis virus (GenBank accession #AF150629), Black queen cell virus (GenBank accession #AF183905), *Triatoma* virus (GenBank accession #AF178440), *Acyrthosiphon*

*pisum* virus (GenBank accession #AF024514), infectious flacherie virus (GenBank accession #AB000906), and/or Sacbrood virus (Genbank accession #AF092924).

Additional examples of IRES sequences are provided in *A Bioinformatical Approach to the Analysis of Viral and Cellular Internal Ribosome Entry Sites* in NEW MESSENGER RNA RESEARCH COMMUNICATIONS 133-166, Nova Science Publishers, Hauppauge, NY (2007). See also http://www.iresite.org.

An IRES sequence can also be a synthetic sequence that has been designed to mimic the function of naturally occurring IRES sequences according to methods know in the art. See, for example, Chappell et al. *Proc Natl Acad Sci USA.* 97:1536-41 (2000).

An example of an IRES sequence is the following:

```
                                              (SEQ ID NO: 29)
  1  GCCCCTCTCC CTCCCCCCCC CCTAACGTTA CTGGCCGAAG

41  CCGCTTGGAA TAAGGCCGGT GTGCGTTTGT CTATATGTTA

81  TTTTCCACCA TATTGCCGTC TTTTGGCAAT GTGAGGGCCC

121  GGAAACCTGG CCCTGTCTTC TTGACGAGCA TTCCTAGGGG

161  TCTTTCCCCT CTCGCCAAAG GAATGCAAGG TCTGTTGAAT

201  GTCGTGAAGG AAGCAGTTCC TCTGGAAGCT TCTTGAAGAC

241  AAACAACGTC TGTAGCGACC CTTTGCAGGC AGCGGAACCC

281  CCCACCTGGC GACAGGTGCC TCTGCGGCCA AAAGCCACGT

321  GTATAAGATA CACCTGCAAA GGCGGCACAA CCCCAGTGCC

361  ACGTTGTGAG TTGGATAGTT GTGGAAAGAG TCAAATGGCT

401  CTCCTCAAGC GTATTCAACA AGGGGCTGAA GGATGCCCAG

441  AAGGTACCCC ATTGTATGGG ATCTGATCTG GGGCCTCGGT

481  GCACATGCTT TACATGTGTT TAGTCGAGGT TAAAAAAACG

521  TCTAGGCCCC CCGAACCACG GGGACGTGGT TTTCCTTTGA

561  AAAACACGAT GATAAGCTTG CCACA
```

Additional examples of IRES sequences are shown below.
From Hepatitis A virus (CF53), partial 5' nontranslated region (Genbank accession no: M63025)

```
                                              (SEQ ID NO: 30)
     GTTTGCCTAGGCTATAGGCTATTTCTCCCCTTCCCTT

TTCCCTGTTTTGTGTAAATATTAATTCCTGCAGGTTC

AGGGTTCTTTAATCTGTTTCTCTATAAGAACACTCAT

TTTCACGCTTTCTGTCTGCTTTCTTCCAGGGCTCTCC

CCTTGCCCTAGGCTCTGGCCGTTGCGCCCGGCGGGGT

CAACTCCATGATTAGCATGGAGCTGTAGGAGTCTAAA

TTGGGGACGCAGATGTTTGGGACGTCACCTTGCAGTA

TTAACTTGGCTCTCATGAAGCTCTTTGATCTTCCACA

AGAGGTAGGCTACGGGTGAAACCTCTTAAGCTAGTAC

TTCTATGAAGAGATGCTTTGGATAGGGTAACAGCGGC

GGATATTGGTGAGTTGTTAAGACAAAAACCTTTCAAC

GCCGGAGGACTGGCTCTCATCCAGTGGATGCATTGAG

TGGATTGTTTGTCAGGGCTGTCTCTAGGCTTAATCTC

AGACCTCTCTGTGCTTAGGGCAAACATTACTTGGCCT

TAAATGGGATTCTGTGAGAGGGGATCCCTCCATTGAT

AGCTGGACTTTTCTTTGGGGCCTTAGGTGGTGTTTGC

CTCTGAGGTACTCAGGGGCATTTAGGTTTTTCCTCAC

TCTCAAATAACTATGAATATGTCTAG
```

From human T-cell lymphotropic virus type 1 BCI1-2 long terminal repeat region (U32552):

```
                                              (SEQ ID NO: 31)
     GGGGAGTTAGAGCCTCCCAGTGAAAAACATTTCCGCG

AAACAGAAGTCTGAAAAGGTCAGGGCCCAGACTAAGG

CTCTGACGTCTCCCCCCGGAGGGACAGCTCAGCACCG

GCTCAGGCTAGGCCCTGACGTGTCCCCCTGAAGACAA

ATCATAAGCTCAGACCTCCGGGAAGCCACCGGAACCA

CCCATTTCCTCCCCATGTTTGTCGAGCCGCCCTCAGG

CGTTGACGACAACCCCTCACCTCAAAAAACTTTTCAT

GGCACGCATATGGCTGAATAAACTAACAGGAGTCTAT

AAAAGCGTGGAGACAGTTCAGGAGGGGCTCGCATCT

CTCCTTCACGCGCCCGCCGCCCTACCTGAGGCCGCCA

TCCACGCCGGTTGAGTCGCGTTCTGCCGCCTCCCGCC

TGTGGTGCCTCCTGAACTGCGTCCGCCGTCTAGGTAA

GTTTAGAGCTCAGGTCGAGACCGGGCCTTTGTCCGGC

GCTCCCTTGGAGCCTACCTAGACTCAGCCGGCTCTCC

ACGCTTTGCCTGACCCTGCTTGCTCAACTCTGCGTCT

TTGTTTCGTTTTCTGTTCTGCGCCGCTACAGATCGAA

AGTTCCACCCCTTTCCCTTTCATTCACGACTGACTGC

CGGCTTGGCCCACGGCCAAGTACCGGCGACTCCGTTG

GCTCGGAGCCAGCGACAGCCCATTCTA
```

From hog cholera virus (Classical swine fever virus) "Chinese" strain (C-strain; EP 0 351 901 B1) encoding polyprotein (Z46258):

```
                                              (SEQ ID NO: 32)
     GTATACGAGGTTAGTTCATTCTCGTATACACGATTGG

ACAAATCAAAATTATAATTTGGTTCAGGGCCTCCCTC

CAGCGACGGCCGAACTGGGCTAGCCATGCCCATAGTA

GGACTAGCAAAACGGAGGGACTAGCCATAGTGGCGAG

CTCCCTGGGTGGTCTAAGTCCTGAGTACAGGACAGTC

GTCAGTAGTTCGACGTGAGCAGAAGCCCACCTCGAGA

TGCTACGTGGACGAGGGCATGCCAAGACACACCTTAA

CCCTAGCGGGGTCGCTAGGGTGAAATCACACCACGT

GATGGGAGTACGACCTGATAGGGCGCTGCAGAGGCCC
```

From Equine rhinitis A virus, nt 1-881 (NC_003982)

(SEQ ID NO: 33)
TTAATTAAAAGTTGAACCTGTAGCGTCAGTAAAACGC

AGTAACCGCAAGCAATTGCCTGTAGCGTCAGTAAAAC

GCAATACACAAGATTTGAGCCTGTAGCGTCAGTAAAA

CGCTGCAACCACAAGCTATTGACTGTAGCGTCAGTAA

AACGCAAACATTCTTGTGGCGCTCGCGTAGCGCTCAA

GTGCAGAGCTTCCCGGCTTTAAGGGTTACTGCTCGTA

ATGAGAGCACATGACATTTTGCCAAGATTTCCTAGCA

ATTGTCACGGGAGAGAGGAGCCCGTTCTCGGGCACTT

TTCTCTCAAACAATGTTGGCGCGCCTCGGCGCGCCCC

CCCTTTTTCAGCCCCCTGTCATTGACTGGTCGAAGGC

GCTCGCAATAAGACTGGTCGTTGCTTGGCTTTTCTAT

TGTTTCAGGCTTTAGCGCGCCCTTGCGCGGCGGGCCG

TCAAGCCCGTGTGCTGTACAGCACCAGGTAACCGGAC

AGCGGCTTGCTGGATTTTCCCGGTGCCATTGCTCTGG

ATGGTGTCACCAAGCTGGCAGATGCGGAGTGAACCTT

ACGAAGCGACACACCTGTGGTAGCGCTGCCCAGAAGG

GAGCGGAGCTCCCCCGCCGCGAGGCGGTCCTCTCTGG

CCAAAAGCCCAGCGTTAATAGCGCCTTCTGGGATGCA

GGAACCCCACCTGCCAGGTGTGAAGTGGACTAAGTGG

ATCTCCAATTTGGCCTGTTCTGAACTACACCATCTAC

TGCTGTGAAGAATGTCCTGAAGGCAAGCTGGTTACAG

CCCTGATCAGGAGCCCCGCTCGTGACTCTCGATCGAC

GCGGGTCAAAAACTGTCTAAGCAGCAGCAGAAACGC

GGGAGCGTTTCTTTTTCCTTATTTGTTTCA

From c-myc 5' UTR IRES 407 nts (SEQ ID NO: 34)
CAGGATCCCCCTAATTCCAGCGAGAGGCAGAGGGAGC

GAGCGGGCGGCCGGCTAGGGTGGAAGAGCCGGGCGAG

CAGAGCTGCGCTGCGGGCGTCCTGGGAAGGGAGATCC

GGAGCGAATAGGGGGCTTCGCCTCTGGCCCAGCCCTC

CCGCTGATCCCCCAGCCAGCGGTCCGCAACCCTTGCC

GCATCCACGAAACTTTGCCCATAGCAGCGGGCGGGCA

CTTTGCACTGGAACTTACAACACCCGAGCAAGGACGC

GACTCTCCCGACGCGGGGAGGCTATTCTGCCCATTTG

GGGACACTTCCCCGCCGCTGCCAGGACCCGCTTCTCT

GAAAGGCTCTCCTTGCAGCTGCTTAGACGCTGGATTT

TTTTCGGGTAGTGGAAAACCAGCAGCCTCCCGCGACC

ATG

From Bovine enterovirus, nt 1-819 (NC_001859)

(SEQ ID NO: 35)
TTAAAACAGCCTGGGGGTTGTACCCACCCCTGGGGCC

CACGTGGCGCTAGTACTCTGGTTCGTTAGAACCTTTG

TACGCCTGTTTTCCCCTCCTTAAACAAATTAAGATCT

CTGCCAATGTGGGGAGTAGTCCGACTCCGCACCGATA

CGTCGCACCAGTAGACCGGTTCGCTTAGGACCCTTCT

ACGGATTGGTATGAGTTCCCCACCCCGTAACTTAGAA

GTACTAGCAAAACCGACCAATAGGAGCGTGGCACCCA

GCTGCGTTAAGGTCAAGCACTTCTGTCTCCCCGGCCA

GAAATGGTCGTCACCCGCCCTCTCTACTACGAGAAGC

CTATTAACCATTGAAGGCGATGAGGAGTTGCGCTCCA

CCACAACCCCAGTGGTAGCTCTGAGAGATGGGGCTCG

CAGTCACCCCCGTGGTAACACGGTTGCTTGCCCGCGT

GTGCTCTCGGGTTCGGCCACTTGGCCGTTCACTCCAA

CTCGTTGTAAGTGGCCAAGAGCCTATTGTGCTAGAGA

GGTTTTCCTCCGGAGCCGTGAATGCTGCTAATCCCAA

CCTCCGAGCGTGTGCGCACAATCCAGTGTTGCTACGT

CGTAACGCGCAAGTTGGAGGCGGAACAGACTACTTTC

GGTACTCCGTGTTTCCTTATTATTTTATACAACAATT

TATGGTGACATTGACTGATACTATTGAGTTCGCCCGC

TTGCCATTGAATATTGCCTTGTATTACCTTATAGCAT

TTCAAAAAGCCACAGATCTCACCCTCGAGCTCATTCA

CTTTGCAGTTTGTTTGAATCGCATACACAAGACATTT

GAACA

As used herein, the term "5' CAP" refers to a nucleotide on the 5' terminus of an RNA molecule that includes a polypeptide coding sequence. The 5'CAP can promote initiation of protein translation from the polypeptide coding sequence if the polypeptide coding sequence is operably-linked to the 5' CAP. Structurally, the 5' CAP includes a guanine nucleotide covalently linked to the 5' terminus of an RNA molecule via a 5' to 5' triphosphate linkage. The guanine nucleotide is methylated on the 7 position.

The viral packaging sequence is a sequence in the nucleic acid molecule, e.g. viral RNA, that interacts with a viral capsid protein and is required for encapsidation of the RNA molecule during the formation of viral particles. Viral packaging sequences are known to those of skill in the art. See, for example, Frolova et al., *Journal of Virology* 71: 248-258 (1997).

A recombinant RNA molecule of the invention can be a single, positive- or negative-stranded RNA viral genome that has a coding sequence for a selected polypeptide. The coding sequence is operably-linked to an IRES sequence or a 5' CAP. Where the viral genome is a negative strand RNA sequence, the polypeptide coding region and IRES sequence are sense sequences in order for translation to occur. A recombinant RNA molecule of the invention can also be an engineered RNA sequence that includes: (1) a coding sequence for the selected polypeptide operably-linked to an IRES sequence or 5' CAP and (2) a viral packaging sequence sufficient for packaging of the RNA expression vector into viral particles.

A recombinant DNA molecule of the invention can be a double stranded expression vector that has a sequence encoding an RNA molecule of the invention, i.e. the expression vector can function as a template from which an RNA molecule of the invention can be transcribed. The recombinant DNA molecule can be a plasmid vector that has a bacterial or mammalian origin of replication, as well as sequences that encode the recombinant RNA molecules of the invention. Recombinant DNA molecules of the invention can serve as a template for the production of RNA molecules of the invention either by in vitro transcription or in vivo expression in an appropriate host cell.

The selected polypeptide encoded by recombinant nucleic acids of the invention can be any polypeptide that can affect the growth or function of the axon of a mammalian neuron. Examples of these polypeptides include, without limitation, the bacterial toxin C3-ADP-ribosyltransferase that is useful for inhibiting the small GTPase RhoA; dominant-negative RhoA mutants, for example, N19-RhoA; dominant-negative RhoA kinase (ROCK) mutants, for example, ROCK I1009A described by Ishizaki et al., *FEBS Lett.* 404:118-124 (1997); a cyclic AMP-producing enzyme such as the soluble adenylyl cyclase (sAC) described by Wu et al., *Nat. Neurosci.* 9:1257-64 (2006); glutamic acid decarboxylase (GAD), an enzyme that synthesizes the neurotransmitter gamma-aminobutyric acid (GABA), which suppresses activity in nerve cells (Hao et al., *Annals of Neurology,* 57: 914-918, (2005)); human proenkephalin, an endogenous opioid peptide with antihyperalgesic properties (Wilson, et al., *PNAS,* 96: 3211-3216, 1999); the dominant-negative Vps24 required for HSV envelopment (Crump et al., *J. Virol.* 81:7380-7387, 2007); GAP43, a gene product of a neuronal regeneration-associated gene and regulator of developmental growth cone motility; CAP23, an activator of intrinsic growth capacity in dorsal root ganglion neurons; Brain-Derived Neurotrophic Factor (BDNF), a neurotrophic factor in the brain and the periphery that act on certain neurons of the central and peripheral nervous systems and helps to support the survival or existing neurons and encourage the growth and differentiation of new neurons and synapses; Neurotrophin-3 (NT-3), a neurotrophic factor in the nerve growth factor family of neurotropins, i.e. a protein growth factor that acts on the nerves of the central and peripheral nervous systems and helps to support the survival and differentiation of existing neurons and encourages the growth and differentiation of new neurons and synapses; and glial-derived neurotropic factor (GDNF), a small protein that promotes survival of neurons, especially dopamiergic and motoneurons. See also U.S. Patent Application No. 2003/0118557.

An example of a C3-ADP-ribosyltransferase sequence is provided by Genbank M74038 and shown below:

(SEQ ID NO: 36)
MKGIRKSILCLVLSAGVIAPVTTSIVQSPQKCYACTVDKGSYADTF

TEFTNVEEAKKWGNAQYKKYGLSKPEQEAIKFYTRDASKINGPLRA

NQGNENGLPADILQKVKLIDQSFSKMKMPQNIILFRGDDPAYLGPE

FQDKILNKDGTINKTVFEQVKAKFLKKDRTEYGYISTSLMSAQFGG

RPIVTKFKVINGSKGGYIDPISYFPGOLEVLLPRNNSYYISDMQIS

PNNRQIMITAMIFK

The sequence of human N19-RhoA, an example of a dominant-negative RhoA mutant is provided by Genbank NM_001664 and shown below:

(SEQ ID NO: 37)
MAAIRKKLVIVGDGACGKNCLLIVFSKDQFPEVYVPTVFENYVADI

EVDGKQVELALWDTAGQEDYDRLRPLSYPDTDVILMCFSIDSPDSL

ENIPEKWTPEVKHFCPNVPIILVGNKKDLRNDEHTRRELAKMKQEP

VKPEEGRDMANRIGAFGYMECSAKTKDGVREVFEMATRAALQARRG

KKKSGCLVL

An example of a dominant-negative RhoA kinase (ROCK) is provided by Genbank NM_005406 and shown below:

(SEQ ID NO: 38)
MSTGDSFETRFEKMDNLLRDPKSEVNSDCLLDGLDALVYDLDEPAL

RKNKNIDNFLSRYKDTINKIRDLRMKAEDYEVVKVIGRGAFGEVQL

VRHKSTRKVYAMKLLSKFEMIKRSDSAFFWEERDIMAFANSPWVVQ

LFYAFQDDRYLYMVMEYMPGGDLVNLMSNYDVPEKWARFYTAEVVL

ALDAIHSMGFIHRDVKPDNMLLDKSGHLKLADFGTCMKMNKEGMVR

CDTAVGTPDYISPEVLKSQGGDGYYGRECDWWSVGVFLYEMLVGDT

PFYADSLVGTYSKIMNHKNSLTFPDDNDISKEAKNLICAFLTDREV

RLGRNGVEEIKRHLFFKNDQWAWEILRDTVAPVVPDLSSDIDTSNF

DDLEEDKGEEETFPIPKAFVGNQLPFVGFTYYSNRRYLSSANPNDN

RTSSNADKSLQESLQKTIYKLEEQLHNEMQLKDEMEQKCRISNIKL

DKIMKELDEEGNORRNLESTVSQIEKEKMLLQHRINEYQRKAEQEN

EKRRNVENEVSTLKDQLEDLKKVSQNSQLANEKLSQLQKQLEEAND

LLRTESDTAVRLRKSHTEMSKSISQLESLNRELQERNRILENSKSQ

TDKDYYQLQAILEAERRDRGHDSEMIGDLQARITSLQEEVKHLKHN

LEKVEGERKEAQDMLNHSEKEKNNLEIDLNYKLKSLQQRLEQEVNE

HKVTKARLTDKHQSIEEAKSVAMCEMEKKLKEEREAREKAENRVVQ

IEKQCSMLDVDLKQSQQKLEHLTGNKERMEDEVKNLTLQLEQESNK

RLLLQNELKTQAFEADNLKGLEKQMKQEINTLLEAKRLLEFELAQL

TKQYRGNEGQMRELQDQLEAEQYFSTLYKTQVKELKEEIEEKNREN

LKKIQELQNEKETLATQLDLAETKAESEQLARGLLEEQYFELTQES

KKAASRNRQEITDKDHTVSRLEEANSMLIKDIEILRRENEELTEKM

KKAEEEYKLEKEEEISNLKAAFEKNINTERTLKTQAVNKLAEIMNR

KDFKIDRKKANTQDLRKKEKENRKLQLELNQEREKFNQMVVKHQKE

LNDMQAQLVEECAHRNELQMQLASKESDIEQLRAKLLDLSDSTSVA

SFPSADETDGNLPESRIEGWLSVPNRGNIKRYGWKKQYVVVSSKKI

-continued

LFYNDEQDKEQSNPSMVLDIDKLFHVRPVTQGDVYRAETEEIPKIF

QILYANEGECRKDVEMEPVQQAEKINFQNHKGHEFIPTLYHFPANC

DACAKPLWHVFKPPPALECRRCHVKCHRDHLDKKEDLICPCKVSYD

VISARDMLLLACSQDEQKKWVTHLVKKIPKNPPSGFVRASPRILST

RSTANQSFRKVVKNTSGKTS

An example of a soluble adenylyl cyclase sequence is provided by Genbank NM_018417 and shown below:

(SEQ ID NO: 39)
MNTPKEEFQDWPIVRIAAHLPDLIVYGHFSPERPFMDYFDGVLMFV

DISGFTAMTEKFSSAMYMDRGAEQLVEILNYHISAIVEKVLIFGGD

ILKFAGDALLALWRVERKQLKNIITVVIKCSLEIHGLFETQEWEEG

LDIRVKIGLAAGHISMLVFGDETHSHFLVIGQAVDDVRLAQNMAQM

NDVILSPNCWQLCDRSMIEIESVPDQRAVKVNFLKPPPNFNFDEFF

TKCTTFMHYYPSGEHKNLLRLACTLKPDPELEMSLQKYVMESILKQ

IDNKQLQGYLSELRPVTIVFVNLMFEDQDKAEEIGPAIQDAYMHIT

SVLKIFQGQINKVFMFDKGCSFLCVFGFPGEKVPDELTHALECAMD

IFDFCSQVHKIQTVSIGVASGIVFCGIVGHTVRHEYTVIGQKVNLA

ARMMMYYPGIVTCDSVTYNGSNLPAYFFKELPKKVMKGVADSGPLY

QYWGRTEKVMFGMACLICNRKEDYPLLGRNKEINYFMYTMKKFLIS

NSSQVLMYEGLPGYGKSQILMKIEYLAQGKNHRIIAISLNKISFHQ

TFYTIQMFMANVLGLDTCKHYKERQTNLRNKVMTLLDEKFYCLLND

IFHVQFPISREISRMSTLKKQKQLEILFMKILKLIVKEERIIFIID

EAQFVDSTSWRFMEKLIRTLPIFIIMSLCPFVNIPCAAARAVIKNR

NTTYIVIGAVQPNDISNKICLDLNVSCISKELDSYLGEGSCGIPFY

CEELLKNLEHHEVLVFQQTESEEKTNRTWNNLFKYSIKLTEKLNMV

TLHSDKESEEVCHLTSGVRLKNLSPPTSLKEISLIQLDSMRLSHQM

LVRCAAIIGLTFTTELLFEILPCWNMKMMIKTLATLVESNIFYCFR

NGKELQKALKQNDPSFEVHYRSLSLKPSEGMDHGEEEQLRELENEV

IECHRIRFCNPMMQKTAYELWLKDQRKAMHLKCARFLEEDAHRCDH

CRGRDFIPYHHFTVNIRLNALDMDAIKKMAMSHGFKTEEKLILSNS

EIPETSAFFPENRSPEEIREKILNFFDHVLTKMKTSDEDIIPLESC

QCEEILEIVILPLAHHFLALGENDKALYYFLEIASAYLIFCDNYMA

YMYLNEGQKLLKTLKKDKSWSQTFESATFYSLKGEVCFNMGQIVLA

KKMLRKALKLLNRIFPYNLISLFLHIHVEKNRHFHYVNRQAQESPP

PGKKRLAQLYRQTVCLSLLWRIYSYSYLFHCKYYAHLAVMMQMNTA

LETQNCFQIIKAYLDYSLYHHLAGYKGVWFKYEVMAMEHIFNLPLK

GEGIEIVAYVAETLVFNKLIMGHLDLAIELGSRALQMWALLQNPNR

HYQSLCRLSRCLLLNSRYPQLIQVLGRLWELSVTQEHIFSKAFFYF

VCLDILLYSGFVYRTFEECLEFIHQYENNRILKFHSGLLLGLYSSV

AIWYARLQEWDNFYKFSNRAKNLLPRRTMTLTYYDGISRYMEGQVL

HLQKQIKEQSENAQASGEELLKNLENLVAQNTTGPVFCPRLYHLMA

YVCILMGDGQKCGLFLNTALRLSETQGNILEKCWLNMNKESWYSTS

ELKEDQWLQTILSLPSWEKIVAGRVNIQDLQKNKFLMRANTVDNHF

An example of a glutamic acid decarboxylase (GAD) is provided by Genbank NM_000817 and shown below:

(SEQ ID NO: 40)
MASSTPSSSATSSNAGADPNTTNLRPTTYDTWCGVAHGCTRKLGLK

ICGFLQRTNSLEEKSRLVSAFKERQSSKNLLSCENSDRDARFRRTE

TDFSNLFARDLLPAKNGEEQTVQFLLEVVDILLNYVRKTFDRSTKV

LDFHHPHQLLEGMEGFNLELSDHPESLEQILVDCRDTLKYGVRTGH

PRFFNQLSTGLDIIGLAGEWLTSTANTNMFTYEIAPVFVLMEQITL

KKMREIVGWSSKDGDGIFSPGGAISNMYSIMAARYKYFPEVKTKGM

AAVPKLVLFTSEQSHYSIKKAGAALGFGTDNVILIKCNERGKIIPA

DFEAKILEAKQKGYVPFYVNATAGTTVYGAFDPIQEIADICEKYNL

WLHVDAAWGGGLLMSRKHRHKLNGIERANSVTWNPHKMMGVLLQCS

AILVKEKGILQGCNQMCAGYLFQPDKQYDVSYDTGDKAIQCGRHVD

IFKFWLMWKAKGTVGFENQINKCLELAEYLYAKIKNREEFEMVFNG

EPEHTNVCFWYIPQSLRGVPDSPQRREKLHKVAPKIKALMMESGTT

MVGYQPQGDKANFFRMVISNPAATQSDIDFLIEEIERLGQDL

An example of human proenkephalin is provided by Genbank NM_006211 and shown below:

(SEQ ID NO: 41)
MARFLTLCTWLLLLGPGLLATVRAECSQDCATCSYRLVRPADINFL

ACVMECEGKLPSLKIWETCKELLQLSKPELPQDGTSTLRENSKPEE

SHLLAKRYGGFMKRYGGFMKKMDELYPMEPEEEANGSEILAKRYGG

FMKKDAEEDDSLANSSDLLKELLETGDNRERSHHQDGSDNEEEVSK

RYGGFMRGLKRSPQLEDEAKELQKRYGGFMRRVGRPEWWMDYQKRY

GGFLKRFAEALPSDEEGESYSKEVPEMEKRYGGFMRF

An example of a dominant-negative Vps24 sequence is provided by Genbank NM_016079 and shown below:

(SEQ ID NO: 42)
MGLFGKTQEKPPKELVNEWSLKIRKEMRVVDRQIRDIQREEEKVKR

SVKDAAKKGQKDVCIVLAKEMIRSRKAVSKLYASKAHMNSVLMGMK

NQLAVLRVAGSLQKSTEVMKAMQSLVKIPEIQATMRELSKEMMKAG

IIEEMLEDTFESMDDQEEMEEEAEMEIDRILFEITAGALGKAPSKV

TDALPEPEPPGAMAASEDEEEEEALEAMQSRLATLRS

An example of a GAP43 sequence is provided by Genbank NM_002045 and shown below:

(SEQ ID NO: 43)
MLCCMRRTKQVEKNDDDQKIEQDGIKPEDKAHKAATKIQASFRGHI

TRKKLKGEKKDDVQAAEAEANKKDEAPVADGVEKKGEGTTTAEAAP

ATGSKPDEPGKAGETPSEEKKGEGDAATEQAAPQAPASSEEKAGSA

-continued

ETESATKASTDNSPSSKAEDAPAKEEPKQADVPAAVTAAAATTPAA

EDAAAKATAQPPTETGESSQAEENIEAVDETKPKESARQDEGKEEE

PEADQEHA

An example of a CAP23 sequence is provided by Genbank NM_006317 and shown below:

(SEQ ID NO: 44)
MGGKLSKKKKGYNVNDEKAKEKDKKAEGAATEEEGTPKESEPQAAA

EPAEAKEGKEKPDQDAEGKAEEKEGEKDAAAAKEEAPKAEPEKTEG

AAEAKAEPPKAPEQEQAAPGPAAGGEAPKAAEAAAAPAESAAPAAG

EEPSKEEGEPKKTEAPAAPAAQETKSDGAPASDSKPGSSEAAPSSK

ETPAATEAPSSTPKAQGPAASAEEPKPVEAPAANSDQTVTVKE

An example of a brain-derived neurotrophic factor (BDNF) are provided by Genbank CAA62632 and shown below:

(SEQ ID NO: 45)
MTILFLTMVISYFGCMKAAPMKEANIRGQGGLAYPGVRTHGTLESV

NGPKAGSRGLTSLADTFEHVIEELLDEDHKVRPNEENNKDADLYTS

RVMLSSQVPLEPPLLFLLEEYKNYLDAANMSMMVLRHSDPARRGEL

SVCDSISEWVTAADKKTAVDMSGGTVTVLEKVPVSKGQLKQYFYET

KCNPMGYTKEGCRGIDKRHWNSQCRTTQSYVRALTMDSKKRIGWRF

IRIDTSCVCTLTIKRGR

Examples of neurotrophin-3 (NT-3) are provided by Genbank AAI07076 & and shown below:

(SEQ ID NO: 46)
MSILFYVIFLAYLRGIQGNNMDQRSLPEDSLNSLIIKLIQADILKN

KLSKQMVDVKENYQSTLPKAEAPREPERGGPAKSAFQPVIAMDTEL

LRQQRRYNSPRVLLSDSTPLEPPPLYLMEDYVGSPVVANRTSRRKR

YAEHKSHRGEYSVCDSESLWVTDKSSAIDIRGHQVTVLGEIKTGNS

PVKQYFYETRCKEARPVKNGCRGIDDKHWNSQCKTSQTYVRALTSE

NNKLVGWRWIRIDTSCVCALSRKIGRT

An example of a glial-derived neurotropic factor (GDNF) is provided by Genbank NM_000514 and shown below:

(SEQ ID NO: 47)
MKLWDVVAVCLVLLHTASAFPLPAGKRPPEAPAEDRSLGRRRAPF

ALSSDSNMPEDYPDQFDDVMDFIQATIKRLKRSPDKQMAVLPRRE

RNRQAAAANPENSRGKGRRGQRGKNRGCVLTAIHLNVTDLGLGYE

TKEELIFRYCSGSCDAAETTYDKILKNLSRNRRLVSDKVGQACCR

PIAFDDDLSFLDDNLVYHILRKHSAKRCGCI

Thus, a recombinant nucleic acid molecule of the invention can be used to promote the growth (regeneration) of axons that have been injured, as well as modify the activity or function of the axons in a mammalian neuron as further described herein in the methods of the invention.

The selected polypeptide encoded by a recombinant nucleic acid molecule of the invention can also be any polypeptide the expression of which can be easily detected. For example, the selected polypeptide can be a green fluorescent protein (GFP) or Cherry. These polypeptides are useful as reporters for gene expression in neuronal axons.

An example of a nucleic acid sequence of the invention is as follows:

(SEQ ID NO: 48)
gcccctctccctcccccccccctaacgttactggccgaagccgct tggaataaggccggtgtgcgtttgtctatatgttattttccacca tattgccgtcttttggcaatgtgagggcccggaaacctggccctg tcttcttgacgagcattcctaggggtctttcccctctcgccaaag gaatgcaaggtctgttgaatgtcgtgaaggaagcagttcctctgg aagcttcttgaagacaaacaacgtctgtagcgaccctttgcaggc agcggaaccccccacctggcgacaggtgcctctgcggccaaaagc cacgtgtataagatacacctgcaaaggcggcacaaccccagtgcc acgttgtgagttggatagttgtggaaagagtcaaatggctctcct caagcgtattcaacaaggggctgaaggatgcccagaaggtacccc attgtatgggatctgatctggggcctcggtgcacatgctttacat gtgtttagtcgaggttaaaaaaaacgtctaggcccccgaaccacg gggacgtggttttcctttgaaaaacacgatgataagcttgccaca acgcgtgccgccaccATGGGTGCAGAAGAACAGAAGCTGATCTCA

GAGGAGGACCTGGGTGTGAGCAAGGGCGAGGAGGATAACATGGCC

ATCATCAAGGAGTTCATGCGCTTCAAGGTGCACATGGAGGGCTCC

GTGAACGGCCACGAGTTCGAGATCGAGGGCGAGGGCGAGGGCCGC

CCCTACGAGGGCACCCAGACCGCCAAGCTGAAGGTGACCAAGGGT

GGCCCCCTGCCCTTCGCCTGGGACATCCTGTCCCCTCAGTTCATG

TACGGCTCCAAGGCCTACGTGAAGCACCCCGCCGACATCCCCGAC

TACTTGAAGCTGTCCTTCCCCGAGGGCTTCAAGTGGGAGCGCGTG

ATGAACTTGGAGGACGGCGGCGTGGTGACCGTGACCCAGGACTCC

TCCCTGCAGGACGGCGAGTTCATCTACAAGGTGAAGCTGCGCGGC

ACCAACTTCCCCTCCGACGGCCCCGTAATGCAGAAGAAGACCATG

GGCTGGGAGGCCTCCTCCGAGCGGATGTACCCCGAGGACGGCGCC

CTGAAGGGCGAGATCAAGCAGAGGCTGAAGCTGAAGGACGGCGGC

CACTACGACGCTGAGGTCAAGACCACCTACAAGGCCAAGAAGCCC

GTGCAGCTGCCCGGCGCCTACAACGTCAACATCAAGTTGGACATC

ACCTCCCACAACGAGGACTACACCATCGTGGAACAGTACGAACGC

GCCGAGGGCCGCCACTCCACCGGCGGCATGGACGAGCTGTACAAG

AGC

In the above sequence, the IRES sequence is shown in small letters and italicized. The polypeptide coding sequence is shown in capital letters with the ATG start codon bolded. There is an eleven-nucleotide spacer between the IRES sequence and the ATG start codon. The underlined sequence encodes for the myc tag and the remaining sequence codes for Cherry. Other nucleic acids of the invention can have the same IRES sequence shown above covalently-linked, i.e. by a phosphodiester bond, to a coding sequence for RhoA or sAC for example. Non-limiting examples of polypeptide-coding sequences that can be ligated to the above sequence, to the above IRES sequence or to any IRES sequence, to form a nucleic acid of the invention are shown below with their 3' untranslated regions.

Nucleic acid encoding a C3-ADP-ribosyltransferase (Genbank M74038):

```
                                                           (SEQ ID NO: 49)
 435           ATGAAA GGGATAAGAA AGTCAATTTT ATGTTTAGTT TTATCAGCAG
 481 GGGTAATAGC TCCGGTAACA ACGAGTATAG TTCAAAGTCC TCAAAAATGT TATGCTTGTA
 541 CTGTTGATAA AGGTTCATAT GCAGATACTT TCACAGAATT TACCAATGTT GAGGAAGCCA
 601 AAAAATGGGG AAATGCTCAA TATAAAAAAT ATGGCCTAAG CAAACCTGAA CAAGAAGCTA
 661 TAAAATTTTA TACAAGAGAT GCAAGTAAGA TCAATGGACC ATTAAGAGCA AATCAAGGGA
 721 ATGAAAATGG ATTACCTGCT GATATATTAC AAAAAGTTAAA TTAATTGAT CAATCTTTTA
 781 GTAAGATGAA GATGCCTCAA AATATTATTC TTTTTAGAGG TGATGACCCT GCTTATTTAG
 841 GTCCAGAATT TCAAGATAAA ATTCTTAATA AAGATGGAAC AATTAATAAA ACTGTTTTTG
 901 AACAAGTTAA AGCGAAATTT TTAAAAAAGG ATAGAACAGA ATATGGATAT ATTAGTACTT
 961 CATTAATGAG TGCGCAATTT GGAGGAAGAC CAATTGTTAC TAAATTTAAA GTAACTAATG
1021 GATCAAAAGG AGGGTATATA GACCCTATTA GCTATTTCCC AGGACAACTT GAAGTGTTGC
1081 TTCCTAGAAA TAATAGTTAT TATATAAGTG ATATGCAAAT ATCTCCTAAT AATAGACAAA
1141 TTATGATTAC AGCAATGATA TTTAAATAGt ttataaaaat aaataaaata tagttatgct
1201 aaataaaaga tttagcatct tgaagtaaga aaaattatag gaacacataa caacaaaaat
1261 aactactttt aattaagtag ttcagattgt tcaaaaagcc tccatgtaat tggaggcttt
1321 tactttcgtc aaatatcttt tatgcgatag catttaaaa agttgctagtt ttgtgtaatg
1381 atttggtata aatttcaatt aaatcatacg aaaaatagtg cgatagcacc atggctatct
1441 ttttcatatt ctgaactgct gctgtaatga agcattgctc ggaaacattt ttaattcctc
1501 gcatgcgaca atagcgcagc ccatgtaatt cttttgaatc agcaaactac gctcaattt
1561 ttctttacgt tttttataaa tacttttacc tttttcagtt ttagtaaatg caaaaatttg
1621 atccttataa tcttcccaaa catgacgacg tatagctttg ttaattgatt tatcagatgt
1681 taagcaatta tttttatatt tgcatgaagc acattcatcc gcattactaa catattcttt
1741 atatccgctt cttgtagtgg ttttgtattt taaaaagaag ttattcatac atacatatcc
1801 atctaattct ttaatatatt gaaatctata tttagtatac ttttctttaa catgaggtcc
1861 taaacggaaa ccaaaaacac cttgataatt tttttctgaa acttgcttac aaataggatt
1921 tgtagaataa ccagcatcag ctactaaata ctttgtatta aaattaaact tttttatttg
1981 cgtctctatt cttttaacat aaggatctac atcattaata ttacctggag ttacatgaac
2041 atcagttata atattatatt ttccgtc
```

A nucleic acid sequence encoding human N19-RhoA 9 Genbank (NM_001664):

```
                                                           (SEQ ID NO: 50)
 277                                         ATGG CTGCCATCCG GAAGAAACTG
 301 GTGATTGTTG GTGATGGAGC CTGTGGAAAG ACATGCTTGC TCATAGTCTT CAGCAAGGAC
 361 CAGTTCCCAG AGGTGTATGT GCCCACAGTG TTTGAGAACT ATGTGGCAGA TATCGAGGTG
 421 GATGGAAAGC AGGTAGAGTT GGCTTTGTGG GACACAGCTG GGCAGGAAGA TTATGATCGC
 481 CTGAGGCCCC TCTCCTACCC AGATACCGAT GTTATACTGA TGTGTTTTTC CATCGACAGC
```

```
 541 CCTGATAGTT TAGAAAACAT CCCAGAAAAG TGGACCCCAG AAGTCAAGCA TTTCTGTCCC

601 AACGTGCCCA TCATCCTGGT TGGGAATAAG AAGGATCTTC GGAATGATGA GCACACAAGG

661 CGGGAGCTAG CCAAGATGAA GCAGGAGCCG GTGAAACCTG AAGAAGGCAG AGATATGGCA

721 AACAGGATTG GCGCTTTTGG GTACATGGAG TGTTCAGCAA AGACCAAAGA TGGAGTGAGA

781 GAGGTTTTTG AAATGGCTAC GAGAGCTGCT CTGCAAGCTA GACGTGGGAA GAAAAAATCT

841 GGGTGCCTTG TCTTGTGAAA CCTTGCTGCA AGCACAGCCC TTATGCGGTT AATTTTGAAG

901 TGCTGTTTAT TAATCTTAGT GTATGATTAC TGGCCTTTTT CATTTATCTA TAATTTACCT

961 AAGATTACAA ATCAGAAGTC ATCTTGCTAC CAGTATTTAG AAGCCAACTA TGATTATTAA

1021 CGATGTCCAA CCCGTCTGGC CCACCAGGGT CCTTTTGACA CTGCTCTAAC AGCCCTCCTC

1081 TGCACTCCCA CCTGACACAC CAGGCGCTAA TTCAAGGAAT TTCTTAACTT CTTGCTTCTT

1141 TCTAGAAAGA GAAACAGTTG GTAACTTTTG TGAATTAGGC TGTAACTACT TTATAACTAA

1201 CATGTCCTGC CTATTATCTG TCAGCTGCAA GGTACTCTGG TGAGTCACCA CTTCAGGGCT

1261 TTACTCCGTA ACAGATTTTG TTGGCATAGC TCTGGGGTGG GCAGTTTTTT GAAAATGGGC

1321 TCAACCAGAA AAGCCCAAGT TCATGCAGCT GTGGCAGAGT TACAGTTCTG TGGTTTCATG

1381 TTAGTTACCT TATAGTTACT GTGTAATTAG TGCCACTTAA TGTATGTTAC CAAAAATAAA

1441 TATATCTACC CCAGACTAGA TGTAGTATTT TTTGTATAAT GGATTTCCT AATACTGTCA

1501 TCCTCAAAGA AAGTGTATTG GTTTTTTAAA AAGAAAGTG TATTTGGAAA TAAAGTCAGA

1561 TGGAAAATTC ATTTTTTAAA TTCCCGTTTT GTCACTTTTT CTGATAAAAG ATGGCCATAT

1621 TACCCCTTTT CGGCCCCATG TATCTCAGTA CCCCATGGAG CTGGGCTAAG TAAATAGGAA

1681 TTGGTTTCAC GCCTGAGGCA ATTAGACACT TTGGAAGATG GCATAACCTG TCTCACCTGG

1741 ACTTAAGCAT CTGGCTCTAA TTCACAGTGC TCTTTTCTCC TCACTGTATC CAGGTTCCCT

1801 CCCAGAGGAG CCACCAGTTC TCATGGGTGG CACTCAGTCT CTCTTCTCTC CAGCTGACTA

1861 AACTTTTTTT CTGTACCAGT TAATTTTTCC AACTACTAAT AGAATAAAGG CAGTTTTCTA

1921 AAAAAA
```

40

Nucleic acid encoding a dominant-negative RhoA kinase (ROCK) (Genbank NM_005406)

```
                                                           (SEQ ID NO: 51)
 942                                                ATGTCGACT GGGGACAGTT

961 TTGAGACTCG ATTTGAAAAA ATGGACAACC TGCTGCGGGA TCCCAAATCG AAGTGAATT

1021 CGGATTGTTT GCTGGATGGA TTGGATGCTT TGGTATATGA TTTGGATTTT CCTGCCTTAA

1081 GAAAAAACAA AAATATTGAC AACTTTTTAA GCAGATATAA AGACACAATA AATAAAATCA

1141 GAGATTTACG AATGAAAGCT GAAGATTATG AAGTAGTGAA GGTGATTGGT AGAGGTGCAT

1201 TTGGAGAAGT TCAATTGGTA AGGCATAAAT CCACCAGGAA GGTATATGCT ATGAAGCTTC

1261 TCAGCAAATT TGAAATGATA AAGAGATCTG ATTCTGCTTT TTTCTGGGAA GAAAGGGACA

1321 TCATGGCTTT TGCCAACAGT CCTTGGGTTG TTCAGCTTTT TTATGCATTC CAAGATGATC

1381 GTTATCTCTA CATGGTGATG GAATACATGC CTGGTGGAGA TCTTGTAAAC TTAATGAGCA

1441 ACTATGATGT GCCTGAAAAA TGGGCACGAT TCTATACTGC AGAAGTAGTT CTTGCATTGG

1501 ATGCAATCCA TTCCATGGGT TTTATTCACA GAGATGTGAA GCCTGATAAC ATGCTGCTGG

1561 ATAAATCTGG ACATTTGAAG TTAGCAGATT TTGGTACTTG TATGAAGATG AATAAGGAAG

1621 GCATGGTACG ATGTGATACA GCGGTTGGAA CACCTGATTA TATTTCCCCT GAAGTATTAA
```

-continued

```
1681 AATCCCAAGG TGGTGATGGT TATTATGGAA GAGAATGTGA CTGGTGGTCG GTTGGGGTAT
1741 TTTTATACGA AATGCTTGTA GGTGATACAC CTTTTTATGC AGATTCTTTG GTTGGAACTT
1801 ACAGTAAAAT TATGAACCAT AAAAATTCAC TTACCTTTCC TGATGATAAT GACATATCAA
1861 AAGAAGCAAA AAACCTTATT TGTGCCTTCC TTACTGACAG GGAAGTGAGG TTAGGGCGAA
1921 ATGGTGTAGA AGAAATCAAA CGACATCTCT TCTTCAAAAA TGACCAGTGG GCTTGGGAAA
1981 CGCTCCGAGA CACTGTAGCA CCAGTTGTAC CCGATTTAAG TAGTGACATT GATACTAGTA
2041 ATTTTGATGA CTTGGAAGAA GATAAAGGAG AGGAAGAAAC ATTCCCTATT CCTAAAGCTT
2101 TCGTTGGCAA TCAACTACCT TTTGTAGGAT TTACATATTA TAGCAATCGT AGATACTTAT
2161 CTTCAGCAAA TCCTAATGAT AACAGAACTA GCTCCAATGC AGATAAAAGC TTGCAGGAAA
2221 GTTTGCAAAA AACAATCTAT AAGCTGGAAG AACAGCTGCA TAATGAAATG CAGTTAAAAG
2281 ATGAAATGGA GCAGAAGTGC AGAACCTCAA ACATAAAACT AGACAAGATA ATGAAAGAAT
2341 TGGATGAAGA GGGAAATCAA AGAAGAAATC TAGAATCTAC AGTGTCTCAG ATTGAGAAGG
2401 AGAAAATGTT GCTACAGCAT AGAATTAATG AGTACCAAAG AAAAGCTGAA CAGGAAAATG
2461 AGAAGAGAAG AAATGTAGAA AATGAAGTTT CTACATTAAA GGATCAGTTG GAAGACTTAA
2521 AGAAAGTCAG TCAGAATTCA CAGCTTGCTA ATGAGAAGCT GTCCCAGTTA CAAAAGCAGC
2581 TAGAAGAAGC CAATGACTTA CTTAGGACAG AATCGGACAC AGCTGTAAGA TTGAGGAAGA
2641 GTCACACAGA GATGAGCAAG TCAATTAGTC AGTTAGAGTC CCTGAACAGA GAGTTGCAAG
2701 AGAGAAATCG AATTTTAGAG AATTCTAAGT CACAAACAGA CAAAGATTAT TACCAGCTGC
2761 AAGCTATATT AGAAGCTGAA CGAAGAGACA GAGGTCATGA TTCTGAGATG ATTGGAGACC
2821 TTCAAGCTCG AATTACATCT TTACAAGAGG AGGTGAAGCA TCTCAAACAT AATCTCGAAA
2881 AAGTGGAAGG AGAAAGAAAA GAGGCTCAAG ACATGCTTAA TCACTCAGAA AAGGAAAAGA
2941 ATAATTTAGA GATAGATTTA AACTACAAAC TTAAATCATT ACAACAACGG TTAGAACAAG
3001 AGGTAAATGA ACACAAAGTA ACCAAAGCTC GTTTAACTGA CAAACATCAA TCTATTGAAG
3061 AGGCAAAGTC TGTGGCAATG TGTGAGATGG AAAAAAAGCT GAAAGAAGAA AGAGAAGCTC
3121 GAGAGAAGGC TGAAAATCGG GTTGTTCAGA TTGAGAAACA GTGTTCCATG CTAGACGTTG
3181 ATCTGAAGCA ATCTCAGCAG AAACTAGAAC ATTTGACTGG AAATAAAGAA AGGATGGAGG
3241 ATGAAGTTAA GAATCTAACC CTGCAACTGG AGCAGGAATC AAATAAGCGG CTGTTGTTAC
3301 AAAATGAATT GAAGACTCAA GCATTTGAGG CAGACAATTT AAAAGGTTTA GAAAAGCAGA
3361 TGAAACAGGA AATAAATACT TTATTGGAAG CAAAGAGATT ATTAGAATTT GAGTTAGCTC
3421 AGCTTACGAA ACAGTATAGA GGAAATGAAG GACAGATGCG GGAGCTACAA GATCAGCTTG
3481 AAGCTGAGCA ATATTTCTCG ACACTTTATA AAACCCAGGT AAAGGAACTT AAAGAAGAAA
3541 TTGAAGAAAA AAACAGAGAA AATTTAAAGA AAATACAGGA ACTACAAAAT GAAAAGAAA
3601 CTCCTTGCTAC TCAGTTGGAT CTAGCAGAAA CAAAAGCTGA GTCTGAGCAG TTGGCGCGAG
3661 GCCTTCTGGA AGAACAGTAT TTTGAATTGA CGCAAGAAAG CAAGAAAGCT GCTTCAAGAA
3721 ATAGACAAGA GATTACAGAT AAAGATCACA CTGTTAGTCG GCTTGAAGAA GCAAACAGCA
3781 TGCTAACCAA AGATATTGAA ATATTAAGAA GAGAGAATGA AGAGCTAACA GAGAAAATGA
3841 AGAAGGCAGA GGAAGAATAT AAACTGGAGA GGGAGGAGGA GATCAGTAAT CTTAAGGCTG
3901 CCTTTGAAAA GAATATCAAC ACTGAACGAA CCCTTAAAAC ACAGGCTGTT AACAAATTGG
3961 CAGAAATAAT GAATCGAAAA GATTTTAAAA TTGATAGAAA GAAAGCTAAT ACACAAGATT
4021 TGAGAAAGAA AGAAAAGGAA AATCGAAAGC TGCAACTGGA ACTCAACCAA GAAAGAGAGA
4081 AATTCAACCA GATGGTAGTG AAACATCAGA AGGAACTGAA TGACATGCAA GCGCAATTGG
```

-continued

```
4141 TAGAAGAATG TGCACATAGG AATGAGCTTC AGATGCAGTT GGCCAGCAAA GAGAGTGATA

4201 TTGAGCAATT GCGTGCTAAA CTTTTGGACC TCTCGGATTC TACAAGTGTT GCTAGTTTTC

4261 CTAGTGCTGA TGAAACTGAT GGTAACCTCC CAGAGTCAAG AATTGAAGGT TGGCTTTCAG

4321 TACCAAATAG AGGAAATATC AAACGATATG GCTGGAAGAA ACAGTATGTT GTGGTAAGCA

4381 GCAAAAAAAT TTTGTTCTAT AATGACGAAC AAGATAAGGA GCAATCCAAT CCATCTATGG

4441 TATTGGACAT AGATAAACTG TTTCACGTTA GACCTGTAAC CCAAGGAGAT GTGTATAGAG

4501 CTGAAACTGA AGAAATTCCT AAAATATTCC AGATACTATA TGCAAATGAA GGTGAATGTA

4561 GAAAAGATGT AGAGATGGAA CCAGTACAAC AAGCTGAAAA AACTAATTTC CAAAATCACA

4621 AAGGCCATGA GTTTATTCCT ACACTCTACC ACTTTCCTGC CAATTGTGAT GCCTGTGCCA

4681 AACCTCTCTG GCATGTTTTT AAGCCACCCC CTGCCCTAGA GTGTCGAAGA TGCCATGTTA

4741 AGTGCCACAG AGATCACTTA GATAAGAAAG AGGACTTAAT TTGTCCATGT AAAGTAAGTT

4801 ATGATGTAAC ATCAGCAAGA GATATGCTGC TGTTAGCATG TTCTCAGGAT GAACAAAAAA

4861 AATGGGTAAC TCATTTAGTA AAGAAAATCC CTAAGAATCC ACCATCTGGT TTTGTTCGTG

4921 CTTCCCCTCG AACGCTTTCT ACAAGATCCA CTGCAAATCA GTCTTTCCGG AAAGTGGTCA

4981 AAAATACATC TGGAAAAACT AGTTAAccat gtgactgagt gccctgtgga atcgtgtggg 5041 atgctacctg ataaaccagg cttctttaac catgcagagc agacaggctg tttctttgac 5101 acaaatatca caggcttcag ggttaagatt gctgttttc tgtccttgct ttggcacaac 5161 acactgaggg ttttttttat tgcgggtttg cctacaggta gattagatta attattacta 5221 tgtaatgcaa gtacagttgg gggaaagctt aggtagatat attttttta aaaggtgctg 5281 ccttttttgga tttataagaa aatgcctgtc agtcgtgata gaacagagtt ttcctcatat 5341 gagtaagagg aagggacttt cactttcaag tggaacagcc atcactatca agatcagctc 5401 atggaaggag taaagaaaat atctcaaaat gagacaaact gaagttttgt ttttttttta 5461 atgacttaag tttttgtgct cttgcaagac tatacaaaac tattttaaga aagcagtgat 5521 atcacttgaa cttcagtgcc ctcactgtag aatttaaaag ccttactgtt gattgcccat 5581 gttggacttg atggagaaat taaatatctt tcattatgct ttacaaaata ctgtatatgt 5641 ttcagcaagt ttggggaatg ggagaggaca aaaaaaagtt acatttaatc tatgcatttt 5701 tgccaagcca tattgagtta ttttactact agagacatta ggaaactaac tgtacaaaag 5761 aaccaagttt aaaagcattt tgtggggtac atcatttcta taattgtata atgtatttct 5821 ttgtggtttt aaatgataaa gacattaagt taacaaacat ataagaaatg tatgcactgt 5881 ttgaaatgta aattattctt agaacacttt caatgggggt tgcattgtcc ttttagtgcc 5941 ttaatttgag ataattattt tactgccatg agtaagtata gaaatttcaa aaaatgtatt 6001 ttcaaaaaat tatgtgtgtc agtgagtttt tcattgataa ttggtttaat ttaaaatatt 6061 tagaggtttg ttggactttc ataaattgag tacaatcttt gcatcaaact acctgctaca 6121 ataatgactt tataaaactg caaaaaatgt agaaggttgc accaacataa aaaggaaata 6181 tggcaataca tccatgatgt tttccagtta acataggaat taccagataa atactgttaa 6241 actcttgtcc agtaacaaga gttgattcat atggacagta tgatttattg tttattttt 6301 taaccaaata cctcctcagt aatttataat ggctttgcag taatgtgtat cagataagaa 6361 gcactggaaa accgatcgtc tctaggatga tatgcatgtt tcaagtggta ttgaaagccg 6421 cactgatgga tatgtaataa taaacatatc tgttattaat atactaatga ctctgtgctc 6481 atttaatgag aaataaaagt aatttatgga tgggtatctt taatttttac tgcaatgtgt
```

-continued

```
6541 tttctcatgg ctgaaatgaa tggaaaacat acttcaaatt agtctctgat tgtatataaa 6601 tgtttgtgaa attccatggt tagattaaag tgtattttta aaagataaaa
```

5

Nucleic acid encoding a soluble adenylyl cyclase sequence (Genbank NM_018417)

(SEQ ID NO: 52)

```
 299                                                                        AT
 301 GAACACTCCA AAAGAAGAAT TCCAGGACTG GCCCATAGTC AGAATAGCAG CTCATTTACC
 361 AGACCTCATT GTCTATGGAC ATTTCTCCCC AGAGCGACCC TTTATGGATT ATTTTGACGG
 421 AGTCCTGATG TTTGTTGATA TTTCAGGTTT TACTGCAATG ACTGAGAAGT TCAGCAGTGC
 481 CATGTACATG GACAGAGGGG CTGAGCAGTT GGTGGAGATC CTCAACTACC ACATAAGTGC
 541 AATAGTGGAG AAAGTGTTGA TTTTTGGAGG AGACATCCTG AAATTTGCAG GTGATGCACT
 601 GCTAGCCCTG TGGAGGGTGG AGCGAAAGCA GCTGAAAAAC ATTATCACAG TGGTAATTAA
 661 ATGTAGCCTG GAGATCCATG GATTGTTTGA GACCCAGGAG TGGGAAGAAG GCCTAGACAT
 721 CCGAGTCAAG ATAGGACTGG CTGCTGGCCA CATCAGCATG TTGGTCTTTG AGATGAAAC
 781 ACACAGCCAC TTTCTGGTGA TTGGTCAGGC AGTGGACGAT GTGCGCCTTG CCCAGAACAT
 841 GGCTCAGATG AATGATGTTA TTCTGTCACC AAACTGCTGG CAGCTCTGTG ACCGGAGCAT
 901 GATTGAAATT GAGAGTGTTC CAGATCAGAG AGCAGTTAAG GTTAACTTCT TAAAACCACC
 961 CCCCAATTTT AATTTTGATG AATTTTTCAC AAAGTGTACG ACCTTCATGC ATTATTATCC
1021 TTCTGGTGAG CACAAAAACC TCCTGAGGCT TGCATGCACG CTGAAGCCTG ATCCTGAACT
1081 GGAGATGTCC CTACAAAAGT ATGTGATGGA AAGCATTTTG AAGCAGATTG ATAACAAACA
1141 GCTTCAGGGC TATTTATCTG AGCTTCGCCC AGTGACGATT GTGTTTGTGA ACCTGATGTT
1201 TGAAGACCAA GACAAAGCAG AAGAGATAGG CCCAGCCATC CAGGATGCCT ATATGCACAT
1261 CACTTCTGTC CTGAAGATCT TCCAAGGCCA AATCAATAAA GTCTTCATGT TTGACAAGGG
1321 CTGCTCTTTC CTCTGTGTCT TTGGCTTCCC TGGGGAAAAG GTACCTGACG AGCTCACTCA
1381 TGCTCTGGAA TGTGCTATGG ATATATTTGA CTTCTGCTCT CAAGTCCACA AAATCCAAAC
1441 TGTATCCATC GGTGTTGCCA GTGGGATTGT CTTCTGTGGG ATCGTTGGAC ACACTGTGAG
1501 ACACGAGTAC ACAGTCATTG GTCAAAAAGT CAACTTAGCT GCCAGGATGA TGATGTACTA
1561 CCCAGGAATT GTGACCTGCG ACTCTGTCAC CTACAATGGG AGCAACCTAC CAGCGTACTT
1621 TTTTAAAGAG CTTCCAAAGA AAGTTATGAA AGGTGTTGCA GATTCTGGAC CATTGTATCA
1681 GTATTGGGGC CGTACTGAGA AAGTCATGTT TGGTATGGCG TGCCTCATCT GCAACAGAAA
1741 GGAGGATTAC CCTTTGCTGG GACGTAATAA AGAGATCAAC TACTTCATGT ATACTATGAA
1801 GAAATTTTTG ATATCTAACA GCAGCCAAGT CTTAATGTAT GAGGGATTAC CAGGATATGG
1861 AAAAAGCCAG ATACTTATGA AAATTGAGTA CCTGGCCCAA GGTAAGAATC ACAGGATTAT
1921 TGCCATTTCA TTGAATAAGA TCAGCTTCCA TCAAACTTTC TATACCATCC AGATGTTCAT
1981 GGCCAATGTC CTAGGCCTAG ACACTTGTAA ACATTATAAA GAACGACAGA CCAACCTTCG
2041 AAATAAAGTC ATGACACTGT TGGATGAAAA GTTCTACTGT CTTCTTAATG ACATTTTCCA
2101 TGTTCAGTTC CCTATTTCTC GGGAGATTTC CAGGATGAGC ACCTTGAAAA AGCAAAAACA
2161 ATTGGAAATA TTGTTTATGA AGATCTTGAA GCTGATAGTG AAAGAGGAAA GGATTATTTT
2221 TATCATTGAT GAGGCCCAGT TTGTGGATTC GACCTCCTGG AGATTTATGG AGAAGCTTAT
2281 CCGGACTCTT CCTATCTTCA TCATTATGTC CCTGTGTCCC TTCGTTAACA TTCCCTGTGC
```

-continued

```
2341 AGCTGCCAGG GCCGTAATAA AGAACAGGAA CACCACCTAC ATTGTCATTG GTGCAGTACA

2401 GCCTAACGAC ATCTCCAACA AGATCTGTCT TGACCTCAAT GTGAGCTGCA TCTCCAAAGA

2461 ACTGGACTCG TACCTGGGGG AGGGAAGCTG TGGGATTCCA TTTTACTGTG AAGAATTGCT

2521 TAAAAACCTG GAACATCATG AGGTACTCGT TTTCCAACAA ACGGAGTCTG AGGAAAAGAC

2581 AAATAGGACC TGGAATAACC TGTTCAAGTA TTCCATTAAG CTAACAGAGA AGTTAAACAT

2641 GGTTACTCTC CATAGTGATA AGGAAAGTGA AGAAGTCTGT CACCTCACAA GTGGTGTCAG

2701 ACTGAAAAAC CTGTCACCTC AACGTCATT AAAAGAAATC TCTCTGATCC AGCTGGATAG

2761 CATGAGACTT TCCCACCAAA TGCTGGTGAG ATGTGCTGCC ATCATTGGCC TGACCTTCAC

2821 CACTGAGTTG TTGTTTGAGA TTCTCCCCTG TTGGAATATG AAGATGATGA TCAAGACCCT

2881 GGCAACCCTA GTGGAATCTA ACATTTTTTA TTGTTTCCGG AATGGCAAGG AGCTTCAAAA

2941 GGCCCTGAAA CAGAATGATC CCTCATTTGA GGTGCACTAT CGTTCCTTGT CTCTGAAGCC

3001 CAGTGAAGGG ATGGATCACG GTGAAGAGGA ACAGCTTCGT GAACTGGAGA ATGAGGTGAT

3061 CGAGTGCCAC AGGATTCGAT TCTGTAACCC TATGATGCAG AAAACAGCCT ACGAGCTGTG

3121 GCTCAAGGAC CAGAGAAAAG CCATGCACTT GAAATGTGCC CGCTTTTTAG AAGAAGATGC

3181 CCACAGATGT GACCACTGCC GAGGCAGGGA CTTCATTCCC TATCATCACT TCACAGTGAA

3241 TATTCGGCTC AACGCTTTAG ACATGGATGC CATTAAAAAG ATGGCTATGT CTCATGGATT

3301 TAAAACTGAA GAAAAGCTTA TCTTGTCCAA CTCAGAGATT CCTGAGACAT CTGCATTTTT

3361 TCCTGAAAAT CGCAGTCCTG AAGAAATAAG AGAAAAGATC TTGAATTTCT TGACCACGT

3421 TTTAACAAAA ATGAAGACAT CTGACGAAGA CATTATCCCT CTGGAATCTT GCCAGTGTGA

3481 AGAAATCCTA GAGATTGTCA TCTTGCCTCT GGCCCACCAT TTTCTGGCTT TGGGAGAAAA

3541 TGACAAAGCC TTATATTACT TCTTAGAAAT TGCATCTGCT TATCTCATCT TTTGTGATAA

3601 CTACATGGCA TACATGTATT TGAATGAAGG ACAGAAGTTG CTAAAAACTC TCAAGAAGGA

3661 CAAATCTTGG AGCCAGACAT TTGAGTCTGC CACCTTTTAC AGCCTCAAAG GTGAGGTCTG

3721 TTTCAATATG GGCCAGATAG TGCTTGCCAA GAAAATGCTG AGGAAGGCAC TGAAGCTCCT

3781 CAACCGAATC TTTCCTTACA ACTTAATCTC CTTGTTTCTC CATATCCATG TCGAGAAAAA

3841 CAGACACTTT CATTATGTGA ATCGGCAGGC CCAAGAGAGC CCACCTCCAG GGAAGAAGAG

3901 GCTGGCACAA CTTTACCGGC AAACTGTCTG CCTTTCCTTG CTGTGGCGCA TCTATAGCTA

3961 CAGTTATCTT TTTCACTGCA AGTATTATGC CCACCTGGCA GTTATGATGC AAATGAATAC

4021 TGCACTGGAA ACTCAAAATT GTTTCCAGAT CATTAAGGCT TACCTAGACT ATTCGCTATA

4081 CCACCACCTG GCTGGCTACA AAGGTGTGTG GTTCAAATAT GAAGTCATGG CCATGGAGCA

4141 CATCTTCAAC CTCCCCCTGA AAGGCGAGGG CATTGAAATC GTGGCATACG TGGCTGAGAC

4201 ACTGGTCTTC AACAAGCTCA TAATGGGACA CCTGGATTTG GCCATTGAGT TAGGCTCCCG

4261 AGCCCTTCAG ATGTGGGCAC TGCTCCAGAA TCCCAACCGA CATTATCAGT CCCTCTGCAG

4321 ACTTAGCAGA TGTCTCCTTC TGAACAGCAG ATACCCGCAA TTGATCCAGG TGCTGGGGCG

4381 GCTGTGGGAG CTTTCTGTAA CACAGGAACA CATCTTCAGC AAGGCATTTT TCTATTTTGT

4441 CTGCTTGGAC ATCCTGCTTT ATTCTGGTTT TGTTTATAGA ACATTTGAAG AATGTTTGGA

4501 ATTCATACAC CAATACGAAA ACAACAGAAT CCTCAAGTTC ACAGTGGAC TCCTCCTGGG

4561 ACTTTATTCC TCTGTAGCTA TCTGGTATGC CAGACTTCAG GAATGGGACA ACTTTTACAA

4621 ATTTTCCAAT AGAGCTAAAA ATCTTTTGCC AAGAAGAACC ATGACACTTA CTTACTATGA

4681 CGGAATATCT AGGTACATGG AGGGGCAAGT TCTTCACCTT CAAAAACAAA TCAAAGAACA

4741 GTCAGAGAAT GCCCAAGCCA GTGGGGAGGA GCTACTCAAG AACTTGGAGA ATCTGGTGGC
```

-continued

```
4801 TCAAAATACC ACTGGCCCTG TCTTTTGCCC AAGGCTCTAC CACCTGATGG CTTACGTCTG
4861 TATATTAATG GGAGATGGGC AGAAATGTGG CCTCTTCCTG AACACAGCCT TGCGGCTCTC
4921 TGAAACACAG GGGAATATAC TGGAGAAATG CTGGCTGAAC ATGAACAAAG AATCATGGTA
4981 CTCAACCTCT GAGTTAAAAG AAGACCAATG GCTTCAGACG ATCTTGAGTC TCCCATCATG
5041 GGAAAAAATT GTAGCAGGCA GGGTAAACAT TCAGGATCTT CAAAAAAACA AATTCCTGAT
5101 GAGAGCTAAT ACCGTGGACA ATCATTTCTA Acatgtcaaa gaaaaaagat tttaataagc
5161 actatgtcct tgtgattatc tattattgac ctttctccgt ggctggcc
```

Nucleic acid encoding a glutamic acid decarboxylase (GAD) (Genbank NM_000817)

(SEQ ID NO: 53)
```
 423 ATGGCGTC TTCGACCCCA TCTTCGTCCG CAACCTCCTC GAACGCGGGA GCGGACCCCA
 481 ATACCACTAA CCTGCGCCCC ACAACGTACG ATACCTGGTG CGGCGTGGCC CATGGATGCA
 541 CCAGAAAACT GGGGCTCAAG ATCTGCGGCT TCTTGCAAAG GACCAACAGC CTGGAAGAGA
 601 AGAGTCGCCT TGTGAGTGCC TTCAAGGAGA GGCAATCCTC CAAGAACCTG CTTTCCTGTG
 661 AAAACAGCGA CCGGGATGCC CGCTTCCGGC GCACAGAGAC TGACTTCTCT AATCTGTTTG
 721 CTAGAGATCT GCTTCCGGCT AAGAACGGTG AGGAGCAAAC CGTGCAATTC CTCCTGGAAG
 781 TGGTGGACAT ACTCCTCAAC TATGTCCGCA AGACATTTGA TCGCTCCACC AAGGTGCTGG
 841 ACTTTCATCA CCCACACCAG TTGCTGGAAG GCATGGAGGG CTTCAACTTG AGCTCTCTG
 901 ACCACCCCGA GTCCCTGGAG CAGATCCTGG TTGACTGCAG AGACACCTTG AAGTATGGGG
 961 TTCGCACAGG TCATCCTCGA TTTTTCAACC AGCTCTCCAC TGGATTGGAT ATTATTGGCC
1021 TAGCTGGAGA ATGGCTGACA TCAACGGCCA ATACCAACAT GTTTACATAT GAAATTGCAC
1081 CAGTGTTTGT CCTCATGGAA CAAATAACAC TTAAGAAGAT GAGAGAGATA GTTGGATGGT
1141 CAAGTAAAGA TGGTGATGGG ATATTTTCTC CTGGGGGCGC CATATCCAAC ATGTACAGCA
1201 TCATGGCTGC TCGCTACAAG TACTTCCCGG AAGTTAAGAC AAAGGGCATG GCGGCTGTGC
1261 CTAAACTGGT CCTCTTCACC TCAGAACAGA GTCACTATTC CATAAAGAAA GCTGGGGCTG
1321 CACTTGGCTT TGGAACTGAC AATGTGATTT TGATAAAGTG CAATGAAAGG GGGAAAATAA
1381 TTCCAGCTGA TTTTGAGGCA AAAATTCTTG AAGCCAAACA GAAGGGATAT GTTCCCTTTT
1441 ATGTCAATGC AACTGCTGGC ACGACTGTTT ATGGAGCTTT TGATCCGATA CAAGAGATTG
1501 CAGATATATG TGAGAAATAT AACCTTTGGT TGCATGTCGA TGCTGCCTGG GGAGGTGGGC
1561 TGCTCATGTC CAGGAAGCAC CGCCATAAAC TCAACGGCAT AGAAAGGGCC AACTCAGTCA
1621 CCTGGAACCC TCACAAGATG ATGGGCGTGC TGTTGCAGTG CTCTGCCATT CTCGTCAAGG
1681 AAAAGGGTAT ACTCCAAGGA TGCAACCAGA TGTGTGCAGG ATACCTCTTC CAGCCAGACA
1741 AGCAGTATGA TGTCTCCTAC GACACCGGGG ACAAGGCAAT TCAGTGTGGC CGCCACGTGG
1801 ATATCTTCAA GTTCTGGCTG ATGTGGAAAG CAAAGGGCAC AGTGGGATTT GAAAACCAGA
1861 TCAACAAATG CCTGGAACTG GCTGAATACC TCTATGCCAA GATTAAAAAC AGAGAAGAAT
1921 TTGATGGT TTTCAATGGC GAGCCTGAGC ACACAAACGT CTGTTTTTGG TATATTCCAC
1981 AAAGCCTCAG GGGTGTGCCA GACAGCCCTC AACGACGGGA AAAGCTACAC AAGGTGGCTC
2041 CAAAAATCAA AGCCCTGATG ATGGAGTCAG GTACGACCAT GGTTGGCTAC CAGCCCCAAG
2101 GGGACAAGGC CAACTTCTTC CGGATGGTCA TCTCCAACCC AGCCGCTACC CAGTCTGACA
2161 TTGACTTCCT CATTGAGGAG ATAGAAAGAC TGGGCCAGGA TCTGTAAtca tccttcgcag
```

-continued

```
2221 aacatgagtt tatgggaatg ccttttccct ctggcactcc agaacaaacc tctatatgtt 2281 gctgaaacac acaggccatt tcattgaggg aaaacataat atcttgaaga atattgttaa 2341 aaccttactt aaagcttgtt tgttctagtt agcaggaaat agtgttcttt ttaaaaagtt 2401 gcacattagg aacagagtat atatgtacag ttatacatac ctctctctat atatacatgt 2461 atagtgagtg tggcttagta atagatcacg gcatgtttcc cgctccaaga gaattcactt 2521 taccttcagc agttaccgag gagctaaaca tgctgccaac cagcttgtcc aacaactcca 2581 ggaaaactgt ttttcaaaac gccatgtcct aggggccaag ggaaatgctg ttggtgagaa 2641 tcgacctcac tgtcagcgtt tctccacctg aagtgatgat ggatgagaaa aaacaccacc 2701 aaatgacaag tcacaccctc cccattagta tcctgttagg ggaaaatagt agcagagtca 2761 ttgttacagg tgtactatgg ctgtattttt agagattaat ttgtgtagat tgtgtaaatt 2821 cctgttgtct gaccttggtg gtgggagggg gagactatgt gtcatgattt caatgattgt 2881 ttaattgtag gtcaatgaaa tatttgctta tttatattca gagatgtacc atgttaaaga 2941 ggcgtcttgt attttcttcc catttgtaat gtatcttatt tatatatgaa gtaagttctg 3001 aaaactgttt atggtatttt cgtgcatttg tgagccaaag agaaaagatt aaaattagtg 3061 agatttgtat ttatattaga gtgcccttaa aataatgatt taagcatttt actgtctgta 3121 agagaattct aagattgtac ataaagtcat atatatggaa atcctgttac ttaaatagca 3181 tctgctcttc tcttacgctc tctgtctggc tgtacgtctg gtgttctcaa tgcttttcta 3241 gcaactgttg gataataact agatctcctg taattttgta gtagttgatg accaatctct 3301 gtgactcgct tagctgaaac ctaaggcaac atttccgaag accttctgaa gatctcagat 3361 aaagtgacca ggctcacaac tgttttttgaa gaagggaaat tcacactgtg cgttttagag 3421 tatgcaagaa gaatatataaa aaataaaaat attctccatg gagaatttga acaaaaaaaa 3481 aaaaaaaa
```

Nucleic acid encoding human proenkephalin (Genbank NM_006211):

```
                                                          (SEQ ID NO: 54)
  82                     ATGGCGCGG TTCCTGACAC TTTGCACTTG GCTGCTGTTG

121 CTCGGCCCCG GGCTCCTGGC GACCGTGCGG GCCGAATGCA GCCAGGATTG CGCGACGTGC

181 AGCTACCGCC TAGTGCGCCC GGCCGACATC AACTTCCTGG CTTGCGTAAT GGAATGTGAA

241 GGTAAACTGC CTTCTCTGAA AATTTGGGAA ACCTGCAAGG AGCTCCTGCA GCTGTCCAAA

301 CCAGAGCTTC CTCAAGATGG CACCAGCACC CTCAGAGAAA ATAGCAAACC GGAAGAAAGC

361 CATTTGCTAG CCAAAAGGTA TGGGGGCTTC ATGAAAAGGT ATGGAGGCTT CATGAAGAAA

421 ATGGATGAGC TTTATCCCAT GGAGCCAGAA GAAGAGGCCA ATGGAAGTGA GATCCTCGCC

481 AAGCGGTATG GGGGCTTCAT GAAGAAGGAT GCAGAGGAGG ACGACTCGCT GGCCAATTCC

541 TCAGACCTGC TAAAAGAGCT TCTGGAAACA GGGGACAACC GAGAGCGTAG CCACCACCAG

601 GATGGCAGTG ATAATGAGGA AGAAGTGAGC AAGAGATATG GGGGCTTCAT GAGAGGCTTA

661 AAGAGAAGCC CCCAACTGGA AGATGAAGCC AAAGAGCTGC AGAAGCGATA TGGGGGCTTC

721 ATGAGAAGAG TAGGTCGCCC AGAGTGGTGG ATGGACTACC AGAAACGGTA TGGAGGTTTC

781 CTGAAGCGCT TTGCCGAGGC TCTGCCCTCC GACGAAGAAG GCGAAAGTTA CTCCAAAGAA

841 GTTCCTGAAA TGGAAAAAAG ATACGGAGGA TTTATGAGAT TTTAAtatct tttcccacta 901 gtggccccag gccccagcaa gcctccctcc atcctccagt gggaaactgt tgatggtgtt
```

-continued

```
 961 ttattgtcat gtgttgcttg ccttgtatag ttgacttcat tgtctggata actatacaac
1021 ctgaaaactg tcatttcagg ttctgtgctc tttttggagt ctttaagctc agtattagtc
1081 tattgcagct atctcgtttt catgctaaaa tagttttgt tatcttgtct cttattttg
1141 acaaacatca ataaatgctt acttgtatat agagataata aacctattac cccaagtgca
1201 taaaaaaaaa aaaaaaaaaa a
```

Nucleic acid encoding a dominant-negative Vps24 sequence (Genbank NM_016079):

(SEQ ID NO: 55)
```
 130        A TGGGGCTGTT TGGAAAGACC CAGGAGAAGC CGCCCAAAGA ACTGGTCAAT
 181 GAGTGGTCAT TGAAGATAAG AAAGGAAATG AGAGTTGTTG ACAGGCAAAT AAGGGATATC
 241 CAAAGAGAAG AAGAAAAAGT GAAACGATCT GTGAAAGATG CTGCCAAGAA GGGCCAGAAG
 301 GATGTCTGCA TAGTTCTGGC CAAGGAGATG ATCAGGTCAA GGAAGGCTGT GAGCAAGCTG
 361 TATGCATCCA AAGCACACAT GAACTCAGTG CTCATGGGGA TGAAGAACCA GCTCGCGGTC
 421 TTGCGAGTGG CTGGTTCCCT GCAGAAGAGC ACAGAAGTGA TGAAGGCCAT GCAAAGTCTT
 481 GTGAAGATTC CAGAGATTCA GGCCACCATG AGGGAGTTGT CCAAAGAAAT GATGAAGGCT
 541 GGGATCATAG AGGAGATGTT AGAGGACACT TTTGAAAGCA TGGACGATCA GGAAGAAATG
 601 GAGGAAGAAG CAGAAATGGA AATTGACAGA ATTCTCTTTG AAATTACAGC AGGGGCCTTG
 661 GGCAAAGCAC CCAGTAAAGT GACTGATGCC CTTCCAGAGC CAGAACCTCC AGGAGCGATG
 721 GCTGCCTCAG AGGATGAGGA GGAGGAGGAA GAGGCTCTGG AGGCCATGCA GTCCCGGCTG
 781 GCCACACTCC GCAGCTAGgg gctgcctacc ccgctgggtg tgcacacact cctctcaaga
 841 gctgccattt tatgtgtctc ttgcactaca cctctgttgt gaggactacc attttggaga
 901 aggttctgtt tgtctctttt cattctctgc ccaggttttg ggatcgcaaa gggattgttc
 961 ttataaaagt ggcataaata aatgcatcat ttttaggagt atagacagat atatcttatt
1021 gtggggaggg gaaagaaatc catctgctca tgaagcactt ctgaaaatat aggtgattgc
1081 ctgaatgtcg aagactctac ttttgtctat aaacactat ataaatgaat tttaataaat
1141 ttttgcttta gcacttggcc ccattgtaga ttgccctgtg cagtaaactt tcaaggtgtc
1201 ggctgcccca gattgcttca tttgctgggt gtggaaagag ttgctatggc caggcatatg
1261 ggatttggaa gctcagcaga agtgacttct gctctgtggt tgctgctccc cggctttcac
1321 agacatggta tggcagccat tottttatct atttaaccaa gaggatgctg gggaattgtg
1381 ctgcttgtcc tgttggctgg tggctgcatt atgtcctggg gtgtgcatgt gggtctattt
1441 agagcttctg tcccttcctt cccattgcaa gttgcaccca gatgagacag ctgtagtact
1501 aggtctcttt cacctctcat tgcctgtccc tgcttcgagc tggttgtctt gtgcgtggga
1561 catgggcctt cctatctgtg ttttctcaaa gtcaggagct gaccaggagc acactaaggt
1621 gtggtcatgc atcataacca acattcactc atctgggaca ttcttaagat acatttataa
1681 atcatttcag cagtagtact ttgtatgtgt tgagagttta cagagctctt tgacatacgc
1741 gatcttagtc tttacaaata aggaaaacag ctcagtttgg gaagtatcag agatgggatt
1801 caaacccaga tcctctggtc caagttgtat gtgcactgaa ctaatcaggc aggaaaaaag
1861 cccagccact gtctcacaga ttgttttttg tatattgtag caaaatcctg aaacaatggg
1921 gtccttccag tctcatcata caaaatggca atcttggctg ggtgcggtgg ttcatgccta
1981 taatcccagt gctttacaag gctgaggcag gaggctctct tgagaatagg agttcaagac
```

-continued

```
2041 cagcctgggc aacatagcaa gatcctgtct ctccaaaaaa aaaaaaaaaa aaaaaaaaaa
2101 atttcatttt tgagtccaga ggaccctcct attactcttg atttcatctt cagagtgtag
2161 ttaaaaaatt attttaaata attatttttt taaatcagtt gtaggttcac agcaaaagtg
2221 gacaaaaaga aatttctcat atatcccctg ccctcacaca tgcatagcct cccaccacta
2281 tcagtatccc acaccagagt ggtacatttg ttacaatcaa taaacctcca ttgacacatc
2341 attatcaccc aaagtccata gtttacatga agattcactc tggtgttgta cattgtatgg
2401 gcttagacaa atgtatgatg atatctacaa ttatagaatc atacagaata gtttcactgc
2461 cctaaaactt ctctatgctt cacctgttca tcccttttott ccctaatccc ctggcaacca
2521 ctttaaaaaa aaaattaggt tcaggggggta catgtgcagg taaactcgtg acaaggggggt
2581 ttgttataca gattatttag tgacccaggt actaagccta gtacccaata gttacttttc
2641 tggtcctgtc ccttttccca ccctccaccc tcaggtaggc cccagtatgt tattcctttg
2701 tgtccatgtt atttcactcc cacttgtgag aacatggaat atttggtttc ctgttcctat
2761 gttagtttgt taaggataat ggcctccagc cccatccatg ttcctgcaaa ggacatgatc
2821 tttctttggc aaccacttttt tactgtcgcc atagttcttc cttttctaga atgtcatatt
2881 ggaatcatat agtatgtagc cttttcagac tggcttcttt cacttaataa tatgcaatta
2941 aggttcctcc atgtcatttc atggcttaat agtgcattta tttttagcac tgaataatac
3001 tccattgtct agatgaatag tttatccatt cacctattga aagacttctt ggtggtttcc
3061 aagttttggc aattatgaat aaagctgttg taaacatctt tgtgcaggtt tttctatggg
3121 catgttttta attcatttga ataaatacca agagcttcag tgctggatca taaa
```

Nucleic acid encoding a GAP43 sequence (Genbank NM_002045):

```
                                                            (SEQ ID NO: 56)
 387                    ATGC TGTGCTGTAT GAGAAGAACC AAACAGGTTG
 421 AAAAAAATGA TGACGACCAA AAGATTGAAC AAGATGGTAT CAAACCAGAA GATAAAGCTC
 481 ATAAGGCCGC AACCAAAATT CAGGCTAGCT TCCGTGGACA CATAACAAGG AAAAAGCTCA
 541 AAGGAGAGAA GAAGGATGAT GTCCAAGCTG CTGAGGCTGA AGCTAATAAG AAGGATGAAG
 601 CCCCTGTTGC CGATGGGGTG GAGAAGAAGG AGAAGGCAC CACTACTGCC GAAGCAGCCC
 661 CAGCCACTGG CTCCAAGCCT GATGAGCCCG GCAAAGCAGG AGAAACTCCT TCCGAGGAGA
 721 AGAAGGGGGA GGGTGATGCT GCCACAGAGC AGGCAGCCCC CCAGGCTCCT GCATCCTCAG
 781 AGGAGAAGGC CGGCTCAGCT GAGACAGAAA GTGCCACTAA AGCTTCCACT GATAACTCGC
 841 CGTCCTCCAA GGCTGAAGAT GCCCCAGCCA AGGAGGAGCC TAAACAAGCC GATGTGCCTG
 901 CTGCTGTCAC TGCTGCTGCT GCCACCACCC TGCCGCAGA GGATGCTGCT GCCAAGGCAA
 961 CAGCCCAGCC TCCAACGGAG ACTGGGGAGA GCAGCCAAGC TGAAGAGAAC ATAGAAGCTG
1021 TAGATGAAAC CAAACCTAAG GAAAGTGCCC GGCAGGACGA GGGTAAAGAA GAGGAACCTG
1081 AGGCTGACCA AGAACATGCC TGAactctaa gaaatggctt tccacatccc caccctcccc
1141 tctcctgagc ctgtctctcc ctaccctctt ctcagctcca tctgaagtc ccttcctgtc
1201 ctgctcacgt ctgtgagtct gtcctttccc acccactagc cctctttctc tctgtgtggc
1261 aaacatttaa aaaaaaaaaa aaaaagcagg aaagatccca agtcaaacag tgtggcttaa
1321 acattttttg tttcttggtg ttgttatggc aagttttttgg taatgatgat tcaatcatttt
1381 tgggaaattc ttgcactgta tccaagttat ttgatctggt gcgtgtggcc ctgtgggagt
```

-continued

```
1441 ccactttcct ctctctctct ctctctgttc caagtgtgtg tgcaatgttc cgttcatctg 1501 aggagtccaa aatatcgagt gaattcaaaa tcattttttt tttcctcctt ttcaatgtga 1561 tggaatgaac aaaaaggaaa aaattcaaaa aacccagttt gttttaaaaa taaataaata 1621 aagcaaatgt gccaattagc gtaaacttgc ggctctaagg ctccttttc aacccgaata 1681 ttaataaatc atgagagtaa tcaaggtcaa aaaaaaaaaa aaaaaaaaa aaaaaaaaaa 1741 aaaaaaa
```

Nucleic acid encoding a CAP23 sequence (Genbank NM_006317):

(SEQ ID NO: 57)

```
180                                                                A

181 TGGGAGGCAA GCTCAGCAAG AAGAAGAAGG GCTACAATGT GAACGACGAG AAAGCCAAGG

241 AGAAAGACAA GAAGGCCGAG GGCGCGGCGA CGGAAGAGGA GGGGACCCCG AAGGAGAGTG

301 AGCCCCAGGC GGCCGCAGAG CCCGCCGAGG CCAAGGAGGG CAAGGAGAAG CCCGACCAGG

361 ACGCCGAGGG CAAGGCCGAG GAGAAGGAGG GCGAGAAGGA CGCGGCGGCT GCCAAGGAGG

421 AGGCCCCGAA GGCGGAGCCC GAGAAGACGG AGGGCGCGGC AGAGGCCAAG GCTGAGCCCC

481 CGAAGGCGCC CGAGCAGGAG CAGGCGGCCC CCGGCCCCGC TGCGGGCGGC GAGGCCCCCA

541 AAGCTGCTGA GGCCGCCGCG GCCCCGGCCG AGAGCGCGGC CCCTGCCGCC GGGGAGGAGC

601 CCAGCAAGGA GGAAGGGGAA CCCAAAAAGA CTGAGGCGCC CGCAGCTCCT GCCGCCCAGG

661 AGACCAAAAG TGACGGGGCC CCAGCTTCAG ACTCAAAACC CGGCAGCTCG GAGGCTGCCC

721 CCTCTTCCAA GGAGACCCCC GCAGCCACGG AAGCGCCTAG TTCCACACCC AAGGCCCAGG

781 GCCCCGCAGC CTCTGCAGAA GAGCCCAAGC CGGTGGAGGC CCCGGCAGCT AATTCCGACC

841 AAACCGTAAC CGTGAAAGAG TGAcaaggac agcctatagg aaaaacaata ccacttaaaa 901 caatctcctc tctctctctc tctctctctc tctatctctc tctctatctc ctctctctct 961 ctcctctcct atctctcctc tctctctctc ctatactaac ttgtttcaaa ttggaagtaa 1021 tgatatgtat tgcccaagga aaaatacagg atgttgtccc atcaagggag ggaggggtg 1081 ggagaatcca aatagtattt ttgtggggaa atatctaata taccttcagt caactttacc 1141 aagaagtcct ggatttccaa gatccgcgtc tgaaagtgca gtacatcgtt tgtacctgaa 1201 actgccgcca catgcactcc tccaccgctg agagttgaat agcttttctt ctgcaatggg 1261 agttgggagt gatgcgtttg attctgccca cagggcctgt gccaaggcaa tcagatcttt 1321 atgagagcag tattttctgt gttttcttt taatttacag cctttcttat tttgatattt 1381 ttttaatgtt gtggatgaat gccagctttc agacagagcc cacttagctt gtccacatgg 1441 atctcaatgc caatcctcca ttcttcctct ccagatattt tgggagtga caaacattct 1501 ctcatcctac ttagcctacc tagatttctc atgacgagtt aatgcatgtc cgtggttggg 1561 tgcacctgta gttctgttta ttggtcagtg gaaatgaaaa aaaaaaaaaa aaaaagtctg 1621 cgttcattgc agttccagtt tctcttccat tctgtgtcac agacaccaac acaccactca 1681 ttggaaaatg gaaaaaaaaa acaaaaaaaa aacaaaaaaa tgtacaatgg atgcattgaa 1741 attatatgta attgtataaa tggtgcaaca gtaataaagt taaacaatta aaagaaaaa 1801 aaaaaaaaaa aaaaaaaaa
```

Nucleic acid encoding a brain-derived neurotrophic factor (BDNF) (Genbank X91251):

(SEQ ID NO: 58)

```
 285                                         ATGACC ATCCTTTTCC
 301 TTACTATGGT TATTTCATAC TTTGGTTGCA TGAAGGCTGC CCCCATGAAA GAAGCAAACA
 361 TCCGAGGACA AGGTGGCTTG GCCTACCCAG GTGTGCGGAC CCATGGGACT CTGGAGAGCG
 421 TGAATGGGCC CAAGGCAGGT TCAAGAGGCT TGACATCATT GGCTGACACT TTCGAACACG
 481 TGATAGAAGA GCTGTTGGAT GAGGACCATA AGTTCGGCC CAATGAAGAA AACAATAAGG
 541 ACGCAGACTT GTACACGTCC AGGGTGATGC TCAGTAGTCA AGTGCCTTTG GAGCCTCCTC
 601 TTCTCTTTCT GCTGGAGGAA TACAAAAATT ACCTAGATGC TGCAAACATG TCCATGATGG
 661 TCCTGCGCCA CTCTGACCCT GCCCGCCGAG GGAGCTGAG CGTGTGTGAC AGTATTAGTG
 721 AGTGGGTAAC GGCGGCAGAC AAAAAGACTG CAGTGGACAT GTCGGGCGGG ACGGTCACAG
 781 TCCTTGAAAA GGTCCCTGTA TCAAAAGGCC AACTGAAGCA ATACTTCTAC GAGACCAAGT
 841 GCAATCCCAT GGGTTACACA AAAGAAGGCT GCAGGGGCAT AGACAAAAGG CATTGGAACT
 901 CCCAGTGCCG AACTACCCAG TCGTACGTGC GGGCCCTTAC CATGGATAGC AAAAAGAGAA
 961 TTGGCTGGCG ATTCATAAGG ATAGACACTT CTTGTGTATG TACATTGACC ATTAAAAGGG
1021 GAAGATAGtg gatttatgtt gtatagatta gattatattg agacaaaaat tatctatttg
1081 tatatataca taacagggta aattattcag ttaagaaaaa aataattta ttaactgcat
1141 gtataaatga agtttataca gtacagtggt tctacaatct atttattgga catgtccatg
1201 accagaaggg aaacagtcat ttgcgcacaa cttaaaaagt ctgcattaca ttccttgata
1261 atgttgtggt ttgttgccgt tgccaagaac tgaaaacata aaaatttaaa aaaataatc
1321 ccttgcatgc tgccc
```

Nucleic acid encoding neurotrophin-3 (NT-3) (Genbank BC107075):

(SEQ ID NO: 59)

```
  71            ATGTCCATCT TGTTTTATGT GATATTTCTC GCTTATCTCC GTGGCATCCA
 121 AGGTAACAAC ATGGATCAAA GGAGTTTGCC AGAAGACTCG CTCAATTCCC TCATTATTAA
 181 GCTGATCCAG GCAGATATTT TGAAAAACAA GCTCTCCAAG CAGATGGTGG ACGTTAAGGA
 241 AAATTACCAG AGCACCCTGC CCAAAGCTGA GGCTCCCCGA GAGCCGGAGC GGGGAGGGCC
 301 CGCCAAGTCA GCATTCCAGC CAGTGATTGC AATGGACACC GAACTGCTGC GACAACAGAG
 361 ACGCTACAAC TCACCGCGGG TCCTGCTGAG CGACAGCACC CCCTTGGAGC CCCCGCCCTT
 421 GTATCTCATG GAGGATTACG TGGGCAGCCC CGTGGTGGCG AACAGAACAT CACGGCGGAA
 481 ACGGTACGCG GAGCATAAGA GTCACCGAGG GGAGTACTCG GTATGTGACA GTGAGAGTCT
 541 GTGGGTGACC GACAAGTCAT CGGCCATCGA CATTCGGGGA CACCAGGTCA CGGTGCTGGG
 601 GGAGATCAAA ACGGGCAACT CTCCTGTCAA ACAATATTTT TATGAAACGC GATGTAAGGA
 661 AGCCAGGCCG GTCAAAAACG GTTGCAGGGG TATTGATGAT AAACACTGGA ACTCTCAGTG
 721 CAAAACATCC CAAACCTACG TCCGAGCACT GACTTCAGAG AACAATAAAC TCGTGGGCTG
 781 GCGGTGGATA CGGATAGACA CGTCCTGTGT GTGTGCCTTG TCGAGAAAAA TCGGAAGAAC
 841 ATGAattggc atctctcccc atatataaat tattacttta aattatatga tatgcatgta
 901 gcatataaat gtttatattg tttttatata ttataagttg acctttattt attaaacttc
 961 agcaaccta cagtatataa gcttttttct caataaaatc agtgtgcttg ccttccctca
1021 ggcctctccc atct
```

A nucleic acid encoding a glial-derived neurotropic factor (GDNF) (Genbank NM_000514):

```
201                        ATGAAGTTAT GGGATGTCGT GGCTGTCTGC CTGGTGCTGC

241 TCCACACCGC GTCCGCCTTC CCGCTGCCCG CCGGTAAGAG GCCTCCCGAG GCGCCCGCCG

301 AAGACCGCTC CCTCGGCCGC CGCCGCGCGC CCTTCGCGCT GAGCAGTGAC TCAAATATGC

361 CAGAGGATTA TCCTGATCAG TTCGATGATG TCATGGATTT TATTCAAGCC ACCATTAAAA

421 GACTGAAAAG GTCACCAGAT AAACAAATGG CAGTGCTTCC TAGAAGAGAG CGGAATCGGC

481 AGGCTGCAGC TGCCAACCCA GAGAATTCCA GAGGAAAAGG TCGGAGAGGC CAGAGGGGCA

541 AAAACCGGGG TTGTGTCTTA ACTGCAATAC ATTTAAATGT CACTGACTTG GGTCTGGGCT

601 ATGAAACCAA GGAGGAACTG ATTTTTAGGT ACTGCAGCGG CTCTTGCGAT GCAGCTGAGA

661 CAACGTACGA CAAAATATTG AAAAACTTAT CCAGAAATAG AAGGCTGGTG AGTGACAAAG

721 TAGGGCAGGC ATGTTGCAGA CCCATCGCCT TGATGATGA  CCTGTCGTTT TTAGATGATA

781 ACCTGGTTTA CCATATTCTA AGAAAGCATT CCGCTAAAAG GTGTGGATGT ATCTGA
```

Any of the above sequences could be expressed in an axon of a mammalian cell when operably linked to an IRES sequence. Coding sequences for polypeptides of interest can be at any distance downstream of the IRES sequences. For example, a polypeptide-coding sequence can be within 10 nucleotides, e.g. within 8, 6, 4 or fewer nucleotides, of the 3' end of an IRES. Coding sequences can also be as distant as about 200 to 300 or more nucleotides away from the 3' end of IRES. In general, translation begins at the first start codon, e.g. ATG, GTG, ATT, downstream, i.e. 3', of an IRES.

Viruses of the Invention

The invention provides recombinant RNA viruses and pseudo-viruses that can be used to deliver selected polypeptide-coding sequences into the axons of mammalian neurons for expression of the encoded polypeptides in the axons. Thus, a virus of the invention contains a recombinant RNA molecule of the invention and is capable of transducing the RNA molecule into an axon of a mammalian neuron.

A virus of the invention can be recombinant RNA virus, as well as a pseudo-virus. A pseudovirus or pseudo-viral particle differs from a recombinant RNA virus of the invention in that the genome of the pseudo-virus or viral particle lacks one or more coding sequences required to generate viral particles upon infection of a mammalian host cell.

A virus of the invention can be any single-stranded RNA virus that can infect a mammalian cell, or which can selectively infect neurons or neuronal subtypes, or which may selectively infect axons. For example, a virus of the invention can be an alphavirus, a virus of the group IV Togaviridae family of viruses. Non-limiting examples of alphaviruses include such as a Sindbis virus or a Semliki Forest virus. A virus of the invention can be an attenuated form of an alphavirus that is less cytotoxic to a mammalian cell.

A virus of the invention can be formulated as a pharmaceutical composition for administration to a mammal as discussed below.

Methods of Generating Nucleic Acids and Viruses of the Invention

Recombinant nucleic acid molecules, as well as viruses of the invention can be produced using methods known to those of skill in the art. See, for example, the methods described MOLECULAR CLONING: A LABORATORY MANUAL, Sambrook & Russell eds., Cold Spring Harbor Laboratory Press, Cold Spring Harbor, New York (2001) [hereinafter MOLECULAR CLONING] or CURRENT PROTOCOLS IN MOLECULAR BIOLOGY, eds. Ausubel et al., John Wiley & Sons, Inc. (1994) [hereinafter CURRENT PROTOCOLS]. Briefly, a coding sequence for a selected polypeptide can be cloned into a DNA expression vector, which serves as a template from which the recombinant RNA molecule of the invention can be generated by in vitro transcription. The expression vector includes sequences coding for a viral replicase, a promoter for subgenomic transcription operably-linked to a sequence that encode the selected polypeptide. Alternatively, the RNA molecule can be produced by in vivo transcription from a DNA plasmid or from a DNA sequence that is stably integrated in the genome of a suitable mammalian host cell.

Recombinant RNA viruses or pseudo-viruses can be produced by (1) transfecting a suitable mammalian host cell with a recombinant RNA molecule of the invention or (2) expressing the recombinant RNA molecule of the invention from a DNA expression vector or from a DNA sequence that is stably integrated in the genome of a suitable mammalian host cell. Where the recombinant RNA molecule does not encode one or more viral proteins required for viral packaging and assembly, a helper RNA molecule having sequences that encode viral structural proteins required for viral assembly can be co-transfected. Alternatively, a helper virus can be used to infect the host cell and provide the sequences for expression of viral proteins required for viral packaging and assembly.

Any mammalian host cell can be used for the in vivo packaging of recombinant RNA molecules of the invention. Non-limiting examples include BHK-21 cells and 293 cells. Viruses so prepared can be purified using methods known to those of skill in the art. Methods for the (1) preparation, enzymatic manipulation and analysis of DNA and RNA nucleic acids; (2) construction, screening and analysis of recombinant nucleic acid vectors; and (3) introduction of DNA and RNA into mammalian cells such as electroporation, transfection (e.g. liposome mediated), and transduction are known to those of skill in the art. See MOLECULAR CLONING; see also CURRENT PROTOCOLS. See also Frolov et al., *Proc. Natl. Acad. Sci. USA*, 93:11371-11377 (1996); Pekosz et al., *Proc. Natl. Acad. Sci. USA* 96:8804-8806 (1999) & Wu et al., *Nature* 436: 1020-1024 and accompanying supplemental materials (2005).

An example of a method for the production of nucleic acids and viruses that can be used to express a mammalian protein in the axon of a mammalian neuron is described below. Additional nucleic acids and methods for generating the nucleic acids of the invention are described in U.S. Pat. Nos. 6,451,592; 6,458,560; & 6,465,634, as well as U.S. Patent Application No. 2007/0166820.

Figure 15:
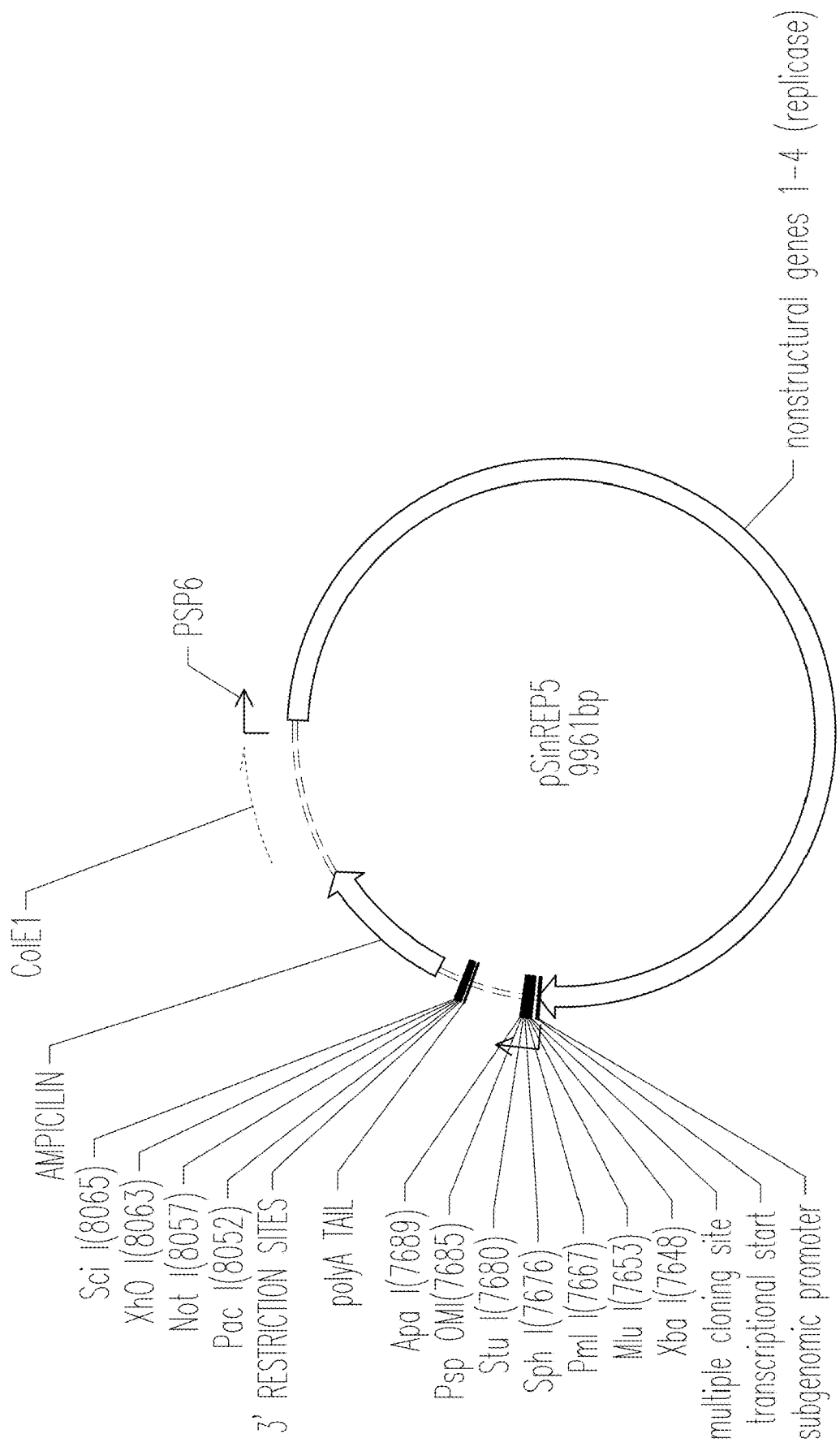
FIG. 15 is a schematic diagram of the structure of pSinRep5. An IRES sequence can be inserted into the pSinRep5 vector at the XbaI & MluI restriction sites to produce pSinRep5-IRES (FIG. 16).
Figure 16:
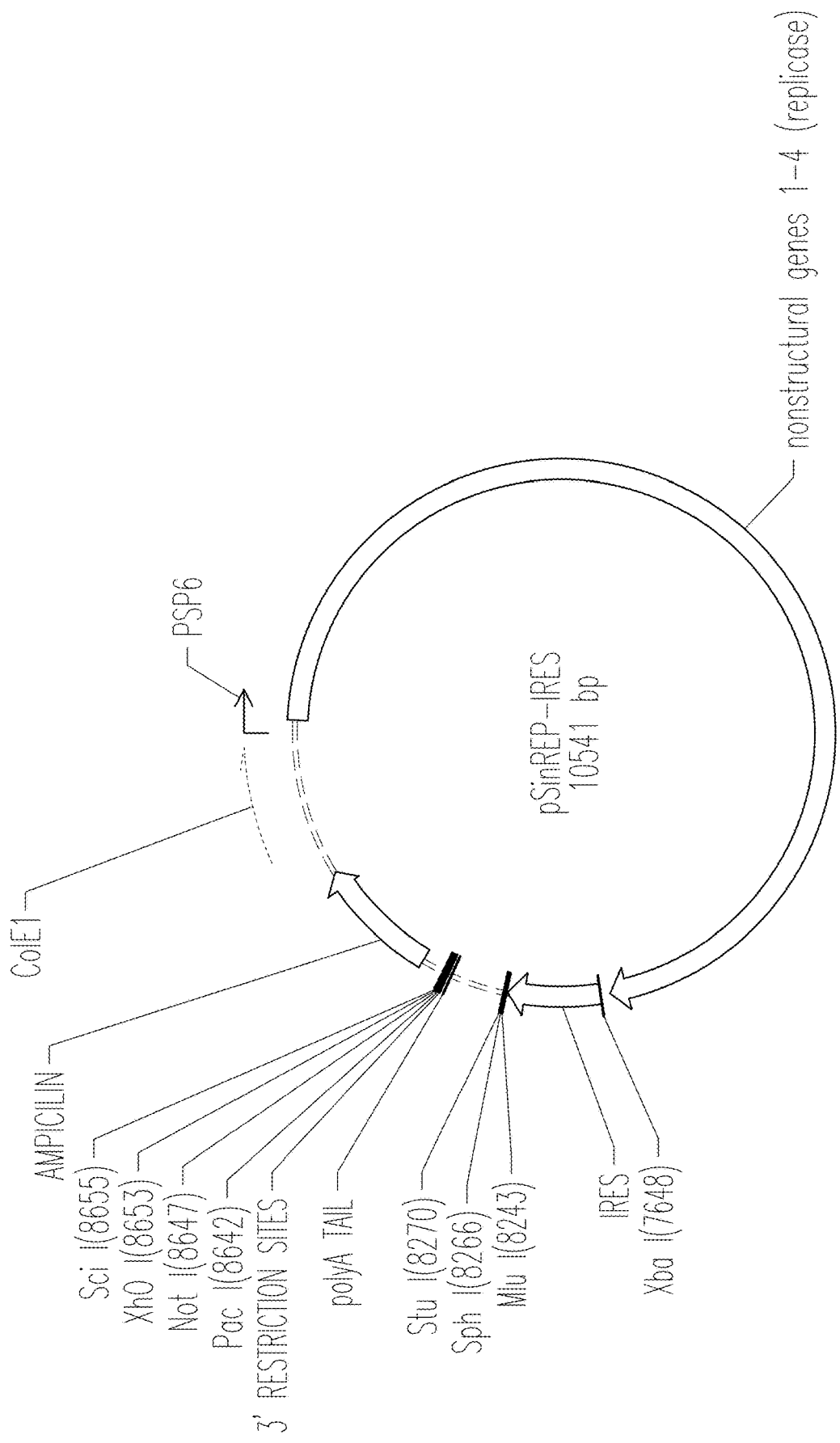
FIG. 16 is a schematic diagram of pSinRep5-IRES.

Sindbis virus is a (+)-strand RNA virus, and can be generated with coat proteins that allow the transduction of an mRNA into cells including neurons. The viral genome contains a subgenomic promoter from which a second mRNA encoding the gene of interest can transcribed. To produce a recombinant RNA molecule from which a select polypeptide can be expressed in the axon of a mammalian neuron, pSinRep5, a DNA expression vector that encodes the genome of an attenuated form of Sindbis virus can be used. A schematic diagram of the structure of pSinRep5 is shown in FIG. 15. An IRES sequence can be inserted into the pSinRep5 vector at the XbaI-MluI restriction site. A schematic diagram of the resulting expression vector is shown in FIG. 16. The full-length sequence of the pSinRep5-IRES is shown below, in which restriction enzyme sites are bolded, IRES is shown in capital letters and the ATG start codon underlined.

```
                                                  (SEQ ID NO: 61)
   1 cgcgtagatc tcacgtgagc atgcaggcct tgggcccaat gatccgacca
  51 gcaaaactcg atgtacttcc gaggaactga tgtgcataat gcatcaggct
 101 ggtacattag atccccgctt accgcgggca atatagcaac actaaaaact
 151 cgatgtactt ccgaggaagc gcagtgcata atgctgcgca gtgttgccac
 201 ataaccacta tattaaccat ttatctagcg gacgccaaaa actcaatgta
 251 tttctgagga agcgtggtgc ataatgccac gcagcgtctg cataactttt
 301 attatttctt ttattaatca acaaaatttt gttttttaaca tttcaaaaaa
 351 aaaaaaaaaa aaaaaaaaaa aaaaaaaaaa agggaattcc tgattaatt
 401 aagcggccgc tcgagcggaa ttaattcttg aagacgaaag ggccaggtgg
 451 cacttttcgg ggaaatgtgc gcggaacccc tatttgttta ttttctaaa
 501 tacattcaaa tatgtatccg ctcatgagac ataacccctg ataaatgctt
 551 caataatatt gaaaaaggaa gagtatgagt attcaacatt tccgtgtcgc
 601 ccttattccc ttttttgcgg cattttgcct tcctgttttt gctcacccag
 651 aaacgctggt gaaagtaaaa gatgctgaag atcagttggg tgcacgagtg
 701 ggttacatcg aactggatct caacagcggt aagatccttg agagttttcg
 751 ccccgaagaa cgttttccaa tgatgagcac ttttaaagtt ctgctatgtg
 801 gcgcggtatt atcccgtgtt gacgccgggc aagagcaact cggtcgccgc
 851 atacactatt ctcagaatga cttggttgag tactcaccag tcacagaaaa
 901 gcatcttacg gatggcatga cagtaagaga attatgcagt gctgccataa
 951 ccatgagtga taacactgcg gccaacttac ttctgacaac gatcggagga
1001 ccgaaggagc taaccgcttt tttgcacaac atggggatc atgtaactcg
1051 ccttgatcgt tgggaaccgg agctgaatga agccatacca aacgacgagc
1101 gtgacaccac gatgcctgta gcaatggcaa caacgttgcg caaactatta
1151 actggcgaac tacttactct agcttcccgg caacaattaa tagactggat
1201 ggaggcggat aaagttgcag gaccacttct gcgctcggcc cttccggctg
1251 gctggtttat tgctgataaa tctggagccg gtgagcgtgg gtctcgcggt
1301 atcattgcag cactggggcc agatggtaag ccctcccgta tcgtagttat
1351 ctacacgacg gggagtcagg caactatgga tgaacgaaat agacagatcg
1401 ctgagatagg tgcctcactg attaagcatt ggtaactgtc agaccaagtt
1451 tactcatata tactttagat tgatttaaaa cttcattttt aatttaaaag
1501 gatctaggtg aagatccttt tgataatct catgaccaaa atcccttaac
1551 gtgagttttc gttccactga gcgtcagacc ccgtagaaaa gatcaaagga
1601 tcttcttgag atccttttt tctgcgcgta atctgctgct tgcaaacaaa
```

-continued

```
1651 aaaaccaccg ctaccagcgg tggttttttt gccggatcaa gagctaccaa
1701 ctcttttttcc gaaggtaact ggcttcagca gagcgcagat accaaatact
1751 gtccttctag tgtagccgta gttaggccac cacttcaaga actctgtagc
1801 accgcctaca tacctcgctc tgctaatcct gttaccagtg gctgctgcca
1851 gtggcgataa gtcgtgtctt accgggttgg actcaagacg atagttaccg
1901 gataaggcgc agcggtcggg ctgaacgggg ggttcgtgca cacagcccag
1951 cttggagcga acgacctaca ccgaactgag atacctacag cgtgagcatt
2001 gagaaagcgc cacgcttccc gaagggagaa aggcggacag gtatccggta
2051 agcggcaggg tcggaacagg agagcgcacg agggagcttc caggggggaaa
2101 cgcctggtat ctttatagtc ctgtcgggtt cgccacctc tgacttgagc
2151 gtcgattttt gtgatgctcg tcagggggggc ggagcctatg gaaaaacgcc
2201 agcaacgcga gctcgtatgg acatattgtc gttagaacgc ggctacaatt
2251 aatacataac cttatgtatc atacacatac gatttagggg acactataga
2301 ttgacggcgt agtacacact attgaatcaa acagccgacc aattgcacta
2351 ccatcacaat ggagaagcca gtagtaaacg tagacgtaga cccccagagt
2401 ccgtttgtcg tgcaactgca aaaaagcttc ccgcaatttg aggtagtagc
2451 acagcaggtc actccaaatg accatgctaa tgccagagca ttttcgcatc
2501 tggccagtaa actaatcgag ctggaggttc ctaccacagc gacgatcttg
2551 gacataggca gcgcaccggc tcgtagaatg ttttccgagc accagtatca
2601 ttgtgtctgc cccatgcgta gtccagaaga cccggaccgc atgatgaaat
2651 acgccagtaa actggcggaa aaagcgtgca agattacaaa caagaacttg
2701 catgagaaga ttaaggatct ccggaccgta cttgatacgc cggatgctga
2751 aacaccatcg ctctgctttc acaacgatgt tacctgcaac atgcgtgccg
2801 aatattccgt catgcaggac gtgtatatca acgctcccgg aactatctat
2851 catcaggcta tgaaaggcgt ggggacccctg tactggattg gcttcgacac
2901 cacccagttc atgttctcgg ctatggcagg ttcgtaccct gcgtacaaca
2951 ccaactgggc cgacgagaaa gtccttgaag cgcgtaacat cggactttgc
3001 agcacaaagc tgagtgaagg taggacagga aaattgtcga taatgaggaa
3051 gaaggagttg aagcccgggt cgcgggttta tttctccgta ggatcgacac
3101 tttatccaga acacagagcc agcttgcaga gctggcatct tccatcggtg
3151 ttccacttga atggaaagca gtcgtacact tgccgctgtg atacagtggt
3201 gagttgcgaa ggctacgtag tgaagaaaat caccatcagt cccgggatca
3251 cgggagaaac cgtgggatac gcggttacac acaatagcga gggcttcttg
3301 ctatgcaaag ttactgacac agtaaaagga gaacgggtat cgttccctgt
3351 gtgcacgtac atcccggcca ccatatgcga tcagatgact ggtataatgg
3401 ccacggatat atcacctgac gatgcacaaa aacttctggt tgggctcaac
3451 cagcgaattg tcattaacgg taggactaac aggaacacca acaccatgca
3501 aaattacctt ctgccgatca tagcacaagg gttcagcaaa tgggctaagg
3551 agcgcaagga tgatcttgat aacgagaaaa tgctgggtac tagagaacgc
3601 aagcttacgt atggctgctt gtgggcgttt cgcactaaga aagtacattc
3651 gttttatcgc ccacctggaa cgcagacctg cgtaaaagtc ccagcctctt
```

-continued

```
3701 ttagcgcttt tcccatgtcg tccgtatgga cgacctcttt gcccatgtcg
3751 ctgaggcaga aattgaaact ggcattgcaa ccaaagaagg aggaaaaact
3801 gctgcaggtc tcggaggaat tagtcatgga ggccaaggct gcttttgagg
3851 atgctcagga ggaagccaga gcggagaagc tccgagaagc acttccacca
3901 ttagtggcag acaaaggcat cgaggcagcc gcagaagttg tctgcgaagt
3951 ggaggggctc caggcggaca tcggagcagc attagttgaa accccgcgcg
4001 gtcacgtaag gataatacct caagcaaatg accgtatgat cggacagtat
4051 atcgttgtct cgccaaactc tgtgctgaag aatgccaaac tcgcaccagc
4101 gcacccgcta gcagatcagg ttaagatcat aacacactcc ggaagatcag
4151 gaaggtacgc ggtcgaacca tacgacgcta agtactgat gccagcagga
4201 ggtgccgtac catggccaga attcctagca ctgagtgaga gcgccacgtt
4251 agtgtacaac gaaagagagt ttgtgaaccg caaactatac cacattgcca
4301 tgcatggccc cgccaagaat acagaagagg agcagtacaa ggttacaaag
4351 gcagagcttg cagaaacaga gtacgtgttt gacgtggaca agaagcgttg
4401 cgttaagaag gaagaagcct caggtctggt cctctcggga gaactgacca
4451 accctcccta tcatgagcta gctctggagg gactgaagac ccgacctgcg
4501 gtcccgtaca aggtcgaaac aataggagtg ataggcacac cggggtcggg
4551 caagtcagct attatcaagt caactgtcac ggcacgagat cttgttacca
4601 gcggaaagaa agaaaattgt cgcgaaattg aggccgacgt gctaagactg
4651 aggggtatgc agattacgtc gaagacagta gattcggtta tgctcaacgg
4701 atgccacaaa gccgtagaag tgctgtacgt tgacgaagcg ttcgcgtgcc
4751 acgcaggagc actacttgcc ttgattgcta tcgtcaggcc ccgcaagaag
4801 gtagtactat gcggagaccc catgcaatgc ggattcttca acatgatgca
4851 actaaaggta catttcaatc accctgaaaa agacatatgc accaagacat
4901 tctacaagta tatctcccgg cgttgcacac agccagttac agctattgta
4951 tcgacactgc attacgatgg aaagatgaaa accacgaacc cgtgcaagaa
5001 gaacattgaa atcgatatta caggggccac aaagccgaag ccagggggata
5051 tcatcctgac atgtttccgc gggtgggtta agcaattgca aatcgactat
5101 cccggacatg aagtaatgac agccgcggcc tcacaagggc taaccagaaa
5151 aggagtgtat gccgtccggc aaaaagtcaa tgaaaaccca ctgtacgcga
5201 tcacatcaga gcatgtgaac gtgttgctca cccgcactga ggacaggcta
5251 gtgtggaaaa ccttgcaggg cgacccatgg attaagcagc ccactaacat
5301 acctaaagga aactttcagg ctactataga ggactgggaa gctgaacaca
5351 agggaataat tgctgcaata aacagcccca ctccccgtgc caatccgttc
5401 agctgcaaga ccaacgtttg ctgggcgaaa gcattggaac cgatactagc
5451 cacggccggt atcgtactta ccggttgcca gtggagcgaa ctgttcccac
5501 agtttgcgga tgacaaacca cattcggcca tttacgcctt agacgtaatt
5551 tgcattaagt ttttcggcat ggacttgaca agcggactgt tttctaaaca
5601 gagcatccca ctaacgtacc atcccgccga ttcagcgagg ccggtagctc
5651 attgggacaa cagcccagga acccgcaagt atgggtacga tcacgccatt
```

```
5701 gccgccgaac tctcccgtag atttccggtg ttccagctag ctgggaaggg 5751 cacacaactt gatttgcaga cggggagaac cagagttatc tctgcacagc 5801 ataacctggt cccggtgaac cgcaatcttc ctcacgcctt agtccccgag 5851 tacaaggaga agcaacccgg cccggtcaaa aaattcttga accagttcaa 5901 acaccactca gtacttgtgg tatcagagga aaaaattgaa gctccccgta 5951 agagaatcga atggatcgcc ccgattggca tagccggtgc agataagaac 6001 tacaacctgg ctttcgggtt tccgccgcag gcacggtacg acctggtgtt 6051 catcaacatt ggaactaaat acagaaacca ccactttcag cagtgcgaag 6101 accatgcggc gaccttaaaa acccttcgc gttcggccct gaattgcctt 6151 aacccaggag gcaccctcgt ggtgaagtcc tatggctacg ccgaccgcaa 6201 cagtgaggac gtagtcaccg ctcttgccag aaagtttgtc agggtgtctg 6251 cagcgagacc agattgtgtc tcaagcaata cagaaatgta cctgattttc 6301 cgacaactag acaacagccg tacacggcaa ttcaccccgc accatctgaa 6351 ttgcgtgatt tcgtccgtgt atgagggtac aagagatgga gttggagccg 6401 cgccgtcata ccgcaccaaa agggagaata ttgctgactg tcaagaggaa 6451 gcagttgtca acgcagccaa tccgctgggt agaccaggcg aaggagtctg 6501 ccgtgccatc tataaacgtt ggccgaccag ttttaccgat tcagccacgg 6551 agacaggcac cgcaagaatg actgtgtgcc taggaaagaa agtgatccac 6601 gcggtcggcc ctgatttccg gaagcaccca gaagcagaag ccttgaaatt 6651 gctacaaaac gcctaccatg cagtggcaga cttagtaaat gaacataaca 6701 traagtctgt cgccattcca ctgctatcta caggcattta ccagccgga 6751 aaagaccgcc ttgaagtatc acttaactgc ttgacaaccg cgctagacag 6801 aactgacgcg gacgtaacca tctattgcct ggataagaag tggaaggaaa 6851 gaatcgacgc ggcactccaa cttaaggagt ctgtaacaga gctgaaggat 6901 gaagatatgg agatcgacga tgagttagta tggattcatc cagacagttg 6951 cttgaaggga agaaagggat tcagtactac aaaaggaaaa ttgtattcgt 7001 acttcgaagg caccaaattc catcaagcag caaaagacat ggcggagata 7051 aaggtcctgt tccctaatga ccaggaaagt aatgaacaac tgtgtgccta 7101 catattgggt gagaccatgg aagcaatccg cgaaaagtgc ccggtcgacc 7151 ataacccgtc gtctagcccg cccaaaacgt tgccgtgcct ttgcatgtat 7201 gccatgacgc cagaaagggt ccacagactt agaagcaata acgtcaaaga 7251 agttacagta tgctcctcca ccccccttcc taagcacaaa attaagaatg 7301 ttcagaaggt tcagtgcacg aaagtagtcc tttttaatcc gcacactccc 7351 gcattcgttc ccgcccgtaa gtacatagaa gtgccagaac agcctaccgc 7401 tcctcctgca caggccgagg aggcccccga agttgtagcg acaccgtcac 7451 catctacagc tgataacacc tcgcttgatg tcacagacat ctcactggat 7501 atggatgaca gtagcgaagg ctcactttt tcgagcttta gcggatcgga 7551 caactctatt actagtatga cagttggtc gtcaggacct agttcactag 7601 agatagtaga ccgaaggcag gtggtggtgg ctgacgttca tgccgtccaa 7651 gagcctgccc ctattccacc gccaaggcta agaagatggg cccgcctggc 7701 agcggcaaga aaagagccca ctccaccggc aagcaatagc tctgagtccc
```

```
7751  tccacctctc ttttggtggg gtatccatgt ccctcggatc aattttcgac
7801  ggagagacgg cccgccaggc agcggtacaa cccctggcaa caggccccac
7851  ggatgtgcct atgtctttcg gatcgttttc cgacggagag attgatgagc
7901  tgagccgcag agtaactgag tccgaacccg tcctgtttgg atcatttgaa
7951  ccgggcgaag tgaactcaat tatatcgtcc cgatcagccg tatcttttcc
8001  actacgcaag cagagacgta gacgcaggag caggaggact gaatactgac
8051  taaccggggt aggtgggtac atattttcga cggacacagg ccctgggcac
8101  ttgcaaaaga agtccgttct gcagaaccag cttacagaac cgaccttgga
8151  gcgcaatgtc ctggaaagaa ttcatgcccc ggtgctcgac acgtcgaaag
8201  aggaacaact caaactcagg taccagatga tgcccaccga agccaacaaa
8251  agtaggtacc agtctcgtaa agtagaaaat cagaaagcca taaccactga
8301  gcgactactg tcaggactac gactgtataa ctctgccaca gatcagccag
8351  aatgctataa gatcacctat ccgaaaccat tgtactccag tagcgtaccg
8401  gcgaactact ccgatccaca gttcgctgta gctgtctgta acaactatct
8451  gcatgagaac tatccgacag tagcatctta tcagattact gacgagtacg
8501  atgcttactt ggatatggta gacgggacag tcgcctgcct ggatactgca
8551  accttctgcc ccgctaagct tagaagttac ccgaaaaaac atgagtatag
8601  agccccgaat atccgcagtg cggttccatc agcgatgcag aacacgctac
8651  aaaatgtgct cattgccgca actaaaagaa attgcaacgt cacgcagatg
8701  cgtgaactgc caacactgga ctcagcgaca ttcaatgtcg aatgctttcg
8751  aaaatatgca tgtaatgacg agtattggga ggagttcgct cggaagccaa
8801  ttaggattac cactgagttt gtcaccgcat atgtagctag actgaaaggc
8851  cctaaggccg ccgcactatt tgcaaagacg tataatttgg tccattgca
8901  agaagtgcct atggatagat tcgtcatgga catgaaaaga gacgtgaaag
8951  ttacaccagg cacgaaacac acagaagaaa gaccgaaagt acaagtgata
9001  caagccgcag aaccccctggc gactgcttac ttatgcggga ttcaccggga
9051  attagtgcgt aggcttacgg ccgtcttgct tccaaacatt cacacgcttt
9101  ttgacatgtc ggcggaggat tttgatgcaa tcatagcaga acacttcaag
9151  caaggcgacc cggtactgga gacggatatc gcatcattcg acaaaagcca
9201  agacgacgct atggcgttaa ccggtctgat gatcttggag gacctgggtg
9251  tggatcaacc actactcgac ttgatcgagt gcgcctttgg agaaatatca
9301  tccacccatc tacctacggg tactcgtttt aaattcgggg cgatgatgaa
9351  atccggaatg ttcctcacac ttttgtcaa cacagttttg aatgtcgtta
9401  tcgccagcag agtactagaa gagcggctta aaacgtccag atgtgcagcg
9451  ttcattggcg acgacaacat catacatgga gtagtatctg acaaagaaat
9501  ggctgagagg tgcgccacct ggctcaacat ggaggttaag atcatcgacg
9551  cagtcatcgg tgagagacca ccttacttct gcggcggatt tatcttgcaa
9601  gattcggtta cttccacagc gtgccgcgtg gcggatcccc tgaaaaggct
9651  gtttaagttg ggtaaaccgc tccagccga cgacgagcaa gacgaagaca
9701  gaagacgcgc tctgctagat gaaacaaagg cgtggtttag agtaggtata
```

```
                         -continued
 9751 acaggcactt tagcagtggc cgtgacgacc cggtatgagg tagacaatat 9801 tacacctgtc ctactggcat tgagaacttt tgcccagagc aaaagagcat 9851 tccaagccat cagaggggaa ataaagcatc tctacggtgg tcctaaatag 9901 tcagcatagt acatttcatc tgactaatac tacaacacca ccacctctag 9951 attccGCCCC TCTCCCTCCC CCCCCCCTAA CGTTACTGGC CGAAGCCGCT

10001 TGGAATAAGG CCGGTGTGCG TTTGTCTATA TGTTATTTTC CACCATATTG

10051 CCGTCTTTTG GCAATGTGAG GGCCCGGAAA CCTGGCCCTG TCTTCTTGAC

10101 GAGCATTCCT AGGGGTCTTT CCCCTCTCGC CAAAGGAATG CAAGGTCTGT

10151 TGAATGTCGT GAAGGAAGCA GTTCCTCTGG AAGCTTCTTG AAGACAAACA

10201 ACGTCTGTAG CGACCCTTTG CAGGCAGCGG AACCCCCCAC CTGGCGACAG

10251 GTGCCTCTGC GGCCAAAAGC CACGTGTATA AGATACACCT GCAAAGGCGG

10301 CACAACCCCA GTGCCACGTT GTGAGTTGGA TAGTTGTGGA AAGAGTCAAA

10351 TGGCTCTCCT CAAGCGTATT CAACAAGGGG CTGAAGGATG CCCAGAAGGT

10401 ACCCCATTGT ATGGGATCTG ATCTGGGGCC TCGGTGCACA TGCTTTACAT

10451 GTGTTTAGTC GAGGTTAAAA AAACGTCTAG GCCCCCCGAA CCACGGGGAC

10501 GTGGTTTTCC TTTGAAAAAC ACGatgataa gcttgccaca a
```

A nucleic acid encoding a selected protein for expression in an axon can be inserted downstream of the IRES sequence, for example, by cloning into the MluI and/or SphI restriction sites shown bolded at nucleotides 10541 & 19 in FIG. 14. Insertion of the sequence encoding the gene of interest can be confirmed by the polymerase chain reaction and sequencing using the following primers: (1) Sindbis forward sequencing primer: 5'-AGCATAGTACATTT-CATCTG-3' (SEQ ID NO: 62); (2) Sindbis reverse sequencing primer: 5'-AAGTACATCGAGTTTTGCTG-3' (SEQ ID NO: 63); (3) Sindbis reverse sequencing primer 2: 5'-ACCTGGCCCTTTCGTCTTCA-3' (SEQ ID NO: 64); and (4) IRES sequencing primer: 5'-AAC-CACGGGGACGTGGTTTTCCTTTGAAA-3' (SEQ ID NO: 65).

The resulting Sindbis vector can be used as an expression vector for RNA production. For example, the DNA expression vector can be linearized by cleavage using a restriction enzyme such as XhoI. A linear form of the DNA expression vector can then be used as a template in an in vitro transcription step to produce a recombinant RNA molecule that has a 5'CAP structure and a polyA (polyadenylyl) tail. The recombinant RNA molecule is in vitro transcribed from the SP6 promoter of the linearized DNA expression vector.

To produce viral particles carrying the above produced recombinant RNA molecule, in vitro transcribed RNA molecules can be transfected into a suitable mammalian host cell using standard electroporation or other standard means of delivery including liposome-mediated. Alternatively, the covalently-closed circular Sindbis vector can be introduced into a host cell from which viral RNA molecules can be transcribed.

If the recombinant RNA molecule encoded by the DNA expression vector does not encode viral structural genes required for packaging and assembly, e.g. genes that encode the capsid or the glycoproteins E1, E2, D3 and 6K, a helper expression plasmid having genes that encode these proteins can be co-transfected or introduced into the host cell for viral production. An example of a suitable host cell is BHK-1.

BHK-1 cells that have been transfected with the RNA molecule and/or helper plasmid release Sindbis viruses or pseudo-viruses into the cell culture medium. The virus-containing cell culture medium can be used directly, i.e. applied to neurons, or viruses can be harvested and purified using methods known in the art such as, for example, centrifugation in a sucrose step gradient, prior to use.

Methods of the Invention

The invention provides a method of expressing a polypeptide in the axon of a mammalian neuron. The method involves contacting the axon with a virus of the invention under conditions effective for the transduction of the recombinant RNA molecule in the virus into the axon. As discussed herein the recombinant RNA molecule includes a mammalian translation initiation element and a coding sequence for a select polypeptide.

Any polypeptide that can be translated from an RNA transcript can be expressed using a method of the invention. The polypeptide can be one that when expressed in the axon, modulates the growth or function of the axon. As used herein, the term "modulate" means to alter or affect in any amount and includes augmenting or attenuating the growth, regeneration or function of the axon. Non-limiting examples of a polypeptide that can be expressed using a method of the invention include a kinase, a transcription factor, a C3-ADP-ribosyltransferase, a dominant-negative RhoA mutant polypeptide, a cAMP-producing enzyme such as a soluble adenylyl cyclase, glutamic acid decarboxylase, human proenkephalin, an inhibitor of a dominant-negative Vps24, an intestinal peptide (VIP), brain-derived neurotrophic factor (BDNF), neurotrophin-3 (NT-3), glial-derived neurotropic factor (GDNF), GAP 43 and CAP23. Alternatively, the polypeptide to be expressed using a method of the invention can be one that generates a readily detectable signal and therefore function as a reporter for gene expression. Non-limiting examples include green fluorescent protein or Cherry.

Thus, a method of the invention can be used to express a polypeptide such as C3-ADP-ribosyltransferase, an inhibitor of the GTPase RhoA, or a dominant-negative RhoA kinase such as I1009A, both of which would promote axon regeneration and recovery in cases of nerve damage such as in spinal cord injury, laceration or diabetic neuropathy. Similarly, since cyclic AMP can induce axon regeneration, expression of a soluble adenylyl cyclase in the axon of a neuron using a method of the invention can also lead to axon sprouting and regeneration. Expression of glutamic acid decarboxylase (CAD), an enzyme that synthesizes the neurotransmitter gamma-aminobutyric acid (GABA), which act at the terminals of sensory neurons, could be used to suppress activity of the neuron and treat chronic pain such as neuropathic or inflammatory pain.

In addition, expression of proteins that could interfere with maturation and/or release of herpes simplex virus from the axons of infected mammalian cells such as a dominant-negative mutant of the ATPase VPs24 can be useful for the treatment of herpes simplex viral infection. A method of the invention can also be used to examine gene expression in the axon of a neuron.

A method of the invention can be used to express a select polypeptide in the axons of neurons in the central or peripheral nervous system. A method of the invention can be used to express a select polypeptide in the axon of a sensory neuron, a motor neuron or an inter-neuron. As such, a method of the invention can be used to modulate the activity of neurons in the central or peripheral nervous system, and can be used to affect the activity of a sensory neuron, a motor neuron or an inter-neuron.

The method of the invention can also be used to treat a condition associated with aberrant activity in the axon of a neuron. Thus, a method of the invention can be used to treat any other disease or disorder where the injured axon can be specifically located. Such conditions included any axonal injuries or axonal degeneration resulting from laceration, spinal cord injury, other trauma, stroke, or diabetes. Non-limiting examples of diseases or disorders that can be treated using a method of the invention include (1) axonal injuries in the central or peripheral nervous systems; (2) neuropathic or inflammatory pain as well as bone pain; and (3) Herpes simplex viral infections.

In axonal injuries of the central or peripheral nervous systems, expression of proteins that promote axonal growth could improve or hasten functional recovery. For example, expression of proteins that block proteolytic enzymes or $Na^+$ and $Ca^{2+}$ channels can prevent damage due to the influx of $Ca^{2+}$ that occurs during inflammation or during axonal degeneration. In addition, damage to axons often occurs as a result of a cascade of events and biological pathways, with one element of the process activating the next. Thus, a single inhibitor of one part of a cascade may thereby block all of the products downstream from it (Arundine et al., *Journal of Neuroscience* 24(37): 8106-8123 (2004)). Intestinal peptide (VIP) is one example of an inhibitor that may be used to treat axonal injuries. VIP increases the breakdown of glycogen by astrocytes, diminishes the inflammatory response, and may promote the differentiation of oligodendrocyte precursors by agonizing prolactin secretion. Another example is nerve growth factor (NGF).

In chronic pain such as neuropathic pain, inflammatory pain (including arthritis) and bone pain associated with cancer, proteins or peptides that act at the nerve terminals of sensory neurons are useful therapeutic candidates. Non-limiting examples include glutamic acid decarboxylase (GAD), an enzyme that synthesizes the neurotransmitter gamma-aminobutyric acid (GABA), which suppresses activity in nerve cells (Hao et al., Annals of Neurology, 57: 914-918, 2005) and human proenkephalin, an endogenous opioid peptide with antihyperalgesic properties (Wilson, et al., PNAS, 96: 3211-3216, 1999).

For treatment of herpes simplex viral infections, a method of the invention can be used to express polypeptides that interfere with the maturation and/or the release of HSV particles from axons. Anterograde transport of herpes simplex virus (HSV) from the neuronal cell body to the axon terminal is crucial for the spread and transmission of the virus. An example of a polypeptide that could be useful for treating herpes simplex viral infections is a dominant-negative version of the ATPase Vps24 as Vps24 is required for herpes simplex viral envelopment (Crump et al., J. Virol. 81:7380-7387, 2007).

The viruses of the invention can be applied directly to neuronal axons at the site of injury. In some embodiments, the application or administration of the viruses of the invention may include surgical exposure of tissue that contains axons of interest or may involve injection of viral particles into an axon-rich region (e.g. stereotactic or fluoroscopic guided injection into the spinal cord). The site of administration can be a specific area, for example, an area that includes injured axons or axons that could benefit from heterologous protein expression, e.g. site of neuronal or axonal injury. The virus could be applied by injection, or in a gel foam or other excipient, for example, directly to the site where the axon is located. Alternatively, if the virus contains a coat protein that binds to axons, the virus could be delivered systemically or it could be delivered in the cerebrospinal fluid, intraperitoneally, or into another body component (e.g. in a cavity formed after injury such as those that occur after stroke). Thus, viruses of the invention can be applied by injection to a selected location, in the spinal cord for example. Viruses of the invention can also be applied topically to an injured area.

The invention also provides a method for introducing nucleic acids into the axon of a mammalian neuron. Selected nucleic acids can be packaged into virus particles as described above. The virus can be applied to a localized site, i.e. by injection or other form of application, to an area or cavity that contains axons or by application to an axon compartment of neurons grown in compartmentalized culturing device, such as Campenot chambers. The virus can also be administered systematically, for example, by intravenous injection or oral administration.

Viruses of the invention for therapeutic use can be formulated as pharmaceutical compositions for administration to a mammal such as a monkey, a rat, a mouse, a horse, a rabbit, and a human.

Pharmaceutical Compositions

The pharmaceutical compositions of the present invention comprise a therapeutically effective amount of the virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the virus, preferably in purified form, together with a suitable amount of carrier so as to provide the form for proper administration to the patient. The formulation should suit the mode of administration.

The compositions may be systemically administered, e.g., orally, in combination with a pharmaceutically acceptable vehicle such as an inert diluent. For oral administration, the virus may be combined with one or more excipients and used in the form of ingestible capsules, elixirs, suspensions, syrups, wafers, and the like. Such compositions should contain at least 0.1% of the virus. The percentage of the compositions and preparations may, of course, be varied and may conveniently be between about 2 to about 60% of the weight of a given unit dosage form. The amount of active compound in such useful compositions is such that an effective dosage level will be obtained.

The compositions may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. Various other materials may be present. For instance, a syrup or elixir may contain the virus, sucrose or fructose as a sweetening agent, methyl and propylparabens as preservatives, a dye and flavoring such as cherry or orange flavor. Of course, any material used in preparing any unit dosage form, including sustained-release preparations or devices, should be pharmaceutically acceptable and substantially non-toxic in the amounts employed.

The composition also be administered by infusion or injection to a localized site. Solutions of the virus can be prepared in water or a suitable buffer, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of undesirable microorganisms.

The pharmaceutical dosage forms suitable for injection or infusion can include sterile aqueous solutions or dispersions or sterile powders comprising the virus which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of undesirable microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the virus in the required amount in the appropriate solvent with various of the other ingredients enumerated above, as required, followed by filter sterilization.

Useful liquid carriers include water, alcohols or glycols or water-alcohol/glycol blends, in which the present viruses can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the viruses of the invention can be determined by comparing their in vitro activity and in vivo activity in animal models.

The administration of the composition may be for either a "prophylactic" or "therapeutic" purpose. When provided prophylactically, the compositions of the invention are provided before any symptom or clinical sign becomes manifest. The prophylactic administration of the composition serves to prevent or attenuate any subsequent symptom. When provided prophylactically, the viral compositions of the invention, are provided before any symptom or clinical sign of a disease becomes manifest. The prophylactic administration of the composition serves to prevent or attenuate one or more symptoms or clinical signs associated with the disease.

When provided therapeutically, the composition is provided upon the detection of a symptom or clinical sign of an injury or condition. The therapeutic administration of the viruses serves to attenuate further axonal degeneration or aberrant function. When provided therapeutically, a viral composition is provided upon the detection of a symptom or clinical sign of the condition or injury. The therapeutic administration of the compound(s) serves to attenuate a symptom or clinical sign of that condition or injury. Thus, a viral composition of the present invention may be provided either before the onset of the condition or injury (so as to prevent or attenuate an anticipated condition or injury) or after the onset of the condition or injury.

A composition is said to be "pharmacologically acceptable" if its administration can be tolerated by a recipient mammal. Viruses of the invention are administered in a "therapeutically effective amount" if the amount administered is physiologically significant. The amount is physiologically significant if it results in a detectable change in the physiology of a recipient patient, e.g., a decrease in aberrant axon function, an increase in axon growth or regeneration, or a decrease in axon degeneration. Thus, an "effective amount" is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

A composition of the invention can include one or more than one viruses of the invention and may be administered by any means that allow delivery of the viruses to the site of a neuronal axon. A composition of the invention can be administered as a single treatment, or multiple treatments, for instance, over a period up to and including between one week and about 24 months, or any range or value therein.

The invention will be further described in the following examples, which do not limit the scope of the invention described in the claims.

EXAMPLES

Example 1—Intra-axonal Translation and Retrograde Trafficking of CREB Promotes Neuronal Survival The studies describe herein show that new growth factor (NGF) triggers axonal protein synthesis, which is required for NGF-mediated retrograde survival. A cDNA library prepared from the axons of developing sensory neurons reveals that CREB mRNA is an axonally-localized transcript. Results indicate that CREB is selectively translated in axons in response to NGF and retrogradely trafficked to the cell body. Furthermore, selective knockdown of axonal CREB mRNA reveals that axonally-synthesized CREB is required for NGF at axons to promote the accumulation of pCREB in the nucleus, transcription of a CRE-containing reporter gene, and neuronal survival. These data identify a role for axonally-synthesized CREB and identify a signaling mechanism involving intra-axonal translation and retrograde trafficking of transcription factors that may have critical roles in signaling from axons to the nucleus.

Materials & Methods

Primary Cell Culture

E15 rat or E13 mouse embryonic dorsal root ganglion (DRG) explants were plated on glass-bottom culture dishes (MatTek) or glass coverslips pre-coated with 33 µg/ml poly-D-lysine and 1 µg/ml laminin. $CREB^{\alpha/\Delta-/+}$ animals used to generate $CREB^{\alpha/\Delta-/-}$ embryos were from Jackson Labs. E15 dissociated DRG neurons were prepared as described by Wu et al., Nature 436, 1020-1024 (2005). DRGs were cultured in B27/Neurobasal medium (Invitrogen) supplemented with 100 ng/ml nerve growth factor (NGF) and 20µM 5'-fluorodeoxyuridine (5-FdU) for 3 days. siRNA-mediated knockdown in DRG neurons has been described previously by Higuchi et al., *Biochemical & Biophysical Research Communications* 301, 804-809 (2003) and was performed using siRNAs listed in Table S3. For measurements of CREB levels in isolated axons, axons were severed from cell bodies by removing the explant with a flame-sharpened Pasteur pipette (Wu et al., Nature 436, 1020-1024 (2005)). Modified Boyden chambers were based on the procedure of Twiss (Zheng et al., *Journal of Neuroscience* 21, 9291-9303 (2001)) and modified to obtain distal axons as described by Wu et al., Nature 436, 1020-1024 (2005). mRNA from harvested axons (Wu et al., Nature 436, 1020-1024 (2005)) was used to prepare a cDNA library using a modified, unbiased single cell protocol as described below. See also Tietjen et al., Neuron 38, 161-175 (2003). Compartmented (Campenot) cultures were prepared as described below. See also Campenot, *Proc Natl Acad Sci USA* 74, 4516-4519 (1977)).

TABLE S3

| SiRNA | Target mRNA | Sense strand sequence | Source |
|---|---|---|---|
| siControl | Non-targeting | UAGCGACUAA ACACAUCAAUU (SEQ ID NO: 1) | Dharmacon |
| $siCREB_{67}$ | CREB1 | GGUUCGUCUAA UGAAGAACUU (SEQ ID NO: 2) | Ambion |
| $siCREB_{85}$ | | GGAGUCUGUGG AUAGUGUAUU (SEQ ID NO: 3) | Ambion | cDNA Library Amplification

Figure 3A:
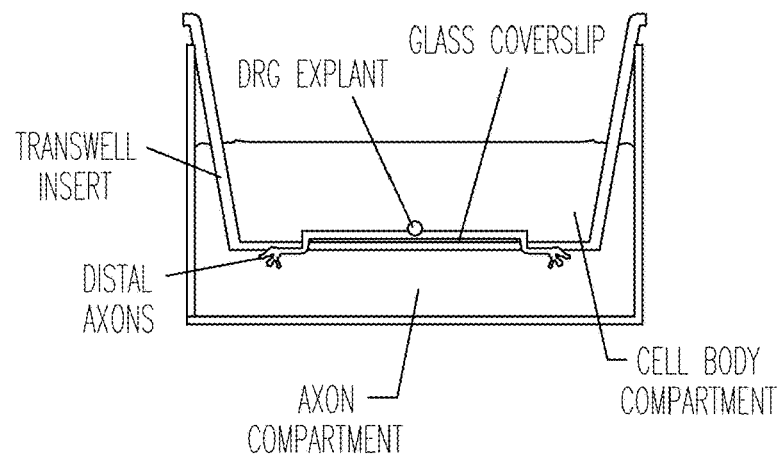
FIGS. 3A-F are results showing that CREB mRNA and protein are localized to developing axons of DRG neurons. (A) Schematic diagram of Boyden chamber. DRGs were cultured in the centre of a glass coverslip placed on top of the microporous membrane. Axons grow across the coverslip and cross through the membrane by DIV4, when they are subjected to experimental conditions and mechanically harvested for analysis. (B) Fluorescent in situ hybridization (FISH) using riboprobes demonstrated the presence of CREB, but not cJun or STAT1 mRNA transcripts in axons. Insets show labeling in cell bodies of dissociated DRG neuron cultures at 10× magnification to demonstrate efficacy of riboprobes. Counterstained images show immunofluorescence using anti-GAP-43 antibody (Red). Scale bar, 10 µm. (C) Quantification of FISH data in (B). CREB levels were monitored with two separate probes (Table S1), and CREB levels were comparable to those of β-actin. Background FISH levels were defined as the average signal obtained using a scrambled β-actin riboprobe and subtracted from all other data. *$p<0.001$. Numbers on bars represent n axons per condition. (D) DRG neurons transfected with non-targeting siRNA demonstrated CREB mRNA FISH signals in axons, while neurons transfected with CREB-specific siRNA demonstrated a near-complete abolishment of CREB mRNA FISH signal. Scale bar, 10 µm. (E) Quantification of data in (D). *$p<0.001$. Numbers on bars represent n axons per condition. (F) CREB was detected in axonal lysates by RT-PCR using two separate primer pairs (Table S2). RT-PCR fidelity was assayed by concurrent RT-PCR from DRG cell body lysates.

Axons were mechanically harvested, deposited directly into ice-cold PBS, and centrifuged at 2000 g for 2 min. The pellet containing purified axons was resuspended in 20 µl Lysis-RT buffer (1×MMLV buffer, 0.5% NP-40, 100 µM dNTPs, 0.1 mg/ml oligo $d(T)_{25}$) and incubated at 65° C. for one minute to lyse axon tissue. 100 U MMLV and 1 U AMV reverse transcriptases (Invitrogen) were added to the mixture and incubated at 37° C. for 15 min for first-strand cDNA synthesis. Reverse transcriptases were inactivated by incubation of the reaction mix at 65° C. for 10 min and then placed on ice. 20 µl PolyA solution (1× TdT buffer, 4 mM $CoCl_2$, 400 µM DTT, 200 µM dATP, 20 U TdT (Invitrogen)) was added and the solution incubated at 37° C. for 15 min for addition of an exogenous 3' poly(A) tail to the first-strand cDNA. TdT was then inactivated by incubation of the reaction at 65° C. for 10 min, and the solution placed on ice. 8 µl of the RT/Poly(A) reaction was added to PCR Mix #1 (1× Amplitaq buffer II, 1×BSA, 2.5 mM $MgCl_2$, 0.05% Triton X-100, 100 µM dNTPs, 1 µM RTLib1 primer (Table S2), 5 U Amplitaq (Roche)), and PCR was performed using the following conditions: 95° C. for 2 min, followed by 25 cycles of [95° C., 1 min: 42° C., 2 min: 72° C. 6 min+10 sec per cycle]. An additional 5 U Amplitaq were added to the reaction and PCR was performed according to the following conditions: 95° C. for 2 min, followed by 25 cycles of [95° C., 1 min: 42° C., 2 min: 72° C. 6 min]. 2.25 µl of the reaction was then added to PCR Mix #2 (1× Amplitaq buffer II, 2.5 mM $MgCl_2$, 20 µM dNTPs, 5 µM RTLib2 primer (Table S2), 5 U Amplitaq) and PCR performed as follows: 95° C. for 2 min, followed by 30 cycles of [94° C., 90 sec: 42° C., 2 min: 72° C., 3 min]. Efficacy of the library was assessed by PCR using oligonucleotide primers against known axon-localized transcripts β-actin and RhoA (FIG. 3D) (Wu et al., Nature 436, 1020-1024 (2005)). Contamination by neuronal cell bodies was assessed by PCR for soma-restricted mRNAs γ-actin and histone H1f0, and contamination by glia was assessed by PCR for glial transcript GFAP.

TABLE S2

| Primer ID | Target mRNA (gene) | Sequence (5' - 3') |
|---|---|---|
| ActinFor | β-Actin | CCATTGAACACGGCATTGTCACCA (SEQ ID NO: 4) |
| ActinRev | | AGGGCAACATAGCACAGCTTCTCT (SEQ ID NO: 5) |

TABLE S2-continued

Oligonucleotide Primers

| Primer ID | Target mRNA (gene) | Sequence (5' - 3') |
|---|---|---|
| ATF2For | ATF2 | ACAAACCATGCCCGTTGCTATTCC (SEQ ID NO: 6) |
| ATF2Rev | | GCTGTTTCAGCTGTGCCACTTCAT (SEQ ID NO: 7) |
| CREBFor | CREB1 | TGCCACATTAGCCCAGGTATCCAT (SEQ ID NO: 8) |
| CREBRev | | TGTACATCACCAGAGGCAGCTTGA (SEQ ID NO: 9) |
| CREBFor2 | | TGCCACATTAGCCCAGGTATCCAT (SEQ ID NO: 10) |
| CREBRev2 | | TGTTAGCCAGCTGTATTGCTCCTC (SEQ ID NO: 11) |
| cJunFor | cJun | TACACAAGATGGACTGGGTTGCGA (SEQ ID NO: 12) |
| cJunRev | | ACACTGGGTAGGACACCCAAACAA (SEQ ID NO: 13) |
| Elk1For | Elk1 | TCTGCTGCAGCTTCTGAGAGAACA (SEQ ID NO: 14) |
| Elk1Rev | | CGCATGTATTCATTCCGGCTGCTT (SEQ ID NO: 15) |
| STAT1For | STAT1 | AGCTTTGAAACCCAGTTGTGCCAG (SEQ ID NO: 16) |
| STAT1Rev | | TCTTCGTGTAGGGCTCAACAGCAT (SEQ ID NO: 17) |
| RTLib1 | Poly(A) + Library tag | ATTGGATCCAGGCCGCTCTGGACAAA ATATGAATTC(T)24 (SEQ ID NO: 18) |
| RTLib2 | | ATTGGATCCAGGCCGCTCTGGACAAA ATATGAATTC (SEQ ID NO: 19) |

Primary Neuronal Cultures and Compartmented Chambers

Figure 1B:
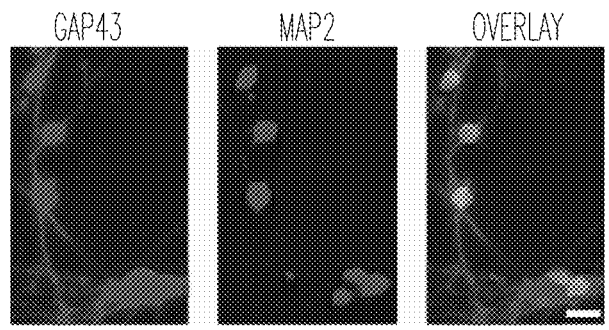

DRG neurons contained only axons and no prominent dendritic processes, as processes were prominently labeled with anti-GAP43 antibodies and did not exhibit MAP2 immunoreactivity (FIG. 1B). DRG cultures were devoid of glial contamination as determined by immunofluorescence using Schwann cell marker GalC (FIG. 1A).

Boyden Chambers were modified for axon harvest as follows: a 12 mm coverslip was placed in the centre of a 24 mm Transwell Polyester (0.3 µm pore) Chamber (Corning), and both were coated in the chamber with poly-D-lysine and laminin, as above. Six E15 DRG explants were plated on the coverslip with the aid of a cloning cylinder placed on each coverslip. At DIV5, axons from 6 separate chambers were harvested from the underside of the membrane and pooled for reverse transcription and cDNA amplification (Tietjen et al., Neuron 38, 161-175 (2003)) (see below for details), or for Western blot analysis. Protein levels were determined by the fluorescent o-phthaldialdehyde assay. Primers for detecting specific transcripts are listed in Table S2.

Campenot chambers were modified for FISH and Immunofluorescence analysis as follows: Teflon dividers were applied to poly-D-lysine, laminin and collagen (1 mg/ml)-coated Lab-Tek chambers (NUNC). The low autofluorescence of the Permanox® plastic in these chambers allows us to perform fluorescence analyses on these cultures much more readily than is possible using traditional cell culture plasticware. E15 dissociated DRG neurons were plated in the cell body compartment in media containing 100 ng/ml NGF and 20 µM 5'-fluorodeoxyuridine to inhibit glial growth. Media was changed every 2 DIV and NGF concentration in the cell body compartment was halved at each media change. At DIV 5, when axons had crossed the divide into the axonal compartment, NGF was withdrawn from the cell body compartment and experimental media containing NGF (0 ng/ml or 30 ng/ml) and/or drug treatments/siRNA transfection reagents was applied to the axon compartment for a further 2 DIV. All media were completely replaced every subsequent 12 hours to ensure purity of the conditions in the respective compartments. Neurons that projected axons across the divide into the axon compartment were retrogradely labeled by addition of Alexa555-conjugated wheat germ agglutinin (WGA) (2 µg/ml, Molecular Probes) to the axon compartment 1 hour before the end of the experiment. Fluidic isolation and the absence of contamination of the chambers were assessed by a number of strict criteria, failure to meet any of which resulted in the culture being discarded from analysis.

Compartments were regularly checked for water-tightness during the frequent media changes. Bulk leakage between compartments is readily visible and excludes cultures from further study. Phenol red was selectively added to compartments, and media from opposing compartments were checked for phenol red exclusion by measuring absorption at 560 nm following subsequent media changes. Detectable presence of phenol red in untreated compartments excluded the culture from analysis.

Batches of compartments were regularly screened by immunofluorescence for Schwann cell marker GalC (FIG. 1A). Our culture media are optimized to prevent glial growth (Wu et al., Nature 436, 1020-1024 (2005)), and the presence of any Schwann cells in screened cultures resulted in discarding the entire batch.

Cultures were routinely counter-stained with DAPI during immunofluorescence and TUNEL assays. The presence of a single DAPI-stained nucleus in the axon compartment or within the divider area was sufficient to reject the culture from analysis.

Axons crossing into the axon compartment were retrogradely labeled with WGA-Alexa555, as above. Cultures were checked to ensure that background Alexa555 staining of the substratum was contained in the axon compartment, with no diffusion across the divider. Presence of background Alexa555 staining outside of the discrete border of the axon compartment excluded the culture from analysis.

Axons crossing the divider were analyzed: as in FIG. 1B, axons fasciculate to form single, discrete bundles that cross the divider. Axon populations that fail to fasciculate into a single pathway for >300 µm were rejected from analysis, due to inference of an incomplete barrier between the compartments.

Figure 1C:
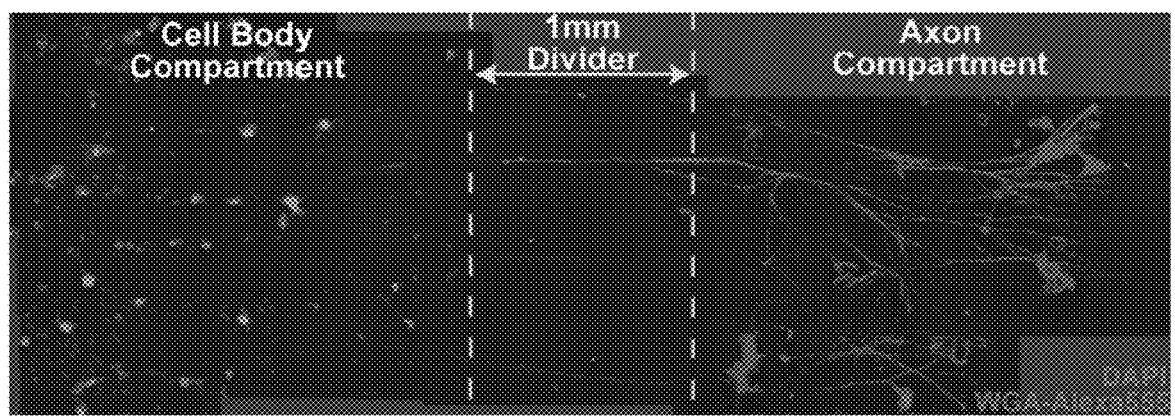
Figure 1D:
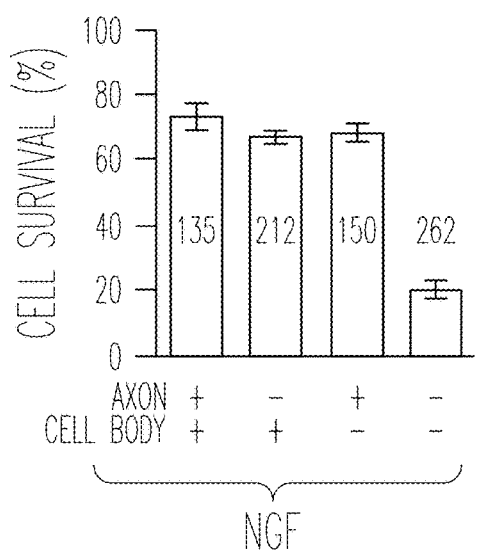

Only WGA-Alexa555-labeled cell bodies are included in the data set. For cell body immunofluorescence measurements, regions of interest (ROI) are defined by the perimeter outline of each WGA-positive cell body. ROIs were transposed to respective immunofluorescence micrographs for analysis of cell body fluorescence levels. FIG. 1C, 10C demonstrate that some cell bodies in the cell body compartment are not WGA-labeled (i.e. fail to extend axons across the divider), and are thus not relevant to the data set. These cells are therefore not used to generate ROIs for fluorescence analysis.

Cultures were fixed at 7 DIV using 4% formaldehyde for 20 min at 25° C., followed by TUNEL assay staining, as per manufacturer's protocol (ApoAlert, Clontech) or in situ hybridization or immunofluorescence, as described below.

In Situ Hybridization

Sense oligonucleotides (Table S1) were synthesized with a T7 promoter site at their 3' end. Antisense riboprobes were in vitro transcribed from the sense oligonucleotides using the MEGAscript T7 transcription kit (Ambion) with digoxigenin-conjugated UTP. DRGs (DIV3) were fixed overnight at 4° C. in 4% paraformaldehyde in cytoskeleton buffer (CSB: 10 mM MES pH 6.1, 138 mM KCl, 3 mM MgCl2, 2 mM EGTA, 0.4 M sucrose). Washes were performed in TBST (20 mM Tris pH 8.0, 150 mM NaCl, 0.1% Triton X-100) for 3×5 min. DRGs were permeabilized in 0.5% Triton X-100/TBS for 10 min and post-fixed in 4% PFA/TBS for 5 min, followed by fresh acetylation buffer (0.25% acetic anhydride, 0.1 M HEPES) for 10 min, and equilibration with 4×SSC/50% formamide for 30 min. Cultures were incubated with 15 ng riboprobes (Table S1) in 15 µl hybridization buffer (10% dextran sulfate, 4×SSC, 1×Denhardt's Solution, 40% formamide, 20 mM ribonucleoside vanadyl complex, 10 mM DTT, 1 mg/ml yeast tRNA, and 1 mg/ml salmon sperm DNA) at 37° C. overnight. The coverslips were washed with 40% formamide/1×SSC at 37° C. for 20 min, and three times each with 1×SSC and 0.1×SSC at RT for 5 min. Neurons were blocked with blocking buffer (100 mM Tris-HCl pH 8.0, 150 mM NaCl, 8% formamide, 5% BSA, 2.5% normal horse serum, and 2.5% normal goat serum) for 30 min. Hybridization was detected with anti-digoxin antibody (Table S4), which was precleared with rat embryo power in blocking buffer for 2 h at 25° C. Mean fluorescence intensity elicited by the scrambled probe was subsequently deducted from all FISH data to produce specific labeling intensity for each probe.

Quantification of CREB Protein Levels

Images and measurements of signals in axons were taken from the terminal 50 µm of the axon, except where indicated. Analyzed axons were a minimum of 2000 µm for all experiments. DRGs were fixed with 4% PFA in CBS overnight at 4° C., permeabilized with 0.5% Triton X-100/TBS, and blocked in 4% BSA/TBS for 1 hour. DRGs were labeled with antibodies (Table S4) in 2% BSA/0.1% Triton X-100/TBS overnight at 4° C. For image acquisition details, see below.

TABLE S4

Primary Antibodies

| Antibody | Target Protein | Dilution (IF/FISH) | Dilution (Western blot) | Source |
| --- | --- | --- | --- | --- |
| CST-9452 | 4E-BP1 | 1:250 | — | Cell Signaling |
| sc-12884 | p-4E-BP1 | 1:200 | — | Santa Cruz |
| CST-9192 | CREB1 | 1:250 | 1:1000 | Cell Signaling |
| sc-186 | CREB1 | 1:250 | 1:250 | Santa Cruz |
| CST-9191 | $^{S133}$pCREB1 | 1:250 | 1:1000 | Cell Signaling |
| sc-7978 | $^{S133}$pCREB1 | 1:250 | 1:250 | Santa Cruz |
| 1333062 | Digoxigenin | 1:500 | — | Roche |
| sc-16564 | pErk5 | 1:100 | — | Santa Cruz |
| CST-2212 | Ribosomal S6 | 1:500 | — | Cell Signaling |
| AB5819 | Staufen | 1:500 | — | Chemicon |
| ab14734 | VDAC/Porin-1 | 1:2000 | — | AbCam |
| sc-12885 | phospho-eIF4E | 1:250 | — | Santa Cruz |
| MAB3420 | Tau | 1:500 | 1:1000 | Chemicon |
| AB5220 | GAP43 | 1:2000 | — | Chemicon |
| MAB378 | MAP2 | 1:500 | — | Chemicon |

TABLE S1

In Situ Riboprobe Template Oligonucleotides

| Oligo. ID | Target mRNA | Target Sequence (5' - 3') |
| --- | --- | --- |
| Scrambled | Non-targeting | TGTACGTCTCGCCTTGCAACTCGTAC TGTGAGGTAGTCGCGCGACAGTGC (SEQ ID NO: 20) |
| HistoneH1FISH | Histone H1f0 | GTACCTGACGGCCGAAATCCTGGAG CTTGCGGCTAATGCGGCGAGGGACA (SEQ ID NO: 21) |
| CREBFISH | CREB1 | CTCAGCCGGGTACTACCATTCTACAA TATGCACAGACCACTGATGGACAG (SEQ ID NO: 22) |
| CREBFISH2 | | CGGCCCAGCCATCAGTTATTCAGTCT CCACAAGTCCAAACAGTTCAGTCT (SEQ ID NO: 23) |
| CREBSense | CREB1 | CTGTCCATCAGTGGTCTGTGCATATT GTAGAATGGTAGTACCCGGCTGAG (SEQ ID NO: 24) |
| CREB2Sense | (Sense strand) | AGACTGAACTGTTTGGACTTGTGGA GACTGAATAACTGATGGCTGGGCCG (SEQ ID NO: 25) |
| cJunFISH | cJun | GACTGTAGATTGCTTCTCTAGTGCTC CGTAAGAACACAAAGCAGGGAGGG (SEQ ID NO: 26) |
| STAT1FISH | STAT1 | CCCTAATGCTGGCCCTGATGGTCTTA TTCCATGGACAAGGTTCTGTAAGG (SEQ ID NO: 27) |
| ActinFISH | β-Actin | GTATGCCTCTGGTCGTACCACTGGCA TTGTGATGGACTCCGGAGACGGG (SEQ ID NO: 28) |

TABLE S4-continued

Primary Antibodies

| Antibody | Target Protein | Dilution (IF/FISH) | Dilution (Western blot) | Source |
| --- | --- | --- | --- | --- |
| sc-118 | TrkA | 1:250 | — | Santa Cruz |
| CST-9141 | pTrkA | 1:250 | — | Cell Signaling |
| G745A | Luciferase | 1:50 | 1:1000 | Promega |

Image Acquisition and Data Handling

Optimal exposure times for both mRNAs (in situ hybridization) and immunofluorescence (IF), were determined empirically for each riboprobe/antibody and kept constant and below grey scale saturation. Cell body FISH, TUNEL and IF signals were obtained using a 20× objective, while axonal FISH and IF signals were acquired using a 60× objective. Image acquisition was kept within the linear range of the camera by maintaining maximum fluorescence signals below 50% saturation of the photodetector CCD chip. Immunofluorescence and FISH images were taken with a Nikon Eclipse TE2000-U inverted microscope with a Cool-Snap HQ CCD camera. Image stacks were deconvoluted using AutoDeblur v9.3 (AutoQuant). The volumes of individual axons were calculated from GAP43 or WGA counterstains using Metamorph v6.2r1 following 3D deconvolution with AutoDeblur v9.3. Specific fluorescence signals from axons were then normalised to the calculated axon volume and are presented as normalised fluorescence intensities per pixel. Within each experiment, exposure times were kept constant throughout and all data were analysed and images processed using Metamorph v6.2r1 software (Universal Imaging). Dendra fluorescence levels were acquired using an Inverted Olympus IX-70 DeltaVision Image Restoration microscope with a 40× objective and acquired by a CoolSnap QE camera (Photometrics). Photoactivation of Dendra was achieved by a 50 ms illumination (for selected growth cones) or 1 s illumination (for cell body Dendra accumulation analysis in low density dissociated DRG cultures) with a 408 nm laser light source. For all microscopy experiments, sample identities were blindly encoded prior to image acquisition and analysis. Identities of the experimental samples were then revealed after imaging and data analysis.

All statistical p values in this study were determined using ANOVA from experiments repeated a minimum of three times, unless stated otherwise. All data are presented as mean+/−s.e.m. n values are represented on all graphs and defined in legends, unless stated otherwise.

Generation and Infection of Recombinant Viruses

The vectors used were a modified Sindbis vector, pSinRep5, containing a point mutation in nsP2 (P726S) that reduces cytotoxicity in neurons (Jeromin et al., *Journal of Neurophysiology* 90, 2741-2745 (2003)) and the helper plasmid DH-BB (S. Schlesinger, Washington University, St. Louis) as described by Wu et al., *Nature* 436, 1020-1024 (2005). Reporter experiments utilized the myr-dEGFP system (Aakalu et al, *Neuron* 30, 489-502 (2001)), except that a d1EGFP variant (i.e., an EGFP with a 1 hour half-life) was used, as described by Wu et al., *Nature* 436, 1020-1024 (2005). pSinRep5-myr-dEGFP$_{3'CREB}$ and pSinRep5-myr-dEGFP$_{3'RhoA}$ contained the full-length 3'UTR of the human CREB mRNA or the 3'UTR of human RhoA mRNA, fused to the viral 3'CSE. For Sindbis virus encoding Dendra constructs, the virus contained the open reading frame (ORF) of Dendra and, in the case of pSinRep5-Dendra-CREB, the full ORF of human CREB, followed by a 54 nt minimal axonal targeting element (Kislauskis et al., *Journal of Cell Biology* 127, 441-451 (1994)). In the case of IRES-driven Sindbis virus, the pSinRep constructs contained a human encephalomyocarditis viral IRES element from vector pIRES-hyg (BD Biosciences). Sindbis pseudoviruses were prepared according to the manufacturer's instructions (Invitrogen), purified on a sucrose gradient, concentrated on YM-100 microcin columns, resuspended in Neurobasal medium, and titered using BHK-21 cells. We generated a CRE-luciferase adenovirus reporter by subcloning the complete CRE-Luc reporter gene from vector pCRE-Luc (BD Biosciences) into pAd/PL-DEST (Invitrogen). Virus production and amplification was performed in HEK293A cells, according to manufacturer's instructions. Adenovirus was purified using the ViraKit AdenoMini-4 system (Virapur), and titered using HEK293T cells. DRGs were infected with equal infectious units of recombinant virus at DIV6 and luciferase levels were measured 24 hour later.

Results

Retrograde NGF Signalling at Axon Terminals Requires Protein Synthesis

Figure 2A:
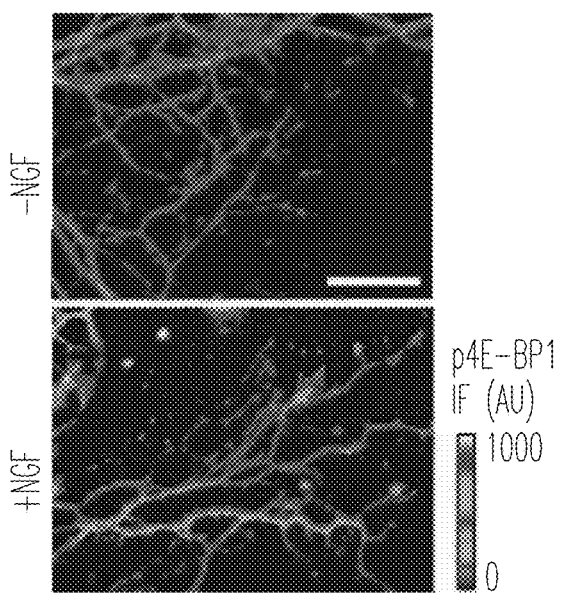
FIGS. 2A-E are results showing that local protein synthesis in axons is required for NGF-dependent survival. (A) Phospho-4E-BP1 levels increase in growth cones in response to NGF treatment. DRG neurons were incubated with NGF-replete or NGF-free media; phospho-4E-BP1 levels in axons were measured by immunofluorescence. Scale bar, 50 µm. (B) Quantification of total and phospho-4EBP1 in (A) $p=0.012$. Numbers on bars represent n axons per condition. (C) Schematic diagram of compartmented (Campenot) chambers. E15 dissociated DRG neurons are cultured in the cell body compartment and axons grow under a thinly applied silicone grease layer that seals the chamber with the Permanox® plastic culture slide. (D) Application of protein synthesis inhibitors to axons blocks NGF-mediated retrograde survival. Dissociated DRG neurons were grown in compartmentalized chambers, and vehicle or NGF was added to the axon compartment. 1 µM cycloheximide (CHX) or 40 µM anisomycin (Aniso) were added to the axon compartment concurrently with NGF media. Cell body compartments were kept NGF-free during the course of the experiment. Cells crossing the divider were retrogradely labeled with WGA-Alexa555 and only WGA-positive cell bodies were counted in the data set. Survival was assessed by TUNEL assay. Examples of non-apoptotic and apoptotic are indicated with closed and open arrows, respectively (Blue=DAPI, Green=TUNEL). Scale bar, 20 µm. (E) Quantification of results from (D). *$p<0.001$. Numbers on bars represent n cells per condition.
Figure 2B:
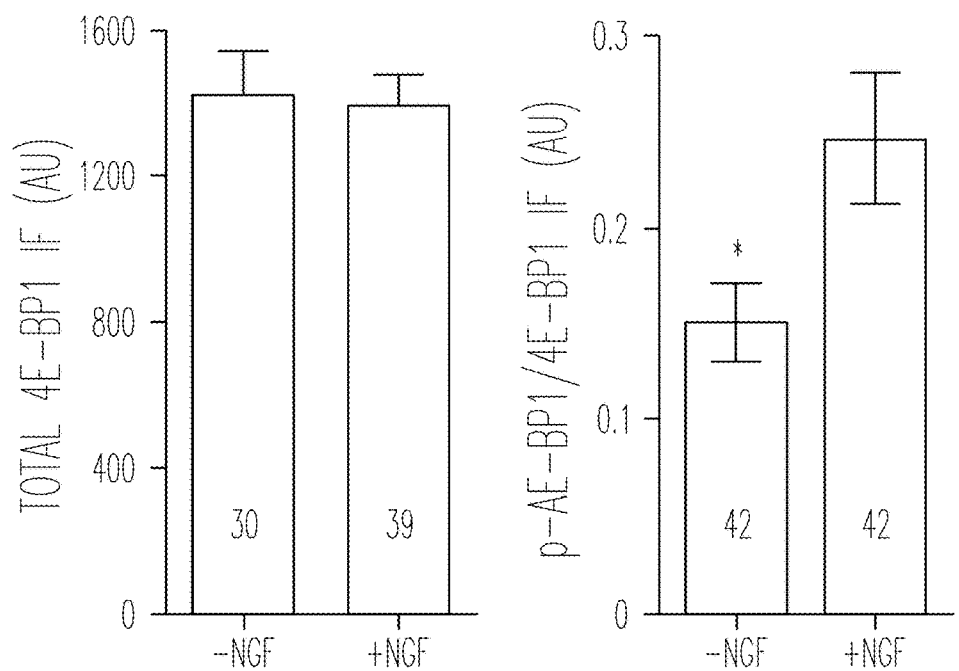
Figure 2C:
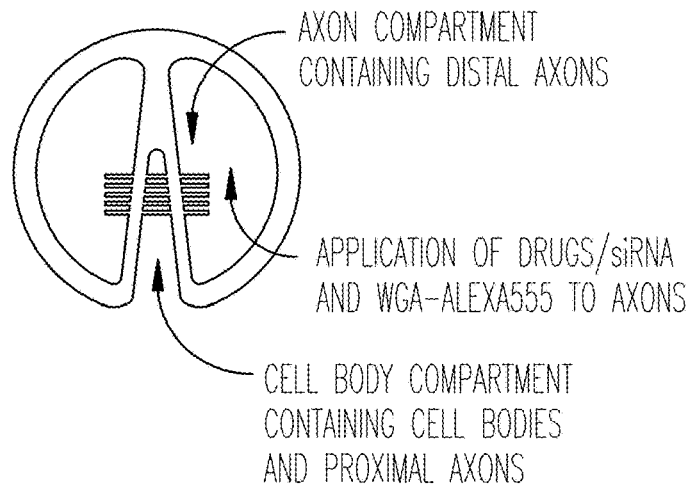

To determine if NGF might regulate local protein synthesis, embryonic day 15 (E15) dorsal root ganglia (DRG) cultures (FIG. 1A, 1B) were transferred to NGF-free media for 2 hour and then stimulated with NGF or vehicle for 1 hour. NGF treatment resulted in increased phosphorylation of 4E-BP1 at S64 and T69 in axons (FIG. 2A, 1B). Multisite phosphorylation of 4E-BP1 is required for mRNA translation (Richter & Sonenberg, *Nature* 433, 477-480 (2005)), indicating that NGF may induce local protein synthesis.

Figure 1E:
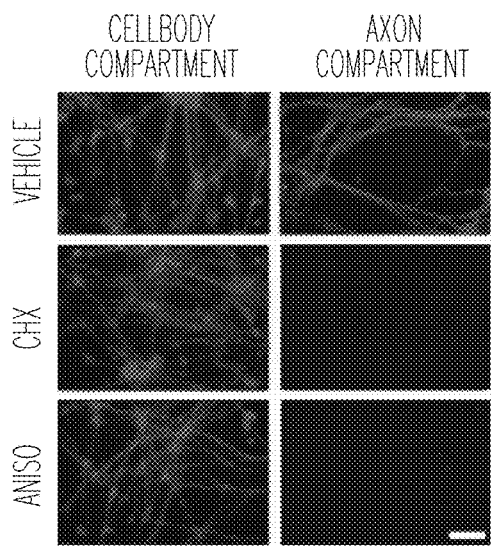
Figure 1F:
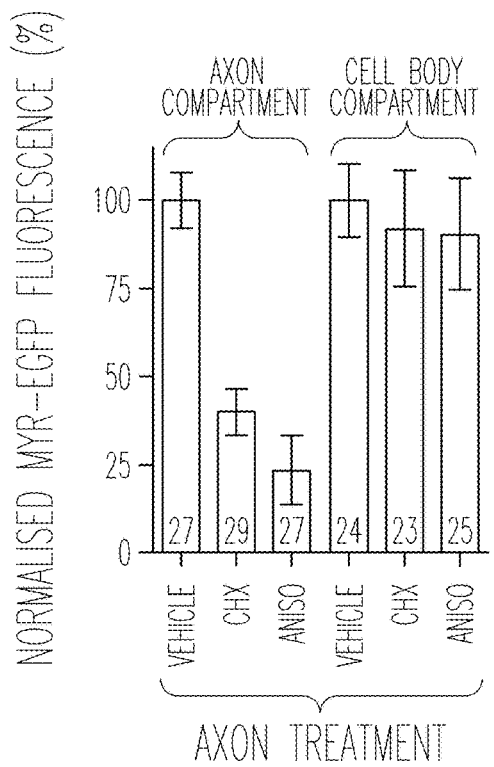
Figure 2D:
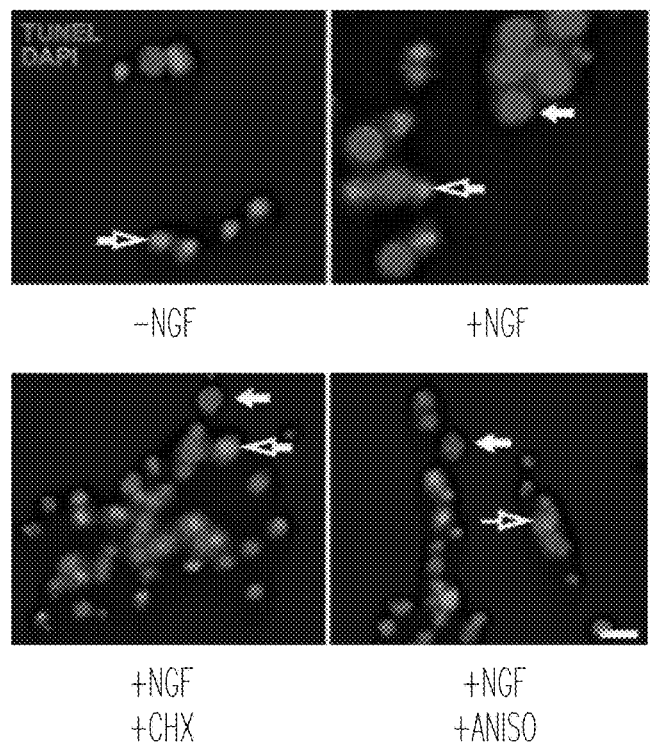
Figure 2E:
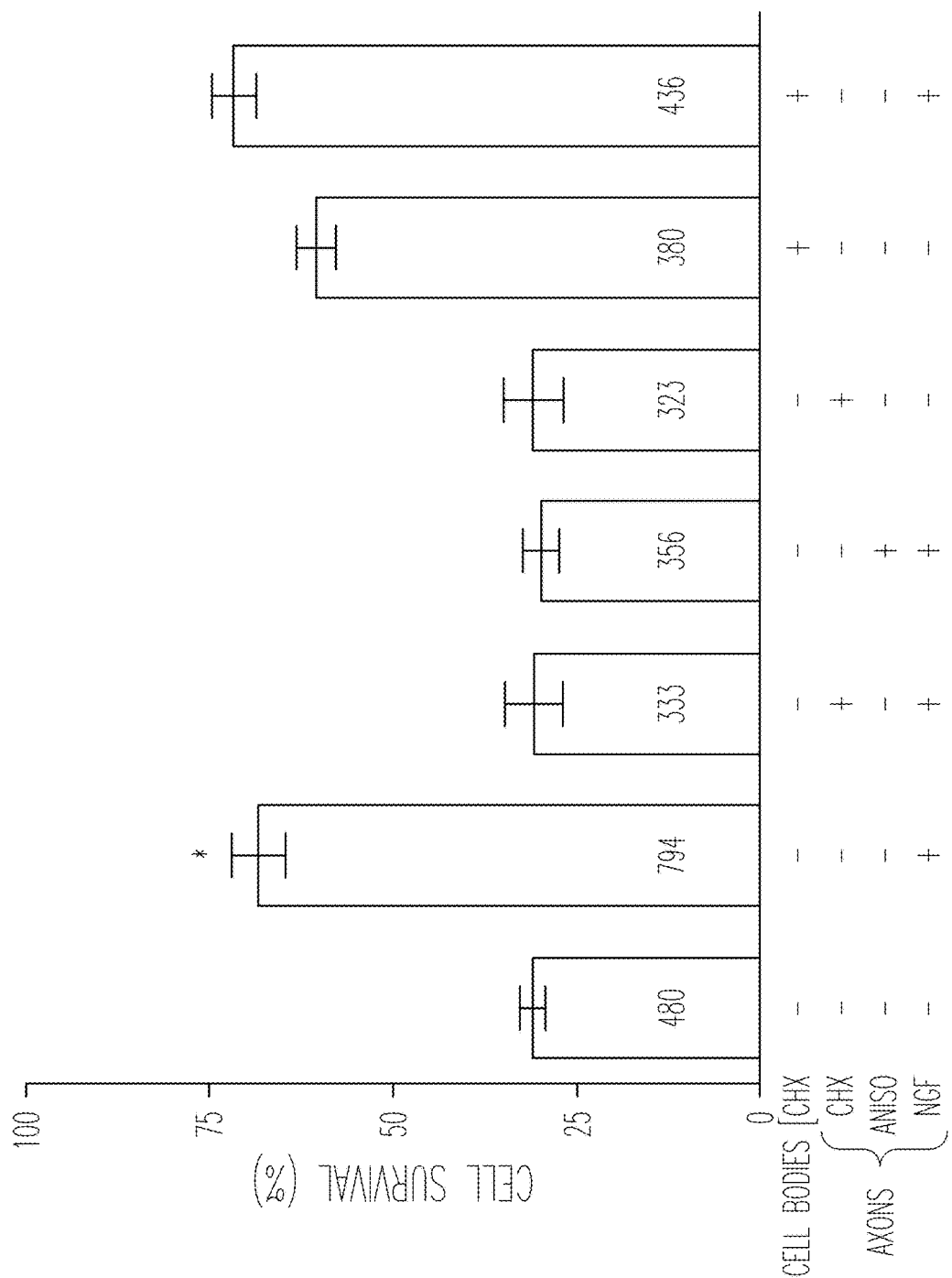

To determine if protein synthesis is required for NGF signaling we cultured neurons in compartmented chambers, which permit selective application of NGF to either distal axons or cell bodies (Campenot, *Proc Natl Acad Sci USA* 74, 4516-4519 (1977)), mimicking the physiologically selective exposure of distal axons to NGF that occurs as axons approach NGF-synthesizing target tissues (FIG. 2C, FIG. 1C-1F). Axonal application of NGF activates a survival pathway that utilizes CREB, resembling the physiologic requirement for CREB (Lonze et al., *Neuron* 34, 371-385 (2002)); bath application appears to utilize different NGF signaling pathways, as it induces survival in the absence of CREB (Lonze et al., *Neuron* 34, 371-385 (2002)). Axons crossed the divider by DIV 5, at which point the media in the cell body compartment was replaced with NGF-free media and the media in the axonal compartment is replaced with either NGF-free or NGF-replete media for an additional 48 hour. Application of NGF exclusively to the axonal compartment resulted in a significant increase in neuronal survival compared to vehicle-treated axons (FIG. 2D, 2E). This effect required intra-axonal protein synthesis, as axonal application of cycloheximide or anisomycin, together with NGF, resulted in a significant reduction in survival compared to NGF alone (FIG. 2D, 2E). The fluidic isolation of treatments was confirmed by our finding that axonal application of translation inhibitors had no effect in the cell body compartment on a membrane-anchored translation reporter (FIG. 1E, 1F). Furthermore, incubation of translation inhibitors in the cell body compartment supported DRG survival, even in the absence of NGF (FIG. 2E), consistent with previous results that have shown that protein synthesis inhibition in various cells, including DRG neurons, promotes survival due to the requirement for new protein synthesis in apoptosis (Tong et al., *J Neurocytol* 26, 771-777

(1997), Martin et al., *J Cell Biol* 106, 829-844 (1988), Wyllie et al., *Journal of Pathology* 142, 67-77 (1984)).

CREB mRNA is Localized to Axons

To identify mRNAs that act downstream of NGF in axons, the Boyden chamber technique for isolating axons (Zheng et al., *Journal of Neuroscience* 21, 9291-9303 (2001)) was modified in order to obtain distal axons (FIG. 3A) (Wu et al., *Nature* 436, 1020-1024 (2005)). DRG explants were cultured on 12-mm coverslips placed in the centre of Boyden chambers. Axons grow across the coverslip and then grow through the membrane towards the higher NGF concentration in the lower chamber. Axons from six chambers were harvested by scraping the underside of the membrane and used for reverse transcription and cDNA amplification using a protocol designed for unbiased amplification of mRNA from single cells (Tietjen et al., *Neuron* 38, 161-175 (2003)) (See Materials & Methods).

Figure 1G:
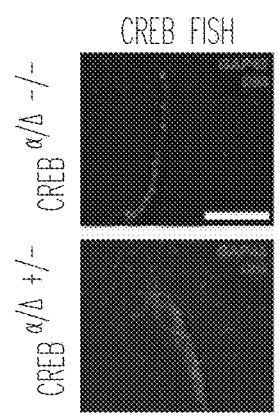
Figure 1I:
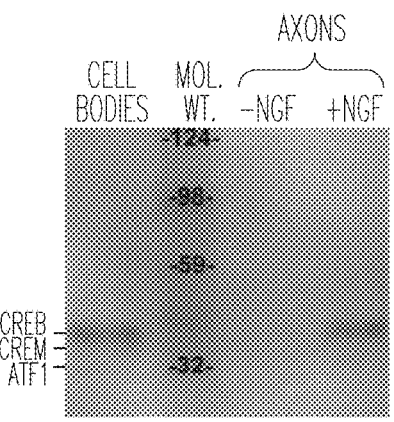
Figure 1H:
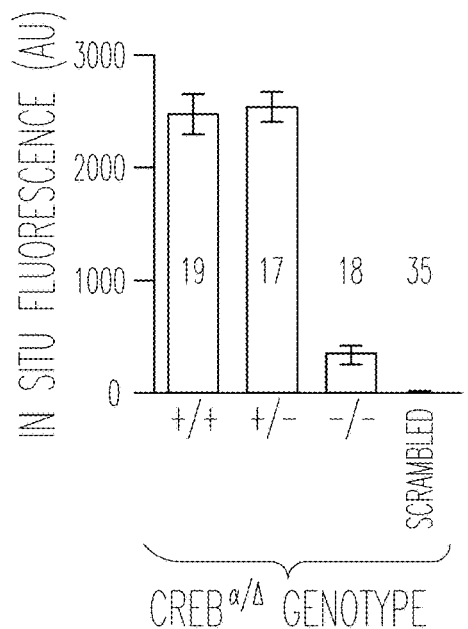
Figure 1J:
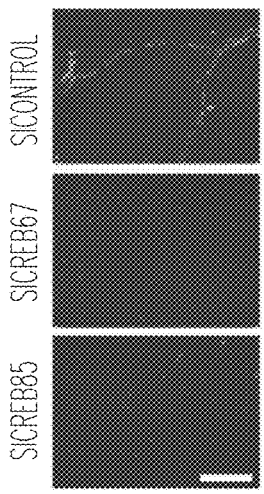
Figure 3B:
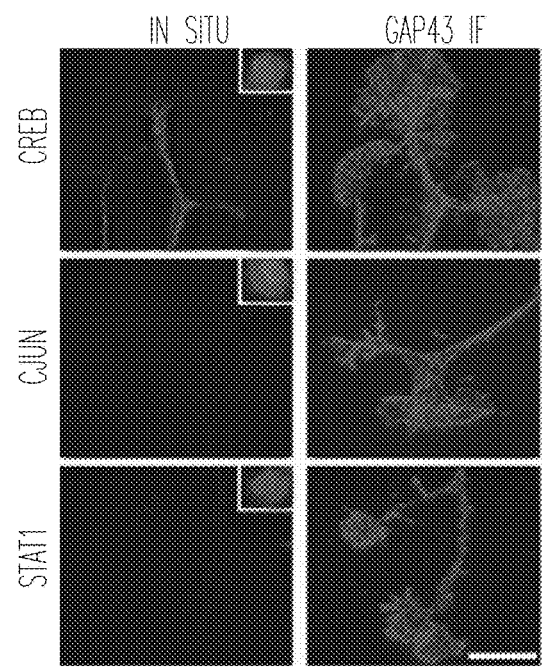
Figure 3C:
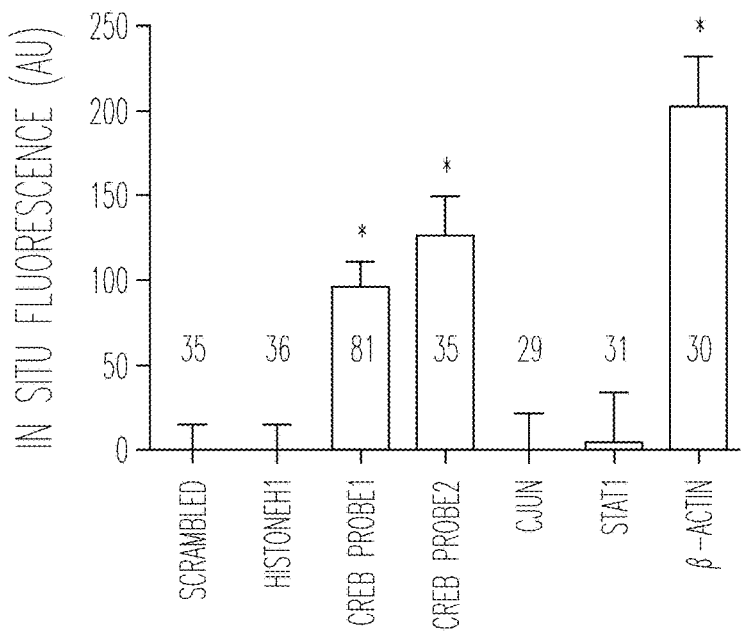
Figure 3D:
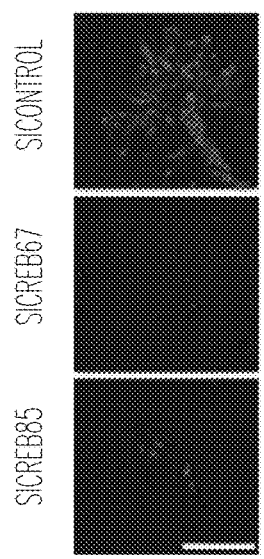
Figure 3E:
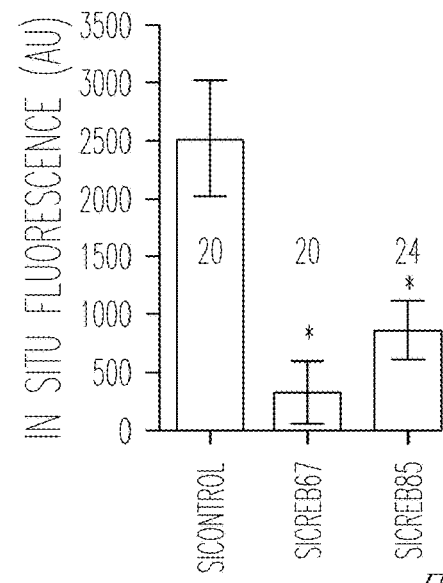
Figure 3F:
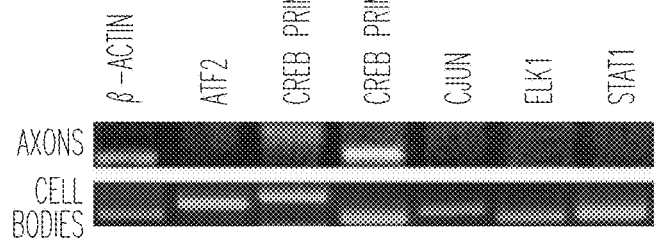

Among the clones in the library, cDNAs encoding specific transcription factors, including CREB were identified. To confirm that CREB transcripts were localized to axons, we performed fluorescent in situ hybridization (FISH) experiments using E15 DRG explant cultures. CREB-specific riboprobes prominently labeled cell bodies (FIG. 3B), with lower levels detectable in axons (FIG. 3B, 3C). Probes directed against other transcription factor transcripts, such as cJun and STAT1, resulted in negligible labeling of axons (FIG. 3B, 3C). CREB FISH signals were markedly reduced in neurons transfected with CREB-specific siRNA (FIG. 3D, 3E), as well as in DRG neurons cultured from mice homozygous for a hypomorphic CREB allele (Blendy et al., *EMBO Journal* 15, 1098-1106 (1996)) (FIG. 1G, 1H). RT-PCR using two distinct primer pairs resulted in amplification of CREB transcripts from distal axon preparations from Boyden chambers (Wu et al., *Nature* 436, 1020-1024 (2005)), as well as amplification of β-actin, a previously-identified axonal mRNA (Olink-Coux & Hollenbeck, *Journal of Neuroscience* 16, 1346-1358 (1996)), while RT-PCR signals for other transcription factor transcripts were absent (FIG. 3F). The axonal localization of CREB mRNA is consistent with the localization of CREB mRNA and protein to dendrites (Crino et al., *Proceedings of the National Academy of Sciences of the United States of America* 95, 2313-2318 (1998)). Together, these data indicate that CREB transcripts are specifically localized to axons of developing DRG neurons.

CREB is Synthesized in Axon Terminals in Response to NGF

Figure 4A:
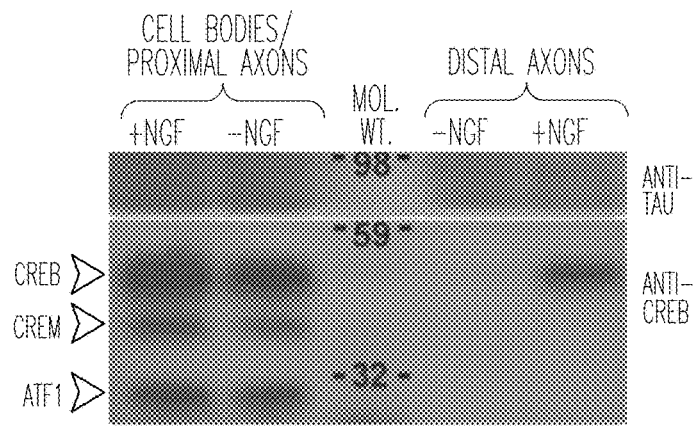
FIGS. 4A-D are results showing that CREB is specifically translated in axons. (A) Selective localization and induction of CREB in distal axons. DRG explants were cultured in Boyden chambers (Wu et al, Nature 436, 1020-1024 (2005)) and the upper compartment was incubated in Ong/ml NGF. The lower compartment was incubated in either 0 ng/ml NGF or 100 ng/ml NGF for 3 hours. Lysates (25 µg protein) were prepared from the coverslip (cell body/proximal axon) or the underside of the membrane (distal axons) and analyzed by Western blot using an antibody that also recognizes CREB family members CREM and ATF-1. (B) NGF and protein synthesis are required for CREB localization in axon terminals. Axons were severed from DIV3 DRG explant cultures, and incubated with 0 or 100 ng/ml NGF, or 100 ng/ml NGF+1 µM cycloheximide (CHX) for 3 hours. CREB was detected by immunofluorescence (IF) using a CREB-specific antibody. Counter-staining shows immunofluorescence using anti-tau antibody (right). Scale bar, 50 µm. (C) Quantification of results in (B). *$p<0.0001$. Numbers on bars represent n axons per condition. (D) Low-power (20×) image of CREB immunofluorescence (IF) in DIV3 E15 DRGs. The majority of cellular CREB protein is associated with the nucleus, although signals are seen in the cytosol and axon. Scale bar 20 µm.

The presence of axonal CREB mRNA raises the possibility of intra-axonal CREB synthesis. To address this, DRG explants were cultured in Boyden chambers; the media in the cell body chamber was replaced with NGF-free media and the media in the axon chamber was replaced with either NGF-replete or NGF-free media for 3 hours. Extracts from the upper surface of the Boyden chamber, containing cell bodies and proximal axons, and the lower surface, containing exclusively distal axons (Wu et al., *Nature* 436, 1020-1024 (2005)), were harvested, and equal amounts of protein were analyzed by Western blot. Western blotting using a CREB family antibody that also recognizes CREM and ATF1 indicated that only CREB was present in distal axons and was dependent on the presence of NGF in the axon compartment (FIG. 4A, FIG. 1I), although all three proteins were detected in the cell body/proximal axon fraction (FIG. 4A).

Figure 4B:
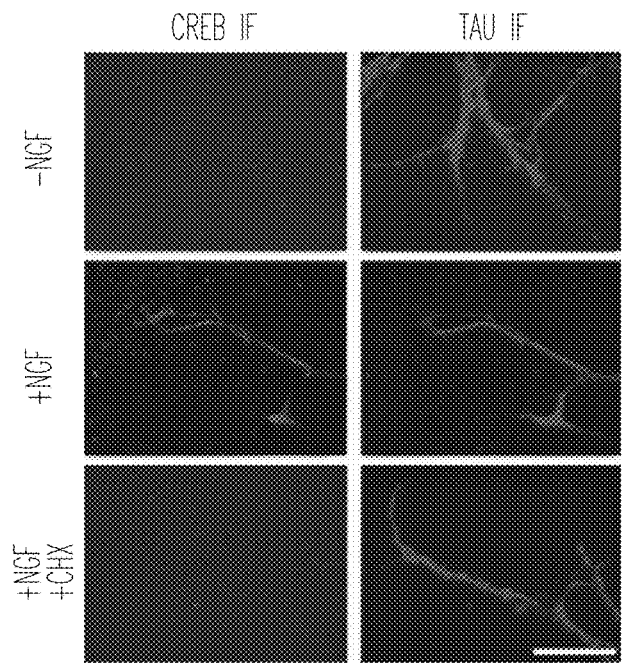
Figure 4C:
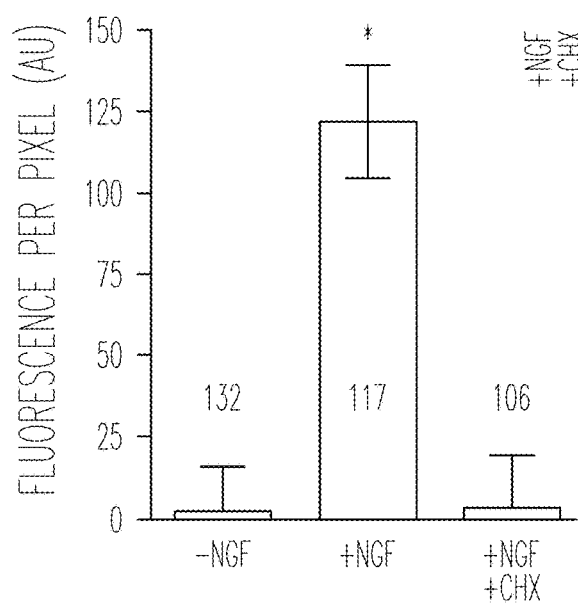
Figure 4D:
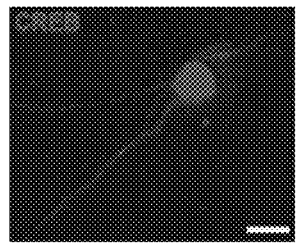

The axonal localization of CREB was also examined by immunofluorescence. Axons were severed from cultured DRG explants to rule out potential contributions from anterograde transport of cell body-derived CREB. Immunofluorescence with a CREB-specific antibody revealed axonal CREB protein was present when the media contained NGF, but not when the media was exchanged with NGF-free media for 3 hour (FIG. 4B, 4C), consistent with the Western blot data. Although the majority of CREB protein localized to the nucleus, with substantially lower levels in axons (FIG. 4D), the immunofluorescence signal in axons was specific. Similar immunofluorescence staining was seen using a different CREB-specific antibody that recognized a non-overlapping epitope. In addition, immunofluorescence staining was substantially reduced in DRG neurons transfected with CREB-specific siRNA and in DRG neurons prepared from mouse embryos homozygous for a hypomorphic CREB allele (Blendy et al., *EMBO Journal* 15, 1098-1106 (1996)) (FIG. 1J-1O). The presence of CREB in severed axons was dependent upon NGF and local translation since replacement of the media with NGF-free media or NGF-replete media containing cycloheximide resulted in a loss of CREB immunoreactivity (FIG. 4B, 4C). These data indicate that CREB is found in axons and its levels are dependent on NGF.

CREB mRNA is Selectively Translated in Response to NGF

NGF-dependent axonal CREB translation was examined using a GFP-based reporter assay (Aakalu et al., *Neuron* 30, 489-502 (2001)). This reporter expresses a transcript encoding a destabilized enhanced GFP with a cellular half-life of 1 hour (dEGFP) that enables dynamic changes in translational activity to be reflected by changes in fluorescence intensity (Aakalu et al., *Neuron* 30, 489-502 (2001)). The dEGFP construct also contains a myristoylation sequence, resulting in reduced diffusion of the reporter in the membrane (Wu et al., *Nature* 436, 1020-1024 (2005), Aakalu et al., *Neuron* 30, 489-502 (2001)). As a result of these two features, fluorescence signals reflect newly-synthesized protein near the site of translation as evidenced by their proximity to ribosomes (Aakalu et al., *Neuron* 30, 489-502 (2001)).

Figure 5C:
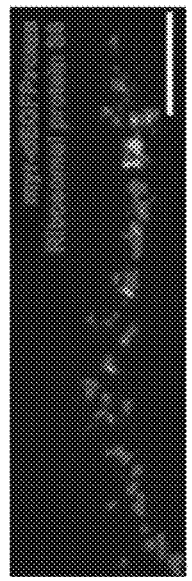
FIGS. 5A-C are results showing NGF-dependent translation of a CREB reporter mRNA in axons. (A) Schematic diagram of the Sindbis viral reporter construct used to monitor CREB translation. The reporter contains a myristoylated, destabilized EGFP (myr-dEGFP) with the 3'UTR of CREB, expressed under control of the Sindbis subgenomic promoter (PSG). (B) E15 DRG explant cultures were infected with Sindbis constructs expressing myr-dEGFP3'CREB on DIV3 and fluorescence (bottom panel) and phase (top panel) images, approximately 1000 µm from the cell body were collected after 24 hours. Fluorescence images are shown in inverted contrast in order to more readily visualize puncta. Scale bar, 25 µm. (C) myr-dEGFP$_{3'CREB}$ puncta co-localize with ribosomal markers. myr-dEGFP$_{3'CREB}$-expressing axons were counter-stained by immunofluorescence using a ribosomal protein S6-specific antibody. EGFP fluorescence co-localizes with a population of S6-labeled ribosomal clusters. Scale bar, 10 µm.
Figure 5A:
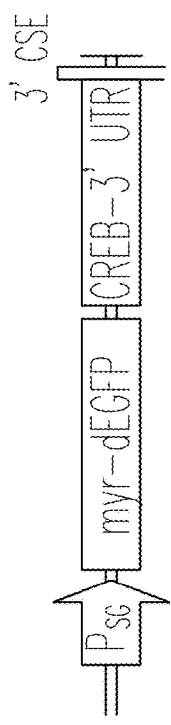
Figure 5B:
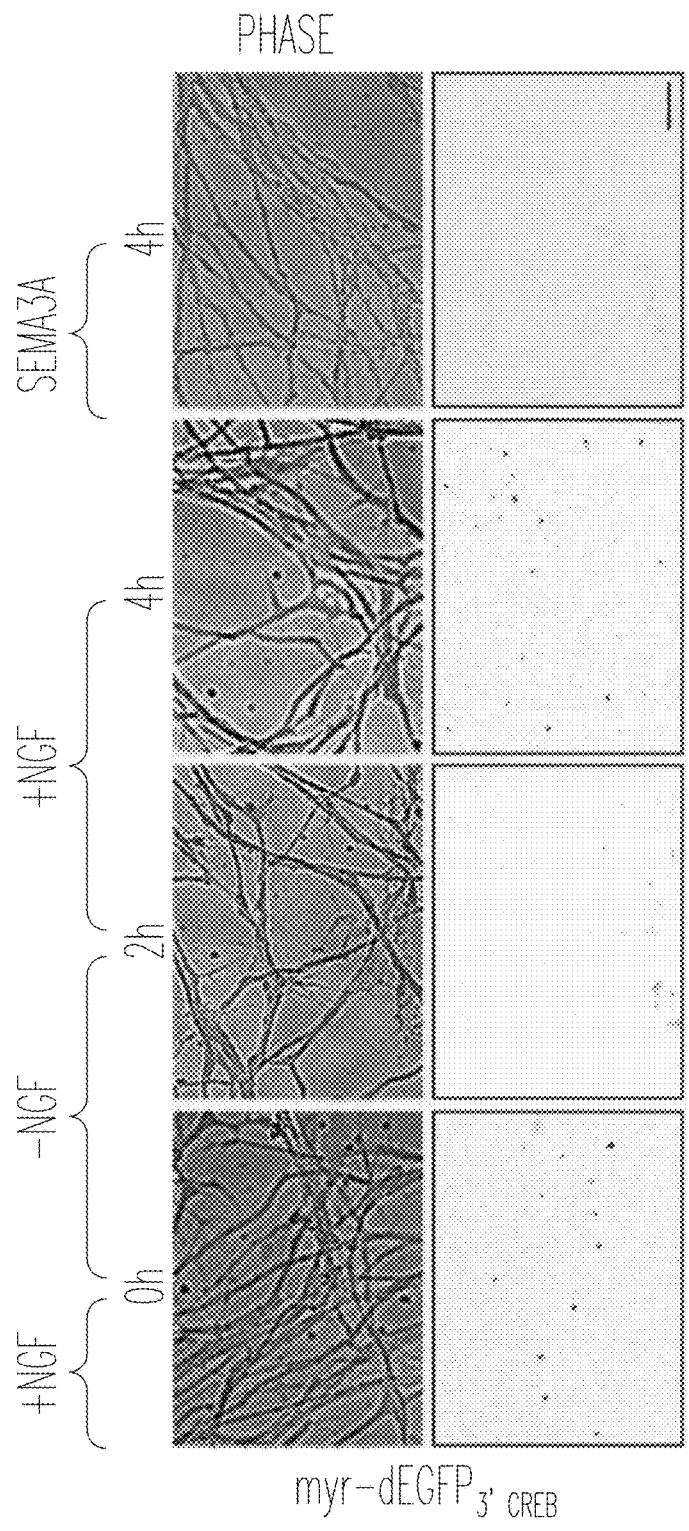
Figure 6A:
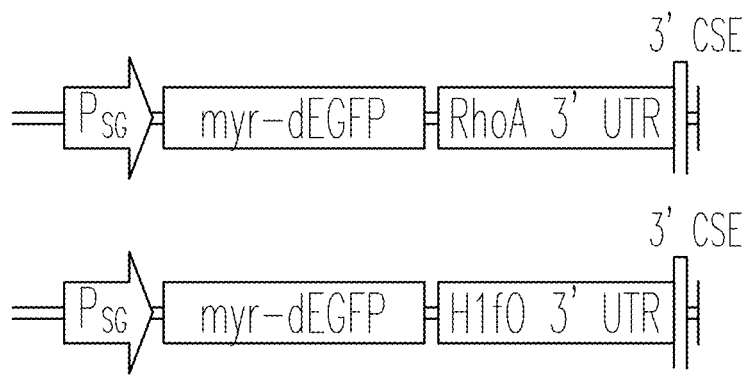
FIGS. 6A-H are data showing that axonal CREB is specifically translated in response to NGF. (A) Schematic diagram of the Sindbis reporters construct used to monitor RhoA and histone H1f0 translation (Wu et al., Nature 436, 1020-1024 (2005)). The reporter contains a myristoylated, destabilised EGFP (dEGFP) with the 3'UTR of RhoA or histone H1f0, expressed under control of the Sindbis subgenomic promoter ($P_{SG}$). (B) E15 DRG explant cultures were infected with Sindbis constructs expressing myr-dEGFP$_{3'RhoA}$ or myr-dEGFP$_{3'H1f0}$ on DIV3 and fluorescence images were collected after 24 h. Explants infected with myr-dEGFP$_{P\ 3'RhoA}$ and cultured in the presence of NGF exhibited fluorescent puncta distributed throughout axons (0 h). Following replacement of the media with NGF-free media for 2 hours, puncta intensity was not significantly affected (2 hours). Explants infected with myr-dEGFP$_{3'H1f0}$ and cultured in the presence of NGF did not exhibit fluorescent puncta in axons. Scale bar, 25 µm. (C) myr-dEGFP$_{3'CREB}$-infected axons were counterstained by immunofluorescence using antibodies specific to translational marker p-eIF4E, RNPassociating protein Staufen, and mitochondrial marker VDAC/Porin1. myr-dEGFP was found in some, but not all ribosomal clusters (FIG. 5C), suggesting that myr-dEGFP-negative clusters are either translationally inactive, that they translate CREB mRNA in response to different stimuli, or that their function involves the translation of other mRNAs. Scale bar, 10 µm. (D) Axons from DIV3 DRGs were analyzed for CREB and mitochondrial localizations by immunofluorescence using CREB-specific and VDAC/porin1-specific antibodies. Scale bar, 10 µm. (E) Axons were severed from DIV3 DRG explant cultures, and incubated with 0 or 100 ng/ml NGF for 3 hours. CREB mRNA was detected by FISH using a CREB specific riboprobe. CREB mRNA levels did not significantly change during the course of the 23 experiments. Numbers on bars represent n axons per condition. (F) 40 µM LLnL was added to myrdEGFP$_{3'CREB}$-infected axons. Within 5 min, the eGFP fluorescence signal increased twofold, due to inhibition of proteasome-dependent degradation of the destabilized EGFP. Scale bar, 10 µm. (G) 3 DIV dissociated DRGs were treated with NGF-free and NGF-replete media as in FIG. 7. CREB levels were assayed by immunofluorescence in contiguous axons: distal segments (450-500 µm), medial segments (250-300 µm) and proximal segments (50-100 µm) from the same axon were determined by their distances from the cell body. n≥10 axons per data point. *p<0.01. (H) Axons of DIV3 DRG explant cultures were analyzed by immunofluorescence for NGF effectors CREB, pTrkA and pErk5 at 3 DIV. Scale bar, 5 µm.
Figure 6B:
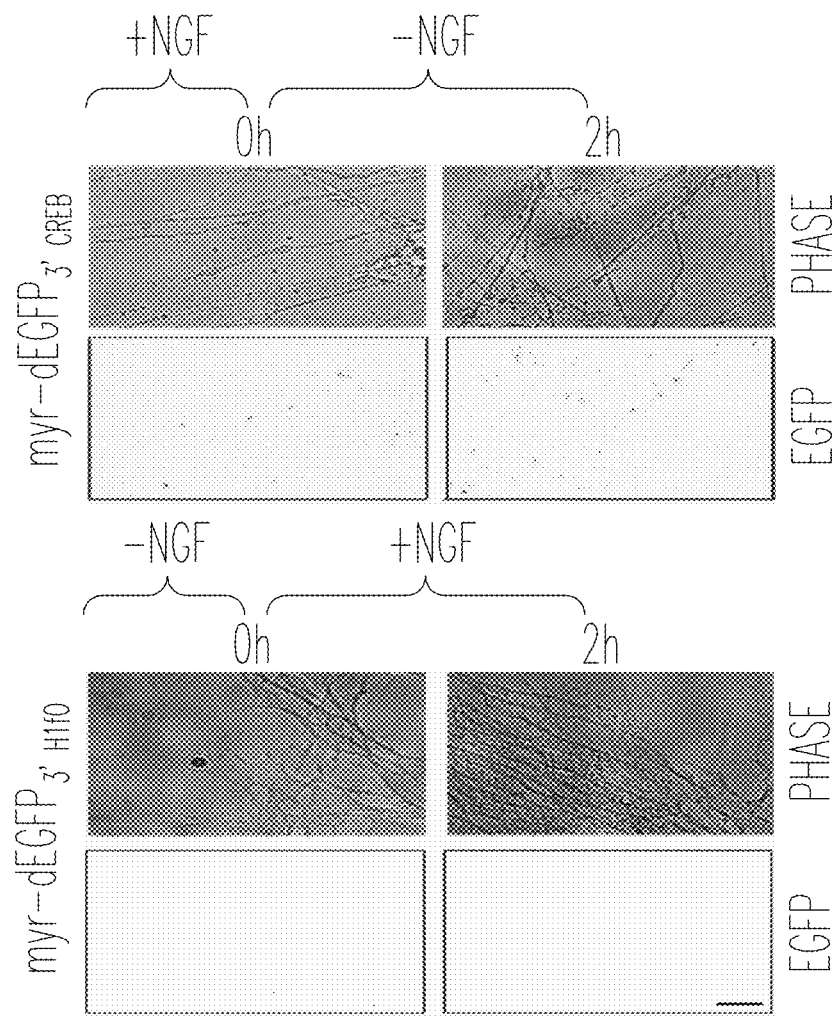

DRG explant cultures were infected with Sindbis virus (Wu et al., *Nature* 436, 1020-1024 (2005), Jeromin et al., *Journal of Neurophysiology* 90, 2741-2745 (2003)) expressing an mRNA comprising the myr-dEGFP coding sequence and the 3'UTR of CREB (myr-dEGFP$_{3'CREB}$) (FIG. 5A). Infection resulted in the appearance of fluorescent puncta throughout infected axons (FIG. 5B), as has previously been found in cultures infected with myr-dEGFP$_{3'RhoA}$ (Wu et al., *Nature* 436, 1020-1024 (2005)). No fluorescent signals are detected in axons of DRGs infected with a histone H1f0 myr-dEGFP reporter, an mRNA that is not detectable in axons (FIG. 6A, 6B). Fluorescent myr-dEGFP$_{3'CREB}$ puncta disappeared following replacement of the media with NGF-free media and reappeared following restoration of NGF, but not Semaphorin 3A (Sema3A), an axonal guidance cue that regulates the translation of axonal RhoA mRNA (FIG. 5B) (Wu et al., *Nature* 436, 1020-1024 (2005)). Expressing the RhoA reporter myr-dEGFP$_{3'RhoA}$ led to fluorescent puncta throughout axons that were only slightly affected by removal of NGF (FIG. 6B). These observations indicate that the CREB reporter is responsive to NGF but not to Sema3A, suggesting that the CREB 3'UTR contains a NGF-response element and that axons contain distinct signaling pathways that regulate the translation of different mRNA transcripts. The punctuate myr-dEGFP signals may reflect "hotspots" of protein translation (Aakalu et al., *Neuron* 30, 489-502

Figure 6C:
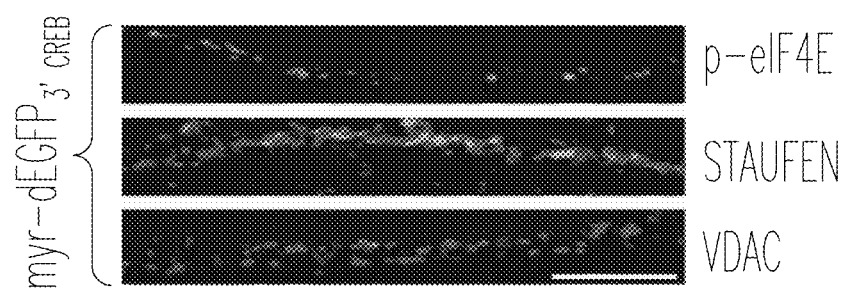
Figure 6D:

(2001), as these puncta co-localized with ribosomal protein S6, phospho-eIF4E, and Staufen, but not mitochondria (FIG. 5C, FIG. 6C, 6D).

Locally Synthesized CREB is Retrogradely Trafficked to the Nucleus

Figure 6E:
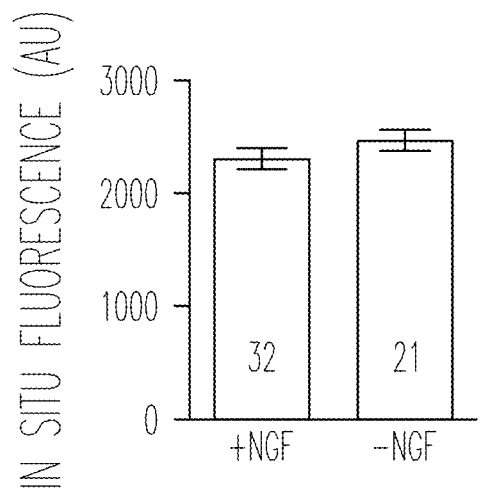
Figure 6F:
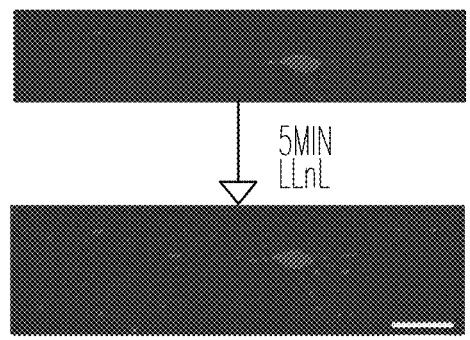
Figure 6G:
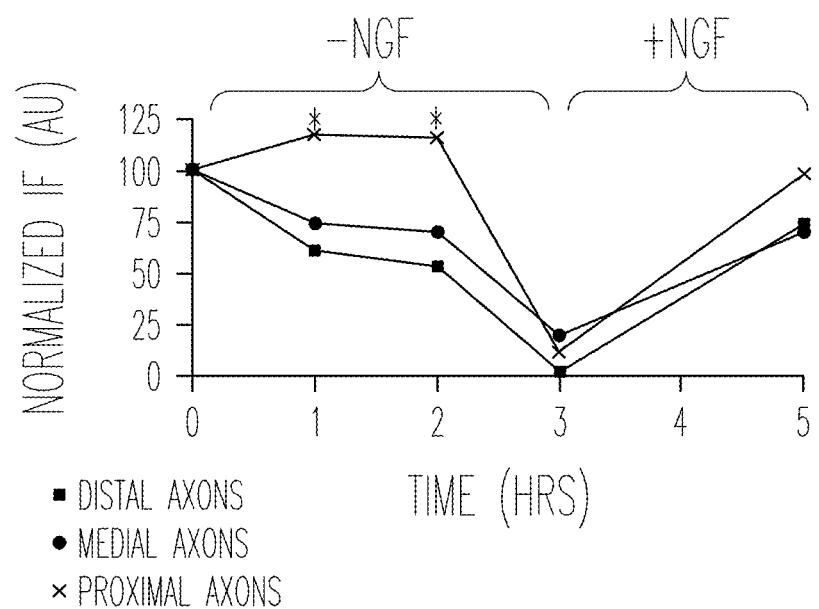
Figure 7A:
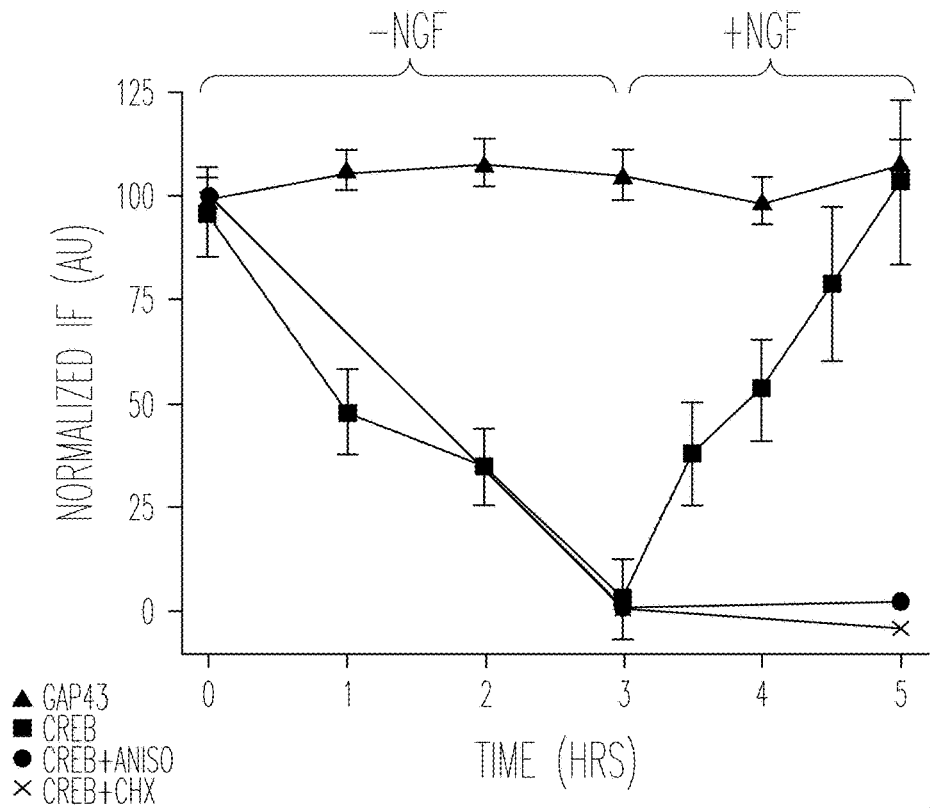
FIGS. 7A-B are results showing the axonal translation and retrograde transport of endogenous CREB. (A) CREB levels in severed axons of E15 DRGs were assayed by immunofluorescence with a CREB-specific antibody. CREB was depleted on removal of NGF, with near complete loss of fluorescence signals by 3 hours. Restoration of NGF resulted in a return of CREB to starting levels within 2 hours. Levels of GAP43 were not significantly affected by NGF removal or by restoration of NGF, indicating that changes in fluorescence intensity were not due to significant changes in axonal volume. Application of 1 µM cycloheximide or 40 µM anisomycin, concurrent with NGF replacement, prevented the restoration of CREB immunofluorescence, indicating that the NGF-dependent increase in CREB levels requires protein synthesis. The error bars represent s.e.m. (n=40). (B) CREB is depleted from axon terminals in a microtubule-dependent manner. CREB levels in severed axons were monitored, as in A, after removal and restoration of NGF, in the presence of LLnL or colchicine. Colchicine, but not LLnL, blocked the reduction in CREB levels following removal of NGF. The error bars represent s.e.m. (n=40).
Figure 7B:
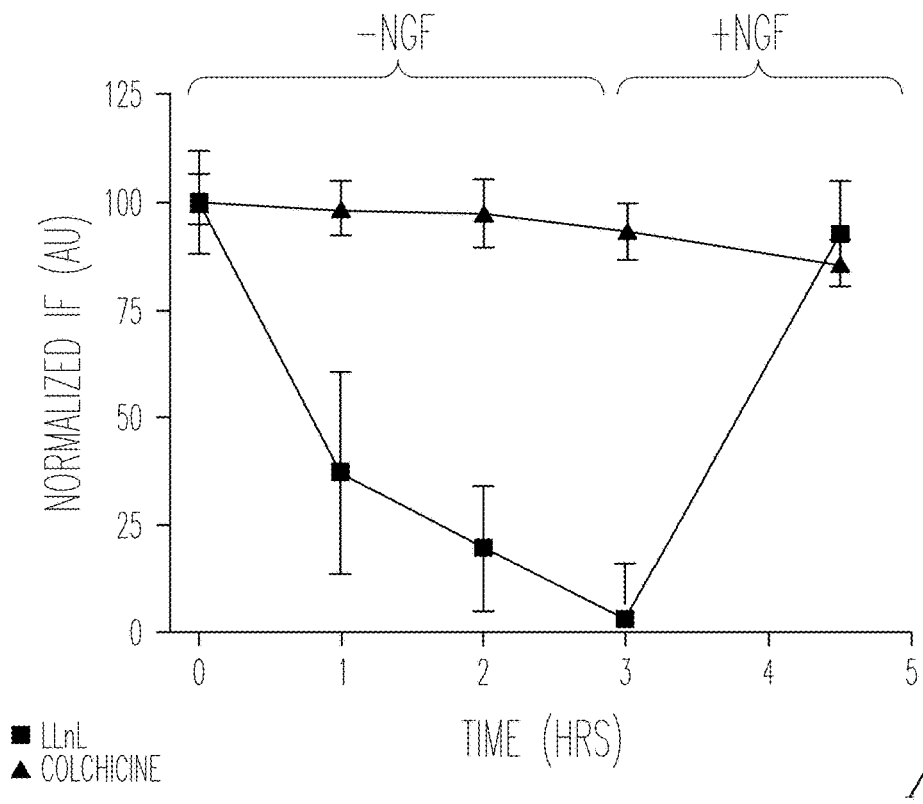

The importin proteins, which bind nuclear-localization sequences (NLS) (Goldfarb et al., *Trends in Cell Biology* 14, 505-514 (2004)), are present in axons and mediate the retrograde trafficking of axonally-injected fluorescently-labeled NLS peptides (Hanz et al., *Neuron* 40, 1095-1104 (2003)). Since CREB contains a NLS that mediates its nuclear localization (Waeber & Habener, *Mol Endocrinol* 5, 1418-1430 (1991)), axonal CREB may be retrogradely transported to the cell body. To determine if endogenously-expressed CREB is retrogradely trafficked, we examined the time course of CREB reduction in axons upon replacement of media with NGF-free media. CREB levels decreased to baseline within 3 hours of NGF removal, and returned to original levels 2 hours following restoration of NGF, although significant recovery in CREB levels (~40%) was observed within 30 min of NGF restoration (FIG. 7A). These treatments did not affect GAP-43 (FIG. 7A) or axonal CREB mRNA levels (FIG. 6E). The NGF-dependent restoration of CREB levels was abolished by ribosomal inhibitors (FIG. 7A). The reduction of CREB levels upon removal of NGF was unaffected by the presence of the proteasome inhibitor LLnL (FIG. 7B, FIG. 6F), indicating a proteasome-independent pathway for CREB removal from axons. Application of colchicine, which prevents microtubule-dependent transport, abolished the reduction in CREB levels following removal of NGF (FIG. 7B), indicating a microtubule-dependent process for the loss of CREB protein from axons. The possibility of retrograde transport is supported by the finding that the loss of CREB protein occurs first in distal axons, and then subsequently in medial and proximal axon segments (FIG. 6G).

Figure 8A:
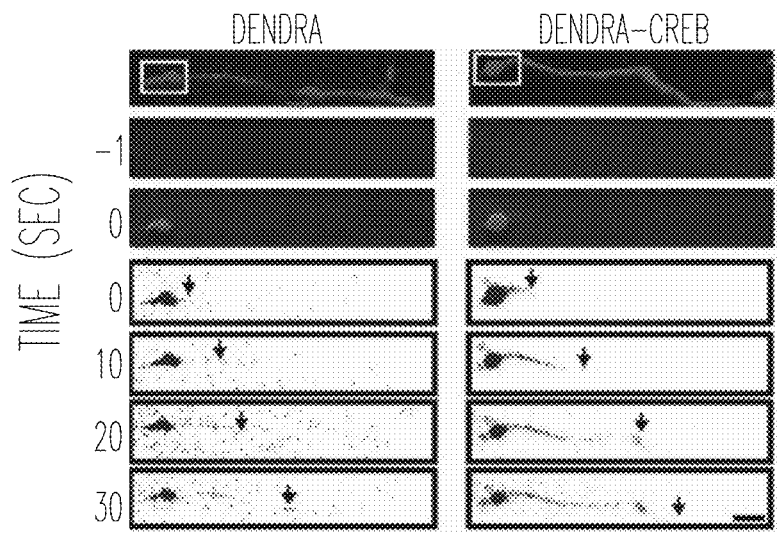
FIGS. 8A-D are results showing the retrograde transport of a photoactivatable fluorescent CREB reporter protein. (A) E15 DRG explant cultures were infected with Sindbis constructs expressing Dendra or Dendra-CREB transcripts. Dendra and Dendra-CREB were visualized as green fluorescence (top panel), and growth cone-localized Dendra[-CREB] was photoactivated to its red form by 50 ms illumination of the boxed regions with a 408 nm laser. Movement of photoactivated Dendra signals was analyzed within the axon determined by green Dendra fluorescence mask. The leading edge (arrows) of red fluorescence for photoactivated Dendra-CREB was observed to move along the axon at a significantly faster rate than photoactivated Dendra. Photoactivated Dendra[-CREB] images are shown inverted in order to more readily visualize signals. Scale bar, 10 µm. (B) Quantification of data in (A). Grey line indicates the predicted diffusion rate of photoconverted Dendra-CREB, based on neuronal viscosity measurements (Bloodgood & Sabatini, Science 310, 866-869 (2005)). The expected diffusion rate of Dendra-CREB was calculated at various elapsed time points, using a previously measured diffusion coefficient (D) in neurons (Bloodgood & Sabatini, Science 310, 866-869 (2005)), in the formula $x^2=(2Dt)$, where x is the average displacement. No significant differences in axon diameter or morphology were observed between the neurons assayed. n≥20 axons per data point. *p<0.0001. (C) Dendra or Dendra-CREB was photoactivated by 1 s illumination of a 40 µm axon segment approximately 1 mm from its respective cell body and levels of photoactivated Dendra fluorescence were analyzed in the respective cell nucleus. Scale bar, 20 µm. (D) Quantification of data in (C). n=10 cells per data point. *p=0.0012.
Figure 8B:
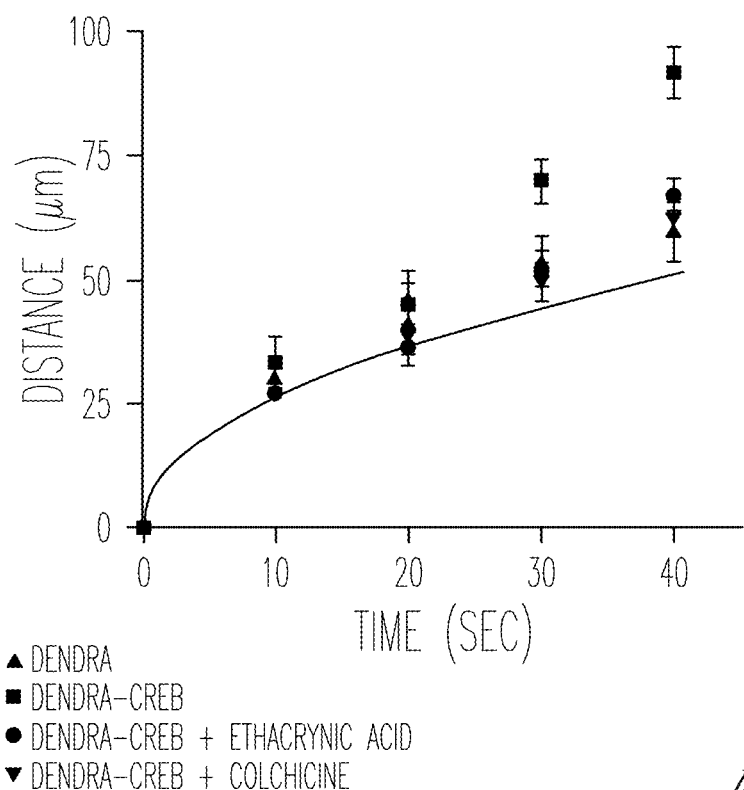
Figure 8C:
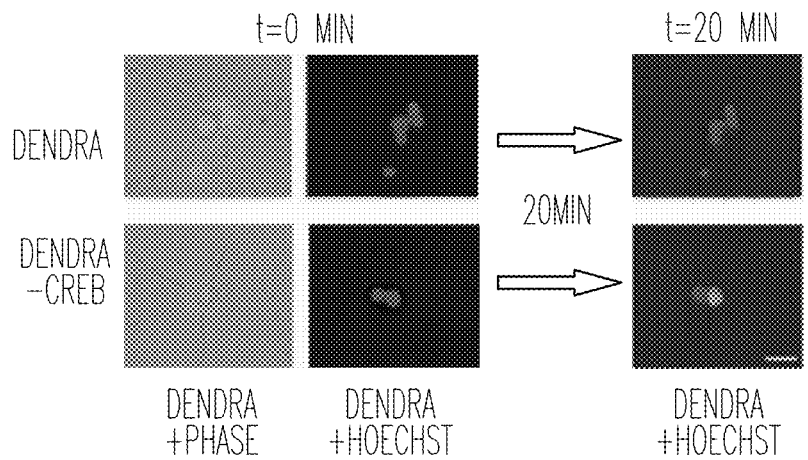
Figure 8D:
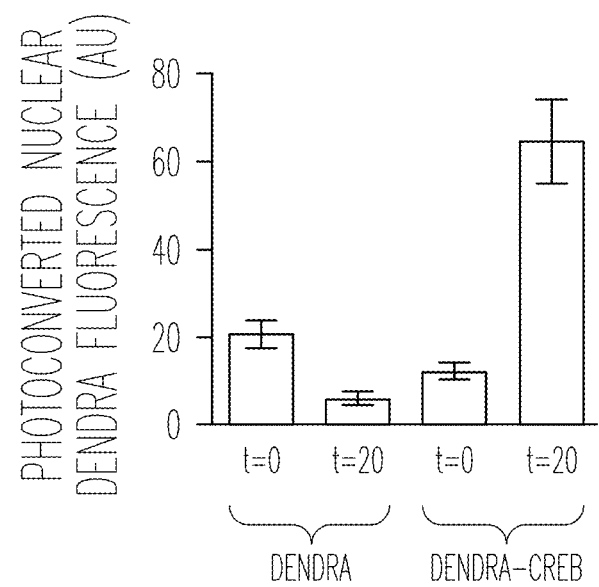

To further examine retrograde trafficking of CREB, Dendra, a monomeric GFP relative that converts from green to red fluorescence upon irradiation with blue or ultraviolet light (Kislauskis et al., *Journal of Cell Biology* 127, 441-451 (1994)) was used. DRG explant cultures were infected with Sindbis virus encoding either Dendra or Dendra-CREB transcripts that contained a minimal 3'UTR axon-targeting element (Kislauskis et al., *Journal of Cell Biology* 127, 441-451 (1994), Zhang et al., *Neuron* 31, 261-275 (2001)). Dendra and Dendra-CREB were photoconverted in selected growth cones (FIG. 8A). The rate of Dendra movement towards the cell body matched the rate predicted by passive diffusion (FIG. 8B). In contrast, photoconverted Dendra-CREB was observed to move at a substantially higher, and constant, rate towards the cell body of 7.8-8.8 mm h−1 (FIG. 8A, 8B), similar to previously measured rates of retrograde trafficking (Brimijoin & Helland, *Brain Research* 102, 217-228 (1976), Ure et al., *Journal of Neuroscience* 17, 1282-1290 (1997)). Retrograde transport was significantly blocked by colchicine or ethacrynic acid, a dynein inhibitor (Martenson et al., *Toxicol Appl Pharmacol* 133, 73-81 (1995)), suggesting a microtubule motor-dependent active transport of Dendra-CREB from the axon (FIG. 8B). Photoconversion of a 40-μm section of axon approximately 1000 μm from the cell body was associated with accumulation of photoconverted Dendra-CREB, but not Dendra, in the nucleus within 20 min (FIG. 8C, 8D).

Figure 6H:
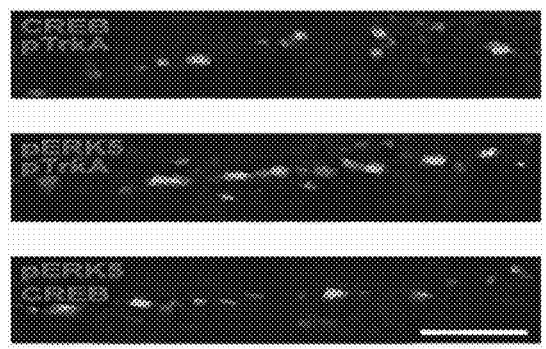

TrkA-containing signaling endosomes are trafficked from distal axons to the cell body (Zweifel et al., *Nature Reviews Neuroscience* 6, 615-625 (2005)) and mediate the activation of Erk5, which is required for CREB phosphorylation in response to axonally-applied NGF (Watson et al., *Nature Neuroscience* 4, 981-988 (2001)). Punctate regions of phospho-TrkA (pTrkA) immunoreactivity were found along the length of axons of DRG neurons cultured in the presence of NGF (FIG. 6H), in a distribution consistent with previous reports of TrkA-signaling endosomes in axons (Cui et al., *Proc Natl Acad Sci USA* 104, 13666-13671 (2007). These regions of pTrkA reactivity also contain phosphorylated Erk5 (FIG. 6H). Interestingly, axonal CREB protein exhibits co-localization with these sites of pTrkA immunoreactivity along axons (FIG. 6H), indicating that axonal CREB may be in proximity to TrkA-signaling complexes in axons.

Figure 10A:
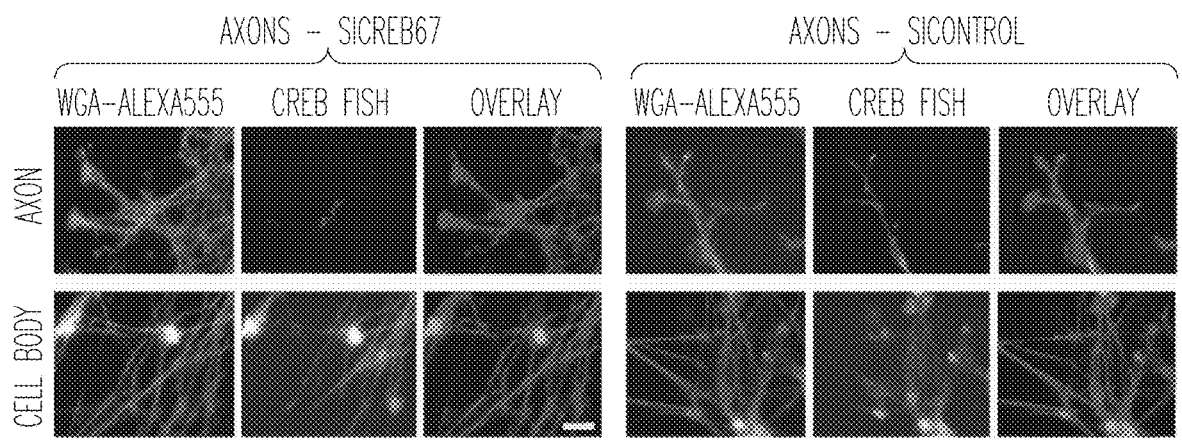

Axonal CREB is Required for the Accumulation of pCREB in the Nucleus Induced by Application of NGF to Axons To determine whether the amounts of CREB synthesized in axons make a substantial contribution to nuclear levels of CREB, the following study was performed. Axonal CREB mRNA was knocked down by compartmentalized siRNA transfection (Hengst et al., *J Neurosci* 26, 5727-5732 (2006)), while BOC-Asp(OMe)-FMK (BAF), a caspase inhibitor, was included in the cell body compartment to prevent neuronal death (Kuruvilla et al., *Cell* 118, 243-255 (2004)). Transfection of CREB-specific siRNA into the axon compartment of dissociated DRG neurons in compartmented chambers resulted in axonal knockdown of CREB protein (72.8+/−5.2%) and CREB mRNA (82.5+/−4.3%), but did not lead to a reduction in CREB mRNA or protein levels in the cell body compartment (FIG. 9A, 9B, FIG. 10A, 10B). Similarly, selective reductions in axonal CREB protein levels are seen by Western blotting (FIG. 10C). These effects are specific, as β-actin mRNA levels in axons or cell bodies were not affected by axonal transfection of CREB-specific siRNA (FIG. 10B).

Figure 9A:
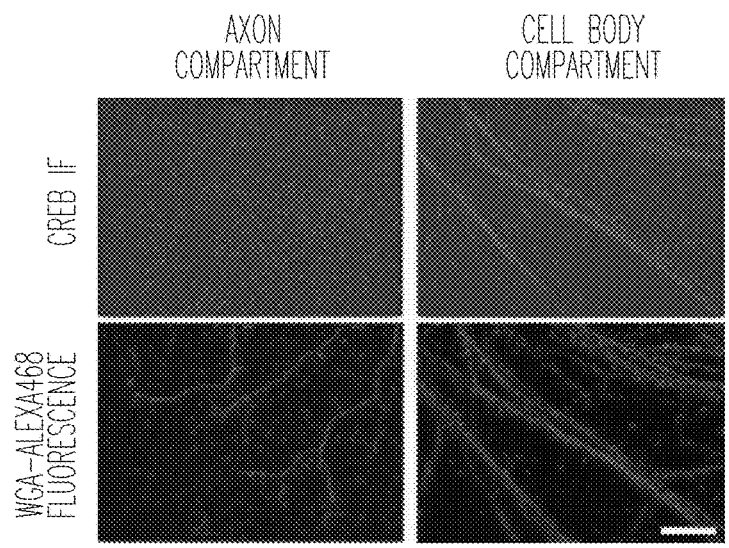
FIGS. 9A-E are data showing that axonal CREB is required for CRE-dependent transcription and NGF-mediated DRG survival. (A) DRG axons in compartmented cultures were transfected with CREB siRNA in the axon compartment only, and CREB levels were detected using a CREB antibody. Axons crossing the compartment divider were retrogradely labeled with WGA-Alexa488. All compartments were maintained in NGF-containing media throughout the experiment. Scale bar, 50 µm. (B) Quantification of data in (A). Immunofluorescence levels in each compartment were normalized to fluorescence signals from cultures treated with non-targeting siRNA. *p<0.0001. Numbers on bars represent n axons per condition. (C) DRGs in compartmented cultures were incubated in NGF-free media, supplemented with BAF to suppress apoptosis. Axon compartments were treated with CREB-specific or non-targeting siRNA. After 48 hours, 30 ng/ml NGF was added to the axon compartment for 20 min, after which pCREB levels in nuclei were quantified by immunofluorescence. *p=0.0004. Numbers on bars represent n cells per condition. (D) DRGs in compartmented chambers were infected with adenovirus encoding luciferase under the control of a CRE transcriptional element and treated with NGF as in (C). *p<0.001. Numbers on bars represent n cells per condition. (E) E15 dissociated DRG were cultured in compartmented chambers as in FIG. 2C. NGF-induced neuronal survival at DIV7 was assayed following transfection of control or CREB-specific siRNA into the axon compartment at DIV5. *p<0.001. Numbers on bars represent n cells per condition.
Figure 9B:
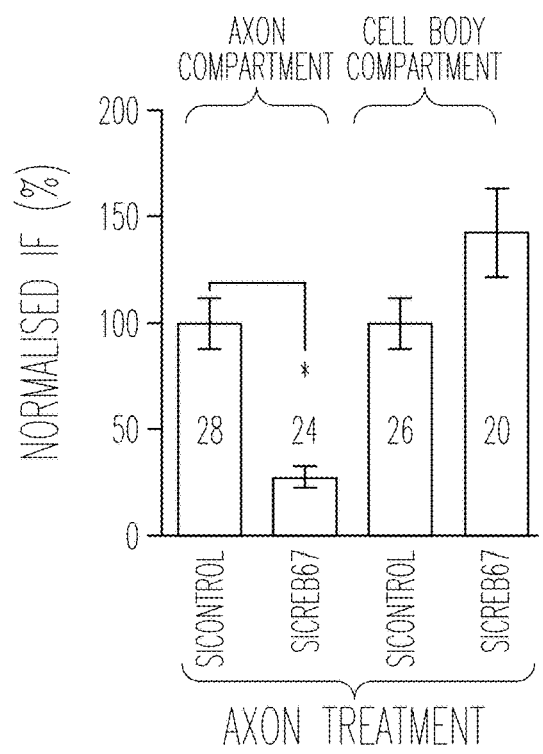
Figure 9C:
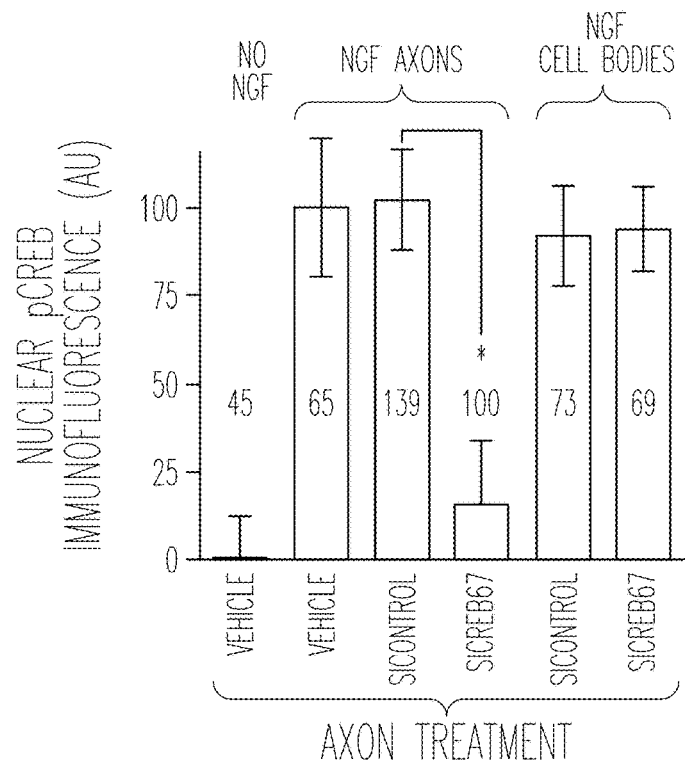
Figure 10E:
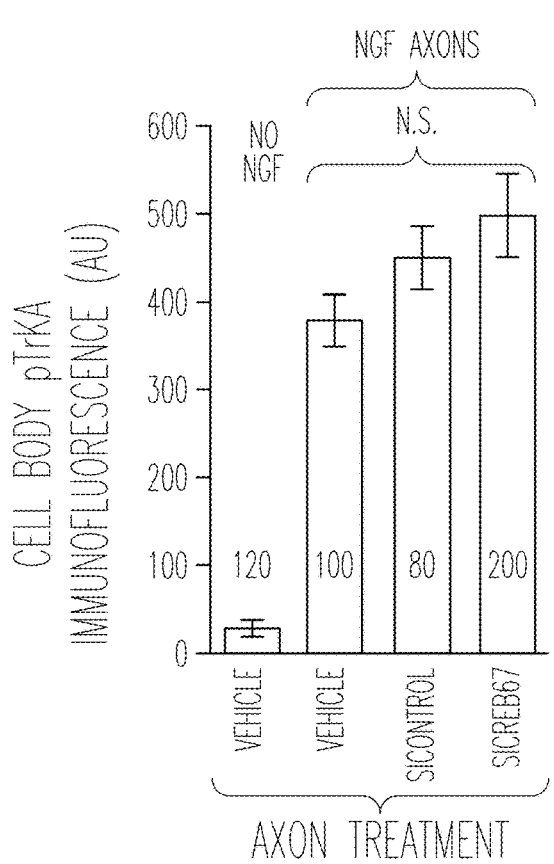
Figure 10F:
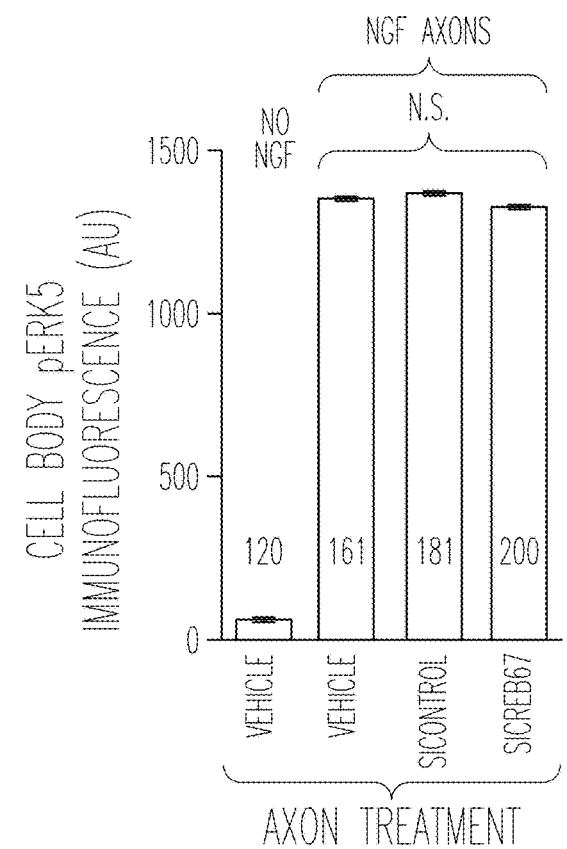

Unlike CREB, which is readily detected in the nucleus, Ser133-phosphorylated CREB (pCREB) is present at negligible levels in the nuclei of unstimulated sensory neurons (Riccio et al., *Science* 277, 1097-1100 (1997), Watson et al., *J Neurosci.* 19, 7889-7900 (1999)). The low basal level of pCREB makes neurons highly responsive to increases in pCREB levels, which occurs upon application of neurotrophin to axons (Watson et al., *J Neurosci.* 19, 7889-7900 (1999)) (FIG. 9C, FIG. 10D). Treatment of axons with NGF resulted in increased levels of pCREB in the nucleus within 20 min, which was unaffected by axonal transfection of a control siRNA. Axonal transfection of CREB-specific siRNA significantly reduced the ability of axonally-applied NGF to induce this rapid increase in nuclear pCREB levels (FIG. 9C, FIG. 10D), but did not have a significant effect on cell body accumulation of pTrkA or pERK5 (FIG. 10E, 10F), suggesting that this effect is not due to inhibition of retrograde transport of signaling endosomes. Knockdown of axonal CREB mRNA also did not affect nuclear pCREB accumulation induced by stimulation of cell bodies with NGF (FIG. 9C), demonstrating that axon-specific CREB knockdown does not have a general inhibitory effect on NGF signaling or CREB phosphorylation. The appearance of pCREB in the nucleus within 20 min of NGF treatment is consistent with the time required for CREB to be transported across the 1-mm divider, based on the trafficking rates measured for Dendra-CREB (FIG. 8B). Thus, while axonal synthesis does not contribute a substantial portion to the total amount of nuclear CREB, these data indicate that the axonally-synthesized pool of CREB accounts for the majority of the pCREB that appears in the nucleus upon stimulation of distal axons with NGF.

Axonal CREB Mediates the Induction of CRE-dependent Transcription

Figure 9D:
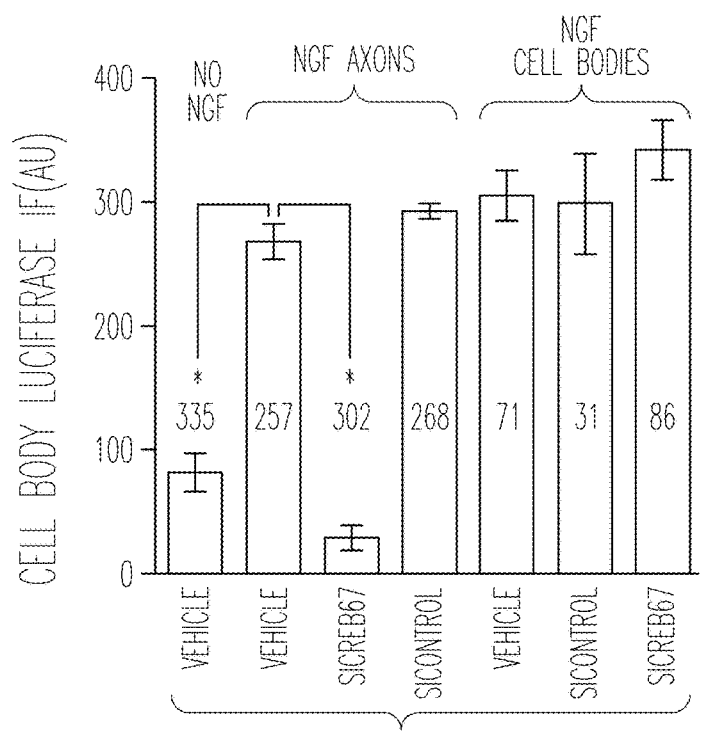
Figure 10G:
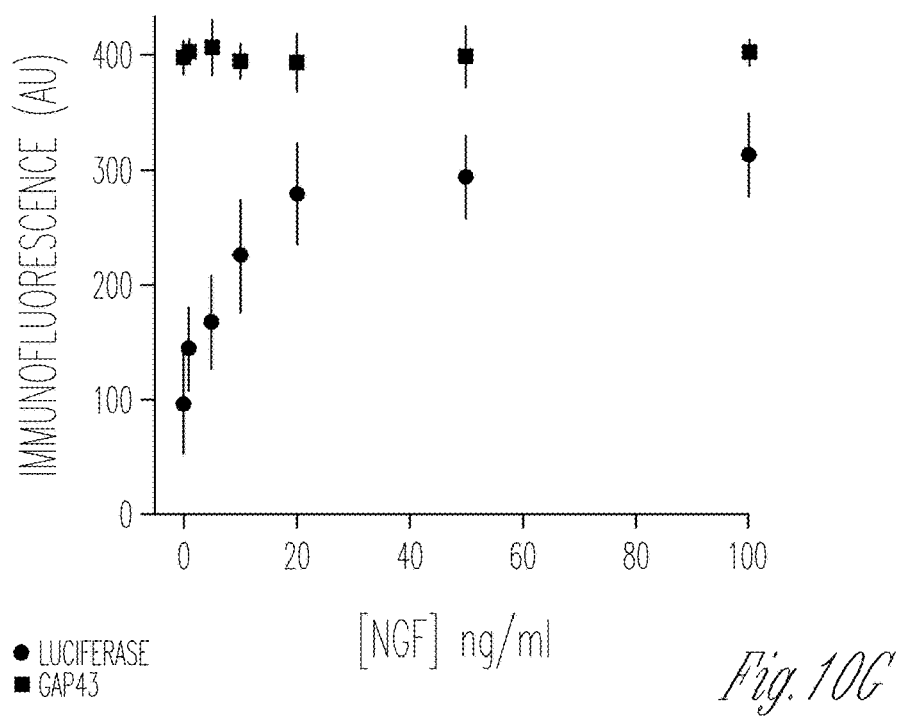

To determine whether axon-derived CREB is capable of affecting CRE-dependent transcription, axons of dissociated DRG neurons in compartmented chambers were subjected to either NGF-replete or NGF-free media and siRNA at 5 DIV. BAF was included in the cell body compartment to prevent neuronal death. At 6 DIV, cell bodies were infected with adenovirus encoding a CRE-luciferase reporter, and cellular luciferase levels were measured 24 hours later. Bath application of NGF to DRG neurons lead to a dose-dependent increase in luciferase immunofluorescence, but did not affect a control protein (FIG. 10G). Axonal application of NGF increased luciferase levels, which was prevented by axon-specific transfection of CREB-specific siRNA, but not control siRNA (FIG. 9D). Knockdown of axonal CREB mRNA did not affect luciferase transcription induced by NGF applied to the cell bodies (FIG. 9D) indicating that axonal CREB knockdown does not non-specifically inhibit the reporter. Axon-derived CREB is thus necessary for CRE-dependent transcription induced by application of NGF to distal axons.

Axonal CREB is Required for NGF-induced Retrograde Survival

Figure 9E:
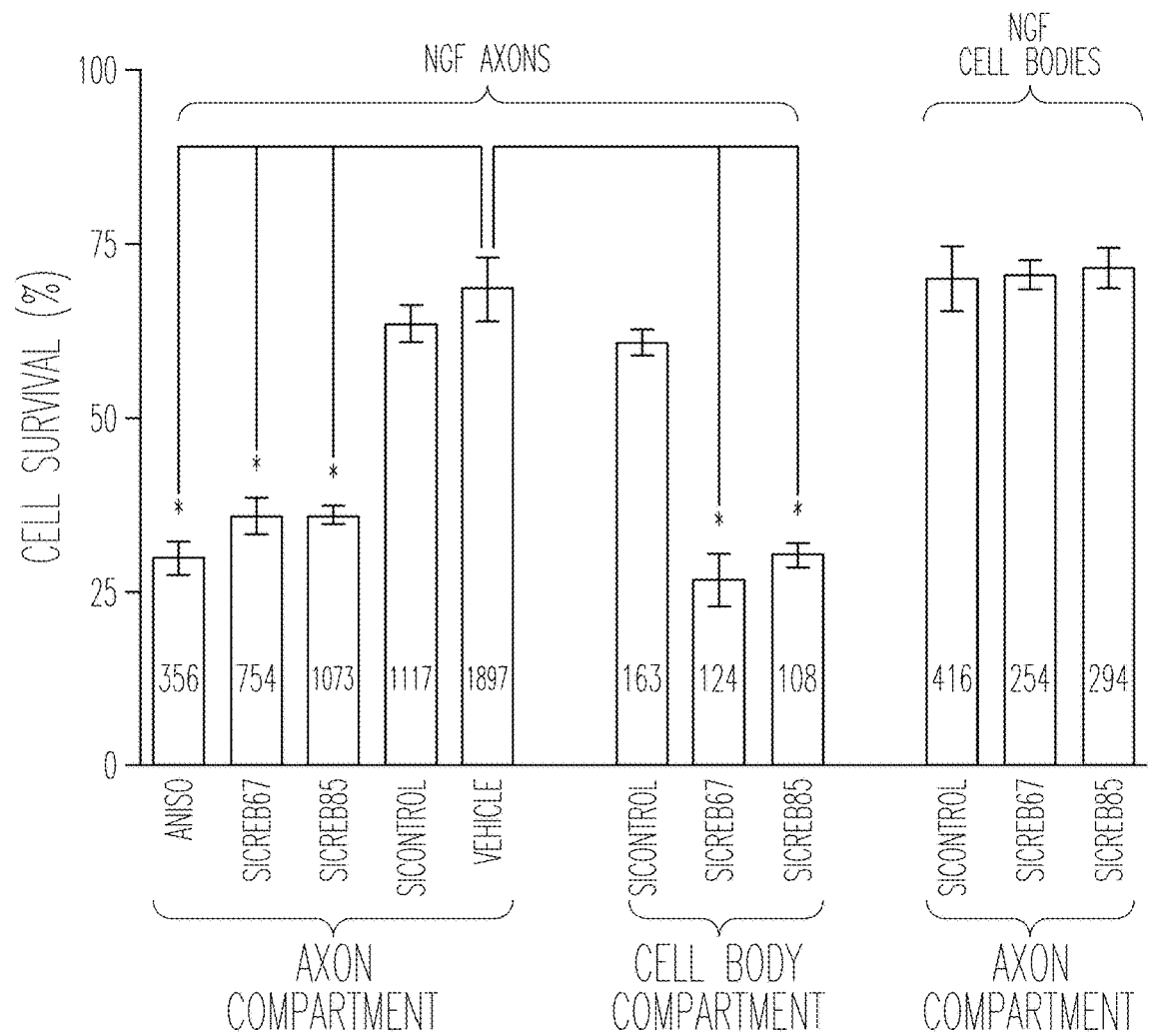

A role for CREB in DRG neuron survival is reflected in the loss of ~75% of these neurons in CREB null mice (Lonze et al., Neuron 34, 371-385 (2002)). To determine the role of the axonal CREB in neuronal survival, DRG neurons were cultured in compartmented chambers, and axons were transfected with either control or CREB-specific siRNA. Neuronal survival induced by axonal application of NGF was unaffected by control siRNA, but was markedly impaired by transfection with either of two CREB-specific siRNAs (FIG. 9E). Axon-specific transfection of CREB-specific siRNA did not affect cell survival elicited by application of NGF to cell bodies (FIG. 9E) indicating that NGF signaling at cell bodies does not require axonal CREB. The impairment in survival seen following knockdown of axonal CREB mRNA was comparable to that seen when CREB mRNA was knocked down throughout both cell bodies and axons by transfection of cell bodies with CREB-specific siRNA (FIG. 9E) and similar to the levels of survival seen when both cell bodies and axons are deprived of NGF (FIG. 2E, FIG. 1D) (Watson et al., Nature Neuroscience 4, 981-988 (2001)). These data indicate that axonal CREB translation is required for survival elicited by NGF signaling in distal axons.

Figure 11:
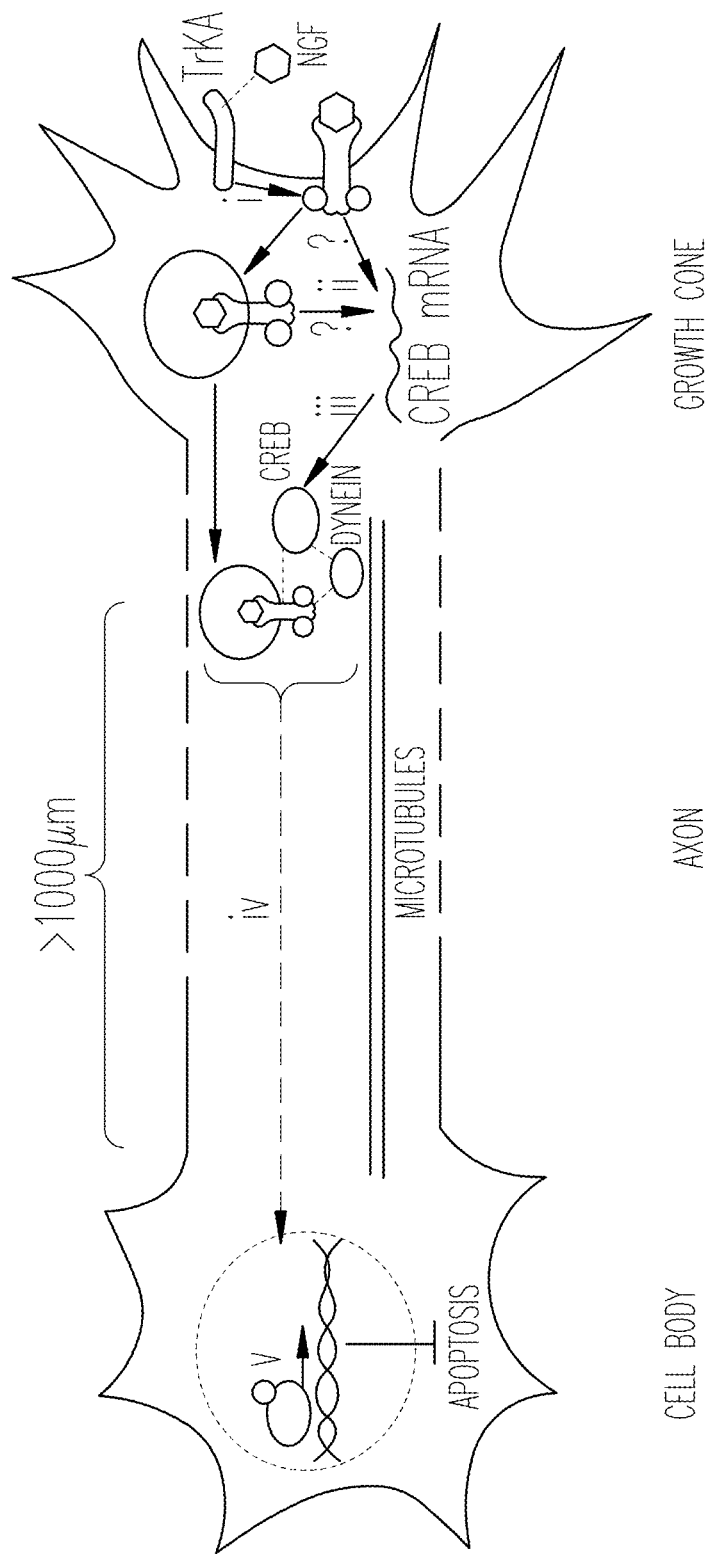
FIG. 11 is a schematic drawing illustrating local translation and retrograde transport of CREB mediates neuronal survival. (i) NGF binds to TrkA receptors causing dimerization and autophosphorylation. (ii) TrkA activation leads to translation of axonal CREB mRNA and (iii) the production of CREB protein. NGF-bound, activated TrkA receptors are internalized into endosomes and initiate formation of a signaling complex containing downstream effectors and the motor protein dynein. Axonally translated CREB protein associates with this NGF-pTrkA signaling endosome, which is required for downstream activation of CREB signaling in the cell body. (iv) CREB is retrogradely transported to the nucleus via microtubules and is phosphorylated at S133 downstream of internalized TrkA signaling endosomes, via a kinase cascade including Mek5/Erk533. (v) Axonally-derived pCREB initiates the transcription of anti-apoptotic genes in the nucleus, leading to neuronal cell survival.
Figure 12A:
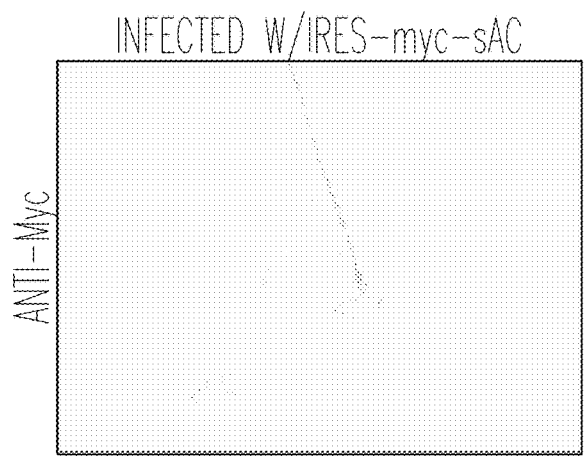
FIGS. 12A-D are results showing that the axons of embryonic day (E) 14 sensory neurons can express a virally-encoded protein. (A) Neurons from embryonic day (E) 14 sensory neurons were cultured in compartmentalized devices, and Sindbis-IRES virus expressing myc-sAC was applied exclusively to axons. Labeling in axons was shown with inverted contrast to facilitate visualization. Labeling was seen in axons, demonstrating expression of myc-sAC directly within the axon as a result of axon-specific viral application. Green staining in (B) shows the outline of axons. No myc labeling was seen in mock-treated axons (C). The outline of the axons in (C) is shown in (D).
Figure 12C:
Figure 12B:
Figure 12D:

These studies reveal a role for intra-axonal mRNA translation in mediating communication between distal axons and the nucleus. CREB mRNA is localized to axons of DRG neurons and translated in response to NGF signaling. Axon-derived CREB is the source of the pCREB that appears in the nucleus following exposure of distal axons to NGF, and is required for the increase in CRE-dependent transcription seen upon stimulation of distal axons with NGF. Furthermore, neuronal survival elicited by NGF signaling at distal axons requires axon-derived CREB. These data indicate that the retrograde signal generated upon axonal application of NGF includes axonally synthesized CREB (FIG. 11). These findings identify a novel function for local translation involving the translation and retrograde trafficking of transcription factors from the axon to the neuronal nucleus. The regulation of local protein synthesis within axons adds to the previously described signaling pathways downstream of NGF/TrkA. NGF signaling is selective as it leads to the induction of the CREB mRNA translational reporter, but not the RhoA reporter, which is regulated by Sema3A4. This selectivity suggests the presence of sequence elements in the CREB 3'UTR that specifically confer NGF-responsiveness.

A common feature of many types of growth factor signaling pathways, including NGF signaling, is the occurrence of intracellular "signaling platforms" that function as localized signal transduction units (Hoeller et al., Curr Opin Cell Biol 17, 107-111 (2005)). NGF-mediated TrkA signaling can occur through TrkA at the plasma membrane as well as TrkA localized to endosomes that form upon internalization of NGF/TrkA complexes (Howe et al., Neuron 32, 801-814 (2001), Delcroix et al., Neuron 39, 69-84 (2003)). These distinct platforms are characterized by unique cohorts of proximally localized TrkA effectors (Howe et al., Neuron 32, 801-814 (2001), Delcroix et al., Neuron 39, 69-84 (2003)). Retrograde trafficking of TrkA signaling endosomes, containing both catalytically-active TrkA as well as specific TrkA effectors, is associated with an increase in pCREB levels in the nucleus in a Mek5 and Erk5-dependent pathway (Watson et al., Nature Neuroscience 4, 981-988 (2001)). However, whether CREB is similarly compartmentalized into an effector pool that is preferentially regulated by the signaling endosome has not previously been addressed. We find that CREB is found colocalized with pTrkA in axons: since both CREB and TrkA-signaling endosomes are retrogradely trafficked, the proximity of the pool of axonally-derived CREB may make it preferentially accessible to phosphorylation by TrkA effectors such as Erk5 (Watson et al., Nature Neuroscience 4, 981-988 (2001)). As TrkA kinase activity in the cell body is required for CREB phosphorylation (Riccio et al., Science 277, 1097-1100 (1997)), several models could explain how CREB phosphorylation is regulated: (1) CREB is not phosphorylated until it arrives in the cell body; (2) CREB is readily dephosphorylated, and TrkA activity is required to maintain CREB in a phosphorylated state when it arrives in the cell body; or (3) TrkA activity is required to inactivate a cell body phosphatase.

Transcriptional effects elicited by axonal signaling require that an axon-derived signal be conveyed to the cell body. An inherent requirement in this type of signaling is that the axon-derived signal must somehow be distinguished from what would presumably be a much larger amount of similar molecules in the cell body. The low basal level of pCREB in the nucleus of unstimulated neurons (Watson et al., Nature Neuroscience 4, 981-988 (2001)) may allow small increases in the amount of pCREB derived from the axon to result in a substantial fold elevation in pCREB-dependent transcriptional activity. These results indicate that axonally-synthesized CREB is capable of exerting transcriptional effects in the nucleus by serving as the source of the pCREB that appears in the nucleus following axonal application of NGF. Because the transcriptional effects of CREB are affected by its phosphorylation at sites other than Ser133 (Kornhauser et al., Neuron 34, 221-233 (2002); Johannessen et al., Cell Signal 16, 1211-1227 (2004)) as well as by protein-protein interactions (Johannessen et al., Cell Signal 16, 1211-1227 (2004)), axon-specific CREB modifications may also impart axonally-synthesized CREB with unique transcriptional effects that differ from cell body-localized CREB.

Several examples of transcription factors or transcriptional regulators localized to dendrites, and less frequently, developing axons have been described; these include CREB (Crino et al., Proceedings of the National Academy of Sciences of the United States of America 95, 2313-2318 (1998)) and NF-κB (Meffert et al., Nature Neuroscience 6, 1072-1078 (2003)) in dendrites, and nervy in axons (Terman & Kolodkin, Science 303, 1204-1207 (2004)). These transcription factors may have non-nuclear functions; for example, in axons, nervy acts as an adapter protein for signaling from Plexin receptors (Terman & Kolodkin, *Science* 303, 1204-1207 (2004)). In the case of dendritic NF-κB, a role for transcriptional regulation has been proposed (Meffert et al., *Nature Neuroscience* 6, 1072-1078 (2003); however, these studies have not been able to differentiate the role of the somatic and dendritic pool of NF-κB. Similarly, while it is clear that CREB can be synthesized in dendrites (Crino et al., *Proceedings of the National Academy of Sciences of the United States of America* 95, 2313-2318 (1998)), the inherent difficulties in selectively abolishing the dendritic CREB pool have prevented a thorough elucidation of the exact role of dendritically-synthesized CREB in neuronal signaling. By selectively abolishing axonal CREB mRNA, the data presented here supports a nuclear role for extrasomatic pools of CREB.

During development, axons encounter a variety of signals that affect multiple aspects of neuronal development, such as axonal elongation, branching, and pathfinding, as well as synaptogenesis and neuronal differentiation (Hodge et al., *Neuron* 55, 572-586 (2007), Allan et al., *Cell* 113, 73-86 (2003), Marques et al., *Development* 130, 5457-5470 (2003)). Increasing evidence suggests that many of these processes involve retrograde signals that affect gene transcription. Translation and retrograde trafficking of axonally-localized transcription factor mRNAs in response to target derived signaling molecules could therefore constitute a general mechanism by which signaling at growth cones can selectively and temporally regulate gene transcription during neuronal development.

In sum, these studies show that axons of developing mammalian neurons contain mRNA encoding the cAMP-responsive element (CRE)-binding protein (CREB). CREB is translated within axons in response to new growth factor (NGF) and is retrogradely trafficked to the cell body. In neurons that are selectively deficient in axonal CREB transcripts, increases in nuclear pCREB, CRE-mediated transcription, and neuronal survival elicited by axonal application of NGF are abolished, indicating a signaling function for axonally synthesized CREB. These studies identify a signaling role for axonally-derived CREB, and indicate that signal-dependent synthesis and retrograde trafficking of transcription factors enables specific transcriptional responses to signaling events at distal axons.

Example 2—Viral-Mediated Protein Expression in Axons

It is unclear whether protein translation occurs in the axons of the mature nervous. The synthetic capacity of the axon is considered to be low and may be insufficient to make meaningful or detectable quantitates of proteins. Furthermore, direct introduction of RNA into an axon is considered unlikely to be able to be translated since current thinking suggests that RNAs that are meant to be translated in axons are prepackaged into RNA granules bound to ribosomes in the cell body. The translational capacity of axons is thought to be very different from the cell body due to the absence of standard protein translational machinery such as golgi or endoplasmic reticulum. Other aspects of the translational capacity of axons, such as the ability to utilize an IRES sequence, are unknown. Therefore, current thinking is not consistent with the idea that direct RNA insertion into the axon would result in translation.

The following experiments were performed to determine whether axonal regeneration could be achieved by expressing proteins in axons that are linked to axonal growth. To express proteins in axons, RNA is transduced into the axoplasms using Sindbis, an alphavirus that has an RNA genome (Ehrengruber, *Molecular Neurobiology.* 26:183-201 (2002)). An internal ribosome entry site (IRES) was inserted into the RNA genome (Wu, *Nature.* 436:1020-1024 (2005)) allowing ribosomes to bind directly to the IRES and initiate translation of the RNA sequence downstream of the IRES.

Expression of Sindbis-IRES Viruses in Axons

More specifically, Sindbis viral sequences were modified by replacing the subgenomic promoter with an IRES (Sindbis-IRES) (Wu, *Nature.* 436:1020-1024 (2005)). A sequence encoding (myr-GFP) was placed downstream of the IRES sequence. Myristoylated GFP does not diffuse away from the site where it is translated (Aakalu, *Neuron.* 30:489-502 (2001)). Rat embryonic (E) day 14 neurons were grown in compartmentalized culturing devices (Campenot, *Dev Biol.* 93:13-21 (1982); Taylor, *Nature Methods.* 2:599-605 (2005)). Neurons were plated in a cell body compartment connected to an axonal compartment via micrometer-thick grooves. After four days in vitro (DIV), axons had crossed into an axonal compartment. Sindbis-IRES virus expressing myr-GFP was applied to the axonal compartment. As shown in above, myr-GFP was only detected in axons, not in cell bodies or axons within the cell body compartment. This demonstrates that the virus had infected the axons and the myr-GFP was translated within the axons. The virus was not retrogradely trafficked to the cell body, since this would result in myr-GFP in the cell body compartment, and possibly the axonal compartment.

Expression of Soluble Adenylyl Cyclase in Axons

Treatments that result in increased cAMP levels in axons result in increased axonal growth rates and reduce the sensitivity to myelin. Sindbis-IRES viruses expressing soluble adenylyl cyclase with a myc epitope tage (FIG. 12) was prepared. Adenylyl cyclase is a cAMP-generating enzyme (Chen, *Science.* 289:625-628 (2000)) that promotes axonal growth Wu, *Nat Neurosci.* 9:1257-1264 (2006). As shown in FIG. 12, this protein was also readily detectable in E14 DIV4 rat sensory neurons cultured in microfluidic culturing devices when Sindbis-IRES-myc-sAC was applied to the axonal compartment. As before, no significant labeling was seen in the cell bodies or axons that lie in the cell body compartment.

Expression of a Dominant Negative RhoA in "Mature" Regenerating Axons

Inhibition of RhoA can lead to improved axonal growth and reduced sensitivity to the effects of myelin. To determine if axons that are regenerating can be infected by Sindbis-IRES viruses, and if these viruses can lead to protein expression, sensory neuron ganglia were harvested from postnatal (P) animals that were six days old. Harvesting these ganglia results in transection of their axons. The explants were dissociated and the neurons were cultured in microfluidic culturing devices, as above. After four DIV, axons crossed into the axonal compartment, and were infected with Sindbis-IRES-RhoA DN, bearing a mutation that renders RhoA inactive. As seen in FIG. 13, myc immunoreactivity was detected throughout the axons in the axonal compartment. No labeling was seen under control uninfected conditions. Additionally, negligible labeling was seen in cell bodies or in axons in the cell body compartment. These data indicate that regenerating axons from mature neurons can express a heterologous protein using the Sindbis-IRES system.

To further validate that cell bodies were not labeled when Sindbis-IRES viruses were applied to axons, Sindbis-IRES-myc-Cherry was used. This construct allowed for the detection of the transgene as a fluorescent protein. As can be seen in FIG. 14, application of virus to the axons did not lead to cell body labeling, while application of the virus to the cell body led to robust labeling. This demonstrates that the virus acted exclusively within axons in order to increase protein levels in axons.

In sum, these results demonstrate a viral approach to selectively modify gene expression in distal axons allowing for the introduction of proteins in injured distal axons and providing a new avenue to promote axonal growth in cases of traumatic nerve injury or axonopathies.

CITED DOCUMENTS

1. Czaplinski, K. & Singer, R. H. Pathways for mRNA localization in the cytoplasm. *Trends Biochem Sci* 31, 687-693 (2006).
2. Piper, M. & Holt, C. RNA translation in axons. *Annual Review of Cell and Developmental Biology* 20, 505-523 (2004).
3. Bassell, G. J., Zhang, H., Byrd, A. L., Femino, A. M., Singer, R. H., Taneja, K. L., Lifshitz, L. M., Herman, I. M. & Kosik, K. S. Sorting of ß-actin mRNA and protein to neurites and growth cones in culture. *Journal of Neuroscience* 18, 251-265 (1998).
4. Wu, K., Hengst, U., Cox, L. J., Macosko, E. Z., Jeromin, A., Urquhart, E. R. & Jaffrey, S. R. Local translation of RhoA regulates growth cone collapse. *Nature* 436, 1020-1024 (2005).
5. Piper, M., Anderson, R., Dwivedy, A., Weinl, C., van Horck, F., Leung, K. M., Cogill, E. & Holt, C. Signaling mechanisms underlying Slit2-induced collapse of Xenopus retinal growth cones. *Neuron* 49, 215-228 (2006).
6. Haase, G., Dessaud, E., Garces, A., de Bovis, B., Birling, M., Filippi, P., Schmalbruch, H., Arber, S. & deLapeyriere, O. GDNF acts through PEAS to regulate cell body positioning and muscle innervation of specific motor neuron pools. *Neuron* 35, 893-905 (2002).
7. Zweifel, L. S., Kuruvilla, R. & Ginty, D. D. Functions and mechanisms of retrograde neurotrophin signalling. *Nature Reviews Neuroscience* 6, 615-625 (2005).
8. Patel, T. D., Kramer, I., Kucera, J., Niederkofler, V., Jessell, T. M., Arber, S. & Snider, W. D. Peripheral NT3 signaling is required for ETS protein expression and central patterning of proprioceptive sensory afferents. *Neuron* 38, 403-416 (2003).
9. Hodge, L. K., Klassen, M. P., Han, B. X., Yiu, G., Hurrell, J., Howell, A., Rousseau, G., Lemaigre, F., Tessier-Lavigne, M. & Wang, F. Retrograde BMP Signaling Regulates Trigeminal Sensory Neuron Identities and the Formation of Precise Face Maps. *Neuron* 55, 572-586 (2007).
10. Howe, C. L. & Mobley, W. C. Long-distance retrograde neurotrophic signaling. *Curr Opin Neurobiol* 15, 40-48 (2005).
11. Richter, J. D. & Sonenberg, N. Regulation of cap-dependent translation by eIF4E inhibitory proteins. *Nature* 433, 477-480 (2005).
12. Campenot, R. B. Local control of neurite development by nerve growth factor. *Proc Natl Acad Sci USA* 74, 4516-4519 (1977).
13. Lonze, B. E., Riccio, A., Cohen, S. & Ginty, D. D. Apoptosis, axonal growth defects, and degeneration of peripheral neurons in mice lacking CREB. *Neuron* 34, 371-385 (2002).
14. Tong, J. X., Vogelbaum, M. A., Drzymala, R. E. & Rich, K. M. Radiation-induced apoptosis in dorsal root ganglion neurons. *J Neurocytol* 26, 771-777 (1997).
15. Martin, D. P., Schmidt, R. E., DiStefano, P. S., Lowry, O. H., Carter, J. G. & Johnson, E. M., Jr. Inhibitors of protein synthesis and RNA synthesis prevent neuronal death caused by nerve growth factor deprivation. *J Cell Biol* 106, 829-844 (1988).
16. Wyllie, A. H., Morris, R. G., Smith, A. L. & Dunlop, D. Chromatin cleavage in apoptosis: association with condensed chromatin morphology and dependence on macromolecular synthesis. *Journal of Pathology* 142, 67-77 (1984).
17. Zheng, J. Q., Kelly, T. K., Chang, B., Ryazantsev, S., Rajasekaran, A. K., Martin, K. C. & Twiss, J. L. A functional role for intra-axonal protein synthesis during axonal regeneration from adult sensory neurons. *Journal of Neuroscience* 21, 9291-9303 (2001).
18. Tietjen, I., Rihel, J. M., Cao, Y., Koentges, G., Zakhary, L. & Dulac, C. Single-cell transcriptional analysis of neuronal progenitors. *Neuron* 38, 161-175 (2003).
19. Blendy, J. A., Kaestner, K. H., Schmid, W., Gass, P. & Schutz, G. Targeting of the CREB gene leads to up-regulation of a novel CREB mRNA isoform. *EMBO Journal* 15, 1098-1106 (1996).
20. Olink-Coux, M. & Hollenbeck, P. J. Localization and active transport of mRNA in axons of sympathetic neurons in culture. *Journal of Neuroscience* 16, 1346-1358 (1996).
21. Crino, P., Khodakhah, K., Becker, K., Ginsberg, S., Hemby, S. & Eberwine, J. Presence and phosphorylation of transcription factors in developing dendrites. *Proceedings of the National Academy of Sciences of the United States of America* 95, 2313-2318 (1998).
22. Aakalu, G., Smith, W. B., Nguyen, N., Jiang, C. & Schuman, E. M. Dynamic visualization of local protein synthesis in hippocampal neurons. *Neuron* 30, 489-502 (2001).
23. Jeromin, A., Yuan, L. L., Frick, A., Pfaffinger, P. & Johnston, D. A modified Sindbis vector for prolonged gene expression in neurons. *Journal of Neurophysiology* 90, 2741-2745 (2003).
24. Goldfarb, D. S., Corbett, A. H., Mason, D. A., Harreman, M. T. & Adam, S. A. Importin alpha: a multipurpose nuclear-transport receptor. *Trends in Cell Biology* 14, 505-514 (2004).
25. Hanz, S., Perlson, E., Willis, D., Zheng, J. Q., Massarwa, R., Huerta, J. J., Koltzenburg, M., Kohler, M., van-Minnen, J., Twiss, J. L. & Fainzilber, M. Axoplasmic importins enable retrograde injury signaling in lesioned nerve. *Neuron* 40, 1095-1104 (2003).
26. Waeber, G. & Habener, J. F. Nuclear translocation and DNA recognition signals colocalized within the bZIP domain of cyclic adenosine 3',5'-monophosphate response element-binding protein CREB. *Mol. Endocrinol.* 5, 1418-1430 (1991).
27. Gurskaya, N. G., Verkhusha, V. V., Shcheglov, A. S., Staroverov, D. B., Chepurnykh, T. V., Fradkov, A. F., Lukyanov, S. & Lukyanov, K. A. Monomeric green-to-red photoconvertible fluorescent protein activated by a visible blue light. *Nature Biotechnology* 24, 461-465 (2006).
28. Kislauskis, E. H., Zhu, X. & Singer, R. H. Sequences responsible for intracellular localization of beta-actin messenger RNA also affect cell phenotype. *Journal of Cell Biology* 127, 441-451 (1994).
29. Zhang, H. L., Eom, T., Oleynikov, Y., Shenoy, S. M., Liebelt, D. A., Dictenberg, J. B., Singer, R. H. & Bassell, G. J. Neurotrophin-induced transport of a beta-actin mRNP complex increases beta-actin levels and stimulates growth cone motility. *Neuron* 31, 261-275 (2001).

30. Brimijoin, S. & Helland, L. Rapid retrograde transport of dopamine-beta-hydroxylase as examined by the stop-flow technique. *Brain Research* 102, 217-228 (1976).
31. Ure, D. R. & Campenot, R. B. Retrograde transport and steady-state distribution of 125I-nerve growth factor in rat sympathetic neurons in compartmented cultures. *Journal of Neuroscience* 17, 1282-1290 (1997).
32. Martenson, C. H., Odom, A., Sheetz, M. P. & Graham, D. G. The effect of acrylamide and other sulfhydryl alkylators on the ability of dynein and kinesin to translocate microtubules in vitro. *Toxicol Appl Pharmacol* 133, 73-81 (1995).
33. Watson, F. L., Heerssen, H. M., Bhattacharyya, A., Klesse, L., Lin, M. Z. & Segal, R. A. Neurotrophins use the Erk5 pathway to mediate a retrograde survival response. *Nature Neuroscience* 4, 981-988 (2001).
34. Cui, B., Wu, C., Chen, L., Ramirez, A., Bearer, E. L., Li, W. P., Mobley, W. C. & Chu, S. One at a time, live tracking of NGF axonal transport using quantum dots. *Proc Natl Acad Sci USA* 104, 13666-13671 (2007).
35. Hengst, U., Cox, L. J., Macosko, E. Z. & Jaffrey, S. R. Functional and selective RNA interference machinery in axonal growth cones. *J. Neurosci.* 26, 5727-5732. (2006).
36. Kuruvilla, R., Zweifel, L. S., Glebova, N. O., Lonze, B. E., Valdez, G., Ye, H. & Ginty, D. D. A neurotrophin signaling cascade coordinates sympathetic neuron development through differential control of TrkA trafficking and retrograde signaling. *Cell* 118, 243-255 (2004).
37. Riccio, A., Pierchala, B. A., Ciarallo, C. L. & Ginty, D. D. An NGF-TrkA-mediated retrograde signal to transcription factor CREB in sympathetic neurons. *Science* 277, 1097-1100 (1997).
38. Watson, F. L., Heerssen, H. M., Moheban, D. B., Lin, M. Z., Sauvageot, C. M., Bhattacharyya, A., Pomeroy, S. L. & Segal, R. A. Rapid nuclear responses to target-derived neurotrophins require retrograde transport of ligand-receptor complex. *J. Neurosci.* 19, 7889-7900 (1999).
39. Hoeller, D., Volarevic, S. & Dikic, I. Compartmentalization of growth factor receptor signalling. *Curr Opin Cell Biol* 17, 107-111 (2005).
40. Howe, C. L., Valletta, J. S., Rusnak, A. S. & Mobley, W. C. NGF signaling from clathrin-coated vesicles: evidence that signaling endosomes serve as a platform for the Ras-MAPK pathway. *Neuron* 32, 801-814 (2001).
41. Delcroix, J. D., Valletta, J. S., Wu, C., Hunt, S. J., Kowal, A. S. & Mobley, W. C. NGF signaling in sensory neurons: evidence that early endosomes carry NGF retrograde signals. *Neuron* 39, 69-84 (2003).
42. Kornhauser, J. M., Cowan, C. W., Shaywitz, A. J., Dolmetsch, R. E., Griffith, E. C., Hu, L. S., Haddad, C., Xia, Z. & Greenberg, M. E. CREB transcriptional activity in neurons is regulated by multiple, calcium-specific phosphorylation events. *Neuron* 34, 221-233 (2002).
43. Johannessen, M., Delghandi, M. P. & Moens, U. What turns CREB on? *Cell Signal* 16, 1211-1227 (2004).
44. Meffert, M. K., Chang, J. M., Wiltgen, B. J., Fanselow, M. S. & Baltimore, D. NF-kappa B functions in synaptic signaling and behavior. *Nature Neuroscience* 6, 1072-1078 (2003).
45. Terman, J. R. & Kolodkin, A. L. Nervy links protein kinase a to plexin-mediated semaphoring repulsion. *Science* 303, 1204-1207 (2004).
46. Allan, D. W., St Pierre, S. E., Miguel-Aliaga, I. & Thor, S. Specification of neuropeptide cell identity by the integration of retrograde BMP signaling and a combinatorial transcription factor code. *Cell* 113, 73-86 (2003).
47. Marques, G., Haerry, T. E., Crotty, M. L., Xue, M., Zhang, B. & O'Connor, M. B. Retrograde Gbb signaling through the Bmp type 2 receptor wishful thinking regulates systemic FMRFa expression in Drosophila. *Development* 130, 5457-5470 (2003).
48. Higuchi, H., Yamashita, T., Yoshikawa, H. & Tohyama, M. Functional inhibition of the p75 receptor using a small interfering RNA. *Biochemical & Biophysical Research Communications* 301, 804-809 (2003).
49. Bloodgood, B. L. & Sabatini, B. L. Neuronal activity regulates diffusion across the neck of dendritic spines. *Science* 310, 866-869 (2005).
50. Donnerer, J. Regeneration of primary sensory neurons. *Pharmacology.* 67:169-181, 2003.
51. Fawcett, J. W., Keynes, R. J. Peripheral nerve regeneration. *Annu Rev Neurosci.* 13:43-60, 1990.
52. Filbin, M. T. Myelin-associated inhibitors of axonal regeneration in the adult mammalian CNS. *Nature Reviews Neuroscience.* 4:703-713, 2003.
53. Gallo, G., Letourneau, P. C. Regulation of growth cone actin filaments by guidance cues. *Journal of Neurobiology.* 58:92-102, 2004.
54. Hengst, U., Jaffrey, S. R. Function and translational regulation of mRNA in developing axons. *Semin Cell Dev Biol.* 18:209-215, 2007.
55. Verma, P., Chierzi, S., Codd, A. M., Campbell, D. S., Meyer, R. L., Holt, C. E., Fawcett, J. W. Axonal protein synthesis and degradation are necessary for efficient growth cone regeneration. *Journal of Neuroscience.* 25:331-342, 2005.
56. Fournier, A. E., Takizawa, B. T., Strittmatter, S. M. Rho kinase inhibition enhances axonal regeneration in the injured CNS. *Journal of Neuroscience.* 23:1416-1423, 2003.
57. Chan, C. C., Khodarahmi, K., Liu, J., Sutherland, D., Oschipok, L. W., Steeves, J. D., Tetzlaff, W. Dose-dependent beneficial and detrimental effects of ROCK inhibitor Y27632 on axonal sprouting and functional recovery after rat spinal cord injury. *Exp Neurol.* 196:352-364, 2005.
58. Chan, C. C., Wong, A. K., Liu, J., Steeves, J. D., Tetzlaff, W. ROCK inhibition with Y27632 activates astrocytes and increases their expression of neurite growth-inhibitory chondroitin sulfate proteoglycans. *Glia.* 55:369-384, 2007.
59. Qiu, J., Cai, D., Filbin, M. T. A role for cAMP in regeneration during development and after injury. *Progress in Brain Research.* 137:381-387, 2002.
60. Pearse, D. D., Pereira, F. C., Marcillo, A. E., Bates, M. L., Berrocal, Y. A., Filbin, M. T., Bunge, M. B. cAMP and Schwann cells promote axonal growth and functional recovery after spinal cord injury. *Nat Med.* 10:610-616, 2004.
61. Lundstrom, K. Alphavirus vectors as tools in cancer gene therapy. *Technology in Cancer Research & Treatment.* 1:83-88, 2002.
62. Fleming, J., Ginn, S. L., Weinberger, R. P., Trahair, T. N., Smythe, J. A., Alexander, I. E. Adeno-associated virus and lentivirus vectors mediate efficient and sustained transduction of cultured mouse and human dorsal root ganglia sensory neurons. *Human Gene Therapy.* 12:77-86, 2001.
63. Willis, D., Li, K. W., Zheng, J. Q., Chang, J. H., Smit, A., Kelly, T., Merianda, T. T., Sylvester, J., van Minnen, J., Twiss, J. L. Differential transport and local translation of cytoskeletal, injury-response, and neurodegeneration protein mRNAs in axons. *Journal of Neuroscience.* 25:778-791, 2005.

64. Zheng, J. Q., Kelly, T. K., Chang, B., Ryazantsev, S., Rajasekaran, A. K., Martin, K. C., Twiss, J. L. A functional role for intra-axonal protein synthesis during axonal regeneration from adult sensory neurons. *Journal of Neuroscience.* 21:9291-9303, 2001.
65. Ehrengruber, M. U. Alphaviral vectors for gene transfer into neurons. *Molecular Neurobiology.* 26:183-201, 2002.
66. Wu, K. Y., Hengst, U., Cox, L. J., Macosko, E. Z., Jeromin, A., Urquhart, E. R., Jaffrey, S. R. Local translation of RhoA regulates growth cone collapse. *Nature.* 436:1020-1024, 2005.
67. Kiebler, M. A., Bassell, G. J. Neuronal RNA granules: movers and makers. *Neuron.* 51:685-690, 2006.
68. Huttelmaier, S., Zenklusen, D., Lederer, M., Dictenberg, J., Lorenz, M., Meng, X., Bassell, G. J., Condeelis, J., Singer, R. H. Spatial regulation of beta-actin translation by Src-dependent phosphorylation of ZBP1. *Nature.* 438: 512-515, 2005.
69. Aakalu, G., Smith, W. B., Nguyen, N., Jiang, C., Schuman, E. M. Dynamic visualization of local protein synthesis in hippocampal neurons. *Neuron.* 30:489-502, 2001.
70. Campenot, R. B. Development of sympathetic neurons in compartmentalized cultures. II. Local control of neurite survival by nerve growth factor. *Dev Biol.* 93:13-21, 1982.
71. Taylor, A. M., Blurton-Jones, M., Rhee, S. W., Cribbs, D. H., Cotman, C. W., Jeon, N. L. A microfluidic culture platform for CNS axonal injury, regeneration and transport. *Nature Methods.* 2:599-605, 2005.
72. Cox, L. J., Hengst, U., Gurskaya, N. G., Lukyanov, K. A., Jaffrey, S. R. Intra-axonal translation and retrograde trafficking of CREB promotes neuronal survival. *Nature Cell Biology.* 10:149-159, 2008.
73. Chen, Y., Cann, M. J., Litvin, T. N., Iourgenko, V., Sinclair, M. L., Levin, L. R., Buck, J. Soluble adenylyl cyclase as an evolutionarily conserved bicarbonate sensor. *Science.* 289:625-628, 2000.
74. Wu, K. Y., Zippin, J. H., Huron, D. R., Kamenetsky, M., Hengst, U., Buck, J., Levin, L. R., Jaffrey, S. R. Soluble adenylyl cyclase is required for netrin-1 signaling in nerve growth cones. *Nat Neurosci.* 9:1257-1264, 2006.
75. Aakalu, G., Smith, W. B., Nguyen, N., Jiang, C., and Schuman, E. M. (2001). Dynamic visualization of local protein synthesis in hippocampal neurons. *Neuron* 30, 489-502.
76. Brittis, P. A., Lu, Q., and Flanagan, J. G. (2002). Axonal protein synthesis provides a mechanism for localized regulation at an intermediate target. *Cell* 110, 223-235.
77. Ehrengruber, M. U. (2002). Alphaviral vectors for gene transfer into neurons. *Mol. Neurobiol.* 26, 183-201.
78. Jeromin, A., Yuan, L. L., Frick, A., Pfaffinger, P., and Johnston, D. (2003). A modified Sindbis vector for prolonged gene expression in neurons. J. Neurophysiol. 90, 2741-2745.
79. Osten, P., Khatri, L., Perez, J. L., Kohr, G., Giese, G., Daly, C., Schulz, T. W., Wensky, A., Lee, L. M., and Ziff, E. B. (2000). Mutagenesis reveals a role for ABP/GRIP binding to GluR2 in synaptic surface accumulation of the AMPA receptor. Neuron 27, 313-325.
80. Raju, R., Hajjou, M., Hill, K. R., Botta, V., and Botta, S. (1999). In vivo addition of poly(A) tail and AU-rich sequences to the 3' terminus of the Sindbis virus RNA genome: a novel 3'-end repair pathway. J. Virol. 73, 2410-2419.
81. Peters, *The fine structure of the nervous system.* 1st ed. New York: Harper & Row; 1970
82. Willis, *Curr Opin Neurobiol.* 16:111-8 (2006)
83. Kiebler, M. A., Bassell, G. J. Neuronal RNA granules: movers and makers. *Neuron.* 51:685-690, 2006.
84. Hengst, U., Jaffrey, S. R. Function and translational regulation of mRNA in developing axons. *Semin Cell Dev Biol.* 18:209-215, 2007.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for translating a polypeptide in the axon of a mammalian neuron comprising administering a recombinant RNA molecule encoding a cyclic AMP-response element-binding (CREB) protein to the neuron or the axon, and administering a recombinant alphavirus exclusively to the axon of the neuron, wherein the recombinant alphavirus is capable of infecting the axon of a mammalian neuron, wherein the alphavirus comprises a single-stranded RNA comprising:
   (a) a mammalian translation initiation element comprising a 5'CAP or an internal ribosome entry site (IRES); and
   (b) a polypeptide coding sequence operably-linked to the mammalian translation initiation element, wherein the coding sequence of the single-stranded RNA is locally translated within the axon to generate a polypeptide within the axon of a mammalian neuron, and the polypeptide modulates the growth or function of an axon.

2. The method of claim 1, wherein the polypeptide promotes the growth of an injured axon.

3. The method of claim 1, wherein the polypeptide is a kinase or a transcription factor.

4. The method of claim 3, wherein the kinase is a src kinase.

5. The method of claim 3, wherein the transcription factor is nervy.

6. The method of claim 1, wherein the polypeptide is a dominant-negative RhoA mutant polypeptide, a cAMP-producing enzyme, glutamic acid decarboxylase, human proenkephalin, an inhibitor of a dominant-negative Vps24, an intestinal peptide (VIP), brain-derived neurotrophic factor (BDNF), neurotrophin-3 (NT-3), glial-derived neurotropic factor (GDNF), GAP 43, CAP23, a myc-tagged soluble adenylyl cyclase, a green fluorescent protein (GFP), a myristoylated GFP, a destabilized enhanced GFP (dEGFP), a myristoylated dEGFP, Cherry, or a myc-tagged Cherry.

7. The method of claim 6, wherein the dominant-negative RhoA mutant polypeptide is N19-RhoA polypeptide.

8. The method of claim 6, wherein the cAMP-producing enzyme is a soluble adenylyl cyclase.

9. The method of claim 1, further comprising locally applying to the axon a brain-derived neurotrophic factor (BDNF), neurotrophin-3 (NT-3), glial-derived neurotropic factor (GDNF), nerve growth factor or a combination thereof.

10. The method of claim 1, wherein the axon is that of a sensory neuron, an upper motor neuron or a dorsal root ganglion.

11. The method of claim 10, wherein the sensory neuron is a peripheral sensory neuron.

12. The method of claim 1, wherein the CREB protein and the alphavirus are locally applied to the axon at a site of injury.

13. The method of claim 1, wherein the virus is an attenuated form of the alphavirus.

14. The method of claim 1, wherein the alphavirus is a Sindbis virus or a Semliki forest virus.

15. The method of claim 1, wherein the single-stranded RNA further comprises a poly-adenylyl tail.

16. The method of claim 1, wherein the IRES is a eukaryotic sequence.

17. The method of claim 1, wherein the IRES is an encephalomyocarditis sequence, or a Semliki forest viral sequence.

18. The method of claim 1, wherein the IRES comprises the sequence of any one of SEQ ID NO: 29-35.

19. The method of claim 1, wherein the mammalian translation initiation element is an internal ribosome entry site (IRES) that replaces a subgenomic promoter in the isolated nucleic acid.

* * * * *

UNITED STATES PATENT AND TRADEMARK OFFICE
CERTIFICATE OF CORRECTION

| | |
|---|---|
| PATENT NO. | : 12,103,952 B2 |
| APPLICATION NO. | : 17/168774 |
| DATED | : October 1, 2024 |
| INVENTOR(S) | : Jaffrey et al. |

It is certified that error appears in the above-identified patent and that said Letters Patent is hereby corrected as shown below:

On the Title Page

In Column 2, under "Other Publications", Line 46, delete "Action Action" and insert --Action-- therefor On page 2, in Column 2, under "Other Publications", Line 5, delete "ploly(A)" and insert --poly(A)-- therefor In the Drawings Sheet 1 of 28, Fig. 1E6, delete "CELLBODY" and insert --CELL BODY-- therefor In the Specification In Column 3, Line 16, delete "soluable" and insert --soluble-- therefor In Column 5, Line 26, delete "(0)" and insert --(O)-- therefor In Column 6, Line 24, delete "Ong/ml" and insert --0 ng/ml-- therefor In Column 7, Line 6, delete "myr-dEGFP$_{P\ 3'RhoA}$" and insert --myr-dEGFP$_{3'RhoA}$-- therefor In Column 12, Line 44, delete "DAPS;" and insert --DAP5;-- therefor In Column 24, Line 22, delete "catttaaaa agttgctagtt" and insert --catttaaaaa gttgctagtt-- therefor In Column 39, Line 29, delete "tottttatct" and insert --tcttttatct-- therefor Signed and Sealed this
Thirtieth Day of December, 2025

John A. Squires
*Director of the United States Patent and Trademark Office*

CERTIFICATE OF CORRECTION (continued)
U.S. Pat. No. 12,103,952 B2

In Column 41, Line 8, delete "tccctttctt" and insert --tccctttct-- therefor

In Column 43, Line 2, delete "tcatttttt" and insert --tcattttgt-- therefor

In Column 43, Line 29, delete "tcagatcttt" and insert --tcagatcttt-- therefor

In Column 50, Line 19, delete "tcgattaatt" and insert --tcgattaatt-- therefor

In Column 51, Line 1, delete "tggtttttt" and insert --tggtttgttt-- therefor

In Column 51, Line 25, delete "catcaggcta" and insert --catcaggcta-- therefor

In Column 51, Line 25, delete "gcggaccctg" and insert --gcggaccctg-- therefor

In Column 51, Line 25, delete "gcttcgacac" and insert --gcttcgacac-- therefor

In Column 53, Line 6, delete "tcggagcagc" and insert --tcggagcagc-- therefor

In Column 55, Line 21, delete "tcaagtctgt" and insert --tcaagtctgt-- therefor

In Column 55, Line 21, delete "ccagccgga" and insert --cgcagccgga-- therefor

In Column 55, Line 33, delete "tttttaatcc" and insert --tgtttaatcc-- therefor

In Column 55, Line 36, delete "catctacagc" and insert --catctacagc-- therefor

In Column 57, Line 14, delete "gcgaactact" and insert --gcgaactact-- therefor

In Column 57, Line 23, delete "tcccattgca" and insert --tcccattgca-- therefor

In Column 57, Line 27, delete "tccaaacatt" and insert --tccaaacatt-- therefor

In Column 57, Line 39, delete "tcccagccga" and insert --tcccagccga-- therefor

In Column 65, Line 39, delete "2011M" and insert --20 μM-- therefor

In Column 69, Line 8, delete "MgCl2," and insert --$MgCl_2$,-- therefor

In Column 79, Line 52, delete "quantitates" and insert --quantities-- therefor

In Column 81, Line 36, delete "PEAS" and insert --PEA3-- therefor

```
                           SEQUENCE LISTING

<160> NUMBER OF SEQ ID NOS: 67

<210> SEQ ID NO 1
<211> LENGTH: 21
<212> TYPE: RNA
<213> ORGANISM: Artificial Sequence
<220> FEATURE:
<223> OTHER INFORMATION: a synthetic oligonucleotide

<400> SEQUENCE: 1
uagcgacuaa acacaucaau u                                              21

<210> SEQ ID NO 2
<211> LENGTH: 21
<212> TYPE: RNA
<213> ORGANISM: Artificial Sequence
<220> FEATURE:
<223> OTHER INFORMATION: a synthetic oligonucleotide

<400> SEQUENCE: 2
gguucgucua augaagaacu u                                              21

<210> SEQ ID NO 3
<211> LENGTH: 21
<212> TYPE: RNA
<213> ORGANISM: Artificial Sequence
<220> FEATURE:
<223> OTHER INFORMATION: a synthetic oligonucleotide

<400> SEQUENCE: 3
ggagucugug gauaguguau u                                              21

<210> SEQ ID NO 4
<211> LENGTH: 24
<212> TYPE: DNA
<213> ORGANISM: Rattus norvegicus

<400> SEQUENCE: 4
ccattgaaca cggcattgtc acca                                           24

<210> SEQ ID NO 5
<211> LENGTH: 24
<212> TYPE: DNA
<213> ORGANISM: Rattus norvegicus

<400> SEQUENCE: 5
agggcaacat agcacagctt ctct                                           24

<210> SEQ ID NO 6
<211> LENGTH: 24
<212> TYPE: DNA
<213> ORGANISM: Rattus norvegicus

<400> SEQUENCE: 6
acaaaccatg cccgttgcta ttcc                                           24

<210> SEQ ID NO 7
<211> LENGTH: 24
<212> TYPE: DNA
<213> ORGANISM: Rattus norvegicus
```

```
<400> SEQUENCE: 7
gctgtttcag ctgtgccact tcat                                          24

<210> SEQ ID NO 8
<211> LENGTH: 24
<212> TYPE: DNA
<213> ORGANISM: Rattus norvegicus

<400> SEQUENCE: 8
tgccacatta gcccaggtat ccat                                          24

<210> SEQ ID NO 9
<211> LENGTH: 24
<212> TYPE: DNA
<213> ORGANISM: Rattus norvegicus

<400> SEQUENCE: 9
tgtacatcac cagaggcagc ttga                                          24

<210> SEQ ID NO 10
<211> LENGTH: 24
<212> TYPE: DNA
<213> ORGANISM: Rattus norvegicus

<400> SEQUENCE: 10
tgccacatta gcccaggtat ccat                                          24

<210> SEQ ID NO 11
<211> LENGTH: 24
<212> TYPE: DNA
<213> ORGANISM: Rattus norvegicus

<400> SEQUENCE: 11
tgttagccag ctgtattgct cctc                                          24

<210> SEQ ID NO 12
<211> LENGTH: 24
<212> TYPE: DNA
<213> ORGANISM: Rattus norvegicus

<400> SEQUENCE: 12
tacacaagat ggactgggtt gcga                                          24

<210> SEQ ID NO 13
<211> LENGTH: 24
<212> TYPE: DNA
<213> ORGANISM: Rattus norvegicus

<400> SEQUENCE: 13
acactgggta ggacacccaa acaa                                          24

<210> SEQ ID NO 14
<211> LENGTH: 24
<212> TYPE: DNA
<213> ORGANISM: Rattus norvegicus

<400> SEQUENCE: 14
tctgctgcag cttctgagag aaca                                          24

<210> SEQ ID NO 15
<211> LENGTH: 24
<212> TYPE: DNA
<213> ORGANISM: Rattus norvegicus
```

```
<400> SEQUENCE: 15
cgcatgtatt cattccggct gctt                                        24

<210> SEQ ID NO 16
<211> LENGTH: 24
<212> TYPE: DNA
<213> ORGANISM: Rattus norvegicus

<400> SEQUENCE: 16
agctttgaaa cccagttgtg ccag                                        24

<210> SEQ ID NO 17
<211> LENGTH: 24
<212> TYPE: DNA
<213> ORGANISM: Rattus norvegicus

<400> SEQUENCE: 17
tcttcgtgta gggctcaaca gcat                                        24

<210> SEQ ID NO 18
<211> LENGTH: 60
<212> TYPE: DNA
<213> ORGANISM: Artificial Sequence
<220> FEATURE:
<223> OTHER INFORMATION: a synthetic oligonucleotide

<400> SEQUENCE: 18
attggatcca ggccgctctg gacaaaatat gaattctttt tttttttttt tttttttttt    60

<210> SEQ ID NO 19
<211> LENGTH: 36
<212> TYPE: DNA
<213> ORGANISM: Artificial Sequence
<220> FEATURE:
<223> OTHER INFORMATION: a synthetic oligonucleotide

<400> SEQUENCE: 19
attggatcca ggccgctctg gacaaaatat gaattc                           36

<210> SEQ ID NO 20
<211> LENGTH: 50
<212> TYPE: DNA
<213> ORGANISM: Artificial Sequence
<220> FEATURE:
<223> OTHER INFORMATION: a synthetic oligonucleotide

<400> SEQUENCE: 20
tgtacgtctc gccttgcaac tcgtactgtg aggtagtcgc gcgacagtgc              50

<210> SEQ ID NO 21
<211> LENGTH: 50
<212> TYPE: DNA
<213> ORGANISM: Rattus norvegicus

<400> SEQUENCE: 21
gtacctgacg gccgaaatcc tggagcttgc ggctaatgcg gcgagggaca              50

<210> SEQ ID NO 22
<211> LENGTH: 50
<212> TYPE: DNA
<213> ORGANISM: Rattus norvegicus
```

```
<400> SEQUENCE: 22
ctcagccggg tactaccatt ctacaatatg cacagaccac tgatggacag          50

<210> SEQ ID NO 23
<211> LENGTH: 50
<212> TYPE: DNA
<213> ORGANISM: Rattus norvegicus

<400> SEQUENCE: 23
cggcccagcc atcagttatt cagtctccac aagtccaaac agttcagtct          50

<210> SEQ ID NO 24
<211> LENGTH: 50
<212> TYPE: DNA
<213> ORGANISM: Rattus norvegicus

<400> SEQUENCE: 24
ctgtccatca gtggtctgtg catattgtag aatggtagta cccggctgag          50

<210> SEQ ID NO 25
<211> LENGTH: 50
<212> TYPE: DNA
<213> ORGANISM: Rattus norvegicus

<400> SEQUENCE: 25
agactgaact gtttggactt gtggagactg aataactgat ggctgggccg          50

<210> SEQ ID NO 26
<211> LENGTH: 50
<212> TYPE: DNA
<213> ORGANISM: Rattus norvegicus

<400> SEQUENCE: 26
gactgtagat tgcttctcta gtgctccgta agaacacaaa gcagggaggg          50

<210> SEQ ID NO 27
<211> LENGTH: 50
<212> TYPE: DNA
<213> ORGANISM: Rattus norvegicus

<400> SEQUENCE: 27
ccctaatgct ggccctgatg gtcttattcc atggacaagg ttctgtaagg          50

<210> SEQ ID NO 28
<211> LENGTH: 49
<212> TYPE: DNA
<213> ORGANISM: Rattus norvegicus

<400> SEQUENCE: 28
gtatgcctct ggtcgtacca ctggcattgt gatggactcc ggagacggg           49

<210> SEQ ID NO 29
<211> LENGTH: 585
<212> TYPE: DNA
<213> ORGANISM: Artificial Sequence
<220> FEATURE:
<223> OTHER INFORMATION: a synthetic oligonucleotide

<400> SEQUENCE: 29
gcccctctcc ctcccccccc cctaacgtta ctggccgaag ccgcttggaa taaggccggt    60
gtgcgtttgt ctatatgtta ttttccacca tattgccgtc ttttggcaat gtgagggccc   120
```

```
ggaaacctgg ccctgtcttc ttgacgagca ttcctagggg tctttcccct ctcgccaaag      180
gaatgcaagg tctgttgaat gtcgtgaagg aagcagttcc tctggaagct tcttgaagac      240
aaacaacgtc tgtagcgacc cttttgcagg cagcggaacc cccacctggc gacaggtgcc      300
tctgcggcca aaagccacgt gtataagata cacctgcaaa ggcggcacaa ccccagtgcc      360
acgttgtgag ttggatagtt gtggaaagag tcaaatggct ctcctcaagc gtattcaaca      420
aggggctgaa ggatgcccag aaggtacccc attgtatggg atctgatctg ggcctcggt       480 gcacatgctt tacatgtgtt tagtcgaggt taaaaaaacg tctaggcccc ccgaaccacg       540
gggacgtggt tttcctttga aaaacacgat gataagcttg ccaca                     585
```

```
<210> SEQ ID NO 30
<211> LENGTH: 655
<212> TYPE: DNA
<213> ORGANISM: Hepatitis A virus

<400> SEQUENCE: 30
gtttgcctag gctataggct atttctcccc ttccctttc cctgttttgt gtaaatatta       60
attcctgcag gttcagggtt cttaatctg tttctctata agaacactca ttttcacgct       120
ttctgtctgc tttcttccag ggctctcccc ttgccctagg ctctgccgt tgcgccggc        180 ggggtcaact ccatgattag catggagctg taggagtcta aattggggac gcagatgttt      240
gggacgtcac cttgcagtat taacttggct ctcatgaagc tctttgatct tccacaagag      300
gtaggctacg ggtgaaacct cttaagctag tacttctatg aagagatgct ttggataggg      360
taacagcggc ggatattggt gagttgttaa gacaaaaacc tttcaacgcc ggaggactgg      420
ctctcatcca gtggatgcat tgagtggatt gtttgtcagg gctgtctcta ggcttaatct      480
cagacctctc tgtgcttagg gcaaacatta cttggcctta aatgggattc tgtgagaggg      540
gatccctcca ttgatagctg gactttttctt tggggcctta ggtggtgttt gcctctgagg     600
tactcagggg catttaggtt tttcctcact ctcaaataac tatgaatatg tctag          655
```

```
<210> SEQ ID NO 31
<211> LENGTH: 693
<212> TYPE: DNA
<213> ORGANISM: Human T-cell lymphotropic virus 1

<400> SEQUENCE: 31
ggggagttag agcctcccag tgaaaaacat ttccgcgaaa cagaagtctg aaaaggtcag      60
ggcccagact aaggctctga cgtctccccc cggagggaca gctcagcacc ggctcaggct      120
aggccctgac gtgtccccct gaagacaaat cataagctca gacctccggg aagccaccgg      180
aaccacccat ttcctcccca tgtttgtcga gccgccctca ggcgttgacg acaacccctc      240
acctcaaaaa acttttcatg gcacgcatat ggctgaataa actaacagga gtctataaaa      300
gcgtggagac agttcaggag ggggctcgca tctctccttc acgcgcccgc cgccctacct      360
gaggccgcca tccacgccgg ttgagtcgcg ttctgccgcc tcccgcctgt ggtgcctcct      420
gaactgcgtc cgccgtctag gtaagtttag agctcaggtc gagaccgggc ctttgtccgg      480
cgctcccttg gagcctacct agactcagcc ggctctccac gctttgcctg accctgcttg      540
ctcaactctg cgtctttgtt tcgttttctg ttctgcgccg ctacagatcg aaagttccac      600 cccttttccct ttcattcacg actgactgcc ggcttggccc acggccaagt accggcgact     660
ccgttggctc ggagccagcg acagcccatt cta                                  693
```

```
<210> SEQ ID NO 32
<211> LENGTH: 373
<212> TYPE: DNA
<213> ORGANISM: Classical swine fever virus - C

<400> SEQUENCE: 32
gtatacgagg ttagttcatt ctcgtataca cgattggaca aatcaaaatt ataatttggt      60
tcagggcctc cctccagcga cggccgaact gggctagcca tgcccatagt aggactagca     120
aaacggaggg actagccata gtggcgagct ccctgggtgg tctaagtcct gagtacagga     180
cagtcgtcag tagttcgacg tgagcagaag cccacctcga gatgctacgt ggacgagggc     240
atgccaagac acaccttaac cctagcgggg gtcgctaggg tgaaatcaca ccacgtgatg     300
ggagtacgac ctgatagggc gctgcagagg cccactatta ggctagtata aaaatctctg     360
ctgtacatgg cac                                                        373

<210> SEQ ID NO 33
<211> LENGTH: 881
<212> TYPE: DNA
<213> ORGANISM: Equine rhinitis A virus

<400> SEQUENCE: 33
ttaattaaaa gttgaacctg tagcgtcagt aaaacgcagt aaccgcaagc aattgcctgt      60
agcgtcagta aaacgcaata cacaagattt gagcctgtag cgtcagtaaa acgctgcaac     120
cacaagctat tgactgtagc gtcagtaaaa cgcaaacatt cttgtggcgc tcgcgtagcg     180
ctcaagtgca gagcttcccg gctttaaggg ttactgctcg taatgagagc acatgacatt     240
ttgccaagat ttcctagcaa ttgtcacggg agagaggagc ccgttctcgg gcacttttct     300
ctcaaacaat gttggcgcgc tcggcgcgc  cccccttttt tcagccccct gtcattgact     360
ggtcgaaggc gctcgcaata agactggtcg ttgcttggct tttctattgt ttcaggcttt     420
agcgcgccct tgcgcggcgg gccgtcaagc ccgtgtgctg tacagcacca ggtaaccgga     480
cagcggcttg ctggattttc ccggtgccat tgctctggat ggtgtcacca agctggcaga     540
tgcggagtga accttacgaa gcgacacacc tgtggtagcg ctgcccagaa gggagcggag     600 ctccccgcc gcgaggcggt cctctctggc caaaagccca gcgttaatag cgccttctgg      660
gatgcaggaa ccccacctgc caggtgtgaa gtggactaag tggatctcca atttggcctg     720
ttctgaacta caccatctac tgctgtgaag aatgtcctga aggcaagctg gttacagccc     780
tgatcaggag ccccgctcgt gactctcgat cgacgcgggg tcaaaaactg tctaagcagc     840
agcagaaacg cgggagcgtt tcttttttcct tatttgtttc a                        881

<210> SEQ ID NO 34
<211> LENGTH: 410
<212> TYPE: DNA
<213> ORGANISM: Homo sapiens

<400> SEQUENCE: 34
caggatcccc ctaattccag cgagaggcag agggagcgag cgggcggccg gctagggtgg      60
aagagccggg cgagcagagc tgcgctgcgg gcgtcctggg aagggagatc cggagcgaat     120
agggggcttc gcctctggcc cagccctccc gctgatcccc cagccagcgg tccgcaaccc     180
ttgccgcatc cacgaaactt tgcccatagc agcgggcggg cactttgcac tggaacttac     240
aacacccgag caaggacgcg actctcccga cgcggggagg ctattctgcc catttgggga     300
```

```
cacttccccg ccgctgccag gacccgcttc tctgaaaggc tctccttgca gctgcttaga    360
cgctggattt ttttcgggta gtggaaaacc agcagcctcc cgcgaccatg              410
```

<210> SEQ ID NO 35
<211> LENGTH: 819
<212> TYPE: DNA
<213> ORGANISM: Bovine enterovirus

<400> SEQUENCE: 35

```
ttaaaacagc ctgggggttg tacccacccc tggggcccac gtggcgctag tactctggtt     60
cgttagaacc tttgtacgcc tgttttcccc tccttaaaca aattaagatc tctgccaatg    120
tggggagtag tccgactccg caccgatacg tcgcaccagt agaccggttc gcttaggacc    180
cttctacgga ttggtatgag ttccccaccc cgtaacttag aagtactagc aaaaccgacc    240
aataggagcg tggcacccag ctgcgttaag gtcaagcact tctgtctccc cggccagaaa    300
tggtcgtcac ccgccctctc tactacgaga agcctattaa ccattgaagg cgatgaggag    360
ttgcgctcca ccacaacccc agtggtagct ctgagagatg gggctcgcag tcaccccgt    420 ggtaacacgg ttgcttgccc gcgtgtgctc tcgggttcgg ccacttggcc gttcactcca    480
actcgttgta agtggccaag agcctattgt gctagagagg ttttcctccg gagccgtgaa    540
tgctgctaat cccaacctcc gagcgtgtgc gcacaatcca gtgttgctac gtcgtaacgc    600
gcaagttgga ggcggaacag actactttcg gtactccgtg tttccttatt attttataca    660
acaatttatg gtgacattga ctgatactat tgagttcgcc cgcttgccat tgaatattgc    720
cttgtattac cttatagcat ttcaaaaagc cacagatctc accctcgagc tcattcactt    780
tgcagtttgt ttgaatcgca tacacaagac atttgaaca                          819
```

<210> SEQ ID NO 36
<211> LENGTH: 244
<212> TYPE: PRT
<213> ORGANISM: Clostridium botulinum

<400> SEQUENCE: 36

```
Met Lys Gly Ile Arg Lys Ser Ile Leu Cys Leu Val Leu Ser Ala Gly
1               5                   10                  15

Val Ile Ala Pro Val Thr Thr Ser Ile Val Gln Ser Pro Gln Lys Cys
            20                  25                  30

Tyr Ala Cys Thr Val Asp Lys Gly Ser Tyr Ala Asp Thr Phe Thr Glu
        35                  40                  45

Phe Thr Asn Val Glu Glu Ala Lys Lys Trp Gly Asn Ala Gln Tyr Lys
    50                  55                  60

Lys Tyr Gly Leu Ser Lys Pro Glu Gln Glu Ala Ile Lys Phe Tyr Thr
65                  70                  75                  80

Arg Asp Ala Ser Lys Ile Asn Gly Pro Leu Arg Ala Asn Gln Gly Asn
                85                  90                  95

Glu Asn Gly Leu Pro Ala Asp Ile Leu Gln Lys Val Lys Leu Ile Asp
            100                 105                 110

Gln Ser Phe Ser Lys Met Lys Met Pro Gln Asn Ile Ile Leu Phe Arg
        115                 120                 125

Gly Asp Asp Pro Ala Tyr Leu Gly Pro Glu Phe Gln Asp Lys Ile Leu
    130                 135                 140

Asn Lys Asp Gly Thr Ile Asn Lys Thr Val Phe Glu Gln Val Lys Ala
145                 150                 155                 160
```

```
Lys Phe Leu Lys Lys Asp Arg Thr Glu Tyr Gly Tyr Ile Ser Thr Ser
                165                 170                 175

Leu Met Ser Ala Gln Phe Gly Gly Arg Pro Ile Val Thr Lys Phe Lys
            180                 185                 190

Val Thr Asn Gly Ser Lys Gly Gly Tyr Ile Asp Pro Ile Ser Tyr Phe
        195                 200                 205

Pro Gly Gln Leu Glu Val Leu Leu Pro Arg Asn Asn Ser Tyr Tyr Ile
    210                 215                 220

Ser Asp Met Gln Ile Ser Pro Asn Asn Arg Gln Ile Met Ile Thr Ala
225                 230                 235                 240

Met Ile Phe Lys

<210> SEQ ID NO 37
<211> LENGTH: 193
<212> TYPE: PRT
<213> ORGANISM: Homo sapiens

<400> SEQUENCE: 37

Met Ala Ala Ile Arg Lys Lys Leu Val Ile Val Gly Asp Gly Ala Cys
1               5                   10                  15

Gly Lys Asn Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 38
<211> LENGTH: 1354
<212> TYPE: PRT
<213> ORGANISM: Homo sapiens

<400> SEQUENCE: 38

Met Ser Thr Gly Asp Ser Phe Glu Thr Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45
```

```
Asn Lys Asn Ile Asp Asn Phe Leu Ser Arg Tyr Lys Asp Thr Ile Asn
     50                  55                  60
Lys Ile Arg Asp Leu Arg Met Lys Ala Glu Asp Tyr Glu Val Val Lys
 65                  70                  75                  80
Val Ile Gly Arg Gly Ala Phe Gly Glu Val Gln Leu Val Arg His Lys
                 85                  90                  95
Ser Thr Arg Lys Val Tyr Ala Met Lys Leu Leu Ser Lys Phe Glu Met
            100                 105                 110
Ile Lys Arg Ser Asp Ser Ala Phe Phe Trp Glu Glu Arg Asp Ile Met
        115                 120                 125
Ala Phe Ala Asn Ser Pro Trp Val Val Gln Leu Phe Tyr Ala Phe Gln
130                 135                 140
Asp Asp Arg Tyr Leu Tyr Met Val Met Glu Tyr Met Pro Gly Gly Asp
145                 150                 155                 160
Leu Val Asn Leu Met Ser Asn Tyr Asp Val Pro Glu Lys Trp Ala Arg
                165                 170                 175
Phe Tyr Thr Ala Glu Val Val Leu Ala Leu Asp Ala Ile His Ser Met
            180                 185                 190
Gly Phe Ile His Arg Asp Val Lys Pro Asp Asn Met Leu Leu Asp Lys
        195                 200                 205
Ser Gly His Leu Lys Leu Ala Asp Phe Gly Thr Cys Met Lys Met Asn
210                 215                 220
Lys Glu Gly Met Val Arg Cys Asp Thr Ala Val Gly Thr Pro Asp Tyr
225                 230                 235                 240
Ile Ser Pro Glu Val Leu Lys Ser Gln Gly Gly Asp Gly Tyr Tyr Gly
                245                 250                 255
Arg Glu Cys Asp Trp Trp Ser Val Gly Val Phe Leu Tyr Glu Met Leu
            260                 265                 270
Val Gly Asp Thr Pro Phe Tyr Ala Asp Ser Leu Val Gly Thr Tyr Ser
        275                 280                 285
Lys Ile Met Asn His Lys Asn Ser Leu Thr Phe Pro Asp Asp Asn Asp
290                 295                 300
Ile Ser Lys Glu Ala Lys Asn Leu Ile Cys Ala Phe Leu Thr Asp Arg
305                 310                 315                 320
Glu Val Arg Leu Gly Arg Asn Gly Val Glu Glu Ile Lys Arg His Leu
                325                 330                 335
Phe Phe Lys Asn Asp Gln Trp Ala Trp Glu Thr Leu Arg Asp Thr Val
            340                 345                 350
Ala Pro Val Val Pro Asp Leu Ser Asp Ile Asp Thr Ser Asn Phe
        355                 360                 365
Asp Asp Leu Glu Glu Asp Lys Gly Glu Glu Thr Phe Pro Ile Pro
370                 375                 380
Lys Ala Phe Val Gly Asn Gln Leu Pro Phe Val Gly Phe Thr Tyr Tyr
385                 390                 395                 400
Ser Asn Arg Arg Tyr Leu Ser Ser Ala Asn Pro Asn Asp Asn Arg Thr
                405                 410                 415
Ser Ser Asn Ala Asp Lys Ser Leu Gln Glu Ser Leu Gln Lys Thr Ile
            420                 425                 430
Tyr Lys Leu Glu Glu Gln Leu His Asn Glu Met Gln Leu Lys Asp Glu
        435                 440                 445
Met Glu Gln Lys Cys Arg Thr Ser Asn Ile Lys Leu Asp Lys Ile Met
450                 455                 460
```

```
Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
            485                 490                 495

Glu Tyr Gln Arg Lys Ala Glu Gln Asn Glu Lys Arg Arg Asn Val
                500                 505                 510

Glu Asn Glu Val Ser Thr Leu Lys Asp Gln Leu Glu Asp Leu Lys Lys
            515                 520                 525

Val Ser Gln Asn Ser Gln Leu Ala Asn Glu Lys Leu Ser Gln Leu Gln
    530                 535                 540

Lys Gln Leu Glu Glu Ala Asn Asp Leu Leu Arg Thr Glu Ser Asp Thr
545                 550                 555                 560

Ala Val Arg Leu Arg Lys Ser His Thr Glu Met Ser Lys Ser Ile Ser
            565                 570                 575

Gln Leu Glu Ser Leu Asn Arg Glu Leu Gln Glu Arg Asn Arg Ile Leu
            580                 585                 590

Glu Asn Ser Lys Ser Gln Thr Asp Lys Asp Tyr Tyr Gln Leu Gln Ala
            595                 600                 605

Ile Leu Glu Ala Glu Arg Arg Asp Arg Gly His Asp Ser Glu Met Ile
610                 615                 620

Gly Asp Leu Gln Ala Arg Ile Thr Ser Leu Gln Glu Glu Val Lys His
625                 630                 635                 640

Leu Lys His Asn Leu Glu Lys Val Glu Gly Glu Arg Lys Glu Ala Gln
                645                 650                 655

Asp Met Leu Asn His Ser Glu Lys Glu Lys Asn Asn Leu Glu Ile Asp
        660                 665                 670

Leu Asn Tyr Lys Leu Lys Ser Leu Gln Gln Arg Leu Glu Gln Glu Val
            675                 680                 685

Asn Glu His Lys Val Thr Lys Ala Arg Leu Thr Asp Lys His Gln Ser
    690                 695                 700

Ile Glu Glu Ala Lys Ser Val Ala Met Cys Glu Met Glu Lys Lys Leu
705                 710                 715                 720

Lys Glu Glu Arg Glu Ala Arg Glu Lys Ala Glu Asn Arg Val Val Gln
                725                 730                 735

Ile Glu Lys Gln Cys Ser Met Leu Asp Val Asp Leu Lys Gln Ser Gln
            740                 745                 750

Gln Lys Leu Glu His Leu Thr Gly Asn Lys Glu Arg Met Glu Asp Glu
        755                 760                 765

Val Lys Asn Leu Thr Leu Gln Leu Glu Gln Glu Ser Asn Lys Arg Leu
    770                 775                 780

Leu Leu Gln Asn Glu Leu Lys Thr Gln Ala Phe Glu Ala Asp Asn Leu
785                 790                 795                 800

Lys Gly Leu Glu Lys Gln Met Lys Gln Glu Ile Asn Thr Leu Leu Glu
                805                 810                 815

Ala Lys Arg Leu Leu Glu Phe Glu Leu Ala Gln Leu Thr Lys Gln Tyr
            820                 825                 830

Arg Gly Asn Glu Gly Gln Met Arg Glu Leu Gln Asp Gln Leu Glu Ala
        835                 840                 845

Glu Gln Tyr Phe Ser Thr Leu Tyr Lys Thr Gln Val Lys Glu Leu Lys
    850                 855                 860

Glu Glu Ile Glu Glu Lys Asn Arg Glu Asn Leu Lys Lys Ile Gln Glu
865                 870                 875                 880
```

```
Leu Gln Asn Glu Lys Glu Thr Leu Ala Thr Gln Leu Asp Leu Ala Glu
                885                 890                 895

Thr Lys Ala Glu Ser Glu Gln Leu Ala Arg Gly Leu Leu Glu Gln
            900                 905                 910

Tyr Phe Glu Leu Thr Gln Glu Ser Lys Lys Ala Ala Ser Arg Asn Arg
            915                 920                 925

Gln Glu Ile Thr Asp Lys Asp His Thr Val Ser Arg Leu Glu Glu Ala
            930                 935                 940

Asn Ser Met Leu Thr Lys Asp Ile Glu Ile Leu Arg Arg Glu Asn Glu
945                 950                 955                 960

Glu Leu Thr Glu Lys Met Lys Lys Ala Glu Glu Tyr Lys Leu Glu
            965                 970                 975

Lys Glu Glu Glu Ile Ser Asn Leu Lys Ala Ala Phe Glu Lys Asn Ile
                980                 985                 990

Asn Thr Glu Arg Thr Leu Lys Thr Gln Ala Val Asn Lys Leu Ala Glu
            995                 1000                1005

Ile Met Asn Arg Lys Asp Phe Lys Ile Asp Arg Lys Lys Ala Asn Thr
            1010                1015                1020

Gln Asp Leu Arg Lys Lys Glu Lys Glu Asn Arg Lys Leu Gln Leu Glu
1025                1030                1035                1040

Leu Asn Gln Glu Arg Glu Lys Phe Asn Gln Met Val Val Lys His Gln
            1045                1050                1055

Lys Glu Leu Asn Asp Met Gln Ala Gln Leu Val Glu Glu Cys Ala His
            1060                1065                1070

Arg Asn Glu Leu Gln Met Gln Leu Ala Ser Lys Glu Ser Asp Ile Glu
            1075                1080                1085

Gln Leu Arg Ala Lys Leu Leu Asp Leu Ser Asp Ser Thr Ser Val Ala
            1090                1095                1100

Ser Phe Pro Ser Ala Asp Glu Thr Asp Gly Asn Leu Pro Glu Ser Arg
1105                1110                1115                1120

Ile Glu Gly Trp Leu Ser Val Pro Asn Arg Gly Asn Ile Lys Arg Tyr
            1125                1130                1135

Gly Trp Lys Lys Gln Tyr Val Val Val Ser Ser Lys Lys Ile Leu Phe
            1140                1145                1150

Tyr Asn Asp Glu Gln Asp Lys Glu Gln Ser Asn Pro Ser Met Val Leu
            1155                1160                1165

Asp Ile Asp Lys Leu Phe His Val Arg Pro Val Thr Gln Gly Asp Val
            1170                1175                1180

Tyr Arg Ala Glu Thr Glu Glu Ile Pro Lys Ile Phe Gln Ile Leu Tyr
1185                1190                1195                1200

Ala Asn Glu Gly Glu Cys Arg Lys Asp Val Glu Met Glu Pro Val Gln
            1205                1210                1215

Gln Ala Glu Lys Thr Asn Phe Gln Asn His Lys Gly His Glu Phe Ile
            1220                1225                1230

Pro Thr Leu Tyr His Phe Pro Ala Asn Cys Asp Ala Cys Ala Lys Pro
            1235                1240                1245

Leu Trp His Val Phe Lys Pro Pro Ala Leu Glu Cys Arg Arg Cys
            1250                1255                1260

His Val Lys Cys His Arg Asp His Leu Asp Lys Lys Glu Asp Leu Ile
1265                1270                1275                1280

Cys Pro Cys Lys Val Ser Tyr Asp Val Thr Ser Ala Arg Asp Met Leu
            1285                1290                1295
```

-continued

```
Leu Leu Ala Cys Ser Gln Asp Glu Gln Lys Lys Trp Val Thr His Leu
                1300                1305                1310

Val Lys Lys Ile Pro Lys Asn Pro Pro Ser Gly Phe Val Arg Ala Ser
            1315                1320                1325

Pro Arg Thr Leu Ser Thr Arg Ser Thr Ala Asn Gln Ser Phe Arg Lys
        1330                1335                1340

Val Val Lys Asn Thr Ser Gly Lys Thr Ser
1345                1350
```

<210> SEQ ID NO 39
<211> LENGTH: 1610
<212> TYPE: PRT
<213> ORGANISM: Homo sapiens

<400> SEQUENCE: 39

```
Met Asn Thr Pro Lys Glu Glu Phe Gln Asp Trp Pro Ile Val Arg Ile
1               5                   10                  15

Ala Ala His Leu Pro Asp Leu Ile Val Tyr Gly His Phe Ser Pro Glu
                20                  25                  30

Arg Pro Phe Met Asp Tyr Phe Asp Gly Val Leu Met Phe Val Asp Ile
            35                  40                  45

Ser Gly Phe Thr Ala Met Thr Glu Lys Phe Ser Ser Ala Met Tyr Met
        50                  55                  60

Asp Arg Gly Ala Glu Gln Leu Val Glu Ile Leu Asn Tyr His Ile Ser
65                  70                  75                  80

Ala Ile Val Glu Lys Val Leu Ile Phe Gly Gly Asp Ile Leu Lys Phe
                85                  90                  95

Ala Gly Asp Ala Leu Leu Ala Leu Trp Arg Val Glu Arg Lys Gln Leu
                100                 105                 110

Lys Asn Ile Ile Thr Val Val Ile Lys Cys Ser Leu Glu Ile His Gly
            115                 120                 125

Leu Phe Glu Thr Gln Glu Trp Glu Glu Gly Leu Asp Ile Arg Val Lys
        130                 135                 140

Ile Gly Leu Ala Ala Gly His Ile Ser Met Leu Val Phe Gly Asp Glu
145                 150                 155                 160

Thr His Ser His Phe Leu Val Ile Gly Gln Ala Val Asp Asp Val Arg
                165                 170                 175

Leu Ala Gln Asn Met Ala Gln Met Asn Asp Val Ile Leu Ser Pro Asn
                180                 185                 190

Cys Trp Gln Leu Cys Asp Arg Ser Met Ile Glu Ile Glu Ser Val Pro
            195                 200                 205

Asp Gln Arg Ala Val Lys Val Asn Phe Leu Lys Pro Pro Asn Phe
        210                 215                 220

Asn Phe Asp Glu Phe Phe Thr Lys Cys Thr Thr Phe Met His Tyr Tyr
225                 230                 235                 240

Pro Ser Gly Glu His Lys Asn Leu Leu Arg Leu Ala Cys Thr Leu Lys
                245                 250                 255

Pro Asp Pro Glu Leu Glu Met Ser Leu Gln Lys Tyr Val Met Glu Ser
                260                 265                 270

Ile Leu Lys Gln Ile Asp Asn Lys Gln Leu Gly Tyr Leu Ser Glu
            275                 280                 285

Leu Arg Pro Val Thr Ile Val Phe Val Asn Leu Met Phe Glu Asp Gln
        290                 295                 300

Asp Lys Ala Glu Glu Ile Gly Pro Ala Ile Gln Asp Ala Tyr Met His
305                 310                 315                 320
```

-continued

```
Ile Thr Ser Val Leu Lys Ile Phe Gln Gly Gln Ile Asn Lys Val Phe
            325                 330                 335
Met Phe Asp Lys Gly Cys Ser Phe Leu Cys Val Phe Gly Phe Pro Gly
            340                 345                 350
Glu Lys Val Pro Asp Glu Leu Thr His Ala Leu Glu Cys Ala Met Asp
            355                 360                 365
Ile Phe Asp Phe Cys Ser Gln Val His Lys Ile Gln Thr Val Ser Ile
            370                 375                 380
Gly Val Ala Ser Gly Ile Val Phe Cys Gly Ile Val Gly His Thr Val
385                 390                 395                 400
Arg His Glu Tyr Thr Val Ile Gly Gln Lys Val Asn Leu Ala Ala Arg
                405                 410                 415
Met Met Met Tyr Tyr Pro Gly Ile Val Thr Cys Asp Ser Val Thr Tyr
                420                 425                 430
Asn Gly Ser Asn Leu Pro Ala Tyr Phe Phe Lys Glu Leu Pro Lys Lys
            435                 440                 445
Val Met Lys Gly Val Ala Asp Ser Gly Pro Leu Tyr Gln Tyr Trp Gly
            450                 455                 460
Arg Thr Glu Lys Val Met Phe Gly Met Ala Cys Leu Ile Cys Asn Arg
465                 470                 475                 480
Lys Glu Asp Tyr Pro Leu Leu Gly Arg Asn Lys Glu Ile Asn Tyr Phe
                485                 490                 495
Met Tyr Thr Met Lys Lys Phe Leu Ile Ser Asn Ser Ser Gln Val Leu
            500                 505                 510
Met Tyr Glu Gly Leu Pro Gly Tyr Gly Lys Ser Gln Ile Leu Met Lys
            515                 520                 525
Ile Glu Tyr Leu Ala Gln Gly Lys Asn His Arg Ile Ile Ala Ile Ser
            530                 535                 540
Leu Asn Lys Ile Ser Phe His Gln Thr Phe Tyr Thr Ile Gln Met Phe
545                 550                 555                 560
Met Ala Asn Val Leu Gly Leu Asp Thr Cys Lys His Tyr Lys Glu Arg
                565                 570                 575
Gln Thr Asn Leu Arg Asn Lys Val Met Thr Leu Leu Asp Glu Lys Phe
            580                 585                 590
Tyr Cys Leu Leu Asn Asp Ile Phe His Val Gln Phe Pro Ile Ser Arg
            595                 600                 605
Glu Ile Ser Arg Met Ser Thr Leu Lys Lys Gln Lys Gln Leu Glu Ile
            610                 615                 620
Leu Phe Met Lys Ile Leu Lys Leu Ile Val Lys Glu Glu Arg Ile Ile
625                 630                 635                 640
Phe Ile Ile Asp Glu Ala Gln Phe Val Asp Ser Thr Ser Trp Arg Phe
                645                 650                 655
Met Glu Lys Leu Ile Arg Thr Leu Pro Ile Phe Ile Ile Met Ser Leu
            660                 665                 670
Cys Pro Phe Val Asn Ile Pro Cys Ala Ala Arg Ala Val Ile Lys
            675                 680                 685
Asn Arg Asn Thr Thr Tyr Ile Val Ile Gly Ala Val Gln Pro Asn Asp
            690                 695                 700
Ile Ser Asn Lys Ile Cys Leu Asp Leu Asn Val Ser Cys Ile Ser Lys
705                 710                 715                 720
Glu Leu Asp Ser Tyr Leu Gly Glu Gly Ser Cys Gly Ile Pro Phe Tyr
                725                 730                 735
```

```
Cys Glu Glu Leu Leu Lys Asn Leu Glu His His Glu Val Leu Val Phe
            740                 745                 750

Gln Gln Thr Glu Ser Glu Lys Thr Asn Arg Thr Trp Asn Asn Leu
        755                 760                 765

Phe Lys Tyr Ser Ile Lys Leu Thr Glu Lys Leu Asn Met Val Thr Leu
    770                 775                 780

His Ser Asp Lys Glu Ser Glu Glu Val Cys His Leu Thr Ser Gly Val
785                 790                 795                 800

Arg Leu Lys Asn Leu Ser Pro Pro Thr Ser Leu Lys Glu Ile Ser Leu
                805                 810                 815

Ile Gln Leu Asp Ser Met Arg Leu Ser His Gln Met Leu Val Arg Cys
        820                 825                 830

Ala Ala Ile Ile Gly Leu Thr Phe Thr Thr Glu Leu Leu Phe Glu Ile
        835                 840                 845

Leu Pro Cys Trp Asn Met Lys Met Met Ile Lys Thr Leu Ala Thr Leu
    850                 855                 860

Val Glu Ser Asn Ile Phe Tyr Cys Phe Arg Asn Gly Lys Glu Leu Gln
865                 870                 875                 880

Lys Ala Leu Lys Gln Asn Asp Pro Ser Phe Glu Val His Tyr Arg Ser
            885                 890                 895

Leu Ser Leu Lys Pro Ser Glu Gly Met Asp His Gly Glu Glu Glu Gln
            900                 905                 910

Leu Arg Glu Leu Glu Asn Glu Val Ile Glu Cys His Arg Ile Arg Phe
        915                 920                 925

Cys Asn Pro Met Met Gln Lys Thr Ala Tyr Glu Leu Trp Leu Lys Asp
    930                 935                 940

Gln Arg Lys Ala Met His Leu Lys Cys Ala Arg Phe Leu Glu Glu Asp
945                 950                 955                 960

Ala His Arg Cys Asp His Cys Arg Gly Arg Asp Phe Ile Pro Tyr His
            965                 970                 975

His Phe Thr Val Asn Ile Arg Leu Asn Ala Leu Asp Met Asp Ala Ile
            980                 985                 990

Lys Lys Met Ala Met Ser His Gly Phe Lys Thr Glu Glu Lys Leu Ile
        995                 1000                1005

Leu Ser Asn Ser Glu Ile Pro Glu Thr Ser Ala Phe Phe Pro Glu Asn
    1010                1015                1020

Arg Ser Pro Glu Glu Ile Arg Glu Lys Ile Leu Asn Phe Phe Asp His
1025                1030                1035                1040

Val Leu Thr Lys Met Lys Thr Ser Asp Glu Asp Ile Ile Pro Leu Glu
            1045                1050                1055

Ser Cys Gln Cys Glu Glu Ile Leu Glu Ile Val Ile Leu Pro Leu Ala
            1060                1065                1070

His His Phe Leu Ala Leu Gly Glu Asn Asp Lys Ala Leu Tyr Tyr Phe
        1075                1080                1085

Leu Glu Ile Ala Ser Ala Tyr Leu Ile Phe Cys Asp Asn Tyr Met Ala
    1090                1095                1100

Tyr Met Tyr Leu Asn Glu Gly Gln Lys Leu Leu Lys Thr Leu Lys Lys
1105                1110                1115                1120

Asp Lys Ser Trp Ser Gln Thr Phe Glu Ser Ala Thr Phe Tyr Ser Leu
            1125                1130                1135

Lys Gly Glu Val Cys Phe Asn Met Gly Gln Ile Val Leu Ala Lys Lys
            1140                1145                1150
```

```
Met Leu Arg Lys Ala Leu Lys Leu Leu Asn Arg Ile Phe Pro Tyr Asn
            1155                1160                1165

Leu Ile Ser Leu Phe Leu His Ile His Val Glu Lys Asn Arg His Phe
            1170                1175                1180

His Tyr Val Asn Arg Gln Ala Gln Glu Ser Pro Pro Pro Gly Lys Lys
1185                1190                1195                1200

Arg Leu Ala Gln Leu Tyr Arg Gln Thr Val Cys Leu Ser Leu Leu Trp
                1205                1210                1215

Arg Ile Tyr Ser Tyr Ser Tyr Leu Phe His Cys Lys Tyr Tyr Ala His
                1220                1225                1230

Leu Ala Val Met Met Gln Met Asn Thr Ala Leu Glu Thr Gln Asn Cys
                1235                1240                1245

Phe Gln Ile Ile Lys Ala Tyr Leu Asp Tyr Ser Leu Tyr His His Leu
                1250                1255                1260

Ala Gly Tyr Lys Gly Val Trp Phe Lys Tyr Glu Val Met Ala Met Glu
1265                1270                1275                1280

His Ile Phe Asn Leu Pro Leu Lys Gly Glu Gly Ile Glu Ile Val Ala
                1285                1290                1295

Tyr Val Ala Glu Thr Leu Val Phe Asn Lys Leu Ile Met Gly His Leu
                1300                1305                1310

Asp Leu Ala Ile Glu Leu Gly Ser Arg Ala Leu Gln Met Trp Ala Leu
                1315                1320                1325

Leu Gln Asn Pro Asn Arg His Tyr Gln Ser Leu Cys Arg Leu Ser Arg
                1330                1335                1340

Cys Leu Leu Leu Asn Ser Arg Tyr Pro Gln Leu Ile Gln Val Leu Gly
1345                1350                1355                1360

Arg Leu Trp Glu Leu Ser Val Thr Gln Glu His Ile Phe Ser Lys Ala
                1365                1370                1375

Phe Phe Tyr Phe Val Cys Leu Asp Ile Leu Leu Tyr Ser Gly Phe Val
                1380                1385                1390

Tyr Arg Thr Phe Glu Glu Cys Leu Glu Phe Ile His Gln Tyr Glu Asn
                1395                1400                1405

Asn Arg Ile Leu Lys Phe His Ser Gly Leu Leu Gly Leu Tyr Ser
            1410                1415                1420

Ser Val Ala Ile Trp Tyr Ala Arg Leu Gln Glu Trp Asp Asn Phe Tyr
1425                1430                1435                1440

Lys Phe Ser Asn Arg Ala Lys Asn Leu Leu Pro Arg Arg Thr Met Thr
                1445                1450                1455

Leu Thr Tyr Tyr Asp Gly Ile Ser Arg Tyr Met Glu Gly Gln Val Leu
                1460                1465                1470

His Leu Gln Lys Gln Ile Lys Glu Gln Ser Glu Asn Ala Gln Ala Ser
            1475                1480                1485

Gly Glu Glu Leu Leu Lys Asn Leu Glu Asn Leu Val Ala Gln Asn Thr
            1490                1495                1500

Thr Gly Pro Val Phe Cys Pro Arg Leu Tyr His Leu Met Ala Tyr Val
1505                1510                1515                1520

Cys Ile Leu Met Gly Asp Gly Gln Lys Cys Gly Leu Phe Leu Asn Thr
                1525                1530                1535

Ala Leu Arg Leu Ser Glu Thr Gln Gly Asn Ile Leu Glu Lys Cys Trp
            1540                1545                1550

Leu Asn Met Asn Lys Glu Ser Trp Tyr Ser Thr Ser Glu Leu Lys Glu
            1555                1560                1565
```

-continued

```
Asp Gln Trp Leu Gln Thr Ile Leu Ser Leu Pro Ser Trp Glu Lys Ile
    1570                1575                1580

Val Ala Gly Arg Val Asn Ile Gln Asp Leu Gln Lys Asn Lys Phe Leu
1585                1590                1595                1600

Met Arg Ala Asn Thr Val Asp Asn His Phe
                1605                1610

<210> SEQ ID NO 40
<211> LENGTH: 594
<212> TYPE: PRT
<213> ORGANISM: Homo sapiens

<400> SEQUENCE: 40

Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
                20                  25                  30

Cys Gly Val Ala His Gly Cys Thr Arg Lys Leu Gly Leu Lys Ile Cys
            35                  40                  45

Gly Phe Leu Gln Arg Thr Asn Ser Leu Glu Glu Lys Ser Arg Leu Val
    50                  55                  60

Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
    115                 120                 125

Arg Lys Thr Phe Asp Arg Ser Thr Lys Val Leu Asp Phe His His Pro
130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
    195                 200                 205

Ala Asn Thr Asn Met Phe Thr Tyr Glu Ile Ala Pro Val Phe Val Leu
210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
    275                 280                 285

Gln Ser His Tyr Ser Ile Lys Lys Ala Gly Ala Ala Leu Gly Phe Gly
290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335
```

```
Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
            355                 360                 365

Trp Leu His Val Asp Ala Ala Trp Gly Gly Gly Leu Leu Met Ser Arg
        370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
                420                 425                 430

Gly Tyr Leu Phe Gln Pro Asp Lys Gln Tyr Asp Val Ser Tyr Asp Thr
            435                 440                 445

Gly Asp Lys Ala Ile Gln Cys Gly Arg His Val Asp Ile Phe Lys Phe
        450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
            515                 520                 525

Pro Gln Arg Arg Glu Lys Leu His Lys Val Ala Pro Lys Ile Lys Ala
        530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu

<210> SEQ ID NO 41
<211> LENGTH: 267
<212> TYPE: PRT
<213> ORGANISM: Homo sapiens

<400> SEQUENCE: 41

Met Ala Arg Phe Leu Thr Leu Cys Thr Trp Leu Leu Leu Leu Gly Pro
1               5                   10                  15

Gly Leu Leu Ala Thr Val Arg Ala Glu Cys Ser Gln Asp Cys Ala Thr
            20                  25                  30

Cys Ser Tyr Arg Leu Val Arg Pro Ala Asp Ile Asn Phe Leu Ala Cys
        35                  40                  45

Val Met Glu Cys Glu Gly Lys Leu Pro Ser Leu Lys Ile Trp Glu Thr
    50                  55                  60

Cys Lys Glu Leu Leu Gln Leu Ser Lys Pro Glu Leu Pro Gln Asp Gly
65                  70                  75                  80

Thr Ser Thr Leu Arg Glu Asn Ser Lys Pro Glu Glu Ser His Leu Leu
                85                  90                  95

Ala Lys Arg Tyr Gly Gly Phe Met Lys Arg Tyr Gly Gly Phe Met Lys
            100                 105                 110
```

```
Lys Met Asp Glu Leu Tyr Pro Met Glu Pro Glu Glu Ala Asn Gly
            115                 120                 125

Ser Glu Ile Leu Ala Lys Arg Tyr Gly Gly Phe Met Lys Lys Asp Ala
130                 135                 140

Glu Glu Asp Asp Ser Leu Ala Asn Ser Ser Asp Leu Leu Lys Glu Leu
145                 150                 155                 160

Leu Glu Thr Gly Asp Asn Arg Glu Arg Ser His His Gln Asp Gly Ser
                165                 170                 175

Asp Asn Glu Glu Glu Val Ser Lys Arg Tyr Gly Gly Phe Met Arg Gly
                180                 185                 190

Leu Lys Arg Ser Pro Gln Leu Glu Asp Glu Ala Lys Glu Leu Gln Lys
        195                 200                 205

Arg Tyr Gly Gly Phe Met Arg Arg Val Gly Arg Pro Glu Trp Trp Met
        210                 215                 220

Asp Tyr Gln Lys Arg Tyr Gly Gly Phe Leu Lys Arg Phe Ala Glu Ala
225                 230                 235                 240

Leu Pro Ser Asp Glu Glu Gly Glu Ser Tyr Ser Lys Glu Val Pro Glu
                245                 250                 255

Met Glu Lys Arg Tyr Gly Gly Phe Met Arg Phe
            260                 265
```

<210> SEQ ID NO 42
<211> LENGTH: 222
<212> TYPE: PRT
<213> ORGANISM: Homo sapiens
<400> SEQUENCE: 42

```
Met Gly Leu Phe Gly Lys Thr Gln Glu Lys Pro Pro Lys Glu Leu Val
1               5                   10                  15

Asn Glu Trp Ser Leu Lys Ile Arg Lys Glu Met Arg Val Val Asp Arg
                20                  25                  30

Gln Ile Arg Asp Ile Gln Arg Glu Glu Glu Lys Val Lys Arg Ser Val
            35                  40                  45

Lys Asp Ala Ala Lys Lys Gly Gln Lys Asp Val Cys Ile Val Leu Ala
50                  55                  60

Lys Glu Met Ile Arg Ser Arg Lys Ala Val Ser Lys Leu Tyr Ala Ser
65                  70                  75                  80

Lys Ala His Met Asn Ser Val Leu Met Gly Met Lys Asn Gln Leu Ala
                85                  90                  95

Val Leu Arg Val Ala Gly Ser Leu Gln Lys Ser Thr Glu Val Met Lys
            100                 105                 110

Ala Met Gln Ser Leu Val Lys Ile Pro Glu Ile Gln Ala Thr Met Arg
        115                 120                 125

Glu Leu Ser Lys Glu Met Met Lys Ala Gly Ile Ile Glu Glu Met Leu
        130                 135                 140

Glu Asp Thr Phe Glu Ser Met Asp Asp Gln Glu Met Glu Glu Glu
145                 150                 155                 160

Ala Glu Met Glu Ile Asp Arg Ile Leu Phe Glu Ile Thr Ala Gly Ala
                165                 170                 175

Leu Gly Lys Ala Pro Ser Lys Val Thr Asp Ala Leu Pro Glu Pro Glu
            180                 185                 190

Pro Pro Gly Ala Met Ala Ala Ser Glu Asp Glu Glu Glu Glu Glu
        195                 200                 205
```

```
Ala Leu Glu Ala Met Gln Ser Arg Leu Ala Thr Leu Arg Ser
    210                 215                 220
```

<210> SEQ ID NO 43
<211> LENGTH: 238
<212> TYPE: PRT
<213> ORGANISM: Homo sapiens

<400> SEQUENCE: 43

```
Met Leu Cys Cys Met Arg Arg Thr Lys Gln Val Glu Lys Asn Asp Asp
1               5                   10                  15

Asp Gln Lys Ile Glu Gln Asp Gly Ile Lys Pro Glu Asp Lys Ala His
            20                  25                  30

Lys Ala Ala Thr Lys Ile Gln Ala Ser Phe Arg Gly His Ile Thr Arg
        35                  40                  45

Lys Lys Leu Lys Gly Glu Lys Lys Asp Asp Val Gln Ala Ala Glu Ala
    50                  55                  60

Glu Ala Asn Lys Lys Asp Glu Ala Pro Val Ala Asp Gly Val Glu Lys
65                  70                  75                  80

Lys Gly Glu Gly Thr Thr Thr Ala Glu Ala Pro Ala Thr Gly Ser
                85                  90                  95

Lys Pro Asp Glu Pro Gly Lys Ala Gly Glu Thr Pro Ser Glu Glu Lys
            100                 105                 110

Lys Gly Glu Gly Asp Ala Ala Thr Glu Gln Ala Ala Pro Gln Ala Pro
        115                 120                 125

Ala Ser Ser Glu Glu Lys Ala Gly Ser Ala Glu Thr Glu Ser Ala Thr
    130                 135                 140

Lys Ala Ser Thr Asp Asn Ser Pro Ser Ser Lys Ala Glu Asp Ala Pro
145                 150                 155                 160

Ala Lys Glu Glu Pro Lys Gln Ala Asp Val Pro Ala Ala Val Thr Ala
                165                 170                 175

Ala Ala Ala Thr Thr Pro Ala Ala Glu Asp Ala Ala Ala Lys Ala Thr
            180                 185                 190

Ala Gln Pro Pro Thr Glu Thr Gly Glu Ser Ser Gln Ala Glu Glu Asn
        195                 200                 205

Ile Glu Ala Val Asp Glu Thr Lys Pro Lys Glu Ser Ala Arg Gln Asp
    210                 215                 220

Glu Gly Lys Glu Glu Glu Pro Glu Ala Asp Gln Glu His Ala
225                 230                 235
```

<210> SEQ ID NO 44
<211> LENGTH: 227
<212> TYPE: PRT
<213> ORGANISM: Homo sapiens

<400> SEQUENCE: 44

```
Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Ala Lys Glu
65                  70                  75                  80
```

-continued

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala
            115                 120                 125

Pro Ala Glu Ser Ala Ala Pro Ala Ala Gly Glu Glu Pro Ser Lys Glu
        130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
    210                 215                 220

Val Lys Glu
225

<210> SEQ ID NO 45
<211> LENGTH: 247
<212> TYPE: PRT
<213> ORGANISM: Homo sapiens

<400> SEQUENCE: 45

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Val Leu Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

```
Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 46
<211> LENGTH: 257
<212> TYPE: PRT
<213> ORGANISM: Homo sapiens

<400> SEQUENCE: 46

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 47
<211> LENGTH: 211
<212> TYPE: PRT
<213> ORGANISM: Homo sapiens

<400> SEQUENCE: 47

Met Lys Leu Trp Asp Val Val Ala Val Cys Leu Val Leu Leu His Thr
1               5                   10                  15
```

Ala Ser Ala Phe Pro Leu Pro Ala Gly Lys Arg Pro Pro Glu Ala Pro
            20                  25                  30

Ala Glu Asp Arg Ser Leu Gly Arg Arg Ala Pro Phe Ala Leu Ser
        35                  40                  45

Ser Asp Ser Asn Met Pro Glu Asp Tyr Pro Gln Phe Asp Asp Val
50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Gly Gln Arg
            100                 105                 110

Gly Lys Asn Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
        130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
                195                 200                 205

Gly Cys Ile
    210

<210> SEQ ID NO 48
<211> LENGTH: 1353
<212> TYPE: DNA
<213> ORGANISM: Artificial Sequence
<220> FEATURE:
<223> OTHER INFORMATION: a synthetic oligonucleotide

<400> SEQUENCE: 48
gcccctctcc ctccccccccc cctaacgtta ctggccgaag ccgcttggaa taaggccggt      60
gtgcgtttgt ctatatgtta ttttccacca tattgccgtc ttttggcaat gtgagggccc     120
ggaaacctgg ccctgtcttc ttgacgagca ttcctagggg tctttcccct ctcgccaaag     180
gaatgcaagg tctgttgaat gtcgtgaagg aagcagttcc tctggaagct tcttgaagac     240
aaacaacgtc tgtagcgacc ctttgcaggc agcggaaccc cccacctggc gacaggtgcc     300
tctgcggcca aaagccacgt gtataagata cacctgcaaa ggcggcacaa ccccagtgcc     360
acgttgtgag ttggatagtt gtggaaagag tcaaatggct ctcctcaagc gtattcaaca     420
aggggctgaa ggatgcccag aaggtacccc attgtatggg atctgatctg ggcctcggt      480 gcacatgctt tacatgtgtt tagtcgaggt taaaaaaacg tctaggcccc cgaaccacg      540 gggacgtggt tttcctttga aaaacacgat gataagcttg ccacaacgcg tgccgccacc     600
atgggtgcag aagaacagaa gctgatctca gaggaggacc tgggtgtgag caagggcgag     660
gaggataaca tggccatcat caaggagttc atgcgcttca aggtgcacat ggagggctcc     720
gtgaacggcc acgagttcga gatcgagggc gagggcgagg ccgcccccta cgagggcacc     780
cagaccgcca agctgaaggt gaccaagggt ggccccctgc ccttcgcctg ggacatcctg     840
tcccctcagt tcatgtacgg ctccaaggcc tacgtgaagc accccgccga catccccgac     900

```
tacttgaagc tgtccttccc cgagggcttc aagtgggagc gcgtgatgaa cttggaggac      960
ggcggcgtgg tgaccgtgac ccaggactcc tccctgcagg acggcgagtt catctacaag     1020
gtgaagctgc gcggcaccaa cttcccctcc gacggccccg taatgcagaa gaagaccatg     1080
ggctgggagg cctcctccga gcggatgtac cccgaggacg cgccctgaa gggcgagatc      1140 aagcagaggc tgaagctgaa ggacggcggc cactacgacg ctgaggtcaa gaccacctac     1200
aaggccaaga gcccgtgca gctgcccggc gcctacaacg tcaacatcaa gttggacatc      1260
acctcccaca acgaggacta caccatcgtg aacagtacg aacgcgccga gggccgccac      1320
tccaccggcg gcatggacga gctgtacaag agc                                  1353
```

<210> SEQ ID NO 49
<211> LENGTH: 1633
<212> TYPE: DNA
<213> ORGANISM: Homo sapiens

<400> SEQUENCE: 49

```
atgaaaggga taagaaagtc aatttatgt ttagttttat cagcagggt aatagctccg        60 gtaacaacga gtatagttca aagtcctcaa aaatgttatg cttgtactgt tgataaaggt     120
tcatatgcag atactttcac agaatttacc aatgttgagg aagccaaaaa atggggaaat    180
gctcaatata aaaatatgg cctaagcaaa cctgaacaag aagctataaa attttataca    240
agagatgcaa gtaagatcaa tggaccatta agagcaaatc aagggaatga aaatggatta   300
cctgctgata tattacaaaa agttaaatta attgatcaat cttttagtaa gatgaagatg    360
cctcaaaata ttattcttt tagaggtgat gaccctgctt atttaggtcc agaatttcaa    420
gataaaattc ttaataaaga tggaacaatt aataaaactg ttttgaaca gttaaagcg     480 aaatttttaa aaaaggatag aacagaatat ggatatatta gtacttcatt aatgagtgcg   540
caatttggag gaagaccaat tgttactaaa tttaaagtaa ctaatggatc aaaaggaggg   600
tatatagacc ctattagcta tttcccagga caacttgaag tgttgcttcc tagaaataat   660
agttattata taagtgatat gcaaatatct cctaataata gacaaattat gattacagca   720
atgatattta aatagtttat aaaaataaat aaaatatagt tatgctaaat aaaagattta   780
gcatcttgaa gtaagaaaaa ttataggaac acataacaac aaaaataact acttttaatt   840
aagtagttca gattgttcaa aaagcctcca tgtaattgga ggcttttact ttcgtcaaat    900
atcttttatg cgatagcatt taaaaagttg ctagttttgt gtaatgattt ggtataaatt    960
tcaattaaat catacgaaaa atagtgcgat agcaccatgg ctatcttttt catattctga    1020
actgctgctg taatgaagca ttgctcggaa acattttaa ttcctcgcat gcgacaatag    1080
cgcagcccat gtaattcttt tgaatcagca aactacgctc aatttttct ttacgttttt    1140 tataaatact tttacctttt tcagttttag taaatgcaaa aatttgatcc ttataatctt    1200
cccaaacatg acgacgtata gctttgttaa ttgattatc agatgttaag caattatttt    1260
tatatttgca tgaagcacat tcatccgcat tactaacata ttctttatat ccgcttcttg    1320
tagtggtttt gtattttaaa aagaagttat tcatacatac atatccatct aattctttaa    1380
tatattgaaa tctatattta gtatactttt cttaacatg aggtcctaaa cggaaaccaa    1440
aaacaccttg ataattttt tctgaaactt gcttacaaat aggatttgta gaataaccag    1500
catcagctac taaatacttt gtattaaaat taaactttt tatttgcgtc tctattcttt    1560
taacataagg atctacatca ttaatattac ctggagttac atgaacatca gttataatat    1620
tatattttcc gtc                                                       1633
```

<210> SEQ ID NO 50
<211> LENGTH: 1650
<212> TYPE: DNA
<213> ORGANISM: Homo sapiens

<400> SEQUENCE: 50

| | | | | | |
|---|---|---|---|---|---|
| atggctgcca | tccggaagaa | actggtgatt | gttggtgatg | gagcctgtgg | aaagacatgc | 60 |
| ttgctcatag | tcttcagcaa | ggaccagttc | ccagaggtgt | atgtgcccac | agtgtttgag | 120 |
| aactatgtgg | cagatatcga | ggtggatgga | aagcaggtag | agttggcttt | gtgggacaca | 180 |
| gctgggcagg | aagattatga | tcgcctgagg | cccctctcct | acccagatac | cgatgttata | 240 |
| ctgatgtgtt | tttccatcga | cagccctgat | agtttagaaa | catcccaga | aaagtggacc | 300 |
| ccagaagtca | agcatttctg | tcccaacgtg | cccatcatcc | tggttgggaa | taagaaggat | 360 |
| cttcggaatg | atgagcacac | aaggcgggag | ctagccaaga | tgaagcagga | gccggtgaaa | 420 |
| cctgaagaag | gcagagatat | ggcaaacagg | attggcgctt | tgggtacat | ggagtgttca | 480 |
| gcaaagacca | agatggagt | gagagaggtt | tttgaaatgg | ctacgagagc | tgctctgcaa | 540 |
| gctagacgtg | ggaagaaaaa | atctgggtgc | cttgtcttgt | gaaaccttgc | tgcaagcaca | 600 |
| gcccttatgc | ggttaatttt | gaagtgctgt | ttattaatct | tagtgtatga | ttactggcct | 660 |
| ttttcattta | tctataattt | acctaagatt | acaaatcaga | agtcatcttg | ctaccagtat | 720 |
| ttagaagcca | actatgatta | ttaacgatgt | ccaacccgtc | tggcccacca | gggtcctttt | 780 |
| gacactgctc | taacagccct | cctctgcact | cccacctgac | acaccaggcg | ctaattcaag | 840 |
| gaatttctta | acttcttgct | tctttctaga | aagagaaaca | gttggtaact | tttgtgaatt | 900 |
| aggctgtaac | tactttataa | ctaacatgtc | ctgcctatta | tctgtcagct | gcaaggtact | 960 |
| ctggtgagtc | accacttcag | ggctttactc | cgtaacagat | tttgttggca | tagctctggg | 1020 |
| gtgggcagtt | ttttgaaaat | gggctcaacc | agaaaagccc | aagttcatgc | agctgtggca | 1080 |
| gagttacagt | tctgtggttt | catgttagtt | accttatagt | tactgtgtaa | ttagtgccac | 1140 |
| ttaatgtatg | ttaccaaaaa | taaatatatc | taccccagac | tagatgtagt | attttttgta | 1200 |
| taattggatt | tcctaatact | gtcatcctca | agaaagtgt | attggttttt | taaaaaagaa | 1260 |
| agtgtatttg | gaaataaagt | cagatggaaa | attcattttt | taaattcccg | ttttgtcact | 1320 |
| ttttctgata | aaagatggcc | atattacccc | ttttcggccc | catgtatctc | agtaccccat | 1380 |
| ggagctgggc | taagtaaata | ggaattggtt | tcacgcctga | ggcaattaga | cactttggaa | 1440 |
| gatggcataa | cctgtctcac | ctggacttaa | gcatctggct | ctaattcaca | gtgctctttt | 1500 |
| ctcctcactg | tatccaggtt | ccctcccaga | ggagccacca | gttctcatgg | gtggcactca | 1560 |
| gtctctcttc | tctccagctg | actaaacttt | ttttctgtac | cagttaattt | ttccaactac | 1620 |
| taatagaata | aaggcagttt | tctaaaaaaa | | | | 1650 |

<210> SEQ ID NO 51
<211> LENGTH: 5709
<212> TYPE: DNA
<213> ORGANISM: Homo sapiens

<400> SEQUENCE: 51

| | | | | | |
|---|---|---|---|---|---|
| atgtcgactg | gggacagttt | tgagactcga | tttgaaaaaa | tggacaaccct | gctgcgggat | 60 |
| cccaaatcgg | aagtgaattc | ggattgtttg | ctggatggat | tggatgcttt | ggtatatgat | 120 |
| ttggattttc | ctgccttaag | aaaaaacaaa | aatattgaca | acttttttaag | cagatataaa | 180 |

```
gacacaataa ataaaatcag agatttacga atgaaagctg aagattatga agtagtgaag    240
gtgattggta gaggtgcatt tggagaagtt caattggtaa ggcataaatc caccaggaag    300
gtatatgcta tgaagcttct cagcaaattt gaaatgataa agagatctga ttctgctttt    360
ttctgggaag aaagggacat catggctttt gccaacagtc cttgggttgt tcagcttttt    420
tatgcattcc aagatgatcg ttatctctac atggtgatgg aatacatgcc tggtggagat    480
cttgtaaact taatgagcaa ctatgatgtg cctgaaaaat gggcacgatt ctatactgca    540
gaagtagttc ttgcattgga tgcaatccat tccatgggtt ttattcacag agatgtgaag    600
cctgataaca tgctgctgga taaatctgga catttgaagt tagcagattt tggtacttgt    660
atgaagatga ataaggaagg catggtacga tgtgatacag cggttggaac acctgattat    720
atttcccctg aagtattaaa atcccaaggt ggtgatggtt attatggaag agaatgtgac    780
tggtggtcgg ttggggtatt tttatacgaa atgcttgtag gtgatacacc tttttatgca    840
gattctttgg ttggaactta cagtaaaatt atgaaccata aaaattcact tacctttcct    900
gatgataatg acatatcaaa agaagcaaaa aaccttattt gtgccttcct tactgacagg    960
gaagtgaggt tagggcgaaa tggtgtgaaa gaaatcaaac gacatctctt cttcaaaaat    1020
gaccagtggg cttgggaaac gctccgagac actgtagcac cagttgtacc cgatttaagt    1080
agtgacattg atactagtaa ttttgatgac ttggaagaag ataaaggaga ggaagaaaca    1140
ttccctattc ctaaagcttt cgttggcaat caactacctt tgtaggatt tacatatat     1200 agcaatcgta gatacttatc ttcagcaaat cctaatgata acagaactag ctccaatgca    1260
gataaaagct tgcaggaaag tttgcaaaaa acaatctata agctggaaga acagctgcat    1320
aatgaaatgc agttaaaaga tgaaatggag cagaagtgca gaacctcaaa cataaaacta    1380
gacaagataa tgaaagaatt ggatgaagag ggaaatcaaa aagaaatct agaatctaca    1440 gtgtctcaga ttgagaagga gaaaatgttg ctacagcata gaattaatga gtaccaaaga    1500
aaagctgaac aggaaaatga aagagaagaa aatgtagaaa atgaagtttc tacattaaag    1560
gatcagttgg aagacttaaa gaaagtcagt cagaattcac agcttgctaa tgagaagctg    1620
tcccagttac aaaagcagct agaagaagcc aatgacttac ttaggacaga atcggacaca    1680
gctgtaagat tgaggaagag tcacacagag atgagcaagt caattagtca gttagagtcc    1740
ctgaacagag agttgcaaga gagaaatcga attttagaga attctaagtc acaaacagac    1800
aaagattatt accagctgca agctatatta gaagctgaac gaagagacag aggtcatgat    1860
tctgagatga ttggagacct tcaagctcga attcatctt tacaagagga ggtgaagcat    1920
ctcaaacata atctcgaaaa agtggaagga gaaagaaaag aggctcaaga catgcttaat    1980
cactcagaaa aggaaagaa taatttagag atagatttaa actacaaact taaatcatta    2040
caacaacggt tagaacaaga ggtaaatgaa cacaaagtaa ccaaagctcg tttaactgac    2100
aaacatcaat ctattgaaga ggcaaagtct gtggcaatgt gtgagatgga aaaaagctg    2160 aaagaagaaa gagaagctcg agagaaggct gaaaatcggg ttgttcagat tgagaaacag    2220
tgttccatgc tagacgttga tctgaagcaa tctcagcaga actagaaca tttgactgga    2280 aataaagaaa ggatggagga tgaagttaag aatctaaccc tgcaactgga gcaggaatca    2340
aataagcggc tgttgttaca aaatgaattg aagactcaag catttgaggc agacaattta    2400
aaaggtttag aaaagcagat gaaacaggaa ataaatactt tattggaagc aaagagatta    2460
ttagaatttg agttagctca gcttacgaaa cagtatagag gaaatgaagg acagatgcgg    2520
gagctacaag atcagcttga agctgagcaa tatttctcga cactttataa aacccaggta    2580
```

```
aaggaactta aagaagaaat tgaagaaaaa aacagagaaa atttaaagaa aatacaggaa    2640
ctacaaaatg aaaagaaac tcttgctact cagttggatc tagcagaaac aaaagctgag    2700
tctgagcagt tggcgcgagg ccttctggaa gaacagtatt ttgaattgac gcaagaaagc    2760
aagaaagctg cttcaagaaa tagacaagag attacagata aagatcacac tgttagtcgg    2820
cttgaagaag caaacagcat gctaaccaaa gatattgaaa tattaagaag agagaatgaa    2880
gagctaacag agaaaatgaa gaaggcagag gaagaatata aactggagaa ggaggaggag    2940
atcagtaatc ttaaggctgc ctttgaaaag aatatcaaca ctgaacgaac ccttaaaaca    3000
caggctgtta acaaattggc agaaataatg aatcgaaaag atttttaaaat tgatagaaag    3060 aaagctaata cacaagattt gagaagaaa gaaaaggaaa atcgaaagct gcaactggaa    3120
ctcaaccaag aaagagagaa attcaaccag atggtagtga acatcagaa ggaactgaat    3180 gacatgcaag cgcaattggt agaagaatgt gcacatagga atgagcttca gatgcagttg    3240
gccagcaaag agagtgatat tgagcaattg cgtgctaaac ttttggacct ctcggattct    3300
acaagtgttg ctagttttcc tagtgctgat gaaactgatg gtaacctccc agagtcaaga    3360
attgaaggtt ggcttcagt accaaataga ggaaatatca aacgatatgg ctggaagaaa    3420
cagtatgttg tggtaagcag caaaaaaatt ttgttctata atgacgaaca agataaggag    3480
caatccaatc catctatggt attggacata gataaactgt ttcacgttag acctgtaacc    3540
caaggagatg tgtatagagc tgaaactgaa gaaattccta aaatattcca gatactatat    3600
gcaaatgaag gtgaatgtag aaaagatgta gagatggaac cagtacaaca agctgaaaaa    3660
actaatttcc aaaatcacaa aggccatgag tttattccta cactctacca ctttcctgcc    3720
aattgtgatg cctgtgccaa acctctctgg catgttttta agccacccc tgccctagag    3780 tgtcgaagat gccatgttaa gtgccacaga gatcacttag ataagaaaga ggacttaatt    3840
tgtccatgta aagtaagtta tgatgtaaca tcagcaagag atatgctgct gttagcatgt    3900
tctcaggatg aacaaaaaaa atgggtaact catttagtaa agaaaatccc taagaatcca    3960
ccatctggtt ttgttcgtgc ttcccctcga acgctttcta caagatccac tgcaaatcag    4020
tctttccgga aagtggtcaa aaaatacatct ggaaaaacta gttaaccatg tgactgagtg    4080
ccctgtggaa tcgtgtggga tgctacctga taaaccaggc ttcttttaacc atgcagagca    4140 gacaggctgt ttctttgaca caaatatcac aggcttcagg gttaagattg ctgttttttct    4200 gtccttgctt tggcacaaca cactgagggt tttttttatt gcgggttgc ctacaggtag    4260 attagattaa ttattactat gtaatgcaag tacagttggg ggaaagctta ggtagatata    4320 tttttttaa aaggtgctgc cttttgggat ttataagaaa atgcctgtca gtcgtgatag    4380
aacagagttt tcctcatatg agtaagagga agggactttc actttcaagt ggaacagcca    4440
tcactatcaa gatcagctca tggaaggagt aaagaaaata tctcaaaatg agacaaactg    4500 aagtttgtt tttttttaa tgacttaagt ttttgtgctc ttgcaagact atacaaaact    4560
attttaagaa agcagtgata tcacttgaac ttcagtgccc tcactgtaga atttaaaagc    4620
cttactgttg attgcccatg ttggacttga tggagaaatt aaatatcttt cattatgctt    4680
tacaaaatac tgtatatgtt tcagcaagtt tggggaatgg gagaggacaa aaaaagtta    4740 catttaatct atgcatttttt gccaagccat attgagttat tttactacta gagacattag    4800
gaaactaact gtacaaaaga accaagtttaa aaagcatttt gtggggtaca tcatttctat    4860
aattgtataa tgtatttctt tgtggtttta aatgataaag acattaagtt aacaaacata    4920
```

```
taagaaatgt atgcactgtt tgaaatgtaa attattctta gaacactttc aatgggggtt    4980
gcattgtcct tttagtgcct taatttgaga taattatttt actgccatga gtaagtatag    5040
aaatttcaaa aaatgtattt tcaaaaaatt atgtgtgtca gtgagttttt cattgataat    5100
tggtttaatt taaaatattt agaggtttgt tggactttca taaattgagt acaatctttg    5160
catcaaacta cctgctacaa taatgacttt ataaaactgc aaaaaatgta gaaggttgca    5220
ccaacataaa aaggaaatat ggcaatacat ccatgatgtt ttccagttaa cataggaatt    5280
accagataaa tactgttaaa ctcttgtcca gtaacaagag ttgattcata tggacagtat    5340
gatttattgt ttatttttt aaccaaatac ctcctcagta atttataatg ctttgcagt     5400
aatgtgtatc agataagaag cactggaaaa ccgatcgtct ctaggatgat atgcatgttt    5460
caagtggtat tgaaagccgc actgatggat atgtaataat aaacatatct gttattaata    5520
tactaatgac tctgtgctca tttaatgaga aataaaagta atttatggat gggtatcttt    5580
aattttact gcaatgtgtt ttctcatggc tgaaatgaat ggaaaacata cttcaaatta     5640
gtctctgatt gtatataaat gtttgtgaaa ttccatggtt agattaaagt gtatttttaa    5700
aagataaaa                                                            5709

<210> SEQ ID NO 52
<211> LENGTH: 4910
<212> TYPE: DNA
<213> ORGANISM: Homo sapiens

<400> SEQUENCE: 52
atgaacactc caaagaaga attccaggac tggcccatag tcagaatagc agctcattta      60
ccagacctca ttgtctatgg acatttctcc ccagagcgac cctttatgga ttattttgac    120
ggagtcctga tgtttgttga tatttcaggt tttactgcaa tgactgagaa gttcagcagt    180
gccatgtaca tggacagagg ggctgagcag ttggtggaga tcctcaacta ccacataagt    240
gcaatagtgg agaaagtgtt gattttggga ggagacatcc tgaaatttgc aggtgatgca    300
ctgctagccc tgtggagggt ggagcgaaag cagctgaaaa acattatcac agtggtaatt    360
aaatgtagcc tggagatcca tggattgttt gagacccagg agtgggaaga aggcctagac    420
atccgagtca agataggact ggctgctggc cacatcagca tgttggtctt tggagatgaa    480
acacacagcc acttttctgg tgattggtcag gcagtggacg atgtgcgcct tgcccagaac    540
atggctcaga tgaatgatgt tattctgtca ccaaactgct ggcagctctg tgaccggagc    600
atgattgaaa ttgagagtgt tccagatcag agagcagtta aggttaactt cttaaaacca    660
ccccccaatt ttaattttga tgaatttttc acaaagtgta cgaccttcat gcattattat    720
ccttctggtg agcacaaaaa cctcctgagg cttgcatgca cgctgaagcc tgatcctgaa    780
ctggagatgt ccctacaaaa gtatgtgatg gaaagcattt tgaagcagat tgataacaaa    840
cagcttcagg gctatttatc tgagcttcgc ccagtgacga ttgtgtttgt gaacctgatg    900
tttgaagacc aagacaaagc agaagagata ggcccagcca tccaggatgc ctatatgcac    960
atcacttctg tcctgaagat cttccaaggc caaatcaata agtcttcat gtttgacaag    1020
ggctgctctt tcctctgtgt ctttggcttc cctggggaaa aggtacctga cgagctcact    1080
catgctctgg aatgtgctat ggatatattt gacttctgct ctcaagtcca caaatccaa    1140
actgtatcca tcggtgttgc cagtgggatt gtcttctgtg ggatcgttgg acacactgtg    1200
agacacgagt acacagtcat tggtcaaaaa gtcaacttag ctgccaggat gatgatgtac    1260
tacccaggaa ttgtgacctg cgactctgtc acctacaatg ggagcaacct accagcgtac    1320
```

```
tttttttaaag agcttccaaa gaaagttatg aaaggtgttg cagattctgg accattgtat    1380
cagtattggg gccgtactga gaaagtcatg tttggtatgg cgtgcctcat ctgcaacaga    1440
aaggaggatt acccctttgct gggacgtaat aaagagatca actacttcat gtatactatg   1500
aagaaatttt tgatatctaa cagcagccaa gtcttaatgt atgagggatt accaggatat    1560
ggaaaaagcc agatacttat gaaaattgag tacctggccc aaggtaagaa tcacaggatt    1620
attgccattt cattgaataa gatcagcttc catcaaactt tctataccat ccagatgttc    1680
atggccaatg tcctaggcct agacacttgt aaacattata agaacgaca gaccaaccttt    1740 cgaaataaag tcatgacact gttggatgaa aagttctact gtcttcttaa tgacattttc    1800
catgttcagt tccctatttc tcgggagatt ccaggatga gcaccttgaa aaagcaaaaa     1860
caattggaaa tattgtttat gaagatcttg aagctgatag tgaaagagga aaggattatt    1920
tttatcattg atgaggccca gtttgtggat tcgacctcct ggagatttat ggagaagctt    1980
atccggactc ttcctatctt catcattatg tccctgtgtc ccttcgttaa cattccctgt    2040
gcagctgcca gggccgtaat aaagaacagg aacaccacct acattgtcat tggtgcagta   2100
cagcctaacg acatctccaa caagatctgt cttgacctca atgtgagctg catctccaaa    2160
gaactggact cgtacctggg ggagggaagc tgtgggattc cattttactg tgaagaattg    2220
cttaaaaacc tggaacatca tgaggtactc gttttccaac aaacggagtc tgaggaaaag    2280
acaaatagga cctggaataa cctgttcaag tattccatta agctaacaga aagttaaac    2340 atggttactc tccatagtga taaggaaagt gaagaagtct gtcacctcac aagtggtgtc    2400
agactgaaaa acctgtcacc tccaacgtca ttaaaagaaa tctctctgat ccagctggat    2460
agcatgagac tttcccacca aatgctggtg agatgtgctg ccatcattgg cctgaccttc    2520
accactgagt tgttgtttga gattctcccc tgttggaata tgaagatgat gatcaagacc    2580
ctggcaaccc tagtggaatc taacattttt tattgtttcc ggaatggcaa ggagcttcaa    2640
aaggccctga acagaatga tcccctcattt gaggtgcact atcgttcctt gtctctgaag    2700
cccagtgaag ggatggatca cggtgaagag aacagcttc gtgaactgga gaatgaggtg    2760
atcgagtgcc acaggattcg attctgtaac cctatgatgc agaaaacagc ctacgagctg    2820
tggctcaagg accagagaaa agccatgcac ttgaaatgtg cccgctttttt agaagaagat    2880 gcccacagat gtgaccactg ccgaggcagg gacttcattc cctatcatca cttcacagtg    2940
aatattcggc tcaacgcttt agacatggat gccattaaaa agatggctat gtctcatgga    3000
tttaaaactg aagaaaagct tatcttgtcc aactcagaga ttcctgagac atctgcattt    3060
tttcctgaaa atcgcagtcc tgaagaaata agagaaaaga tcttgaatttt ctttgaccac    3120 gttttaacaa aaatgaagac atctgacgaa gacattatcc ctctggaatc ttgccagtgt    3180
gaagaaatcc tagagattgt catcttgcct ctggcccacc attttctggc tttgggagaa    3240
aatgacaaag cctatatatta cttcttagaa attgcatctg cttatctcat cttttgtgat    3300
aactacatgg catacatgta tttgaatgaa ggacagaagt tgctaaaaac tctcaagaag    3360
gacaaatctt ggagccagac atttgagtct gccaccttttt acagcctcaa aggtgaggtc    3420
tgtttcaata tgggccagat agtgcttgcc aagaaaatgc tgaggaaggc actgaagctc    3480
ctcaaccgaa tctttcctta caacttaatc tccttgtttc tccatatcca tgtcgagaaa    3540
aacagacact ttcattatgt gaatcggcag gcccaagaga gcccacctcc agggaagaag    3600
aggctggcac aactttaccg gcaaactgtc tgcctttcct tgctgtggcg catctatagc    3660
```

```
tacagttatc tttttcactg caagtattat gcccacctgg cagttatgat gcaaatgaat    3720
actgcactgg aaactcaaaa ttgtttccag atcattaagg cttacctaga ctattcgcta    3780
taccaccacc tggctggcta caaaggtgtg tggttcaaat atgaagtcat ggccatggag    3840
cacatcttca acctccccct gaaaggcgag ggcattgaaa tcgtggcata cgtggctgag    3900
acactggtct tcaacaagct cataatggga cacctggatt tggccattga gttaggctcc    3960
cgagcccttc agatgtgggc actgctccag aatcccaacc gacattatca gtccctctgc    4020
agacttagca gatgtctcct tctgaacagc agatacccgc aattgatcca ggtgctgggg    4080
cggctgtggg agctttctgt aacacaggaa cacatcttca gcaaggcatt tttctatttt    4140
gtctgcttgg acatcctgct ttattctggt tttgtttata aacatttga agaatgtttg     4200 gaattcatac accaatacga aaacaacaga atcctcaagt tccacagtgg actcctcctg    4260
ggactttatt cctctgtagc tatctggtat gccagacttc aggaatggga caacttttac    4320
aaattttcca atagagctaa aaatcttttg ccaagaagaa ccatgacact tacttactat    4380
gacggaatat ctaggtacat ggaggggcaa gttcttcacc ttcaaaaaca aatcaaagaa    4440
cagtcagaga atgcccaagc cagtggggag gagctactca agaacttgga gaatctggtg    4500
gctcaaaata ccactggccc tgtcttttgc ccaaggctct accacctgat ggcttacgtc    4560
tgtatattaa tgggagatgg gcagaaatgt ggcctcttcc tgaacacagc cttgcggctc    4620
tctgaaacac aggggaatat actggagaaa tgctggctga acatgaacaa agaatcatgg    4680
tactcaacct ctgagttaaa agaagaccaa tggcttcaga cgatcttgag tctcccatca    4740
tgggaaaaaa ttgtagcagg cagggtaaac attcaggatc ttcaaaaaaa caaattcctg    4800
atgagagcta ataccgtgga caatcatttc taacatgtca agaaaaaag atttaataa     4860 gcactatgtc cttgtgatta tctattattg acctttctcc gtggctggcc               4910
```

<210> SEQ ID NO 53
<211> LENGTH: 3066
<212> TYPE: DNA
<213> ORGANISM: Homo sapiens
<400> SEQUENCE: 53

```
atggcgtctt cgaccccatc ttcgtccgca acctcctcga acgcgggagc ggaccccaat     60
accactaacc tgcgcccac aacgtacgat acctggtgcg cgtggcccca tggatgcacc     120
agaaaactgg ggctcaagat ctgcggcttc ttgcaaagga ccaacagcct ggaagagaag     180
agtcgccttg tgagtgcctt caaggagagg caatcctcca agaacctgct ttcctgtgaa     240
aacagcgacc gggatgcccg cttccggcgc acagagactg acttctctaa tctgtttgct     300
agagatctgc ttccggctaa gaacggtgag gagcaaaccg tgcaattcct cctggaagtg     360
gtggacatac tcctcaacta tgtccgcaag acatttgatc gctccaccaa ggtgctggac     420
tttcatcacc acaccagtt gctggaaggc atggagggct tcaacttgga gctctctgac     480
caccccgagt ccctggagca gatcctggtt gactgcagag acaccttgaa gtatgggtt      540 cgcacaggtc atcctcgatt tttcaaccag ctctccactg gattggatat tattggccta     600
gctggagaat ggctgacatc aacggccaat accaacatgt ttacatatga aattgcacca     660
gtgtttgtcc tcatggaaca aataacactt aagaagatga gagagatagt tggatggtca     720
agtaaagatg gtgatgggat attttctcct gggggcgcca tatccaacat gtacagcatc     780
atggctgctc gctacaagta cttccccgaa gttaagacaa agggcatggc ggctgtgcct     840
aaactggtcc tcttcacctc agaacagagt cactattcca taaagaaagc tggggctgca     900
```

```
cttggctttg gaactgacaa tgtgattttg ataaagtgca atgaaagggg gaaataatt    960
ccagctgatt ttgaggcaaa aattcttgaa gccaaacaga agggatatgt tcccttttat  1020
gtcaatgcaa ctgctggcac gactgtttat ggagcttttg atccgataca agagattgca  1080
gatatatgtg agaaatataa cctttggttg catgtcgatg ctgcctgggg aggtgggctg  1140
ctcatgtcca ggaagcaccg ccataaactc aacggcatag aaagggccaa ctcagtcacc  1200
tggaaccctc acaagatgat gggcgtgctg ttgcagtgct ctgccattct cgtcaaggaa  1260
aagggtatac tccaaggatg caaccagatg tgtgcaggat acctcttcca gccagacaag  1320
cagtatgatg tctcctacga caccggggac aaggcaattc agtgtggccg ccacgtggat  1380
atcttcaagt tctggctgat gtggaaagca agggcacag tgggatttga aaaccagatc  1440
aacaaatgcc tggaactggc tgaataccte tatgccaaga ttaaaaacag agaagaattt  1500
gagatggttt tcaatggcga gcctgagcac acaaacgtct gttttggta tattccacaa  1560
agcctcaggg gtgtgccaga cagccctcaa cgacgggaaa agctacacaa ggtggctcca  1620
aaaatcaaag ccctgatgat ggagtcaggt acgaccatgg ttggctacca gccccaaggg  1680
gacaaggcca acttcttccg gatggtcatc tccaacccag ccgctaccca gtctgacatt  1740
gacttcctca ttgaggagat agaaagactg gccaggatc tgtaatcatc cttcgcagaa  1800
catgagttta tgggaatgcc ttttccctct ggcactccag aacaaacctc tatatgttgc  1860
tgaaacacac aggccatttc attgagggaa acataatat cttgaagaat attgttaaaa  1920
ccttacttaa agcttgtttg ttctagttag caggaaatag tgttcttttt aaaaagttgc  1980
acattaggaa cagagtatat atgtacagtt atacatacct ctctctatat atacatgtat  2040
agtgagtgtg gctagtaat agatcacggc atgtttcccg ctccaagaga attcacttta  2100
ccttcagcag ttaccgagga gctaaacatg ctgccaacca gcttgtccaa caactccagg  2160
aaaactgttt ttcaaaacgc catgtcctag gggccaaggg aaatgctgtt ggtgagaatc  2220
gacctcactg tcagcgtttc tccacctgaa gtgatgatgg atgagaaaaa acaccaccaa  2280
atgacaagtc acaccctccc cattagtatc ctgttagggg aaaatagtag cagagtcatt  2340
gttacaggtg tactatggct gtattttag agattaattt gtgtagattg tgtaaattcc  2400
tgttgtctga ccttggtggt gggaggggga gactatgtgt catgatttca atgattgttt  2460
aattgtaggt caatgaaata tttgcttatt tatattcaga gatgtaccat gttaaagagg  2520
cgtcttgtat tttcttccca tttgtaatgt atcttattta tatatgaagt aagttctgaa  2580
aactgtttat ggtattttcg tgcatttgtg agccaaagag aaaagattaa aattagtgag  2640
atttgtattt atattagagt gcccttaaaa taatgattta agcatttac tgtctgtaag  2700
agaattctaa gattgtacat aaagtcatat atatggaaat cctgttactt aaatagcatc  2760
tgctcttctc ttacgctctc tgtctggctg tacgtctggt gttctcaatg cttttctagc  2820
aactgttgga taataactag atctcctgta attttgtagt agttgatgac caatctctgt  2880
gactcgctta gctgaaacct aaggcaacat ttccgaagac cttctgaaga tctcagataa  2940
agtgaccagg ctcacaactg tttttgaaga agggaaattc acactgtgcg ttttagagta  3000
tgcaagaaga atataaataa ataaaatat tctccatgga gaatttgaac aaaaaaaaaa  3060
aaaaaa                                                             3066
```

<210> SEQ ID NO 54
<211> LENGTH: 1140
<212> TYPE: DNA

<213> ORGANISM: Homo sapiens

<400> SEQUENCE: 54

```
atggcgcggt tcctgacact ttgcacttgg ctgctgttgc tcggcccgg gctcctggcg      60
accgtgcggg ccgaatgcag ccaggattgc gcgacgtgca gctaccgcct agtgcgcccg    120
gccgacatca acttcctggc ttgcgtaatg aatgtgaag gtaaactgcc ttctctgaaa    180
atttgggaaa cctgcaagga gctcctgcag ctgtccaaac cagagcttcc tcaagatggc    240
accagcaccc tcagagaaaa tagcaaaccg gaagaaagcc atttgctagc caaaaggtat    300
gggggcttca tgaaaaggta tggaggcttc atgaagaaaa tggatgagct ttatcccatg    360
gagccagaag aagaggccaa tggaagtgag atcctcgcca gcggtatgg gggcttcatg    420
aagaaggatg cagaggagga cgactcgctg gccaattcct cagacctgct aaaagagctt    480
ctggaaacag gggacaaccg agagcgtagc caccaccagg atggcagtga taatgaggaa    540
gaagtgagca agagatatgg gggcttcatg agaggcttaa agagaagccc ccaactggaa    600
gatgaagcca aagagctgca gaagcgatat ggggcttca tgaagagt aggtcgccca    660
gagtggtgga tggactacca gaaacggtat ggaggtttcc tgaagcgctt gccgaggct    720
ctgccctccg acgaagaagg cgaaagttac tccaaagaag ttcctgaaat ggaaaaaga    780
tacggaggat ttatgagatt ttaatatctt ttcccactag tggccccagg ccccagcaag    840
cctcccctcca tcctccagtg ggaaactgtt gatggtgttt tattgtcatg tgttgcttgc    900
cttgtatagt tgacttcatt gtctggataa ctatacaacc tgaaaactgt catttcaggt    960
tctgtgctct ttttggagtc tttaagctca gtattagtct attgcagcta tctcgttttc   1020
atgctaaaat agttttgtt atcttgtctc ttatttttga caaacatcaa taaatgctta   1080
cttgtatata gagataataa acctattacc ccaagtgcat aaaaaaaaaa aaaaaaaaaa   1140
```

<210> SEQ ID NO 55
<211> LENGTH: 3045
<212> TYPE: DNA
<213> ORGANISM: Homo sapiens

<400> SEQUENCE: 55

```
atggggctgt ttggaaagac ccaggagaag ccgcccaaag aactggtcaa tgagtggtca      60
ttgaagataa gaaggaaat gagagttgtt gacaggcaaa taagggatat ccaaagagaa    120
gaagaaaaag tgaaacgatc tgtgaaagat gctgccaaga agggccagaa ggatgtctgc    180
atagttctgg ccaaggagat gatcaggtca aggaaggctg tgagcaagct gtatgcatcc    240
aaagcacaca tgaactcagt gctcatgggg atgaagaacc agctcgcggt cttgcgagtg    300
gctggttccc tgcagaagag cacagaagtg atgaaggcca tgcaaagtct tgtgaagatt    360
ccagagattc aggccaccat gagggagttg tccaaagaaa tgatgaaggc tgggatcata    420
gaggagatgt tagaggacac ttttgaaagc atggacgatc aggaagaaat ggaggaagaa    480
gcagaaatgg aaattgacag aattctcttt gaaattacag caggggcctt gggcaaagca    540
cccagtaaag tgactgatgc ccttccagag ccagaacctc aggagcgat ggctgcctca    600
gaggatgagg aggaggagga agaggctctg gaggccatgc agtcccggct ggccacactc    660
cgcagctagg ggctgcctac cccgctgggt gtgcacacac tcctctcaag agctgccatt    720
ttatgtgtct cttgcactac acctctgttg tgaggactac cattttggag aaggttctgt    780
ttgtctcttt tcattctctg cccaggtttt gggatcgcaa aggattgtt cttataaaag    840
tggcataaat aaatgcatca tttttaggag tatagacaga tatatcttat tgtggggagg    900
```

```
ggaaagaaat ccatctgctc atgaagcact tctgaaaata taggtgattg cctgaatgtc    960
gaagactcta cttttgtcta taaaacacta tataaatgaa ttttaataaa tttttgcttt   1020
agcacttggc cccattgtag attgccctgt gcagtaaact ttcaaggtgt cggctgcccc   1080
agattgcttc atttgctggg tgtggaaaga gttgctatgg ccaggcatat gggatttgga   1140
agctcagcag aagtgacttc tgctctgtgg ttgctgctcc ccggctttca cagacatggt   1200
atggcagcca ttcttttatc tatttaacca agaggatgct ggggaattgt gctgcttgtc   1260
ctgttggctg gtggctgcat tatgtcctgg ggtgtgcatg tgggtctatt tagagcttct   1320
gtcccttcct tcccattgca agttgcaccc agatgagaca gctgtagtac taggtctctt   1380
tcacctctca ttgcctgtcc ctgcttcgag ctggttgtct tgtgcgtggg acatgggcct   1440
tcctatctgt gttttctcaa agtcaggagc tgaccaggag cacactaagg tgtggtcatg   1500
catcataacc aacattcact catctgggac attcttaaga tacatttata aatcatttca   1560
gcagtagtac tttgtatgtg ttgagagttt acagagctct ttgacatacg cgatcttagt   1620
ctttacaaat aaggaaaaca gctcagtttg gaagtatca gagatgggat tcaaacccag   1680
atcctctggt ccaagttgta tgtgcactga actaatcagg caggaaaaaa gcccagccac   1740
tgtctcacag attgtttttt gtatattgta gcaaaatcct gaaacaatgg ggtccttcca   1800
gtctcatcat acaaaatggc aatcttggct gggtgcggtg gttcatgcct ataatcccag   1860
tgctttacaa ggctgaggca ggaggctctc ttgagaatag gagttcaaga ccagcctggg   1920
caacatagca agatcctgtc tctccaaaaa aaaaaaaaaa aaaaaaaaaa aatttcattt   1980
ttgagtccag aggaccctcc tattactctt gatttcatct tcagagtgta gttaaaaaat   2040
tattttaaat aattattttt ttaaatcagt tgtaggttca cagcaaaagt ggacaaaaag   2100
aaatttctca tatatcccct gccctcacac atgcatagcc tcccaccact atcagtatcc   2160
cacaccagag tggtacattt gttacaatca ataaacctcc attgacacat cattatcacc   2220
caaagtccat agtttacatg aagattcact ctggtgttgt acattgtatg ggcttagaca   2280
aatgtatgat gatatctaca attatagaat catacagaat agtttcactg ccctaaaact   2340
tctctatgct tcacctgttc atcccttct tccctaatcc cctggcaacc actttaaaaa   2400
aaaaattagg ttcaggggt acatgtgcag gtaaactcgt gacaagggg tttgttatac   2460
agattattta gtgacccagg tactaagcct agtacccaat agttactttt ctggtcctgt   2520
cccttttccc accctccacc ctcaggtagg ccccagtatg ttattccttt gtgtccatgt   2580
tatttcactc ccacttgtga gaacatggaa tatttggttt cctgttccta tgttagtttg   2640
ttaaggataa tggcctccag ccccatccat gttcctgcaa aggacatgat ctttctttgg   2700
caaccacttt ttactgtcgc catagttctt ccttttctag aatgtcatat ggaatcata   2760
tagtatgtag ccttttcaga ctggcttctt tcacttaata atatgcaatt aaggttcctc   2820
catgtcattt catggcttaa tagtgcattt atttttagca ctgaataata ctccattgtc   2880
tagatgaata gtttatccat tcacctattg aaagacttct tggtggtttc caagttttgg   2940
caattatgaa taaagctgtt gtaaacatct ttgtgcaggt ttttctatgg gcatgttttt   3000
aattcatttg aataaatacc aagagcttca gtgctggatc ataaa              3045
```

<210> SEQ ID NO 56
<211> LENGTH: 1361
<212> TYPE: DNA
<213> ORGANISM: Homo sapiens

<400> SEQUENCE: 56

```
atgctgtgct gtatgagaag aaccaaacag gttgaaaaaa atgatgacga ccaaaagatt    60
gaacaagatg gtatcaaacc agaagataaa gctcataagg ccgcaaccaa aattcaggct   120
agcttccgtg gacacataac aaggaaaaag ctcaaaggag agaagaagga tgatgtccaa   180
gctgctgagg ctgaagctaa taagaaggat gaagcccctg ttgccgatgg ggtggagaag   240
aagggagaag gcaccactac tgccgaagca gccccagcca ctggctccaa gcctgatgag   300
cccggcaaag caggagaaac tccttccgag gagaagaagg gggagggtga tgctgccaca   360
gagcaggcag ccccccaggc tcctgcatcc tcagaggaga aggccggctc agctgagaca   420
gaaagtgcca ctaaagcttc cactgataac tcgccgtcct ccaaggctga agatgcccca   480
gccaaggagg agcctaaaca gccgatgtg cctgctgctg tcactgctgc tgctgccacc    540
acccctgccg cagaggatgc tgctgccaag gcaacagccc agcctccaac ggagactggg   600
gagagcagcc aagctgaaga gaacatagaa gctgtagatg aaaccaaacc taaggaaagt   660
gcccggcagg acgagggtaa agaagaggaa cctgaggctg accaagaaca tgcctgaact   720
ctaagaaatg gctttccaca tccccaccct cccctctcct gagcctgtct ctccctaccc   780
tcttctcagc tccactctga agtcccttcc tgtcctgctc acgtctgtga gtctgtcctt   840
tcccacccac tagccctctt tctctctgtg tggcaaacat ttaaaaaaaa aaaaaaaaag   900
caggaaagat cccaagtcaa acagtgtggc ttaaacattt tttgtttctt ggtgttgtta   960
tggcaagttt ttggtaatga tgattcaatc attttgggaa attcttgcac tgtatccaag  1020
ttatttgatc tggtgcgtgt ggccctgtgg gagtccactt tcctctctct ctctctctct  1080
gttccaagtg tgtgtgcaat gttccgttca tctgaggagt ccaaaatatc gagtgaattc  1140
aaaatcattt ttgttttcct cctttcaat gtgatggaat gaacaaaaag gaaaaaattc    1200
aaaaaaccca gtttgtttta aaaataaata aataaagcaa atgtgccaat tagcgtaaac  1260
ttgcggctct aaggctccctt tttcaacccg aatattaata aatcatgaga gtaatcaagg  1320
tcaaaaaaaa aaaaaaaaaa aaaaaaaaaa aaaaaaaaa a                        1361
```

<210> SEQ ID NO 57
<211> LENGTH: 1641
<212> TYPE: DNA
<213> ORGANISM: Homo sapiens

<400> SEQUENCE: 57

```
atgggaggca agctcagcaa gaagaagaag ggctacaatg tgaacgacga gaaagccaag    60
gagaaagaca agaaggccga gggcgcggcg acggaagagg aggggacccc gaaggagagt   120
gagcccccagg cggccgcaga gcccgccgag gccaaggagg gcaaggagaa gcccgaccag   180
gacgccgagg gcaaggccga ggagaaggag ggcgagaagg acgcggcggc tgccaaggag   240
gaggccccga ggcggagcc cgagaagacg gagggcgcgg cagaggccaa ggctgagccc   300
ccgaaggcgc ccgagcagga gcaggcggcc cccggcccg ctgcgggcgg cgaggccccc   360
aaagctgctg aggccgccgc ggccccggcc gagagcgcgg ccctgccgc cggggaggag   420
cccagcaagg aggaagggga acccaaaaag actgaggcgc ccgcagctcc tgccgccag   480
gagaccaaaa gtgacggggc cccagcttca gactcaaaac ccggcagctc ggaggctgcc   540
cctctcttcca aggagacccc cgcagcacg gaagcgccta gttccacacc caaggcccag   600
ggcccgcag cctctgcaga agagcccaag ccggtggagg cccggcagc taattccgac   660
caaaccgtaa ccgtgaaaga gtgacaagga cagcctatag gaaaaacaat accacttaaa   720
```

```
acaatctcct ctctctctct ctctctctct ctctatctct ctctctatct cctctctctc    780
tctcctctcc tatctctcct ctctctctct cctatactaa cttgtttcaa attggaagta    840
atgatatgta ttgcccaagg aaaaatacag gatgttgtcc catcaaggga gggaggggt     900 gggagaatcc aaatagtatt tttgtgggga aatatctaat ataccttcag tcaactttac    960
caagaagtcc tggatttcca agatccgcgt ctgaaagtgc agtacatcgt ttgtacctga   1020
aactgccgcc acatgcactc ctccaccgct gagagttgaa tagcttttct tctgcaatgg   1080
gagttgggag tgatgcgttt gattctgccc acagggcctg tgccaaggca atcagatctt   1140
tatgagagca gtattttctg tgttttcttt ttaatttaca gcctttctta ttttgatatt   1200 ttttaatgt tgtggatgaa tgccagcttt cagacagagc ccacttagct tgtccacatg    1260
gatctcaatg ccaatcctcc attcttcctc tccagatatt tttgggagtg acaaacattc   1320
tctcatccta cttagcctac ctagattct catgacgagt taatgcatgt ccgtggttgg    1380
gtgcacctgt agttctgttt attggtcagt ggaaatgaaa aaaaaaaaaa aaaaaagtct   1440
gcgttcattg cagttccagt ttctcttcca ttctgtgtca cagacaccaa cacaccactc   1500
attggaaaat ggaaaaaaaa aacaaaaaaa aaacaaaaaa atgtacaatg gatgcattga   1560
aattatatgt aattgtataa atggtgcaac agtaataaag ttaaacaatt aaaaagaaaa   1620
aaaaaaaaaa aaaaaaaaaa a                                              1641

<210> SEQ ID NO 58
<211> LENGTH: 1051
<212> TYPE: DNA
<213> ORGANISM: Homo sapiens

<400> SEQUENCE: 58
atgaccatcc ttttccttac tatggttatt tcatactttg gttgcatgaa ggctgccccc     60
atgaaagaag caaacatccg aggacaaggt ggcttggcct acccaggtgt gcggacccat    120
gggactctgg agagcgtgaa tgggcccaag gcaggttcaa gaggcttgac atcattggct    180
gacactttcg aacacgtgat agaagagctg ttggatgagg accataaagt tcggcccaat    240
gaagaaaaca ataaggacgc agacttgtac acgtccaggg tgatgctcag tagtcaagtg    300
cctttggagc ctcctcttct cttctgctg gaggaataca aaaattacct agatgctgca    360
aacatgtcca tgatggtcct cgccactct gaccctgccc gccaggggga gctgagcgtg    420
tgtgacagta ttagtgagtg ggtaacggcg gcagacaaaa agactgcagt ggacatgtcg    480
ggcgggacgt tcagtcct tgaaaaggtc cctgtatcaa aaggccaact gaagcaatac    540
ttctacgaga ccaagtgcaa tcccatgggt tacacaaaag aaggctgcag gggcatagac    600
aaaaggcatt ggaactccca gtgccgaact acccagtcgt acgtgcgggc ccttaccatg    660
gatagcaaaa agagaattgg ctggcgattc ataaggatag acacttcttg tgtatgtaca    720
ttgaccatta aaggggaag atagtggatt tatgttgtat agattagatt atattgagac    780
aaaaattatc tatttgtata tatacataac agggtaaatt attcagttaa gaaaaaaata    840 atttttattaa ctgcatgtat aaatgaagtt tatacagtac agtggttcta caatctattt    900
attggacatg tccatgacca gaagggaaac agtcatttgc gcacaactta aaagtctgc     960 attacattcc ttgataatgt tgtggtttgt tgccgttgcc aagaactgaa aacataaaaa   1020
tttaaaaaaa ataatcccctt gcatgctgcc c                                 1051

<210> SEQ ID NO 59
```

<211> LENGTH: 964
<212> TYPE: DNA
<213> ORGANISM: Homo sapiens

<400> SEQUENCE: 59

```
atgtccatct tgttttatgt gatatttctc gcttatctcc gtggcatcca aggtaacaac    60
atggatcaaa ggagtttgcc agaagactcg ctcaattccc tcattattaa gctgatccag   120
gcagatattt tgaaaaacaa gctctccaag cagatggtgg acgttaagga aaattaccag   180
agcaccctgc ccaaagctga ggctccccga gagccggagc ggggagggcc cgccaagtca   240
gcattccagc cagtgattgc aatggacacc gaactgctgc gacaacagag acgctacaac   300
tcaccgcggg tcctgctgag cgacagcacc cccttggagc ccccgccctt gtatctcatg   360
gaggattacg tgggcagccc cgtggtggcg aacagaacat cacggcggaa acggtacgcg   420
gagcataaga gtcaccgagg ggagtactcg gtatgtgaca gtgagagtct gtgggtgacc   480
gacaagtcat cggccatcga cattcgggga caccaggtca cggtgctggg ggagatcaaa   540
acgggcaact ctcctgtcaa acaatatttt tatgaaacgc gatgtaagga agccaggccg   600
gtcaaaaacg gttgcagggg tattgatgat aaacactgga actctcagtg caaacatcc    660
caaacctacg tccgagcact gacttcagag aacaataaac tcgtgggctg gcggtggata   720
cggatagaca cgtcctgtgt gtgtgccttg tcgagaaaaa tcggaagaac atgaattggc   780
atctctcccc atatataaat tattacttta aattatatga tatgcatgta gcatataaat   840
gtttatattg tttttatata ttataagttg acctttattt attaaacttc agcaacccta   900
cagtatataa gcttttttct caataaaatc agtgtgcttg ccttccctca ggcctctccc   960
atct                                                                964
```

<210> SEQ ID NO 60
<211> LENGTH: 636
<212> TYPE: DNA
<213> ORGANISM: Homo sapiens

<400> SEQUENCE: 60

```
atgaagttat gggatgtcgt ggctgtctgc ctggtgctgc tccacaccgc gtccgccttc    60
ccgctgcccg ccggtaagag gcctcccgag gcgcccgccg aagaccgctc cctcggccgc   120
cgccgcgcgc ccttcgcgct gagcagtgac tcaaatatgc cagaggatta tcctgatcag   180
ttcgatgatg tcatggattt tattcaagcc accattaaaa gactgaaaag gtcaccagat   240
aaacaaatgg cagtgcttcc tagaagagag cggaatcggc aggctgcagc tgccaaccca   300
gagaattcca gaggaaaagg tcggagaggc cagaggggca aaaaccgggg ttgtgtctta   360
actgcaatac atttaaatgt cactgacttg ggtctgggct atgaaaccaa ggaggaactg   420
atttttaggt actgcagcgg ctcttgcgat gcagctgaga caacgtacga caaaatattg   480
aaaaacttat ccagaaatag aaggctggtg agtgacaaag tagggcaggc atgttgcaga   540
cccatcgcct ttgatgatga cctgtcgttt ttagatgata acctggttta ccatattcta   600
agaaagcatt ccgctaaaag tgtggatgt atctga                              636
```

<210> SEQ ID NO 61
<211> LENGTH: 10541
<212> TYPE: DNA
<213> ORGANISM: Artificial Sequence
<220> FEATURE:
<223> OTHER INFORMATION: a synthetic oligonucleotide

<400> SEQUENCE: 61

```
cgcgtagatc tcacgtgagc atgcaggcct tgggcccaat gatccgacca gcaaaactcg      60
atgtacttcc gaggaactga tgtgcataat gcatcaggct ggtacattag atccccgctt     120
accgcgggca atatagcaac actaaaaact cgatgtactt ccgaggaagc gcagtgcata     180
atgctgcgca gtgttgccac ataaccacta tattaaccat ttatctagcg gacgccaaaa     240
actcaatgta tttctgagga agcgtggtgc ataatgccac gcagcgtctg cataactttt     300
attatttctt ttattaatca acaaaatttt gttttaaaca tttcaaaaaa aaaaaaaaaa     360
aaaaaaaaa aaaaaaaaa agggaattcc tcgattaatt aagcggccgc tcgaggggaa       420
ttaattcttg aagacgaaag gcccaggtgg cacttttcgg ggaaatgtgc gcggaacccc     480
tatttgttta ttttctaaa tacattcaaa tatgtatccg ctcatgagac aataaccctg      540
ataaatgctt caataatatt gaaaaggaa gagtatgagt attcaacatt tccgtgtcgc      600
ccttattccc ttttttgcgg cattttgcct tcctgttttt gctcacccag aaacgctggt     660
gaaagtaaaa gatgctgaag atcagttggg tgcacgagtg ggttacatcg aactggatct     720
caacagcggt aagatccttg agagttttcg ccccgaagaa cgttttccaa tgatgagcac     780
ttttaaagtt ctgctatgtg gcgcggtatt atcccgtgtt gacgccgggc aagagcaact     840
cggtcgccgc atacactatt ctcagaatga cttggttgag tactcaccag tcacagaaaa     900
gcatcttacg gatggcatga cagtaagaga attatgcagt gctgccataa ccatgagtga     960
taacactgcg gccaacttac ttctgacaac gatcggagga ccgaaggagc taaccgcttt    1020
tttgcacaac atgggggatc atgtaactcg ccttgatcgt tgggaaccgg agctgaatga    1080
agccatacca aacgacgagc gtgacaccac gatgcctgta gcaatggcaa caacgttgcg    1140
caaactatta actggcgaac tacttactct agcttcccgg caacaattaa tagactggat    1200
ggaggcggat aaagttgcag gaccacttct gcgctcggcc cttccggctg gctggtttat    1260
tgctgataaa tctggagccg gtgagcgtgg gtctcgcggt atcattgcag cactggggcc    1320
agatggtaag ccctcccgta tcgtagttat ctacacgacg gggagtcagg caactatgga    1380
tgaacgaaat agacagatcg ctgagatagg tgcctcactg attaagcatt ggtaactgtc    1440
agaccaagtt tactcatata ctttagat tgatttaaaa cttcattttt aatttaaaag     1500
gatctaggtg aagatccttt ttgataatct catgaccaaa atcccttaac gtgagttttc    1560
gttccactga gcgtcagacc ccgtagaaaa gatcaaagga tcttcttgag atcctttttt    1620
tctgcgcgta atctgctgct tgcaaacaaa aaaaccaccg ctaccagcgg tggtttgttt    1680
gccggatcaa gagctaccaa ctctttttcc gaaggtaact ggcttcagca gagcgcagat    1740
accaaatact gtccttctag tgtagccgta gttaggccac cacttcaaga actctgtagc    1800
accgcctaca tacctcgctc tgctaatcct gttaccagtg gctgctgcca gtggcgataa    1860
gtcgtgtctt accgggttgg actcaagacg atagttaccg gataaggcgc agcggtcggg    1920
ctgaacgggg ggttcgtgca cacagcccag cttggagcga acgacctaca ccgaactgag    1980
atacctacag cgtgagcatt gagaaagcgc cacgcttccc gaagggagaa aggcggacag    2040
gtatccggta agcggcaggg tcggaacagg agagcgcacg agggagcttc caggggggaaa   2100
cgcctggtat ctttatagtc ctgtcgggtt tcgccacctc tgacttgagc gtcgattttt    2160
gtgatgctcg tcagggggggc ggagcctatg gaaaaacgcc agcaacgcga gctcgtatgg    2220
acatattgtc gttagaacgc ggctacaatt aatacataac cttatgtatc atacacatac    2280
```

```
gatttaggggg acactataga ttgacggcgt agtacacact attgaatcaa acagccgacc    2340
aattgcacta ccatcacaat ggagaagcca gtagtaaacg tagacgtaga ccccccagagt    2400 ccgtttgtcg tgcaactgca aaaaagcttc ccgcaatttg aggtagtagc acagcaggtc    2460
actccaaatg accatgctaa tgccagagca ttttcgcatc tggccagtaa actaatcgag    2520
ctggaggttc ctaccacagc gacgatcttg gacataggca gcgcaccggc tcgtagaatg    2580
ttttccgagc accagtatca ttgtgtctgc cccatgcgta gtccagaaga cccggaccgc    2640
atgatgaaat acgccagtaa actggcggaa aaagcgtgca agattacaaa caagaacttg    2700
catgagaaga ttaaggatct ccggaccgta cttgatacgc cggatgctga acaccatcg     2760 ctctgctttc acaacgatgt tacctgcaac atgcgtgccg aatattccgt catgcaggac    2820
gtgtatatca acgctcccgg aactatctat catcaggcta tgaaaggcgt gcggaccctg    2880
tactggattg gcttcgacac cacccagttc atgttctcgg ctatggcagg ttcgtaccct    2940
gcgtacaaca ccaactgggc cgacgagaaa gtccttgaag cgcgtaacat cggactttgc    3000
agcacaaagc tgagtgaagg taggacagga aaattgtcga taatgaggaa gaaggagttg    3060
aagcccgggt cgcgggttta tttctccgta ggatcgacac tttatccaga acacagagcc    3120
agcttgcaga gctggcatct tccatcggtg ttccacttga atggaaagca gtcgtacact    3180
tgccgctgtg atacagtggt gagttgcgaa ggctacgtag tgaagaaaat caccatcagt    3240
cccgggatca cgggagaaac cgtgggatac gcggttacac acaatagcga gggcttcttg    3300
ctatgcaaag ttactgacac agtaaaagga gaacgggtat cgttccctgt gtgcacgtac    3360
atcccggcca ccatatgcga tcagatgact ggtataatgg ccacggatat atcacctgac    3420
gatgcacaaa aacttctggt tgggctcaac cagcgaattg tcattaacgg taggactaac    3480
aggaacacca acaccatgca aaattacctt ctgccgatca tagcacaagg gttcagcaaa    3540
tgggctaagg agcgcaagga tgatcttgat aacgagaaaa tgctgggtac tagagaacgc    3600
aagcttacgt atgctgctt gtgggcgttt cgcactaaga aagtacattc gttttatcgc    3660
ccacctggaa cgcagacctg cgtaaaagtc ccagcctctt ttagcgcttt tcccatgtcg    3720
tccgtatgga cgacctcttt gcccatgtcg ctgaggcaga aattgaaact ggcattgcaa    3780
ccaaagaagg aggaaaaact gctgcaggtc tcggaggaat tagtcatgga ggccaaggct    3840
gcttttgagg atgctcagga ggaagccaga gcggagaagc tccgagaagc acttccacca    3900
ttagtggcag acaaaggcat cgaggcagcc gcagaagttg tctgcgaagt ggaggggctc    3960
caggcggaca tcggagcagc attagttgaa accccgcgcg gtcacgtaag gataatacct    4020
caagcaaatg accgtatgat cggacagtat atcgttgtct cgccaaactc tgtgctgaag    4080
aatgccaaac tcgcaccagc gcacccgcta gcagatcagg ttaagatcat aacacactcc    4140
ggaagatcag gaaggtacgc ggtcgaacca tacgacgcta agtactgat gccagcagga    4200 ggtgccgtac catggccaga attcctagca ctgagtgaga gcgccacgtt agtgtacaac    4260
gaaagagagt ttgtgaaccg caaactatac cacattgcca tgcatggccc cgccaagaat    4320
acagaagagg agcagtacaa ggttacaaag gcagagcttg cagaaacaga gtacgtgttt    4380
gacgtggaca gaagcgttg cgttaagaag gaagaagcct caggtctggt cctctcggga    4440
gaactgacca cccctcccta tcatgagcta gctctggagg gactgaagac ccgacctgcg    4500
gtcccgtaca aggtcgaaac aataggagtg ataggcacac cggggtcggg caagtcagct    4560
attatcaagt caactgtcac ggcacagat cttgttacca gcgaaagaa agaaaattgt    4620 cgcgaaattg aggccgacgt gctaagactg agggggtatgc agattacgtc gaagacagta    4680
```

```
gattcggtta tgctcaacgg atgccacaaa gccgtagaag tgctgtacgt tgacgaagcg    4740
ttcgcgtgcc acgcaggagc actacttgcc ttgattgcta tcgtcaggcc ccgcaagaag    4800
gtagtactat gcggagaccc catgcaatgc ggattcttca acatgatgca actaaaggta    4860
catttcaatc accctgaaaa agacatatgc accaagacat tctacaagta tatctcccgg    4920
cgttgcacac agccagttac agctattgta tcgacactgc attacgatgg aaagatgaaa    4980
accacgaacc cgtgcaagaa gaacattgaa atcgatatta caggggccac aaagccgaag    5040 ccagggata tcatcctgac atgtttccgc gggtgggtta agcaattgca aatcgactat      5100
cccggacatg aagtaatgac agccgcggcc tcacaagggc taaccagaaa aggagtgtat    5160
gccgtccggc aaaaagtcaa tgaaaaccca ctgtacgcga tcacatcaga gcatgtgaac    5220
gtgttgctca cccgcactga ggacaggcta gtgtggaaaa ccttgcaggg cgacccatgg    5280
attaagcagc ccactaacat acctaaagga aactttcagg ctactataga ggactgggaa    5340
gctgaacaca agggaataat tgctgcaata aacagcccca ctccccgtgc caatccgttc    5400
agctgcaaga ccaacgtttg ctgggcgaaa gcattggaac cgatactagc cacggccggt    5460
atcgtactta ccggttgcca gtggagcgaa ctgttcccac agtttgcgga tgacaaacca    5520
cattcggcca tttacgcctt agacgtaatt tgcattaagt ttttcggcat ggacttgaca    5580
agcggactgt tttctaaaca gagcatccca ctaacgtacc atcccgccga ttcagcgagg    5640
ccggtagctc attgggacaa cagcccagga acccgcaagt atgggtacga tcacgccatt    5700
gccgccgaac tctcccgtag atttccggtg ttccagctag ctgggaaggg cacacaactt    5760
gatttgcaga cggggagaac cagagttatc tctgcacagc ataacctggt cccggtgaac    5820
cgcaatcttc ctcacgcctt agtccccgag tacaaggaga gcaacccggc ccgtgcaaaa    5880
aaattcttga accagttcaa acaccactca gtacttgtgg tatcagagga aaaaattgaa    5940
gctccccgta agagaatcga atggatcgcc ccgattggca tagccggtgc agataagaac    6000
tacaacctgg cttccgggtt tccgccgcag gcacggtacg acctggtgtt catcaacatt    6060
ggaactaaat acagaaacca ccactttcag cagtgcgaag accatgcggc gaccttaaaa    6120 acccttcgc gttcggccct gaattgcctt aacccaggag gcaccctcgt ggtgaagtcc    6180
tatggctacg ccgaccgcaa cagtgaggac gtagtcaccg ctcttgccag aaagtttgtc    6240
agggtgtctg cagcgagacc agattgtgtc tcaagcaata cagaaatgta cctgattttc    6300
cgacaactag acaacagccg tacacggcaa ttcacccccgc accatctgaa ttgcgtgatt    6360
tcgtccgtgt atgagggtac aagagatgga gttggagccg cgccgtcata ccgcaccaaa    6420
agggagaata ttgctgactg tcaagaggaa gcagttgtca acgcagccaa tccgctgggt    6480
agaccaggcg aaggagtctg ccgtgccatc tataaacgtt ggccgaccag ttttaccgat    6540
tcagccacgg agacaggcac cgcaagaatg actgtgtgcc taggaaagaa agtgatccac    6600
gcggtcggcc ctgatttccg gaagcaccca gaagcagaag ccttgaaatt gctacaaaac    6660
gcctaccatg cagtggcaga cttagtaaat gaacataaca tcaagtctgt cgccattcca    6720
ctgctatcta caggcattta cgcagccgga aaagaccgcc ttgaagtatc acttaactgc    6780
ttgacaaccg cgctagacag aactgacgcg gacgtaacca tctattgcct ggataagaag    6840
tggaaggaaa gaatcgacgc ggcactccaa cttaaggagt ctgtaacaga gctgaaggat    6900
gaagatatgg agatcgacga tgagttagta tggattcatc cagacagttg cttgaaggga    6960
agaaagggat tcagtactac aaaaggaaaa ttgtattcgt acttcgaagg caccaaattc    7020
```

```
catcaagcag caaaagacat ggcggagata aaggtcctgt tccctaatga ccaggaaagt    7080
aatgaacaac tgtgtgccta catattgggt gagaccatgg aagcaatccg cgaaaagtgc    7140
ccggtcgacc ataacccgtc gtctagcccg cccaaaacgt tgccgtgcct ttgcatgtat    7200
gccatgacgc cagaaagggt ccacagactt agaagcaata acgtcaaaga agttacagta    7260
tgctcctcca ccccccttcc taagcacaaa attaagaatg ttcagaaggt tcagtgcacg    7320
aaagtagtcc tgtttaatcc gcacactccc gcattcgttc ccgcccgtaa gtacatagaa    7380
gtgccagaac agcctaccgc tcctcctgca caggccgagg aggcccccga agttgtagcg    7440
acaccgtcac catctacagc tgataacacc tcgcttgatg tcacagacat ctcactggat    7500
atggatgaca gtagcgaagg ctcactttttt tcgagcttta gcggatcgga caactctatt    7560
actagtatgg acagttggtc gtcaggacct agttcactag agatagtaga ccgaaggcag    7620
gtggtggtgg ctgacgttca tgccgtccaa gagcctgccc ctattccacc gccaaggcta    7680
aagaagatgg cccgcctggc agcggcaaga aaagagccca ctccaccggc aagcaatagc    7740
tctgagtccc tccacctctc ttttggtggg gtatccatgt ccctcggatc aattttcgac    7800
ggagagacgg cccgccaggc agcggtacaa cccctggcaa caggccccac ggatgtgcct    7860
atgtctttcg gatcgttttc cgacggagag attgatgagc tgagccgcag agtaactgag    7920
tccgaacccg tcctgtttgg atcatttgaa ccgggcgaag tgaactcaat tatatcgtcc    7980
cgatcagccg tatcttttcc actacgcaag cagagacgta gacgcaggag caggaggact    8040
gaatactgac taaccggggt aggtgggtac atattttcga cggacacagg ccctgggcac    8100
ttgcaaaaga agtccgttct gcagaaccag cttacagaac cgaccttgga gcgcaatgtc    8160
ctggaaagaa ttcatgcccc ggtgctcgac acgtcgaaag aggaacaact caaactcagg    8220
taccagatga tgcccaccga agccaacaaa agtaggtacc agtctcgtaa agtagaaaat    8280
cagaaagcca taaccactga gcgactactg tcaggactac gactgtataa ctctgccaca    8340
gatcagccag aatgctataa gatcacctat ccgaaaccat tgtactccag tagcgtaccg    8400
gcgaactact ccgatccaca gttcgctgta gctgtctgta acaactatct gcatgagaac    8460
tatccgacag tagcatctta tcagattact gacgagtacg atgcttactt ggatatggta    8520
gacgggacag tcgcctgcct ggatactgca accttctgcc ccgctaagct tagaagttac    8580
ccgaaaaaac atgagtatag agccccgaat atccgcagtg cggttccatc agcgatgcag    8640
aacacgctac aaaatgtgct cattgccgca actaaaagaa attgcaacgt cacgcagatg    8700
cgtgaactgc caacactgga ctcagcgaca ttcaatgtcg aatgctttcg aaaatatgca    8760
tgtaatgacg agtattggga ggagttcgct cggaagccaa ttaggattac cactgagttt    8820
gtcaccgcat atgtagctag actgaaaggc cctaaggccg ccgcactatt tgcaaagacg    8880
tataatttgg tcccattgca agaagtgcct atggatagat tcgtcatgga catgaaaaga    8940
gacgtgaaag ttacaccagg cacgaaacac acagaagaaa gaccgaaagt acaagtgata    9000
caagccgcag aaccccctggc gactgcttac ttatgcggga ttcaccggga attagtgcgt    9060
aggcttacgg ccgtcttgct tccaaacatt cacacgcttt ttgacatgtc ggcggaggat    9120
tttgatgcaa tcatagcaga acacttcaag caaggcgacc cggtactgga gacggatatc    9180
gcatcattcg acaaaagcca agacgacgct atggcgttaa ccggtctgat gatcttggag    9240
gacctgggtg tggatcaacc actactcgac ttgatcgagt gcgcctttgg agaaatatca    9300
tccacccatc tacctacggg tactcgtttt aaattcgggg cgatgatgaa atccggaatg    9360
ttcctcacac tttttgtcaa cacagttttg aatgtcgtta tcgccagcag agtactagaa    9420
```

-continued

```
gagcggctta aaacgtccag atgtgcagcg ttcattggcg acgacaacat catacatgga    9480
gtagtatctg acaaagaaat ggctgagagg tgcgccacct ggctcaacat ggaggttaag    9540
atcatcgacg cagtcatcgg tgagagacca ccttacttct gcggcggatt tatcttgcaa    9600
gattcggtta cttccacagc gtgccgcgtg gcggatcccc tgaaaaggct gtttaagttg    9660
ggtaaaccgc tcccagccga cgacgagcaa gacgaagaca gaagacgcgc tctgctagat    9720
gaaacaaagg cgtggtttag agtaggtata acaggcactt tagcagtggc cgtgacgacc    9780
cggtatgagg tagacaatat tacacctgtc ctactggcat tgagaacttt tgcccagagc    9840
aaaagagcat tccaagccat cagaggggaa ataaagcatc tctacggtgg tcctaaatag    9900
tcagcatagt acatttcatc tgactaatac acaacacca ccacctctag attccgcccc    9960
tctccctccc cccccctaa cgttactggc cgaagccgct tggaataagg ccggtgtgcg    10020
tttgtctata tgttattttc caccatattg ccgtcttttg gcaatgtgag ggcccggaaa    10080
cctggccctg tcttcttgac gagcattcct aggggtcttt cccctctcgc caaaggaatg    10140
caaggtctgt tgaatgtcgt gaaggaagca gttcctctgg aagcttcttg aagacaaaca    10200
acgtctgtag cgaccctttg caggcagcgg aaccccccac ctggcgacag gtgcctctgc    10260
ggccaaaagc cacgtgtata agatacacct gcaaaggcgg cacaacccca gtgccacgtt    10320
gtgagttgga tagttgtgga aagagtcaaa tggctctcct caagcgtatt caacaagggg    10380
ctgaaggatg cccagaaggt accccattgt atgggatctg atctggggcc tcggtgcaca    10440
tgctttacat gtgtttagtc gaggttaaaa aaacgtctag gcccccccgaa ccacggggac    10500 gtggttttcc tttgaaaaac acgatgataa gcttgccaca a                        10541
```

```
<210> SEQ ID NO 62
<211> LENGTH: 20
<212> TYPE: DNA
<213> ORGANISM: Artificial Sequence
<220> FEATURE:
<223> OTHER INFORMATION: a synthetic oligonucleotide

<400> SEQUENCE: 62
agcatagtac atttcatctg                                                20

<210> SEQ ID NO 63
<211> LENGTH: 20
<212> TYPE: DNA
<213> ORGANISM: Artificial Sequence
<220> FEATURE:
<223> OTHER INFORMATION: a synthetic oligonucleotide

<400> SEQUENCE: 63
aagtacatcg agttttgctg                                                20

<210> SEQ ID NO 64
<211> LENGTH: 20
<212> TYPE: DNA
<213> ORGANISM: Artificial Sequence
<220> FEATURE:
<223> OTHER INFORMATION: a synthetic oligonucleotide

<400> SEQUENCE: 64
acctggccct ttcgtcttca                                                20

<210> SEQ ID NO 65
<211> LENGTH: 29
<212> TYPE: DNA
```

```
<213> ORGANISM: Artificial Sequence
<220> FEATURE:
<223> OTHER INFORMATION: a synthetic oligonucleotide

<400> SEQUENCE: 65
aaccacgggg acgtggtttt cctttgaaa                                           29

<210> SEQ ID NO 66
<211> LENGTH: 621
<212> TYPE: DNA
<213> ORGANISM: Artificial Sequence
<220> FEATURE:
<223> OTHER INFORMATION: a synthetic oligonucleotide

<400> SEQUENCE: 66
tgactaatac tacaacacca ccacctctag attccgcccc tctccctccc cccccctaa          60 cgttactggc cgaagccgct tggaataagg ccggtgtgcg tttgtctata tgttattttc         120
caccatattg ccgtcttttg gcaatgtgag ggcccggaaa cctggccctg tcttcttgac         180
gagcattcct aggggtcttt cccctctcgc caaaggaatg caaggtctgt tgaatgtcgt         240
gaaggaagca gttcctctgg aagcttcttg aagacaaaca acgtctgtag cgacccttttg       300 caggcagcgg aaccccccac ctggcgacag gtgcctctgc ggccaaaagc cacgtgtata         360
agatacacct gcaaaggcgg cacaacccca gtgccacgtt gtgagttgga tagttgtgga        420
aagagtcaaa tggctctcct caagcgtatt caacaagggg ctgaaggatg cccagaaggt        480
accccattgt atgggatctg atctggggcc tcggtgcaca tgctttacat gtgtttagtc        540
gaggttaaaa aaacgtctag gccccccgaa ccacggggac gtggttttcc tttgaaaaac        600
acgatgataa gcttgccaca a                                                  621

<210> SEQ ID NO 67
<211> LENGTH: 420
<212> TYPE: DNA
<213> ORGANISM: Artificial Sequence
<220> FEATURE:
<223> OTHER INFORMATION: a synthetic oligonucleotide

<400> SEQUENCE: 67
cgcgtagatc tcacgtgagc atgcaggcct tgggcccaat gatccgacca gcaaaactcg         60
atgtacttcc gaggaactga tgtgcataat gcatcaggct ggtacattag atccccgctt        120
accgcgggca atatagcaac actaaaaact cgatgtactt ccgaggaagc gcagtgcata        180
atgctgcgca gtgttgccac ataaccacta tattaaccat ttatctagcg gacgccaaaa        240
actcaatgta tttctgagga agcgtggtgc ataatgccac gcagcgtctg cataactttt       300
attatttctt ttattaatca acaaaatttt gtttttaaca tttcaaaaaa aaaaaaaaa         360 aaaaaaaaaa aaaaaaaaa agggaattcc tcgattaatt aagcggccgc tcgagggaa          420
```